United States Patent
Morse et al.

(10) Patent No.: US 10,759,775 B2
(45) Date of Patent: Sep. 1, 2020

(54) ORGANIC SEMICONDUCTING COMPOUNDS

(71) Applicant: Raynergy Tek Incorporation, Hsinchu (TW)

(72) Inventors: Graham Morse, Southampton (GB); Lana Nanson, Southampton (GB); William Mitchell, Chandler's Ford (GB); Michal Krompiec, Southampton (GB); Mansoor D'Lavari, Bude (GB); Agnieszka Pron, Eastleigh (GB)

(73) Assignee: MERCK PATENT GmbH, Darmstadt (DE)

( * ) Notice: Subject to any disclaimer, the term of this patent is extended or adjusted under 35 U.S.C. 154(b) by 0 days.

(21) Appl. No.: 16/315,757

(22) PCT Filed: Jul. 6, 2017

(86) PCT No.: PCT/EP2017/066852
§ 371 (c)(1),
(2) Date: Jan. 7, 2019

(87) PCT Pub. No.: WO2018/007479
PCT Pub. Date: Jan. 11, 2018

(65) Prior Publication Data
US 2019/0389832 A1    Dec. 26, 2019

(30) Foreign Application Priority Data

Jul. 8, 2016 (EP) .................................. 16178589

(51) Int. Cl.
| H01L 51/00 | (2006.01) |
| H01L 51/42 | (2006.01) |
| C07D 333/78 | (2006.01) |
| C07D 495/14 | (2006.01) |
| C07D 495/22 | (2006.01) |
| C07D 513/04 | (2006.01) |

(52) U.S. Cl.
CPC ......... *C07D 333/78* (2013.01); *C07D 495/14* (2013.01); *C07D 495/22* (2013.01); *C07D 513/04* (2013.01); *H01L 51/0047* (2013.01); *H01L 51/0068* (2013.01); *H01L 51/0072* (2013.01); *H01L 51/0074* (2013.01); *H01L 51/4253* (2013.01)

(58) Field of Classification Search
CPC .............. C07D 333/78; H01L 51/0047; H01L 51/0068; H01L 51/0072; H01L 51/0074
USPC ......................................................... 257/78
See application file for complete search history.

(56) References Cited

U.S. PATENT DOCUMENTS

2012/0104940 A1    5/2012   Shin

FOREIGN PATENT DOCUMENTS

| CN | 104557968 A | 4/2015 |
| CN | 105315298 A | 2/2016 |
| CN | 106543200 A | 3/2017 |
| WO | 2010114243 A2 | 10/2010 |

OTHER PUBLICATIONS

International Search Report PCT/EP2017/066852 dated Sep. 26, 2017 (pp. 1-5).
Yongxi Li et al: "Non-fullerene acceptor with low energy loss and high external quantum efficiency: towards high performance polymer solar cells", Journal of Materials Chemistry A: Materials for Energy and Sustainability, vol. 4, No. 16, Feb. 22, 2016 (Feb. 22, 2016), GB, pp. 5890-5897, XP055405362, ISSN: 2050-7488.

*Primary Examiner* — Elias Ullah
(74) *Attorney, Agent, or Firm* — Millen, White, Zelano & Branigan; Csaba Henter

(57) ABSTRACT

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, organic photodetectors (OPD), organic field effect transistors (OFET) and organic light emitting diodes (OLED), and to OE, OPV, OPD, OFET and OLED devices comprising these compounds, compositions or polymer blends.

20 Claims, No Drawings

ORGANIC SEMICONDUCTING COMPOUNDS

TECHNICAL FIELD

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, organic photodetectors (OPD), organic field effect transistors (OFET) and organic light emitting diodes (OLED), and to OE, OPV, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 10%.

Another particular area of importance are OFETs. The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ cm$^2$V$^{-1}$ s$^{-1}$). In addition, it is important that the semiconducting material is stable to oxidation i.e. it has a high ionisation potential, as oxidation leads to reduced device performance. Further requirements for the semiconducting material are good processability, especially for large-scale production of thin layers and desired patterns, and high stability, film uniformity and integrity of the organic semiconductor layer.

Organic photodetectors (OPDs) are a further particular area of importance, for which conjugated light-absorbing polymers offer the hope of allowing efficient devices to be produced by solution-processing technologies, such as spin casting, dip coating or ink jet printing, to name a few only.

The photosensitive layer in an OPV or OPD device is usually composed of at least two materials, a p-type semiconductor, which is typically a conjugated polymer, an oligomer or a defined molecular unit, and an n-type semiconductor, which is typically a fullerene or substituted fullerene, graphene, a metal oxide, or quantum dots.

However, the OSC materials disclosed in prior art for use in OE devices have several drawbacks. They are often difficult to synthesis or purify (fullerenes), and/or do not absorb light strongly in the near IR spectrum >700 nm. In addition, other OSC materials do not often form a favourable morphology and/or donor phase miscibility for use in organic photovoltaics or organic photodetectors.

Therefore there is still a need for OSC materials for use in OE devices like OPVs, OPDs and OFETs, which have advantageous properties, in particular good processability, high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new OSC compounds, especially n-type OSCs, which can overcome the drawbacks of the OSCs from prior art, and which provide one or more of the above-mentioned advantageous properties, especially easy synthesis by methods suitable for mass production, good processability, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

The inventors of the present invention have found that one or more of the above aims can be achieved by providing compounds as disclosed and claimed hereinafter. These comprise an indaceno-type polycyclic central group having a "cis"-configuration, i.e. wherein the unfused atoms in the two five-membered rings fused to the central aromatic group are pointing in the same direction, as exemplarily shown in the following structure, wherein Ar is an aryl group and R are for example alkyl groups.

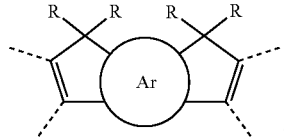

It has been found that compounds comprising such a central polycyclic unit, and further comprising two terminal electron withdrawing groups, can be used as n-type OSCs which show advantageous properties as described above.

Conjugated polymers based on linearly fused polycyclic aromatic units have been disclosed in prior art for use as p-type OSCs, such as indacenodithiophene (IDT) as disclosed for example in WO 2010/020329 A1 and EP 2075274 A1, or indacenodithienothiophene (IDTT) as disclosed for example in WO 2015/154845 A1.

OSC small molecules with an IDT core have been proposed for use as chromophores in OLEDs by K-T. Wong, T-C. Chao, L-C. Chi, Y-Y. Chu, A. Balaiah, S-F. Chiu, Y-H. Liu, and Y. Wang, *Org. Lett.*, 2006, 8, 5033.

More recently, OSC small molecules comprising an IDT or IDTT core that is end capped with 2-(3-oxo-2,3-dihydroinden-1-ylidene)malononitrile have been reported for use as non-fullerene n-type OSCs in OPV devices, for example by Y. Lin, J. Wang, Z.-G. Zhang, H. Bai, Y. Li, D. Zhu and X. Zhan, *Adv. Mater.*, 2015, 27, 1170, and by H. Lin, S. Chen, Z. Li, J. Y. L. Lai, G. Yang, T. McAfee, K. Jiang, Y. Li, Y. Liu, H. Hu, J. Zhao, W. Ma, H. Ade and H. Yan, Zhan, *Adv. Mater.*, 2015, 27, 7299, in CN104557968A and CN105315298 A.

However, the compounds as disclosed and claimed hereinafter have hitherto not been disclosed in prior art.

SUMMARY

The invention relates to a compound of formula I

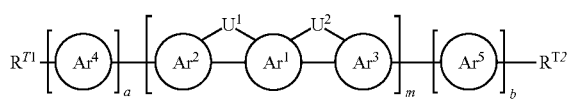

I wherein the individual radicals, independently of each other and on each occurrence identically or differently, have the following meanings $Ar^{1-3}$ arylene or heteroarylene that has from 5 to 20 ring atoms, is mono- or polycyclic, optionally contains fused rings, and is unsubstituted or substituted by one or more identical or different groups L, $Ar^{4,5}$ arylene or heteroarylene that has from 5 to 20 ring atoms, is mono- or polycyclic, optionally contains fused rings, and is unsubstituted or substituted by one or more identical or different groups L, or $CY^1=CY^2$ or —C≡C—, $Y^1$, $Y^2$ H, F, Cl or —CN, $U^1$ $CR^1R^2$, $SiR^1R^2$, $GeR^1R^2$, $NR^1$ or C=O, $U^2$ $CR^3R^4$, $SiR^3R^4$, $GeR^3R^4$, $NR^3$ or C=O, $R^{1-4}$ H, F, Cl or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^o$—, —$SiR^oR^{oo}$—, —$CF_2$—, —$CR^o$=$CR^{oo}$—, —$CY^1$=$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and the pair of $R^1$ and $R^2$ and/or the pair of $R^3$ and $R^4$ together with the C, Si or Ge atom to which they are attached, may also form a spiro group with 5 to 20 ring atoms which is mono- or polycyclic, does optionally contain fused rings, and is unsubstituted or substituted by one or more identical or different groups L, $R^{T1}$, $R^{T2}$ a carbyl or hydrocarbyl group with 1 to 30 C atoms that is optionally substituted by one or more groups L and optionally comprises one or more hetero atoms, and wherein at least one of $R^{T1}$ and $R^{T2}$ is an electron withdrawing group, L F, Cl, —$NO_2$, —CN, —NC, —NCO, —NCS, —OCN, —SCN, $R^o$, $OR^o$, $SR^o$, —C(=O)$X^o$, —C(=O)$R^o$, —C(=O)—$OR^o$, —O—C(=O)—$R^o$, —$NH_2$, —$NHR^o$, —$NR^oR^{oo}$, —C(=O)$NHR^o$, —C(=O)$NR^oR^{oo}$, —$SO_3R^o$, $SO_2R^o$, —OH, —$NO_2$, —$CF_3$, —$SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^o$, —$OR^o$, —$SR^o$, —C(=O)—$R^o$, —C(=O)—$OR^o$, —O—C(=O)—$R^o$, —O—C(=O)—$OR^o$, C(=O)—$NHR^o$, or —C(=O)—$NR^oR^{oo}$, $R^o$, $R^{oo}$ H or straight-chain or branched alkyl with 1 to 20, preferably 1 to 12, C atoms that is optionally fluorinated, $X^o$ halogen, preferably F or Cl, a, b 0, 1, 2 or 3, m 1, 2 or 3.

The invention further relates to novel synthesis methods for preparing compounds of formula I, and novel intermediates used therein.

The invention further relates to the use of compounds of formula I as semiconductor, preferably as electron acceptor or n-type semiconductor, preferably in a semiconducting material, an electronic or optoelectronic device, or a component of an electronic or optoelectronic device.

The invention further relates to the use of compounds of formula I as dyes or pigments.

The invention further relates to a composition comprising one or more compounds of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds of formula I, and further comprising a binder, preferably an electrically inert binder, very preferably an electrically inert polymeric binder.

The invention further relates to a composition comprising a compound of formula I, and further comprising one or more electron donors or p-type semiconductors, preferably selected from conjugated polymers.

The invention further relates to a composition comprising one or more n-type semiconductors, at least one of which is a compound of formula I, and further comprising one or more p-type semiconductors.

The invention further relates to a composition comprising one or more n-type semiconductors, at least one of which is a compound of formula I, and at least one other of which is a fullerene or fullerene derivative, and further comprising one or more p-type semiconductors, preferably selected from conjugated polymers.

The invention further relates to a bulk heterojunction (BHJ) formed from a composition comprising a compound of formula I as electron acceptor or n-type semiconductor, and one or more compounds which are electron donor or p-type semiconductors, and are preferably selected from conjugated polymers.

The invention further relates to the use of a compound of formula I or a composition as described above and below, as semiconducting, charge transporting, electrically conducting, photoconducting, photoactive or light emitting material.

The invention further relates to the use of a compound of formula I or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound of formula I or a composition as described above and below.

The invention further relates to an electronic or optoelectronic device, or a component thereof, or an assembly comprising it, which comprises a compound of formula I or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds of formula I, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells, laser diodes, Schottky diodes, photoconductors, photodetectors and thermoelectric devices.

Preferred devices are OFETs, OTFTs, OPVs, OPDs and OLEDs, in particular OPDs and BHJ OPVs or inverted BHJ OPVs.

The component of the electronic or optoelectronic device includes, without limitation, charge injection layers, charge transport layers, interlayers, planarising layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

In addition the compounds of formula I and compositions as described above and below can be used as electrode materials in batteries, or in components or devices for detecting and discriminating DNA sequences.

Terms and Definitions

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a unit of formula I or a polymer of formula III or IV or their subformulae, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^5$ or $R^6$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —R$^0$, —OR$^0$, —SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O)NR$^0$R$^{00}$, —SO$_3$R$^0$, —SO$_2$R$^0$, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, wherein X$^0$ is halogen, preferably F or Cl, and $R^O$, $R^{OO}$ denote H or straight-chain or branched alkyl with 1 to 20, preferably 1 to 12 C atoms that is optionally fluorinated.

Preferably L is selected from F, —CN, $R^O$, —$OR^O$, —$SR^O$, —C(=O)—$R^O$, —C(=O)—$OR^O$, —O—C(=O)—$R^O$, —O—C(=O)—$OR^O$, —C(=O)—$NHR^O$ and —C(=O)—$NR^OR^{OO}$.

Further preferably L is selected from F or alkyl, alkoxy, oxaalkyl, thioalkyl, fluoroalkyl, fluoroalkoxy, alkylcarbonyl, alkoxycarbonyl, with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

An arylalkyl or heteroarylalkyl group as referred to above and below preferably denotes —$(CH_2)_a$-aryl or —$(CH_2)_a$-heteroaryl, wherein a is an integer from 1 to 6, preferably 1, and "aryl" and "heteroaryl" have the meanings given above and below. A preferred arylalkyl group is benzyl which is optionally substituted by L.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred aryl and heteroaryl groups are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (~$SCH_3$), 1-thioethyl (—$SCH_2CH_3$), 1-thiopropyl (=—SCH$_2$CH$_2$CH$_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH$_2$ group adjacent to the sp$^2$ hybridised vinyl carbon atom is replaced.

A fluoroalkyl group can either be perfluoroalkyl C$_i$F$_{2i+1}$, wherein i is an integer from 1 to 15, in particular CF$_3$, C$_2$F$_5$, C$_3$F$_7$, C$_4$F$_9$, C$_5$F$_{11}$, C$_6$F$_{13}$, C$_7$F$_{15}$ or CO$_8$F$_{17}$, very preferably C$_6$F$_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methyl-pentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl ring are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are optionally replaced by F, or aryl, aryloxy, heteroaryl or heteroaryloxy that is optionally alkylated, alkoxylated, alkylthiolated or esterified and has 4 to 30 ring atoms. Further preferred substituents are selected from the group consisting of the following formulae

SUB1

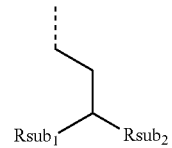

SUB2

SUB3

SUB4

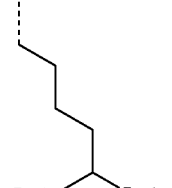

SUB5

SUB6

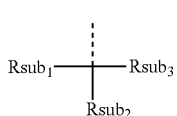

SUB7

SUB8

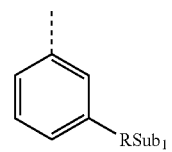

SUB9

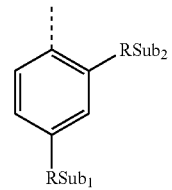

SUB10

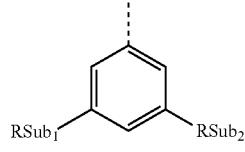

SUB11

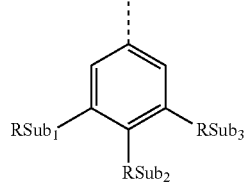

SUB12

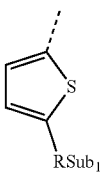

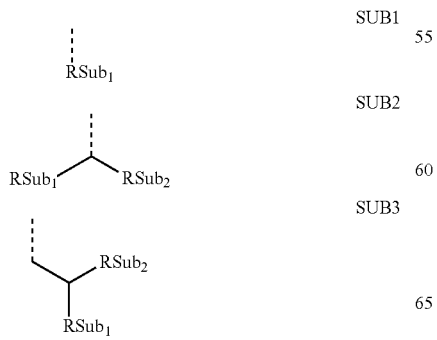

SUB13

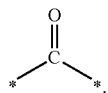

SUB14

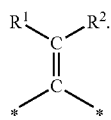

wherein RSub$_{1-3}$ denotes L as defined above and below and where at least one group RSub$_{1-3}$ is alkyl, alkoxy, oxaalkyl, thioalkyl, alkylcarbonyl or alkoxycarbonyl with 1 to 24 C atoms, preferably 1 to 20 C atoms, that is optionally fluorinated, and wherein the dashed line denotes the link to the ring to which these groups are attached. Very preferred among these substituents are those wherein all RSub$_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 20 C-atoms and being straight-chain or branched and wherein one or more H atoms are optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure As used herein, C=CR$^1$R$^2$ will be understood to mean a group having the structure As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

DETAILED DESCRIPTION

The compounds of the present invention are easy to synthesize and exhibit advantageous properties. They show good processibility for the device manufacture process, high solubility in organic solvents, and are especially suitable for large scale production using solution processing methods.

The compounds of formula I are especially suitable as (electron) acceptor or n-type semiconductor, and for the preparation of blends of n-type and p-type semiconductors which are suitable for use in OPD or BHJ OPV devices.

The compounds of formula I are further suitable to replace the fullerene compounds that have hitherto been used as n-type semiconductor in OPV or OPD devices.

Besides, the compounds of formula I show the following advantageous properties:

i) Substitution in positions $R^{1-4}$ and/or $Ar^{1-5}$ for example with solubilising groups enables greater light stability of the bulk heterojunction.

ii) Substitution in positions $R^{1-4}$ and/or $Ar^{1-5}$ for example with solubilising groups enables greater stability towards light illumination of the bulk heterojunction through mediation of the crystallisation and/or phase separation kinetic, thus stabilising the initial equilibrium thermodynamics in the BHJ.

iii) Substitution in positions $R^{1-4}$ and/or $Ar^{1-5}$ for example with solubilising groups enables greater thermal stability of the bulk heterojunction through mediation of the crystallisation and/or phase separation kinetic, thus stabilising the initial equilibrium thermodynamics in the BHJ.

iv) Compared to previously disclosed n-type OSCs for OPV/OPD application, the compounds of formula I provide the advantage that they enable further optimization of the HOMO and LUMO levels of the polycyclic unit through substitution, and careful selection of the $Ar^{1-5}$ units can give improved light absorption.

v) Further optimization of the HOMO and LUMO levels of the polycyclic unit in formula I through substitution and/or careful selection of the $Ar^{1-5}$ units can increase the open circuit potential ($V_{oc}$).

vi) When using the compounds as n-type OSC in a composition with a p-type OSC in the photoactive layer of an OPV or OPD, additional fine-tuning of the HOMO and LUMO levels of the polycyclic unit in formula I, for example through substitution and/or careful selection of the $Ar^{1-5}$ units, can reduce the energy loss in the electron transfer process between the n-type acceptor and the p-type donor material in the photoactive layer.

vii) Substitution in positions $R^{1-4}$ and/or $Ar^{1-5}$ can enable higher solubility in non-halogenated solvents due to the increased number of solubilising groups.

The synthesis of the compounds of formula I can be achieved based on methods that are known to the skilled person and described in the literature, as will be further illustrated herein.

In the compounds of formula I $Ar^4$ and $Ar^5$ are preferably arylene or heteroarylene as defined above.

Preferred groups $Ar^{1-5}$ in formula I are selected from the following formulae and their mirror images:

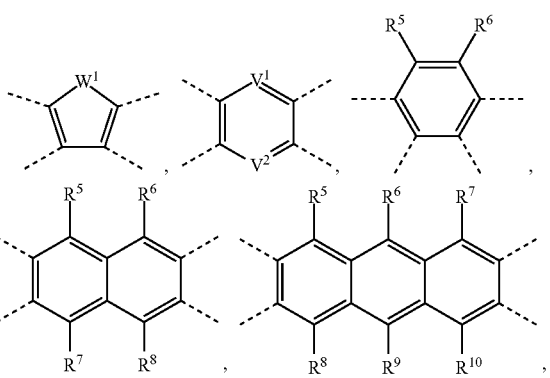

-continued
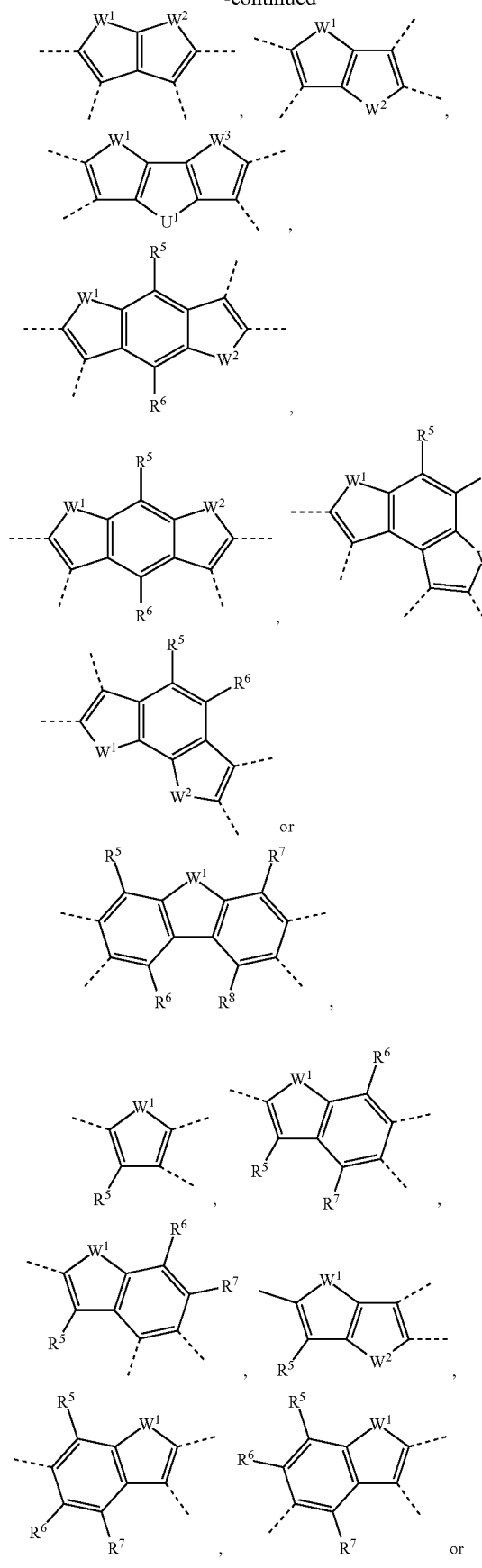
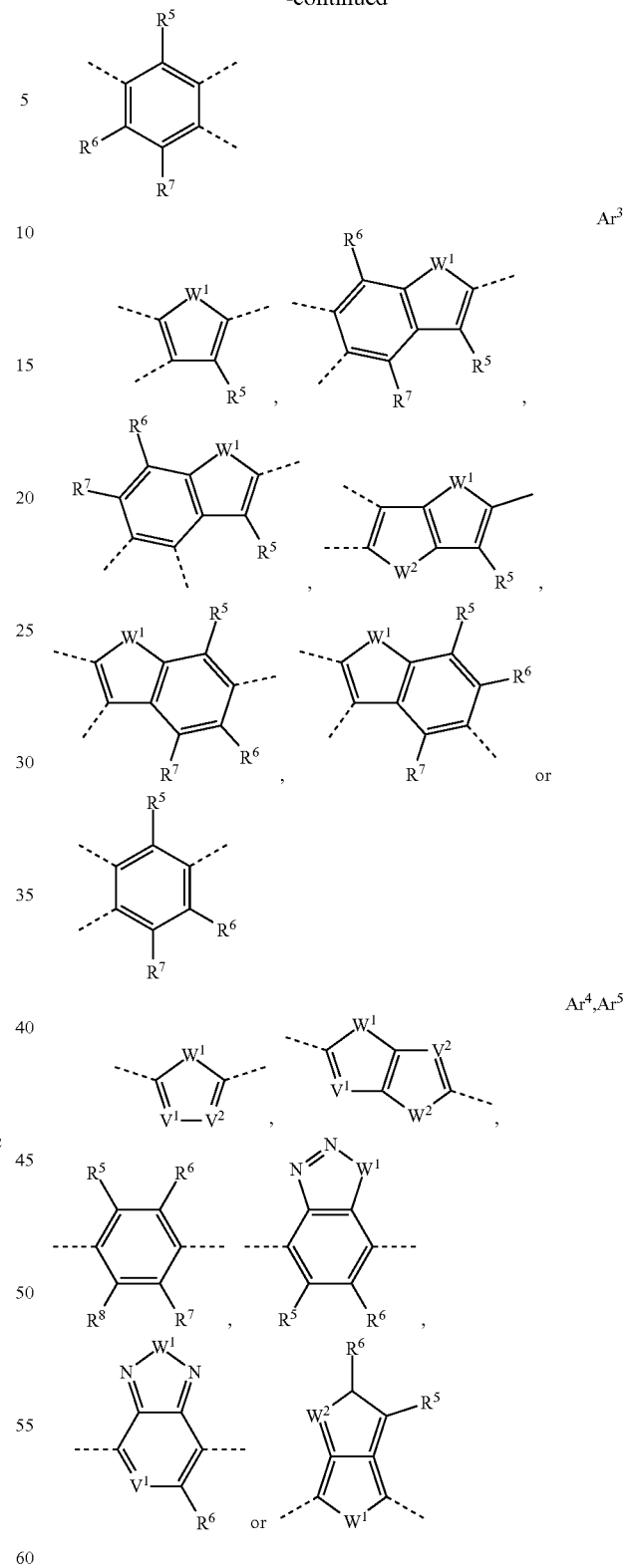
wherein the individual radicals, independently of each other and on each occurrence identically or differently, have the following meanings
$U^1$ one of the meanings of formula I,
$W^{1,2}$ S, O, Se or C=O,
$V^1$ $CR^5$ or N,
$V^2$ $CR^6$ or N, $R^{5-10}$ H, F, Cl, —CN or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L as defined above and below.

Very preferred groups $Ar^{1-3}$ in formula I are selected from the following formulae and their mirror images:

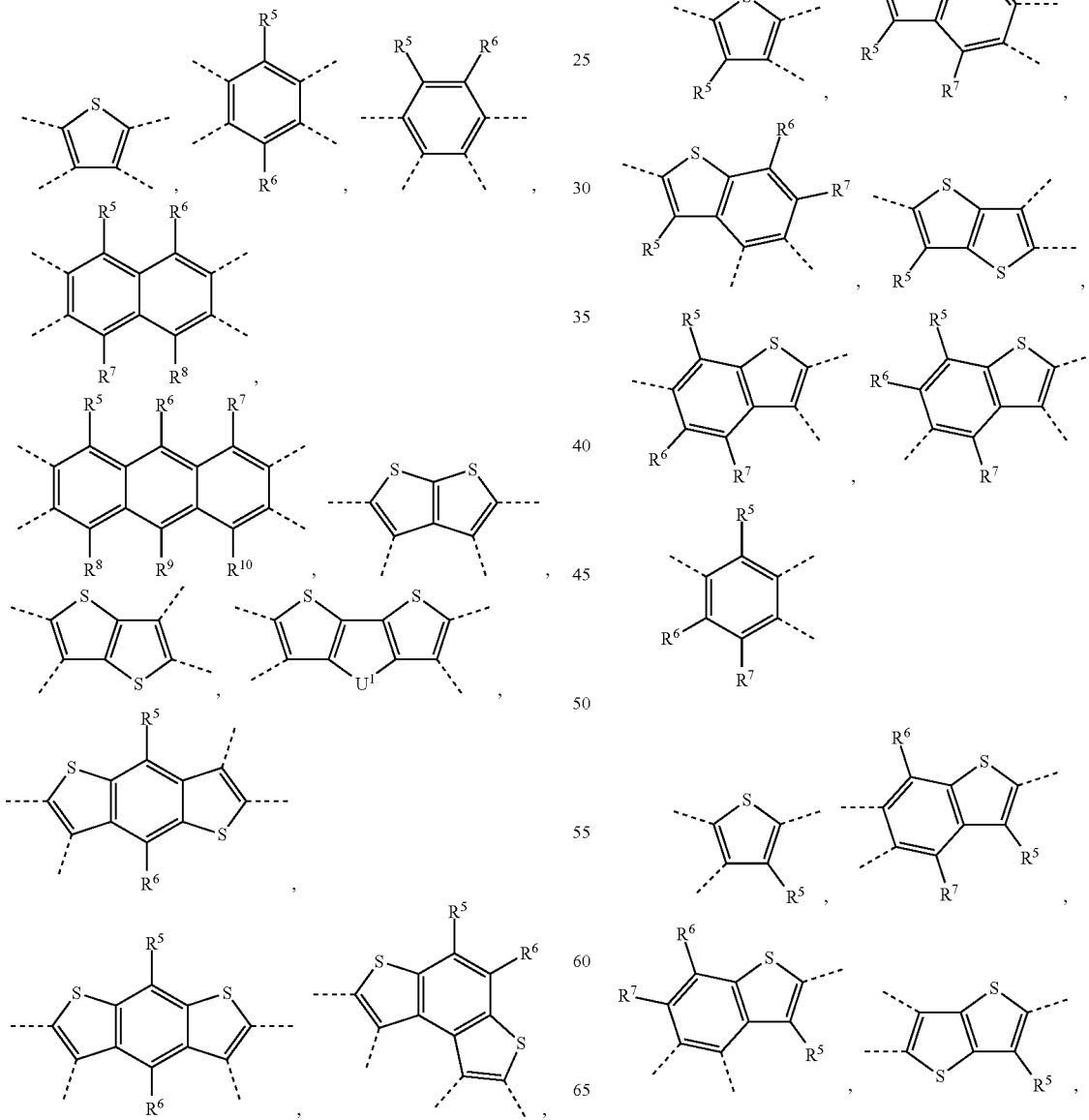

-continued

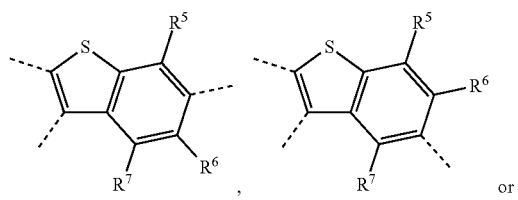

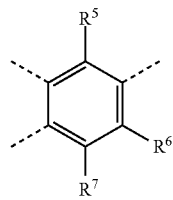

wherein $U^1$ and $R^{5-10}$ have the meanings given above and below.

Very preferred groups $Ar^4$ and $Ar^5$ in formula I are selected from the following formulae and their mirror images.

AR1

AR2

AR3

AR4

AR5

AR6

-continued

AR7

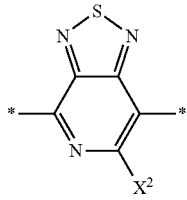

AR8

AR9

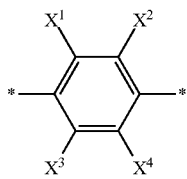

AR10

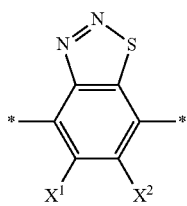

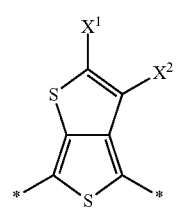

wherein $X^1$ and $X^2$ have one of the meanings given for $R^1$ above and below, and preferably denote H, F, Cl, —CN, —$R^0$, —$OR^0$ or —C(=O)$OR^0$.

Preferred formulae AR1, AR2, AR5, AR6, AR7, AR8, AR9 and AR10 are those containing at least one, preferably one, two or four substituents $X^{1-4}$ selected from F and Cl, very preferably F.

Preferably the groups $R^{T1}$ and $R^{T2}$ in formula I are selected from H, F, Cl, Br, —NO$_2$, —CN, —CF$_3$, R*, —CF$_2$—R*, —O—R*, —S—R*, —SO$_2$—R*, —SO$_3$—R*, —C(=O)—H, —C(=O)—R*, —C(=S)—R*, —C(=O)—CF$_2$—R*, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*, —NR*R**, —CR*=CR*R**, —C≡C—R*, —C≡C— SiR*RR*, SiR*RR*, —CH=CH(CN), —CH=C(CN)$_2$, —C(CN)=C(CN)$_2$, —CH=C(CN)(R$^a$), CH=C(CN)—C(=O)—OR*, —CH=C(CO—OR*)$_2$, —CH=C(CO—NR*R**)$_2$, and the group consisting of the following formulae

T1

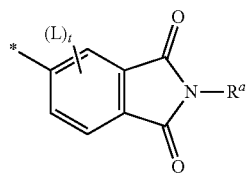

| | |
|---|---|
| T2 | T12 |
| T3 | T13 |
| T4 | T14 |
| T5 | T15 |
| T6 | T16 |
| T7 | |
| T8 | |
| T9 | T17 |
| T10 | |
| T11 | T18 |

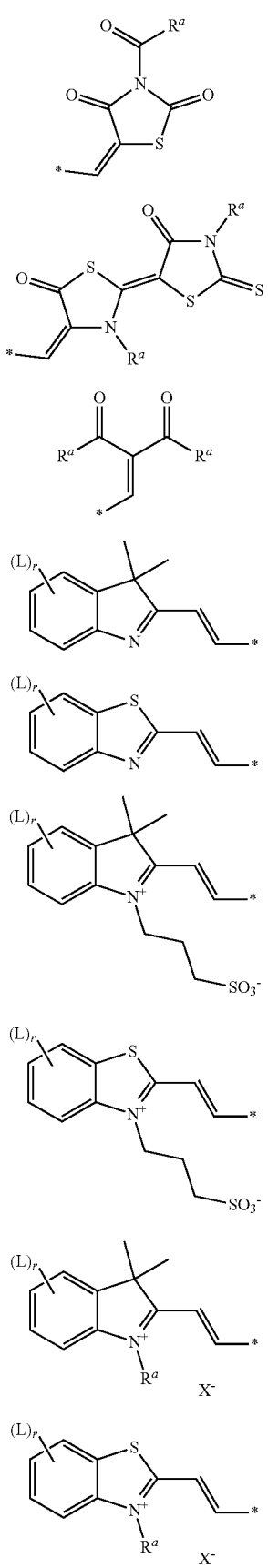
T19
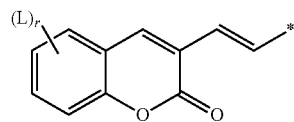
T28
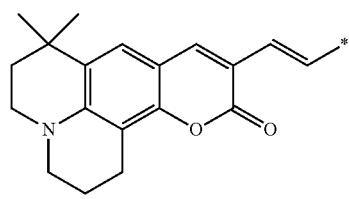
T29
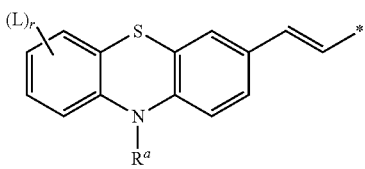
T30
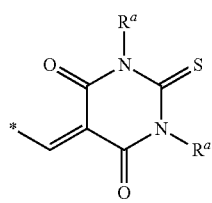
T31
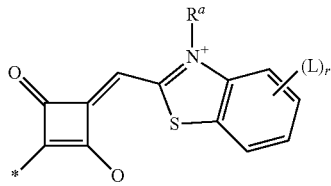
T32
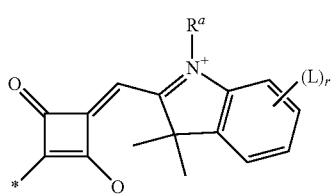
T33
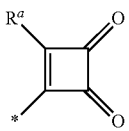
T34
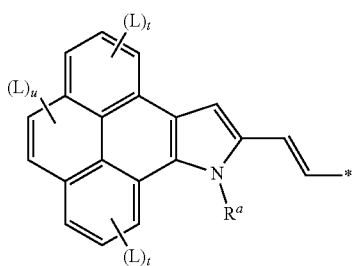
T35

-continued
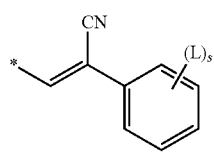 T36
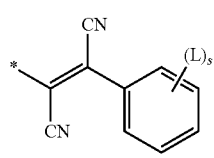 T37
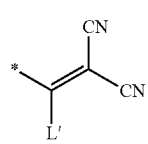 T38
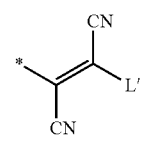 T39
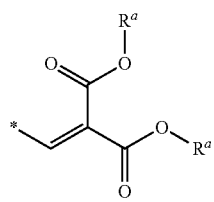 T40
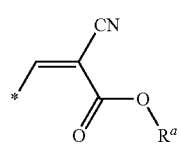 T41
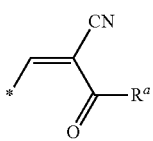 T42
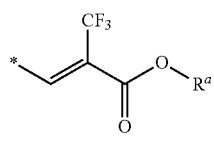 T43
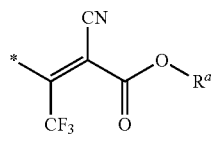 T44
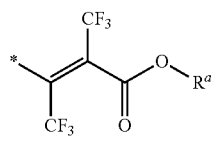 T45
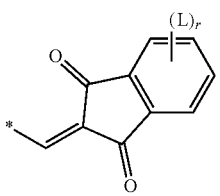 T46
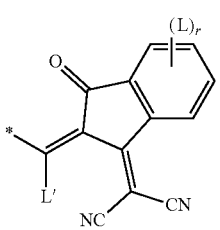 T47
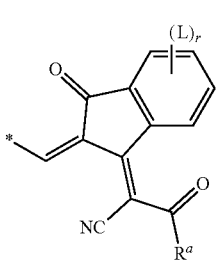 T48
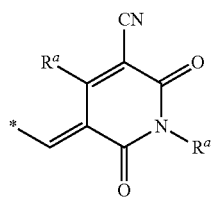 T49
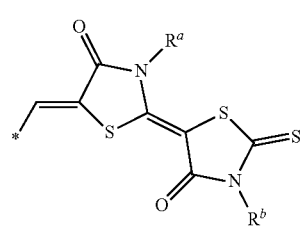 T50
T51

-continued

T52
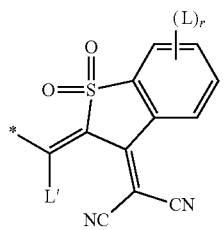

T53
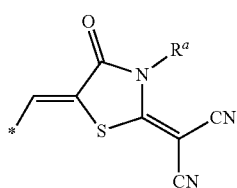

wherein the individual radicals, independently of each other and on each occurrence identically or differently, have the following meanings $R^a$, $R^b$ aryl or heteroaryl, each having from 4 to 30 ring atoms, optionally containing fused rings and being unsubstituted or substituted with one or more groups L, or one of the meanings given for L, R*, R, R* alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(=O)—, —C(=S)—, —SiR°R°°—, —NR°R°°—, —CHR°=CR°°— or —C≡C— such that O- and/or S-atoms are not directly linked to each other, L F, Cl, —NO$_2$, —CN, —NC, —NCO, —NCS, —OCN, —SCN, R°, OR°, SR°, —C(=O)X°, —C(=O)R°, —C(=O)—OR°, —O—C(=O)—R°, —NH$_2$, —NHR°, —NR°R°°, —C(=O)NHR°, —C(=O)NR°R°°, —SO$_3$R°, SO$_2$R°, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, preferably F, —CN, R°, —OR°, —SR°, —C(=O)—R°, —C(=O)—OR°, —O—C(=O)—R°, —O—C(=O)—OR°, C(=O)—NHR°, —C(=O)—NR°R°°, L' H or one of the meanings of L, R°, R°° H or straight-chain or branched alkyl with 1 to 20, preferably 1 to 12 C atoms that is optionally fluorinated, $Y^1$, $Y^2$ H, F, Cl or CN, $X^0$ halogen, preferably F or Cl, r 0, 1, 2, 3 or 4, s 0, 1, 2, 3, 4 or 5, t 0, 1, 2 or 3, u 0, 1 or 2, and wherein at least one of $R^{T1}$ and $R^{T2}$ denotes an electron withdrawing group.

Preferred compounds of formula I are those wherein both of $R^{T1}$ and $R^{T2}$ denote an electron withdrawing group.

Preferred electron withdrawing groups $R^{T1}$ and $R^{T2}$ are selected from —CN, —C(=O)—OR*, —C(=S)—OR*, —CH=CH(CN), —CH=C(CN)$_2$, —C(CN)=C(CN)$_2$, —CH=C(CN)($R^a$), CH=C(CN)—C(=O)—OR*, —CH=C(CO—OR*)$_2$, and formulae T1-T53.

Very preferred groups $R^{T1}$ and $R^{T2}$ are selected from the following formulae T10
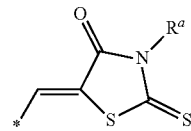

T36
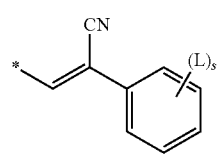

T37
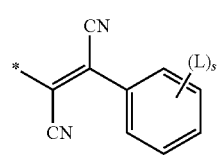

T38
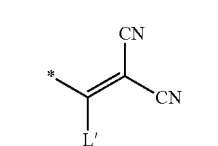

T39
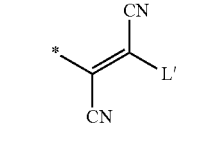

T47
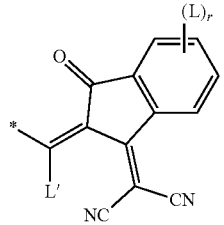

wherein L, r and s have the meanings given above and below, and L' is H or has one of the meanings given for L. Preferably in these formulae L' is H. Further preferably in these formulae r is 0.

The above formulae T1-T53 are meant to also include their respective E- or Z-stereoisomer with respect to the C=C bond in (α-position to the adjacent group $Ar^4$ or $Ar^5$, thus for example the group

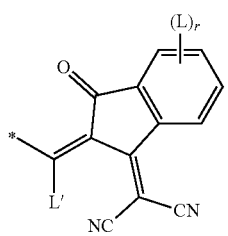

may also denote

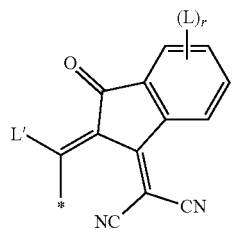

Preferred compounds of formula I are selected from formula Ia

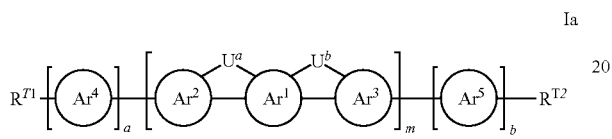

Ia wherein $U^a$ denotes $CR^1R^2$, $SiR^1R^2$ or $GeR^1R^2$, preferably $CR^1R^2$ or $SiR^1R^2$, very preferably $CR^1R^2$, $U^b$ denotes $CR^3R^4$, $SiR^3R^4$ or $GeR^3R^4$, preferably $CR^3R^4$ or $SiR^3R^4$, very preferably $CR^3R^4$, and $R^{1-4}$, $Ar^{1-5}$, $R^{T1,T2}$, a, b and m have the meanings or preferred meanings given above and below.

In the compounds of formula I and Ia preferably $R^{1-4}$ are different from H.

In a preferred embodiment of the present invention, $R^{1-4}$ in formula I and Ia are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, and most preferably is selected from formulae SUB1-SUB6 as defined above.

In another preferred embodiment of the present invention, $R^{1-4}$ in formula I and Ia are selected from mono- or poylcyclic aryl or heteroaryl, each of which is optionally substituted with one or more groups L as defined in formula I and has 4 to 30 ring atoms, and wherein two or more rings may be fused to each other or connected with each other by a covalent bond.

In a preferred embodiment of the present invention, $R^{5-10}$ in formula I and Ia are H.

In another preferred embodiment of the present invention, at least one of $R^{5-10}$ in formula I and Ia is different from H.

In a preferred embodiment of the present invention, $R^{5-10}$ in formula I and Ia, when being different from H, are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated.

In another preferred embodiment of the present invention, $R^{5-10}$ in formula I and Ia, when being different from H, are selected from aryl or heteroaryl, each of which is optionally substituted with one or more groups $R^S$ as defined in formula I and has 4 to 30 ring atoms.

Preferred aryl and heteroaryl groups $R^{1-10}$ are selected from the following formulae

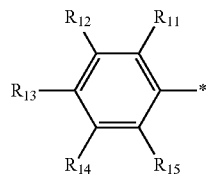
C1

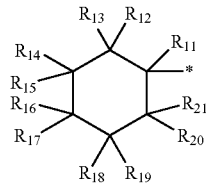
C2

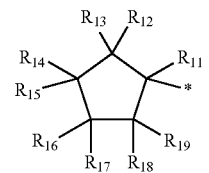
C3

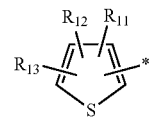
C4

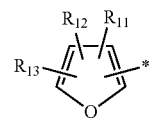
C5

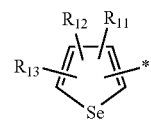
C6

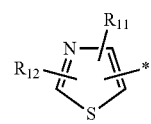
C7

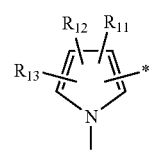
C8

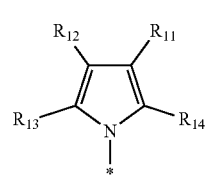
C9

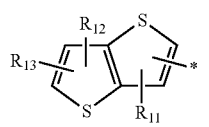
C10

-continued
C11 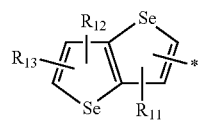
C12 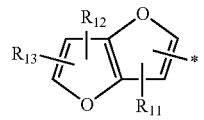
C13 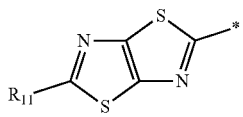
C14 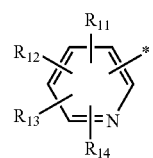
C15 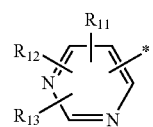
C16 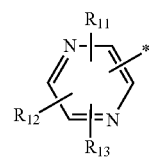
C17 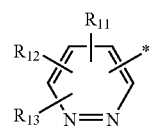
C18 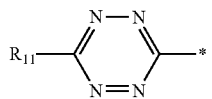
C19 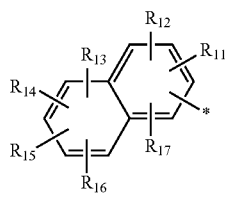
C20 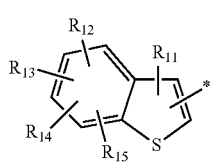
C21 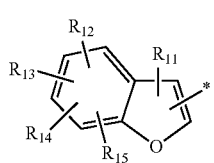
-continued
C22 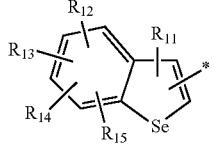
C23 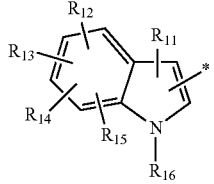
C24 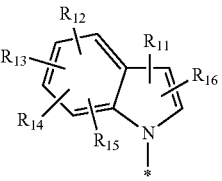
C25 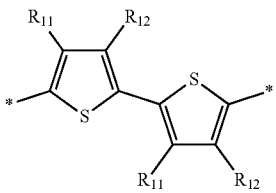
C26 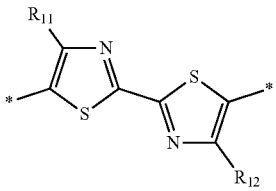
C27 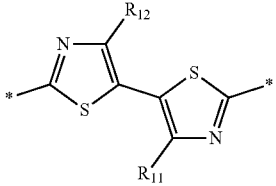
wherein $R^{11-17}$, independently of each other, and on each occurrence identically or differently, denote H or have one of the meanings given for L in formula I or one of its preferred meanings as given above and below.
Very preferred aryl and heteroaryl groups $R^{1-10}$ are selected from the following formulae
C1-1 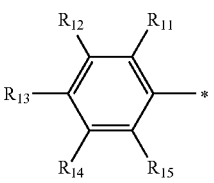

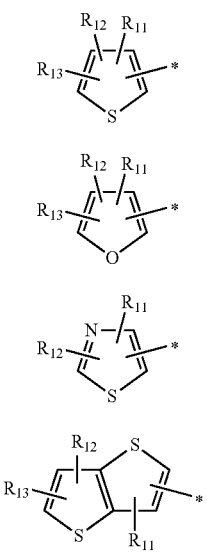

C4-1

C5-1

C7-1

C10-1 wherein $R^{11-15}$ are as defined above. Most preferably $R_1$-$R_{10}$ are selected from formulae SUB7-SUB14 as defined above.

In another preferred embodiment one or more of $R^{1-10}$ denote a straight-chain, branched or cyclic alkyl group with 1 to 50, preferably 2 to 50, very preferably 2 to 30, more preferably 2 to 24, most preferably ≥2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms, or is preferably selected from formulae SUB1-6 as defined above.

Further preferred cationic groups are selected from the group consisting of the following formulae

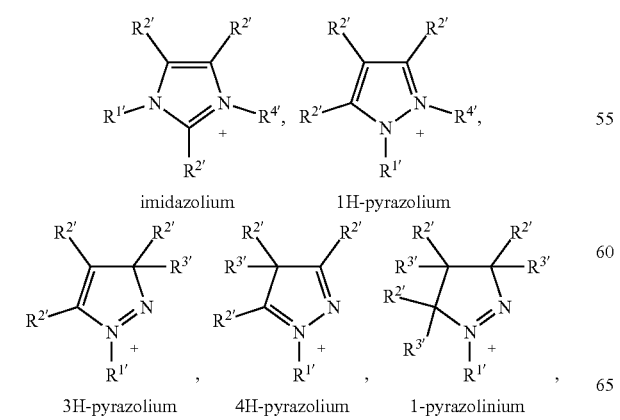

imidazolium, 1H-pyrazolium, 3H-pyrazolium, 4H-pyrazolium, 1-pyrazolinium,

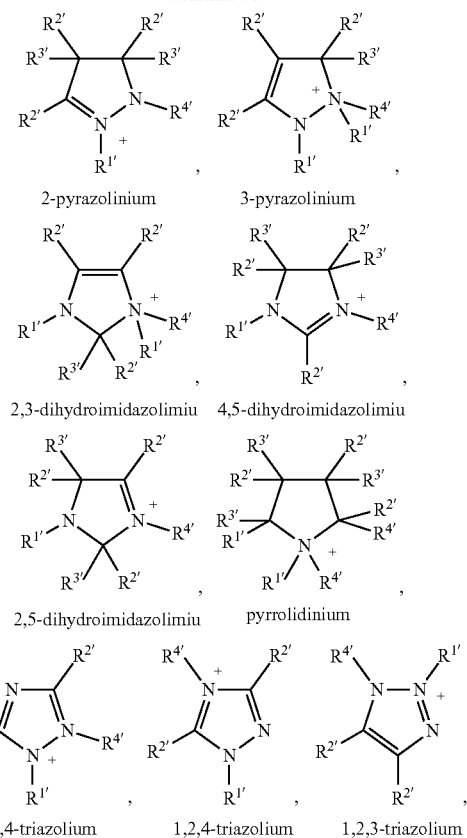

2-pyrazolinium, 3-pyrazolinium, 2,3-dihydroimidazolimiu, 4,5-dihydroimidazolimiu, 2,5-dihydroimidazolimiu, pyrrolidinium, 1,2,4-triazolium, 1,2,4-triazolium, 1,2,3-triazolium,

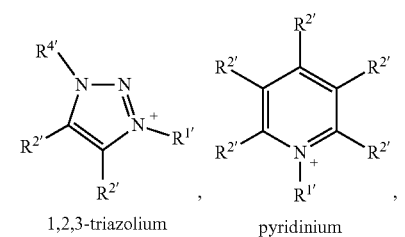

1,2,3-triazolium, pyridinium,

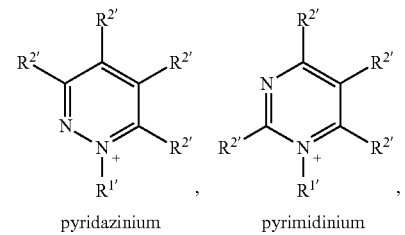

pyridazinium, pyrimidinium,

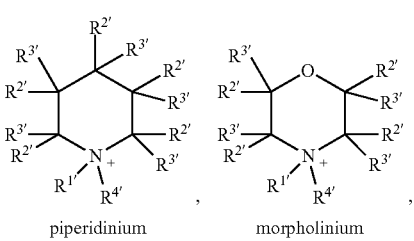

piperidinium, morpholinium,

-continued

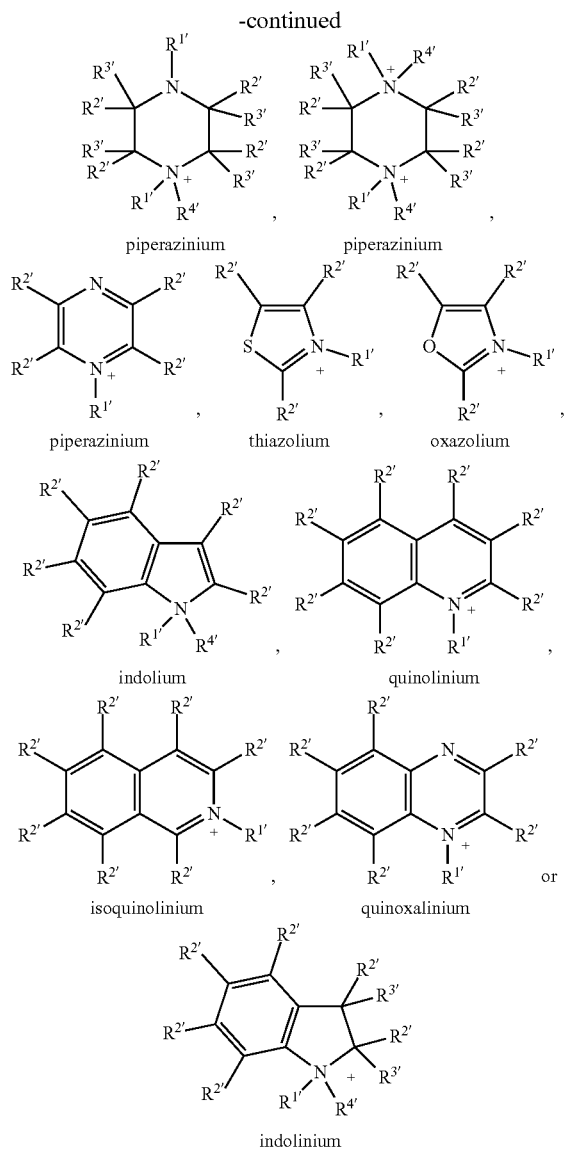

wherein $R^{1\prime}$, $R^{2\prime}$, $R^{3\prime}$ and $R^{4\prime}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents L as defined above, or denote a link to the respective group $R^{1-10}$.

In the above cationic groups of the above-mentioned formulae any one of the groups $R^{1\prime}$, $R^{2\prime}$, $R^{3\prime}$ and $R^{4\prime}$ (if they replace a CH$_3$ group) can denote a link to the respective group $R^{1-10}$, or two neighbored groups $R^{1\prime}$, $R^{2\prime}$, $R^{3\prime}$ or $R^{4\prime}$ (if they replace a CH$_2$ group) can denote a link to the respective group $R^1$.

The anionic group is preferably selected from the group consisting of borate, imide, phosphate, sulfonate, sulfate, succinate, naphthenate or carboxylate, very preferably from phosphate, sulfonate or carboxylate.

In a preferred embodiment of the present invention the groups $R^{T1}$ and $R^{T2}$ in formula I are selected from alkyl with 1 to 16 C atoms which is straight-chain, branched or cyclic, and is unsubstituted, substituted with one or more F or Cl atoms or CN groups, or perfluorinated, and in which one or more C atoms are optionally replaced by —O—, —S—, —C(O)—, —C(S)—, —SiR$^\circ$R$^{\circ\circ}$—, —NR$^\circ$R$^{\circ\circ}$—, —CHR$^\circ$=CR$^{\circ\circ}$— or —C≡C— such that O- and/or S-atoms are not directly linked to each other.

Further preferred compounds of formula I are selected from the following preferred embodiments or any combination thereof:
$W^1$ is S or Se, preferably S,
$W^2$ is S or Se, preferably S,
$U^1$ is $CR^1R^2$ or $SiR^1R^2$ and $U^2$ is $CR^3R^4$ or $SiR^3R^4$,
$U^1$ is $CR^1R^2$ and $U^2$ is $CR^3R^4$,
$Ar^1$ is benzene that is fused in 1-, 2-, 4- and 5-position to $Ar^2$ and $Ar^3$,
$Ar^1$ is thiophene,
$Ar^1$ is thienothiophene,
m=1,
a=b=1 or 2, preferably 1,
a=b=0,
in one or both of $Ar^2$ and $Ar^3$ the substituents $R^{5-10}$ are H,
in one or both of $Ar^2$ and $Ar^3$ one or two of $R^{5-10}$ are different from H,
$V^1$ is $CR^5$ and $V^2$ is $CR^6$,
$V^1$ is $CR^5$ and $V^2$ is N,
$V^1$ and $V^2$ are N,
in one or both of $Ar^4$ and $Ar^5$ $R^5$ and $R^6$ are H,
in one or both of $Ar^4$ and $Ar^5$ one or both of $R^5$ and $R^6$ are H,
$Ar^4$ and $Ar^5$ denote thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene or thiadiazole[3,4-c]pyridine, which are substituted by $X^1$, $X^2$, $X^3$ and $X^4$ as defined above,
$Ar^4$ and $Ar^5$ denote thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene or thiadiazole[3,4-c]pyridine, wherein $X^1$, $X^2$, $X^3$ and $X^4$ are H,
$Ar^4$ and $Ar^5$ denote thiophene, thiazole, thieno[3,2-b]thiophene, thiazolothiazole, benzene, 2,1,3-benzothiadiazole, 1,2,3-benzothiadiazole, thieno[3,4-b]thiophene or thiadiazole[3,4-c]pyridine, wherein one or more of $X^1$, $X^2$, $X^3$ and $X^4$ are different from H, —$R^1$, $R^2$, $R^3$ and $R^4$ are different from H,
$R^1$, $R^2$, $R^3$ and $R^4$ are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, preferably from F, or alkyl or alkoxy having 1 to 12 C atoms that is optionally fluorinated, very preferably methyl, most preferably are selected from formulae SUB1-6 as defined above,
$R^1$, $R^2$, $R^3$ and $R^4$ are selected from aryl or heteroaryl, each of which is optionally substituted with one or more groups L as defined in formula I and has 4 to 30 ring atoms, preferably from benzene that is optionally substituted, preferably in 4-position 3,4,5-positions or in 3,5-positions, with alkyl or alkoxy having 1 to 20 C atoms, preferably 1 to 16 C atoms, very preferably 4-alkylphenyl wherein alkyl is C1-16 alkyl, most preferably 4-methylphenyl, 4-hexylphenyl, 4-octylphenyl or 4-dodecylphenyl, or 4-alkoxyphenyl wherein alkoxy is C1-16 alkoxy, most preferably 4-hexyloxyphenyl, 4-octyloxyphenyl or 4-dodecyloxyphenyl or 3,5-di-alkylphenyl wherein alkyl is C1-16 alkyl, most preferably 3,5-dihexylphenyl or 3,5-dioctylphenyl or 3,5- dialkoxyphenyl wherein alkoxy is C1-16 alkoxy, most preferably 3,5-dihexyloxyphenyl or 3,5-dioctyloxyphenyl, or 4-thioalkylphenyl wherein thioalkyl is C1-16 thioalkyl, most preferably 4-thiohexylphenyl, 4-thiooctylphenyl or 4-thiododecylphenyl or 3,5-dithioalkylphenyl wherein thioalkyl is C1-16 thioalkyl, most preferably 3,5-dithiohexylphenyl or 3,5-dithiooctylphenyl, most preferably selected from formulae SUB7-14 as defined above, L' is H, L, L' denote F, Cl, CN, $NO_2$, or alkyl or alkoxy with 1 to 16 C atoms that is optionally fluorinated, $R^{5-10}$, when being different from H, are selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, without being perfluorinated, preferably from F, or alkyl or alkoxy having 1 to 16 C atoms that is optionally fluorinated.

r is 2 and L is F, Cl, CN, $NO_2$, or alkyl or alkoxy with 1 to 16 C atoms that is optionally fluorinated, r is 1 and L is F, Cl, CN, $NO_2$, or alkyl or alkoxy with 1 to 16 C atoms that is optionally fluorinated, r is 4 and L is F, Cl, CN, $NO_2$, or alkyl or alkoxy with 1 to 16 C atoms that is optionally fluorinated, Preferred compounds of formula I are selected from the following subformulae

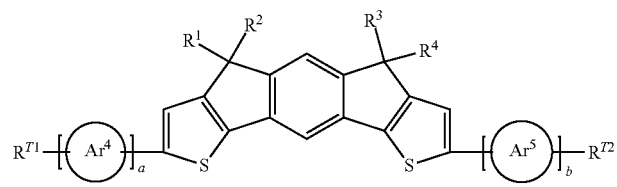

I1

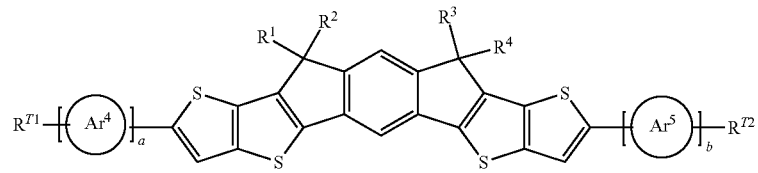

I2

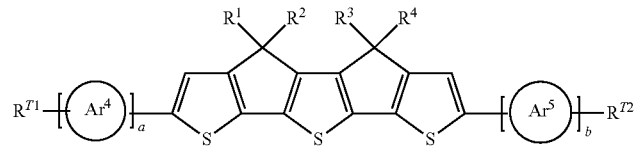

I3

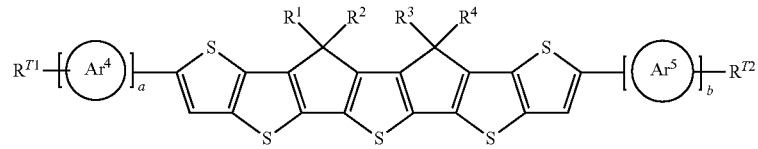

I4

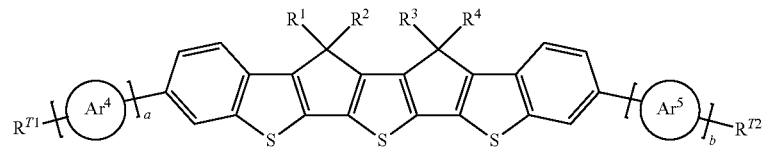

I5

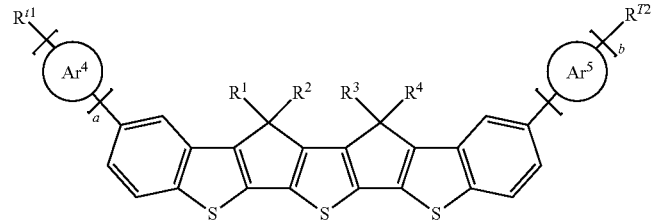

I6

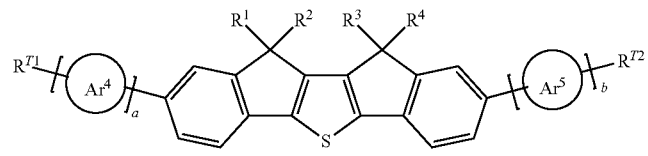

I7

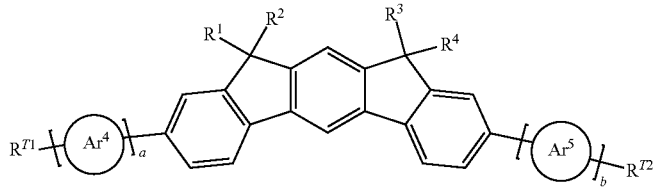

I8

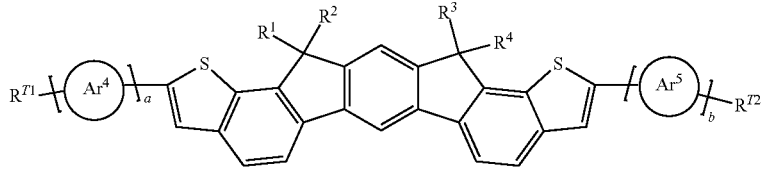

I9

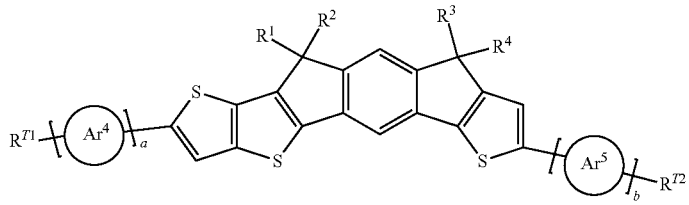

I10

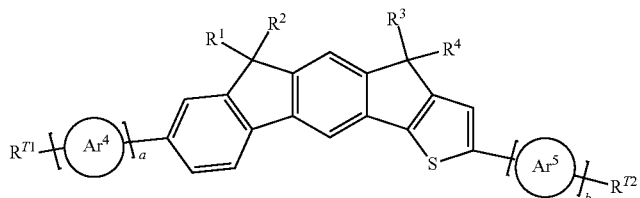

I11

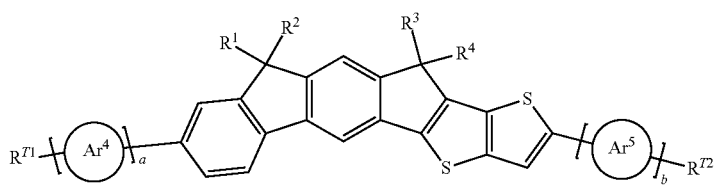

I12

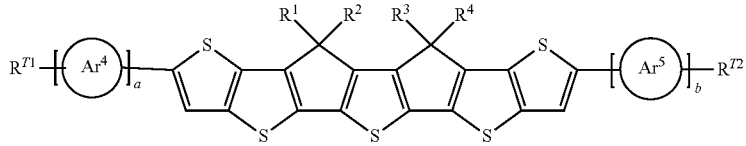

I13 wherein $R^1$, $R^2$, $R^3$, $R^4$, $R^{T1}$, $R^{T2}$, $Ar^4$, $Ar^5$, a and b have the meanings given above.

Very preferred compounds of formula I are selected from the following groups:

1a) The group consisting of compounds of formula I, wherein $Ar^4$ and $Ar^5$ are selected from formulae A1-A10, a and b are 0, 1 or 2, and $R^{T1}$ and $R^{T2}$ are selected from formula T10.

1b) The group consisting of compounds of formula I, wherein $Ar^4$ and $Ar^5$ are selected from formulae A1-A10, a and b are 0, 1 or 2, and $R^{T1}$ and $R^{T2}$ are selected from formula T36.

1c) The group consisting of compounds of formula I, wherein $Ar^4$ and $Ar^5$ are selected from formulae A1-A10, a and b are 0, 1 or 2, and $R^{T1}$ and $R^{T2}$ are selected from formula T37.

1d) The group consisting of compounds of formula I, wherein $Ar^4$ and $Ar^5$ are selected from formulae A1-A10, a and b are 0, 1 or 2, and $R^{T1}$ and $R^{T2}$ are selected from formula T38.

1e) The group consisting of compounds of formula I, wherein $Ar^4$ and $Ar^5$ are selected from formulae A1-A10, a and b are 0, 1 or 2, and $R^{T1}$ and $R^{T2}$ are selected from formula T39.

1f) The group consisting of compounds of formula I, wherein $Ar^4$ and $Ar^5$ are selected from formulae A1-A10, a and b are 0, 1 or 2, and $R^{T1}$ and $R^{T2}$ are selected from formula T47.

2a) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T10.

2b) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T36.

2c) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T37.

2d) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T38.

2e) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T39.

2f) The group consisting of compounds of formula I2, wherein $Ar^4$ and $Ar^5$ are selected from formulae A1-A10, a and b are 0, 1 or 2, and $R^{T1}$ and $R^{T2}$ are selected from formula T47.

3a) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T10.

3b) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T36.

3c) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T37.

3d) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T38.

3e) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T39.

3f) The group consisting of compounds of formula I3, wherein $Ar^4$ and $Ar^5$ are selected from formulae A1-A10, a and b are 0, 1 or 2, and $R^{T1}$ and $R^{T2}$ are selected from formula T47.

4a) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T10.

4b) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T36.

4c) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T37.

4d) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T38.

4e) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T39.

4f) The group consisting of compounds of formula I4, wherein $Ar^4$ and $Ar^5$ are selected from formulae A1-A10, a and b are 0, 1 or 2, and $R^{T1}$ and $R^{T2}$ are selected from formula T47.

5a) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T10.

5b) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T36.

5c) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T37.

5d) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T38.

5e) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T39.

5f) The group consisting of compounds of formula I5, wherein $Ar^4$ and $Ar^5$ are selected from formulae A1-A10, a and b are 0, 1 or 2, and $R^{T1}$ and $R^{T2}$ are selected from formula T47.

6a) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T10.

6b) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T36.

6c) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T37.

6d) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T38.

6e) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T39.

6f) The group consisting of compounds of formula I6, wherein $Ar^4$ and $Ar^5$ are selected from formulae A1-A10, a and b are 0, 1 or 2, and $R^{T1}$ and $R^{T2}$ are selected from formula T47.

7a) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T10.

7b) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T36.

7c) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T37.

7d) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T38.

7e) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T39.

7f) The group consisting of compounds of formula I7, wherein $Ar^4$ and $Ar^5$ are selected from formulae A1-A10, a and b are 0, 1 or 2, and $R^{T1}$ and $R^{T2}$ are selected from formula T47.

8a) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T10.

8b) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T36.

8c) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T37.

8d) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T38.

8e) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T39.

8f) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T47.

9a) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T10.

9b) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T36.

9c) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T37.

9d) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T38.

9e) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T39.

9f) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T47.

10a) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T10.

10b) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T36.

10c) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T37.

10d) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T38.

10e) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T39.

10f) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T47.

11a) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T10.

11b) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T36.

11c) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T37.

11d) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T38.

11e) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T39.

11f) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T47.

12a) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T10.

12b) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T36.

12c) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T37.

12d) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T38.

12e) The group consisting of compounds of formula I8, wherein $Ar^4$ and $Ar^5$ are selected from formulae A1-A10, a and b are 0, 1 or 2, and $R^{T1}$ and $R^{T2}$ are selected from formula T39.

12f) The group consisting of compounds of formula I8, wherein Ar⁴ and Ar⁵ are selected from formulae A1-A10, a and b are 0, 1 or 2, and $R^{T1}$ and $R^{T2}$ are selected from formula T47.

13a) The group consisting of compounds of formula I8, wherein Ar⁴ and Ar⁵ are selected from formulae A1-A10, a and b are 0, 1 or 2, and $R^{T1}$ and $R^{T2}$ are selected from formula T10.

13b) The group consisting of compounds of formula I8, wherein Ar⁴ and Ar⁵ are selected from formulae A1-A10, a and b are 0, 1 or 2, and $R^{T1}$ and $R^{T2}$ are selected from formula T36.

13c) The group consisting of compounds of formula I8, wherein Ar⁴ and Ar⁵ are selected from formulae A1-A10, a and b are 0, 1 or 2, and $R^{T1}$ and $R^{T2}$ are selected from formula T37.

13d) The group consisting of compounds of formula I8, wherein Ar⁴ and Ar⁵ are selected from formulae A1-A10, a and b are 0, 1 or 2, and $R^{T1}$ and $R^{T2}$ are selected from formula T38.

13e) The group consisting of compounds of formula I8, wherein Ar⁴ and Ar⁵ are selected from formulae A1-A10, a and b are 0, 1 or 2, and $R^{T1}$ and $R^{T2}$ are selected from formula T39.

13f) The group consisting of compounds of formula I8, wherein Ar⁴ and Ar⁵ are selected from formulae A1-A10, a and b are 0, 1 or 2, and $R^{T1}$ and $R^{T2}$ are selected from formula T47.

Further preferred embodiments of the invention relate to
compounds selected from the above groups 1a-1f,
compounds selected from the above groups 2a-2f,
compounds selected from the above groups 3a-3f,
compounds selected from the above groups 4a-4f,
compounds selected from the above groups 5a-5f,
compounds selected from the above groups 6a-6f,
compounds selected from the above groups 7a-7f,
compounds selected from the above groups 8a-8f,
compounds selected from the above groups 9a-9f,
compounds selected from the above groups 10a-10f,
compounds selected from the above groups 11a-11f,
compounds selected from the above groups 12a-12f,
compounds selected from the above groups 13a-13f, Further preferred embodiments of the invention relate to compounds selected from each of the individual groups 1a-13f as defined above.

In the above groups 1a-13f, $R^{1-4}$ are preferably selected from alkyl or alkoxy with 1 to 16 C atoms which is optionally fluorinated or aryl or heteroaryl that is mono- or polycyclic, optionally contains fused rings, has 4 to 30 ring atoms, and is optionally substituted by one or more groups L as defined in formula I, and preferably denotes phenyl that is substituted with one or more optionally fluorinated alkyl or alkoxy group with 1 to 16 C atoms.

Very preferred compounds of formula I are selected from the following subformulae:

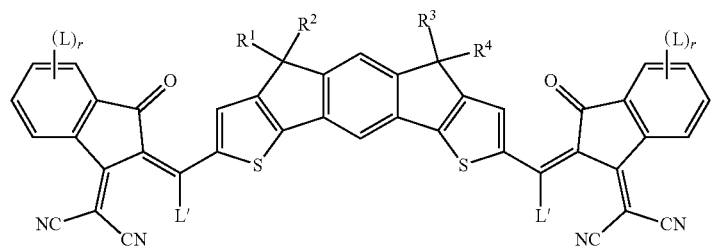

I1a

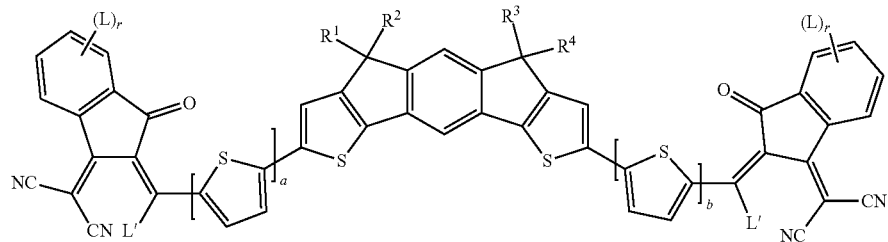

I1b

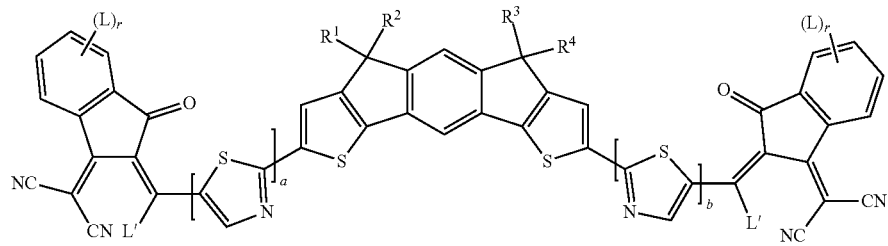

I1c

-continued
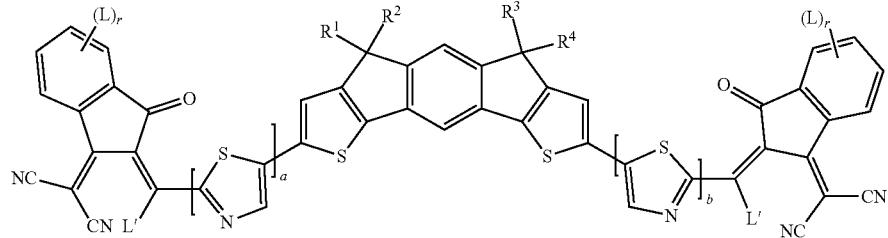
I1d
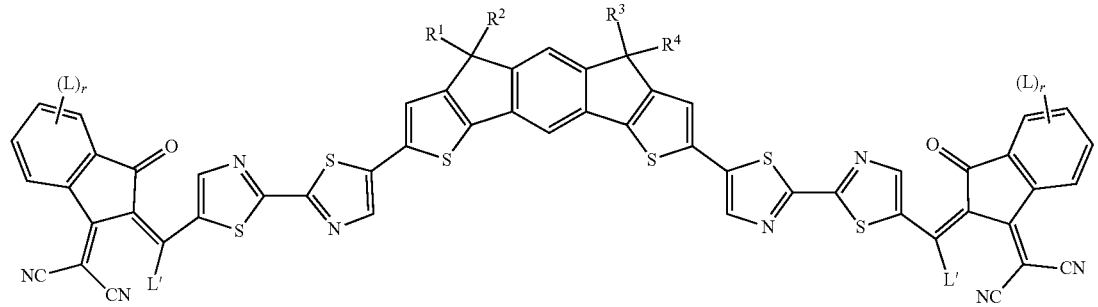
I1e
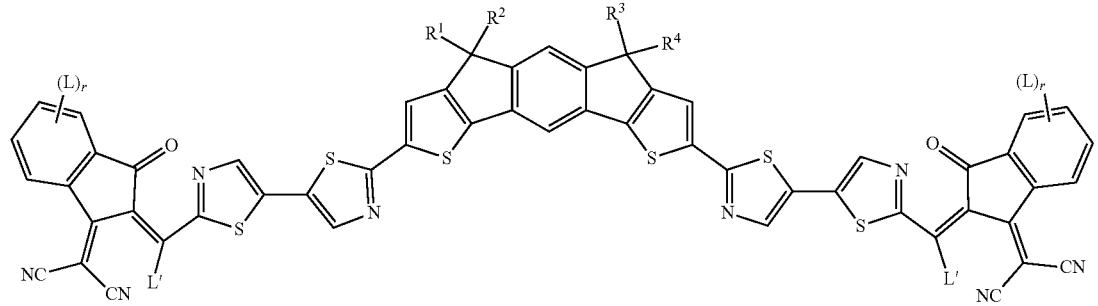
I1f
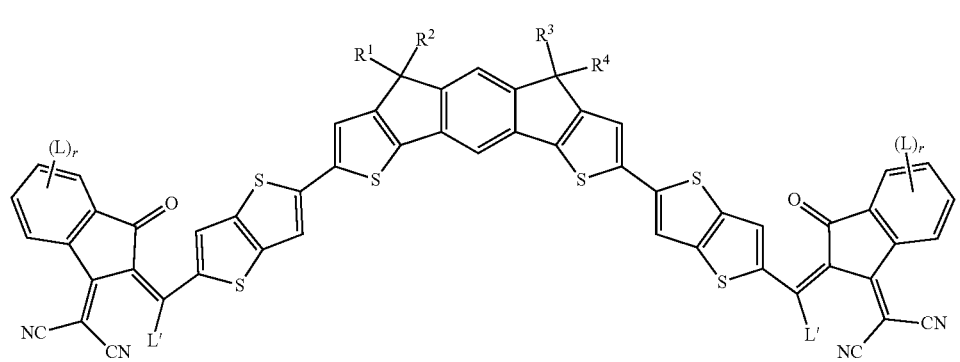
I1g
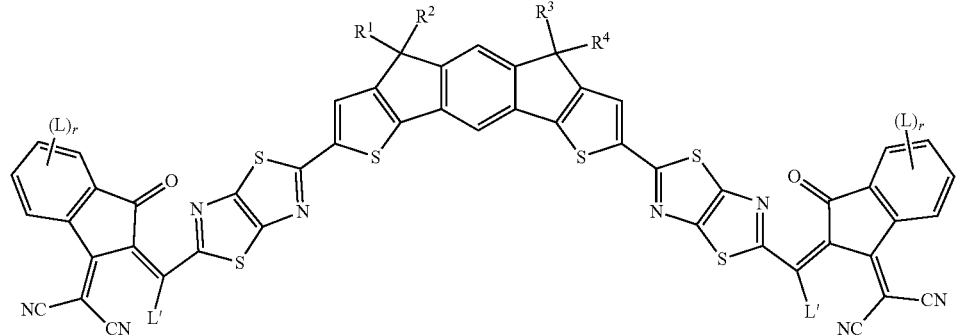
I1h I1i
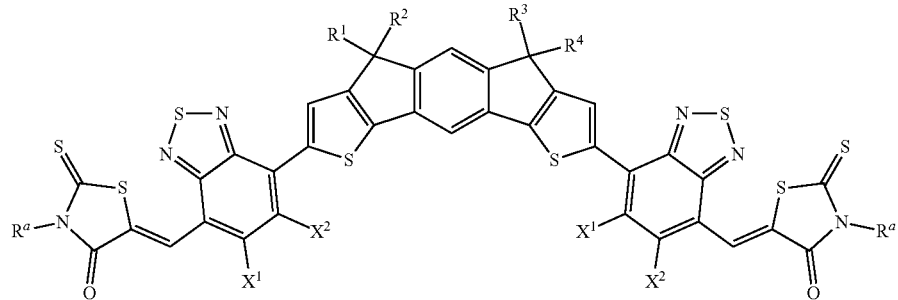
I1k
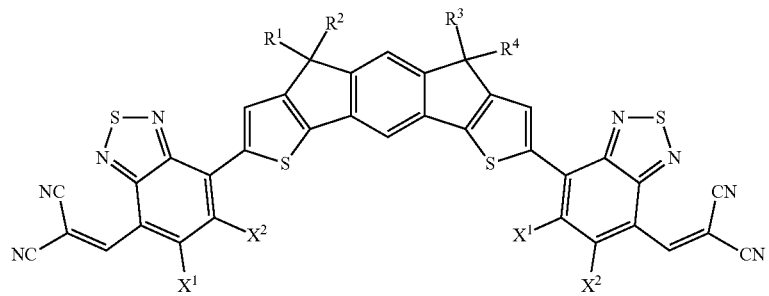
I1m
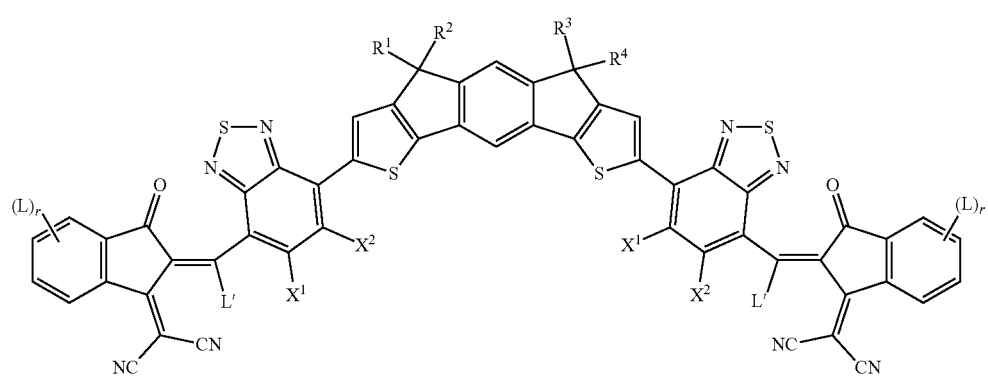
I2a
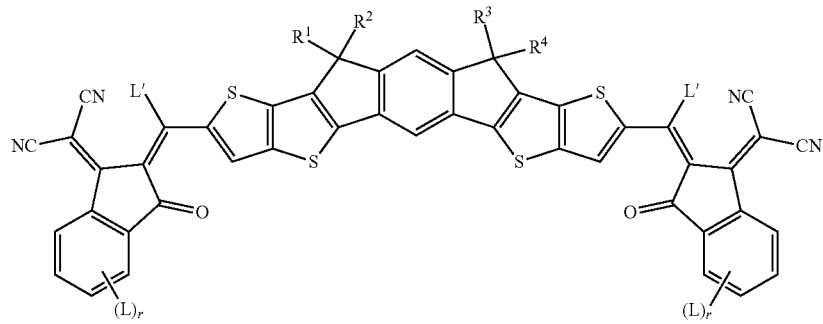
I2b
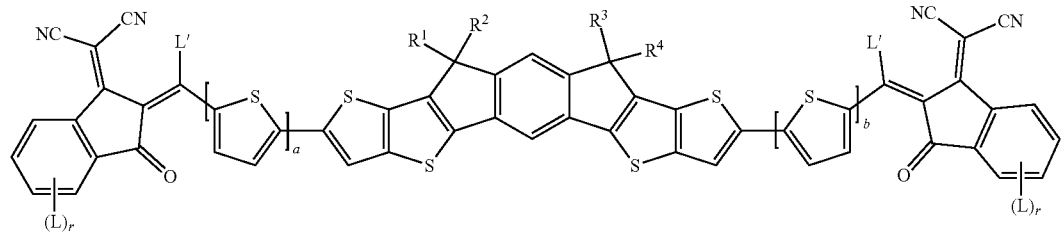

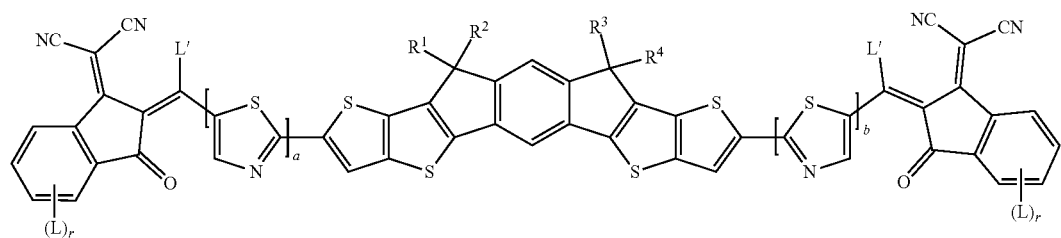
I2c
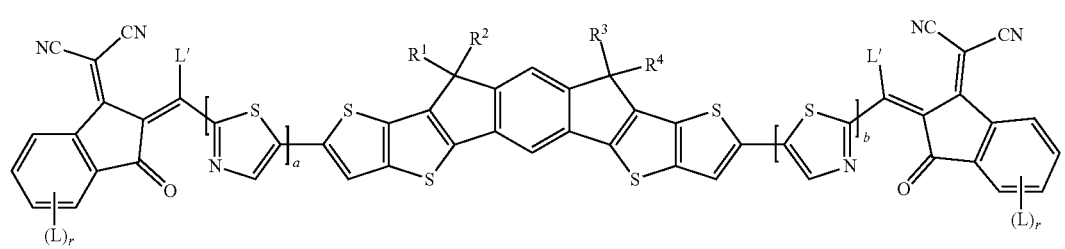
I2d
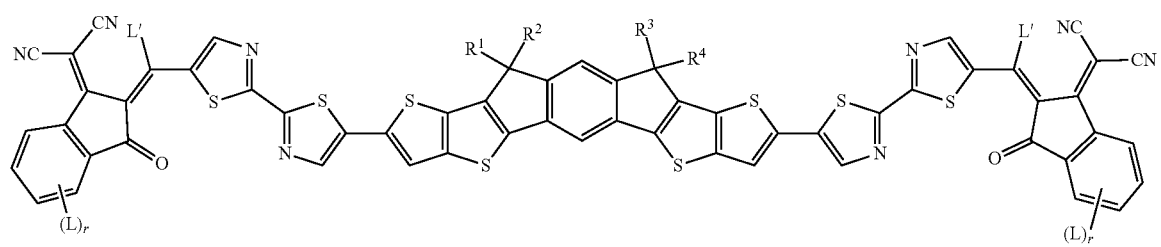
I2e
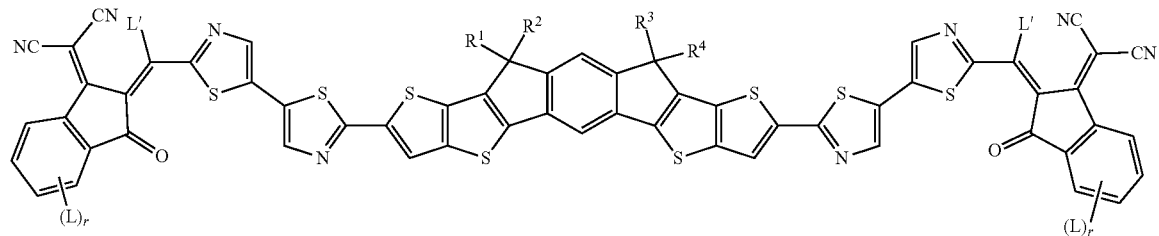
I2f
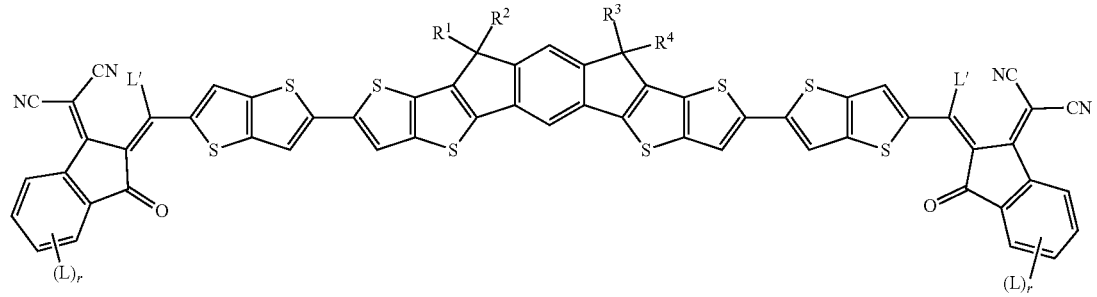
I2g

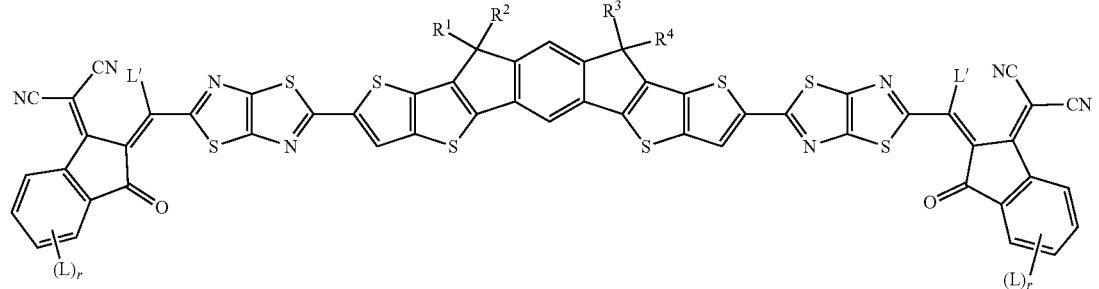
I2h
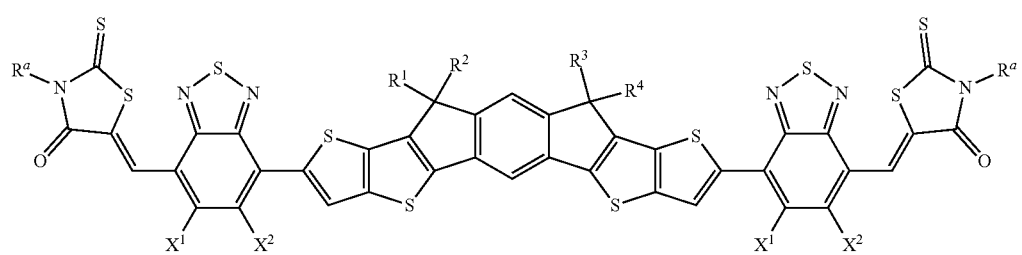
I2i
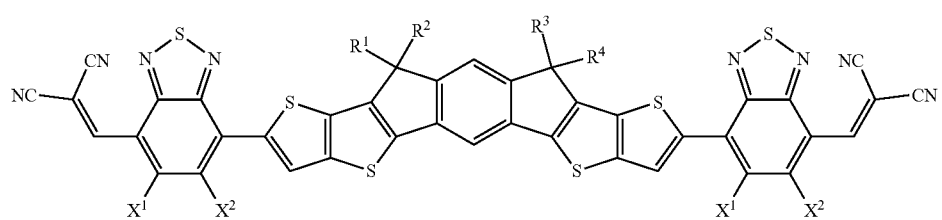
I2k
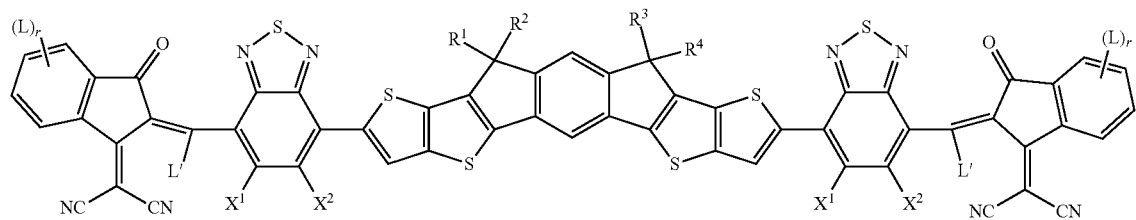
I2m
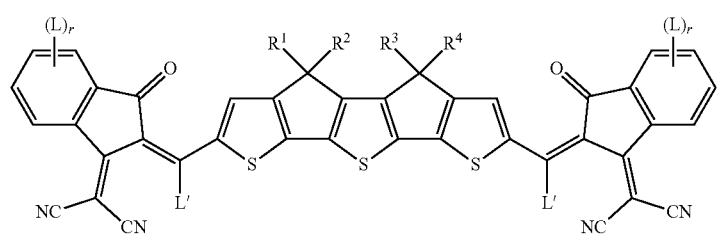
I3a
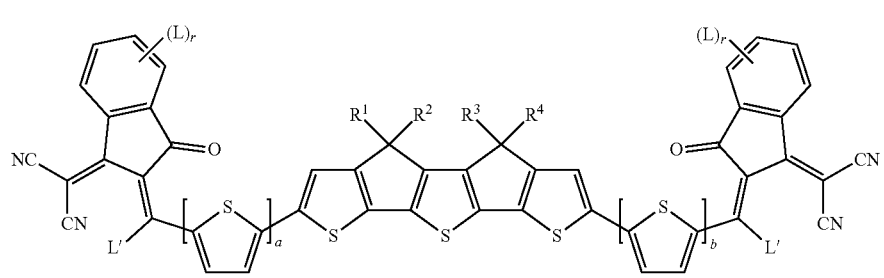
I3b -continued
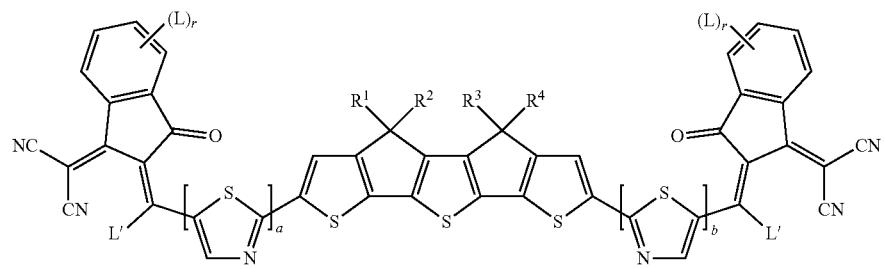
I3c
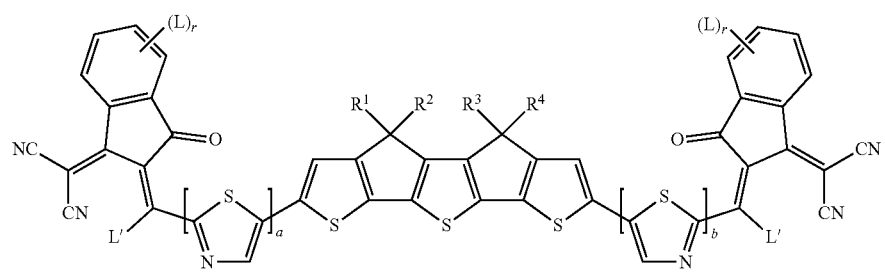
I3d
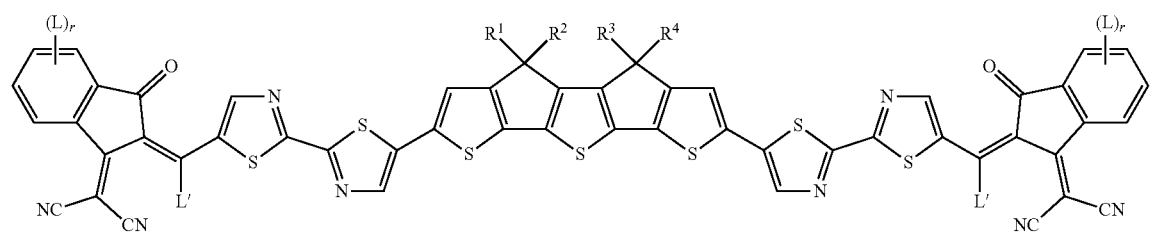
I3e
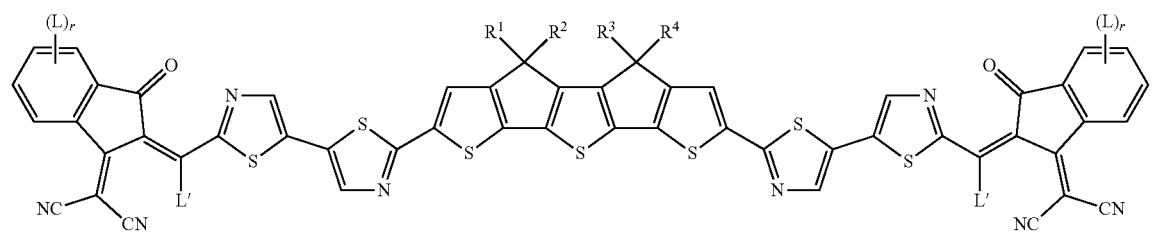
I3f
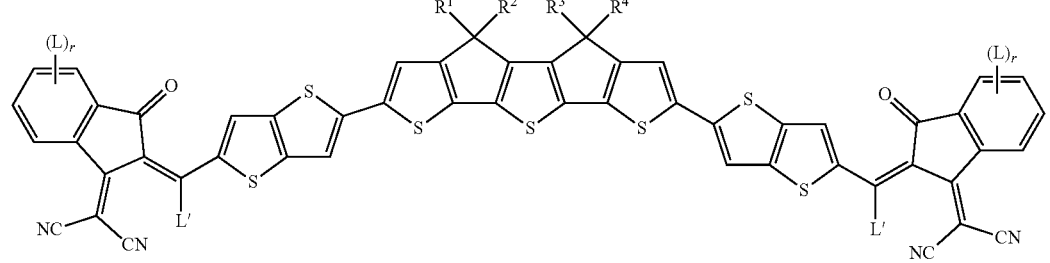
I3g
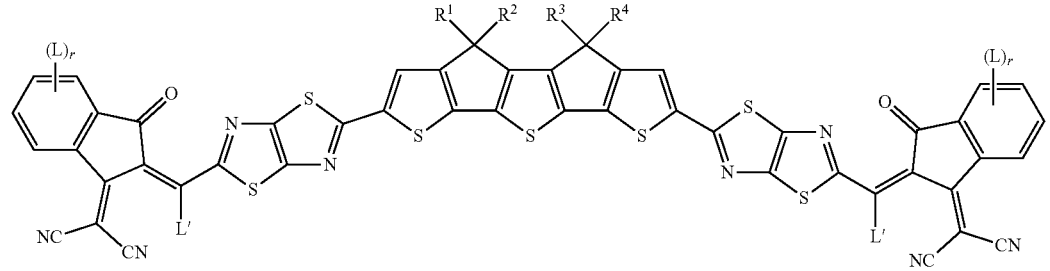
I3h

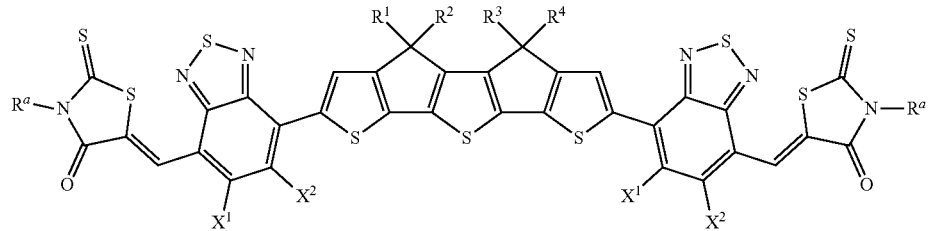
I3i
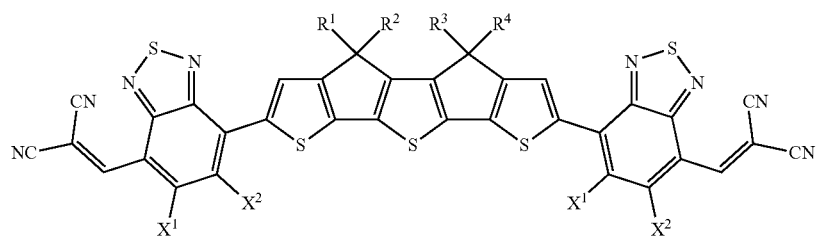
I3k
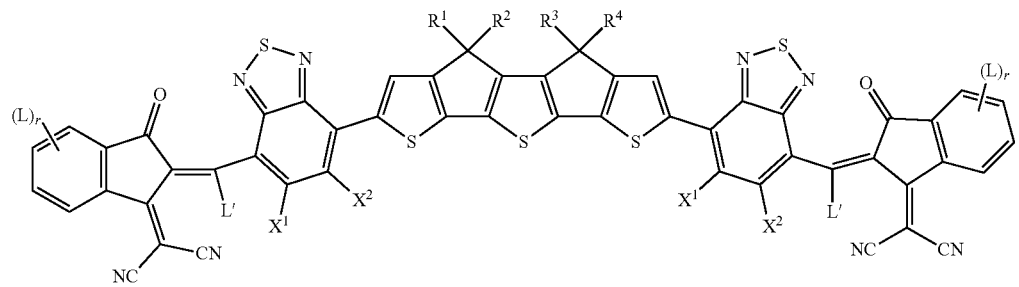
I3m
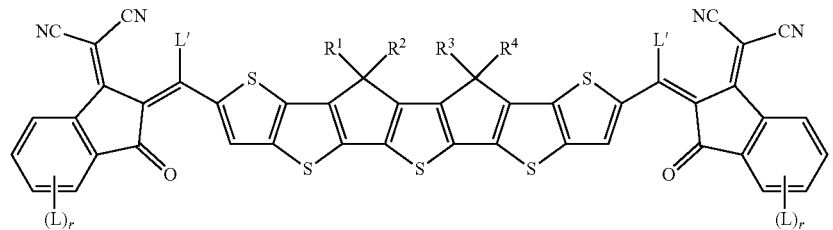
I4a
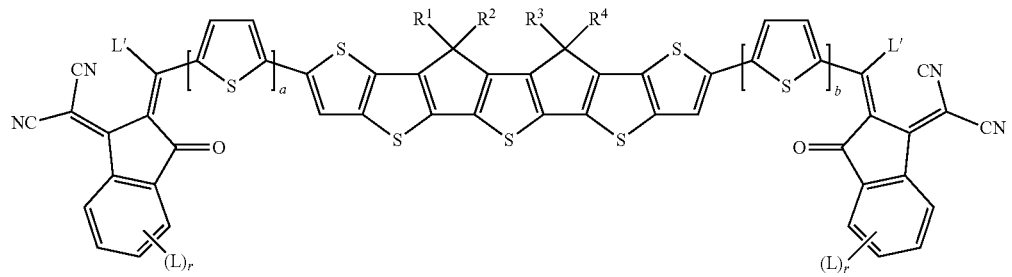
I4b
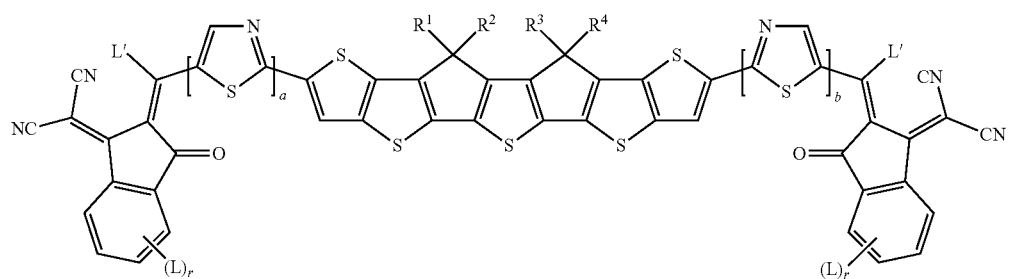
I4c -continued
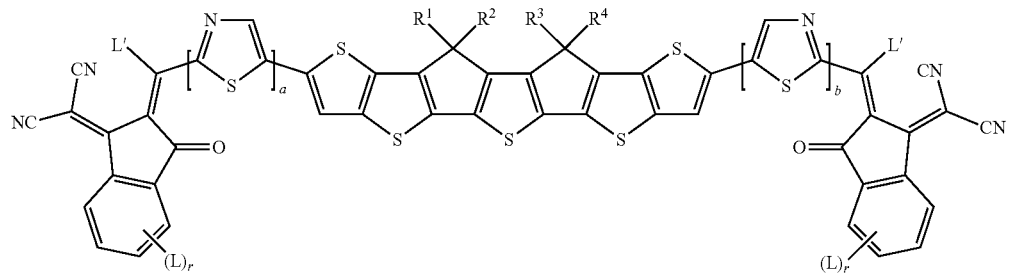
I4d
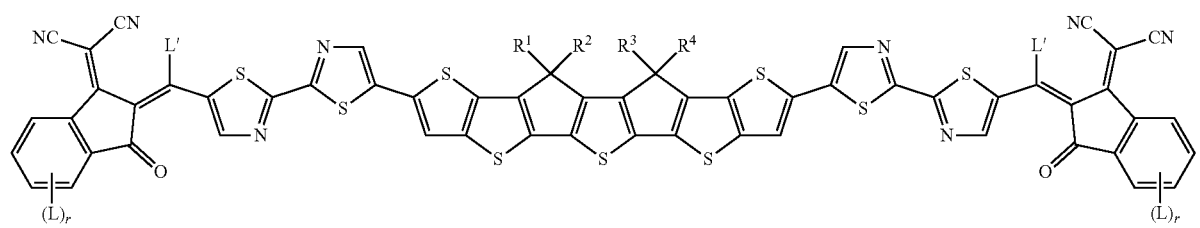
I4e
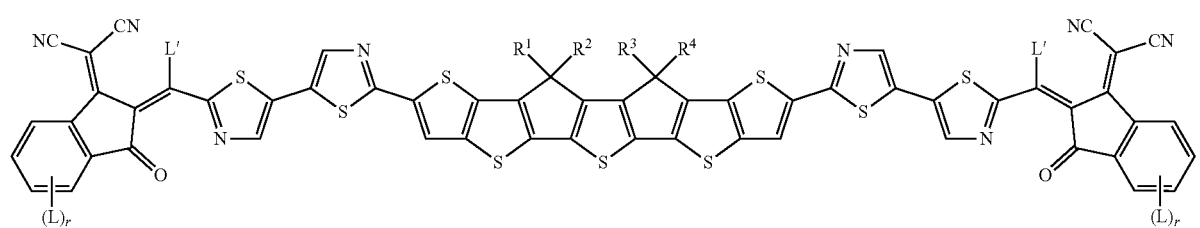
I4f
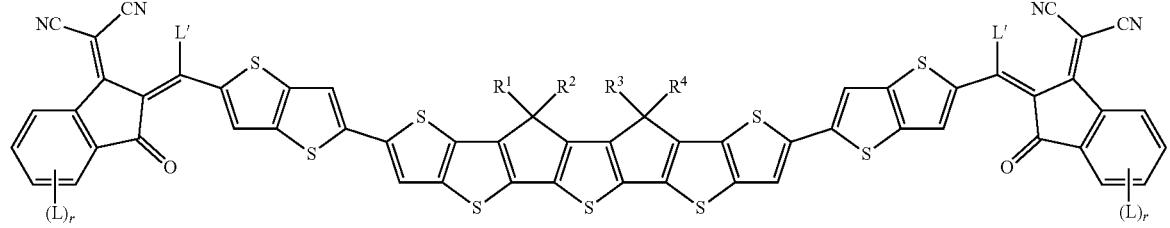
I4g
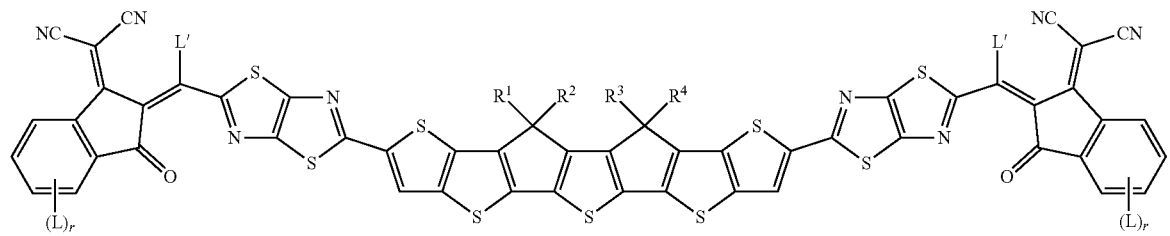
I4h
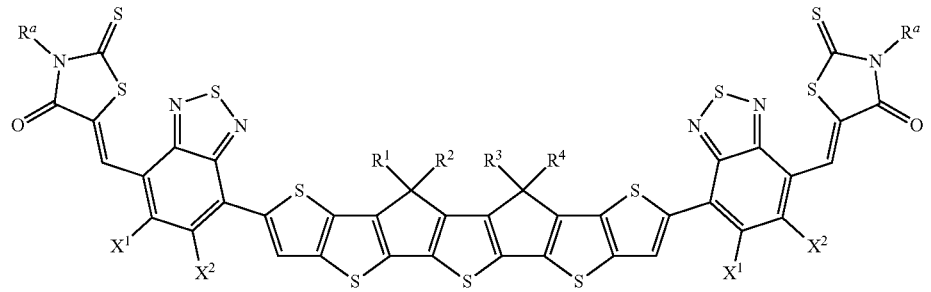
I4i -continued
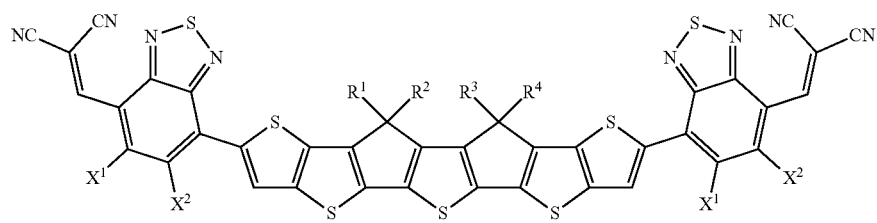
I4k
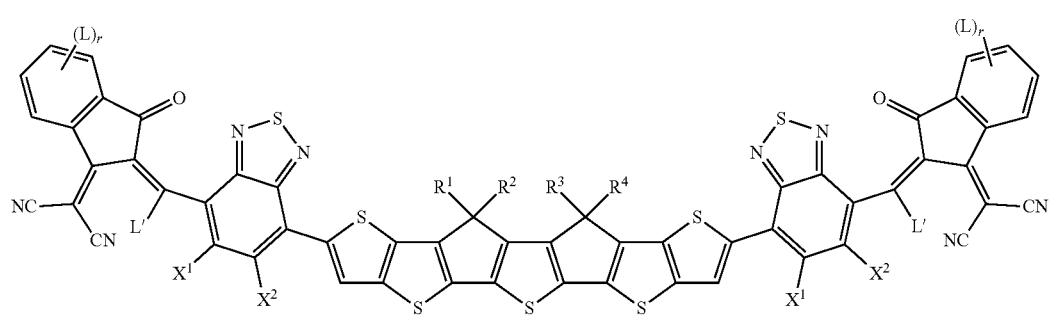
I4m
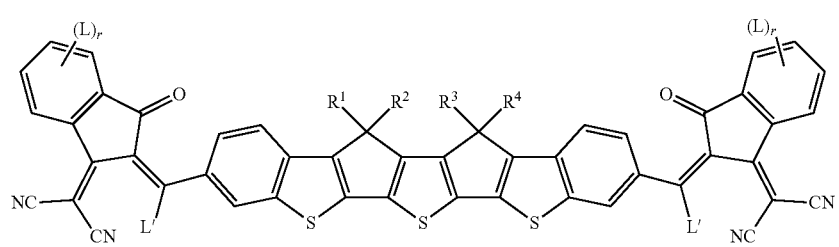
I5a
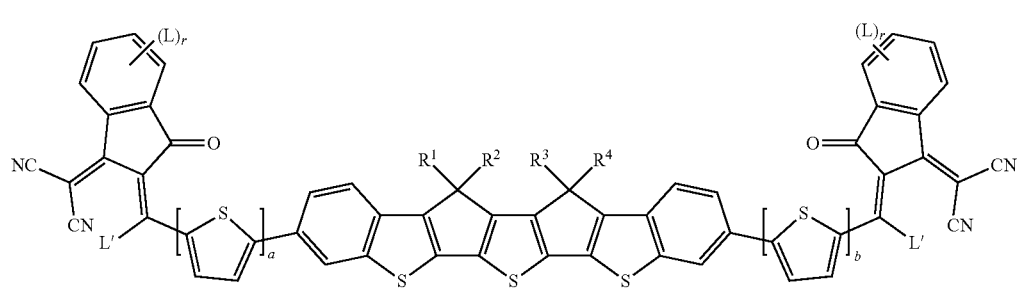
I5b
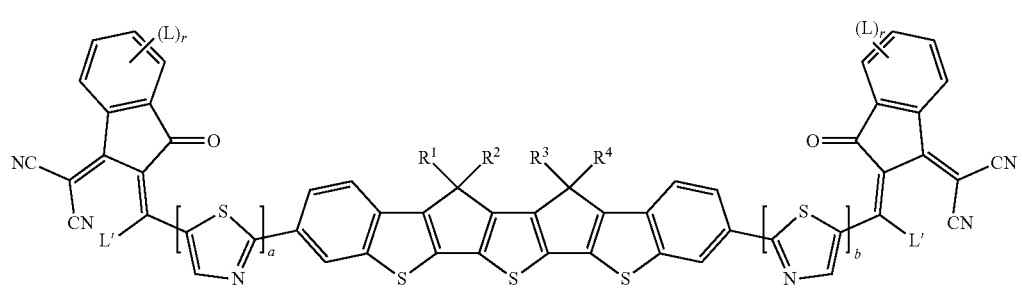
I5c
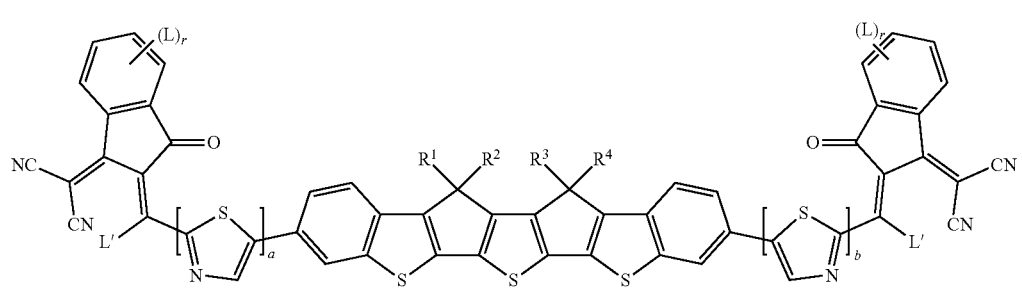
I5d -continued
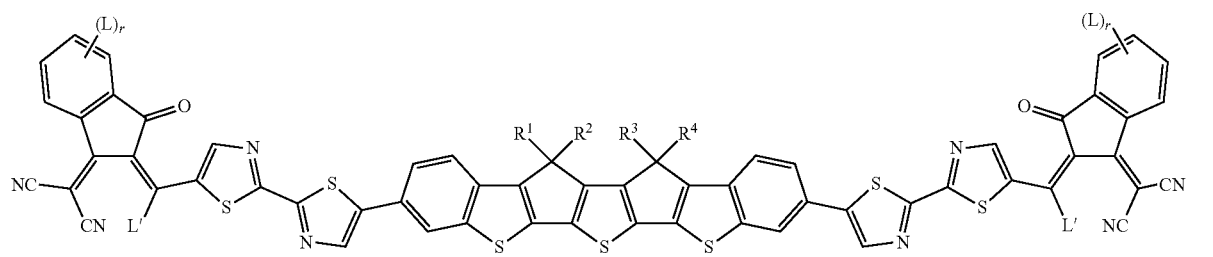
I5e
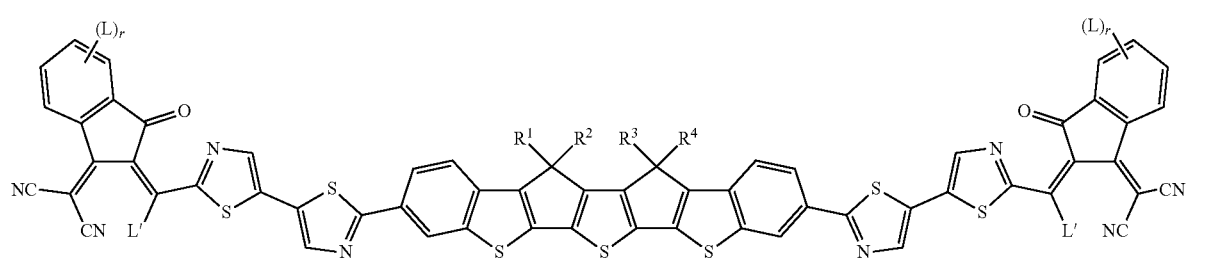
I5f
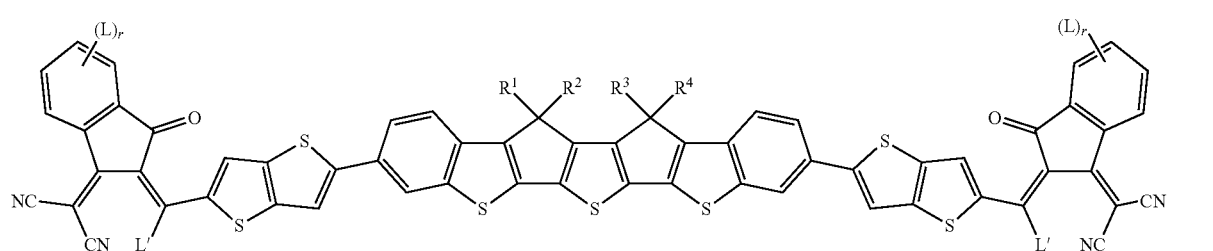
I5g
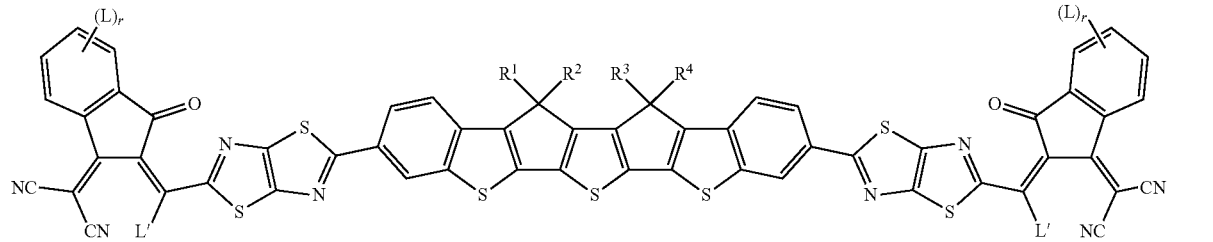
I5h
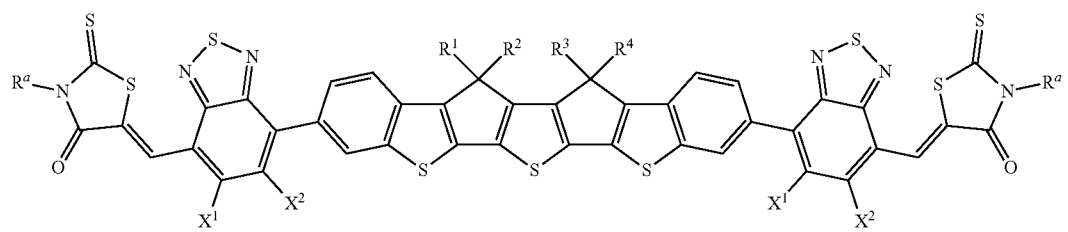
I5i
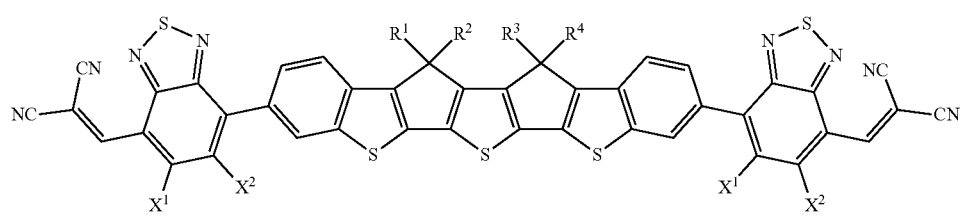
I5k -continued
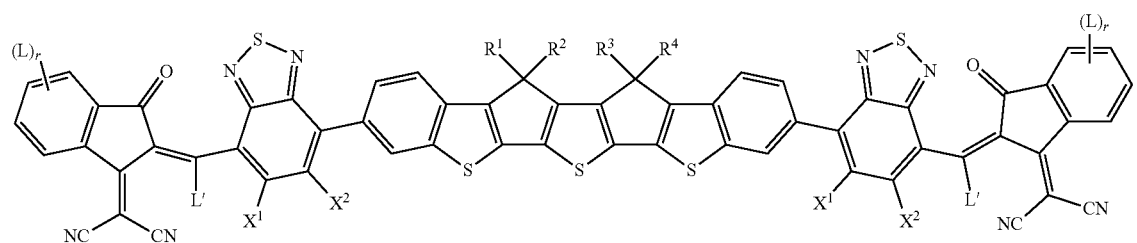
I5m
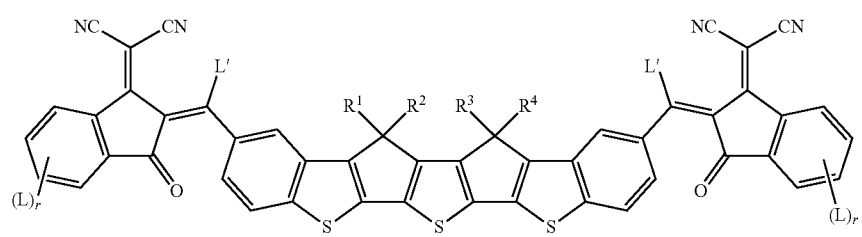
I6a
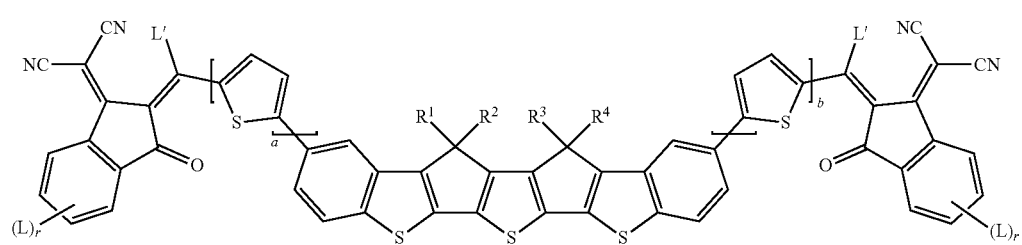
I6b
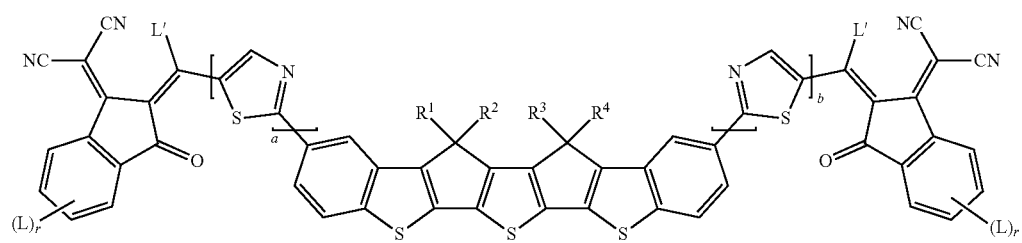
I6c
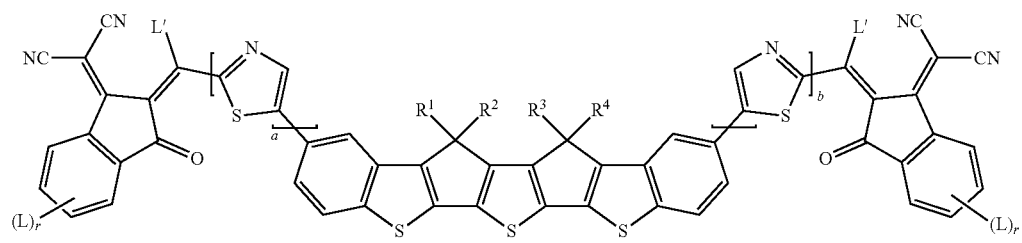
I6d
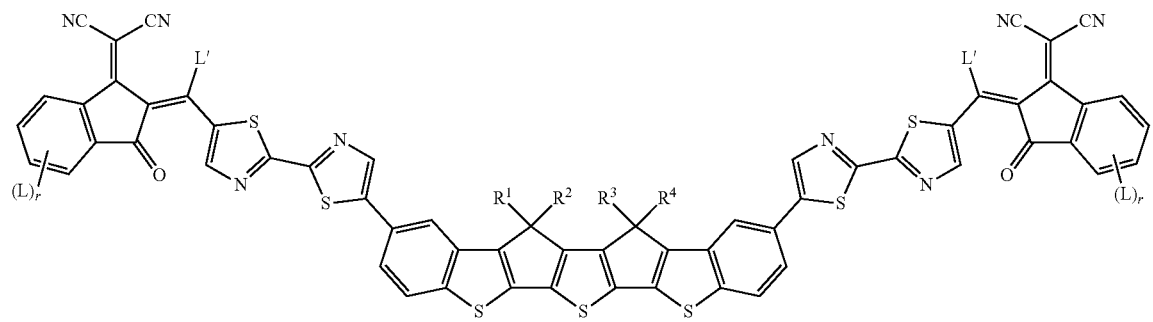
I6e -continued
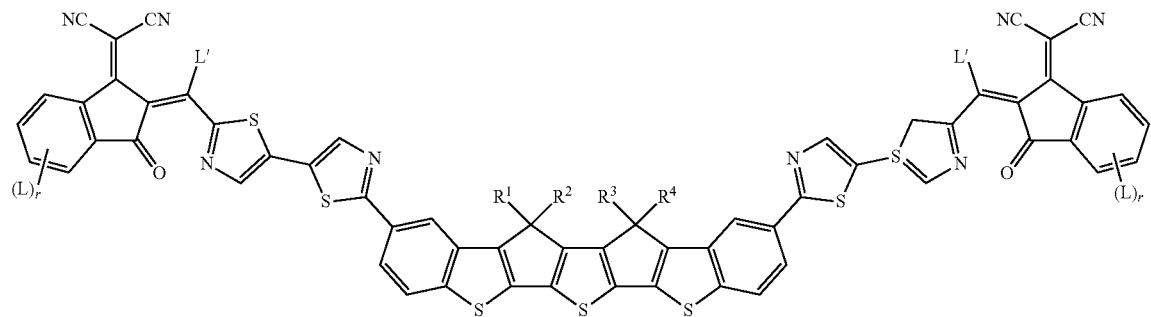
I6f
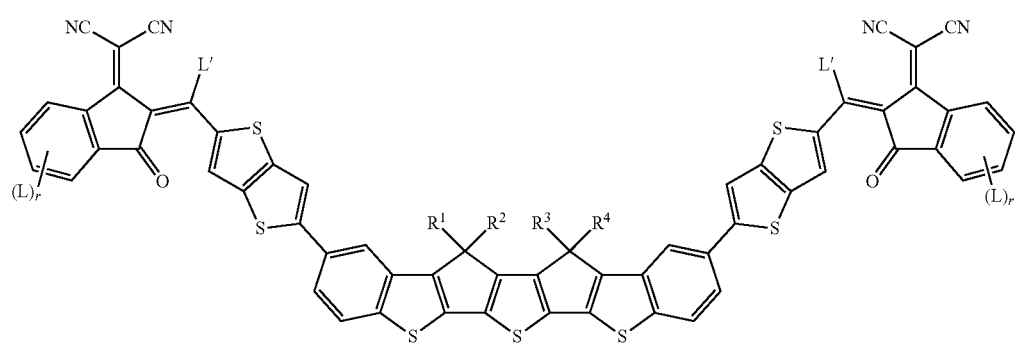
I6g
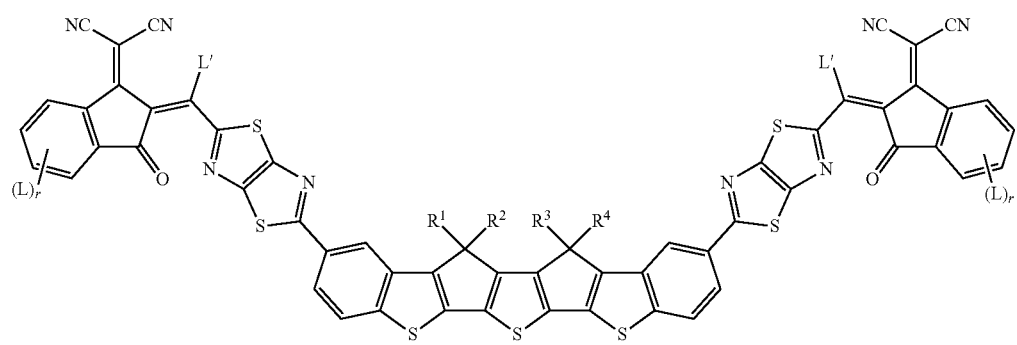
I6h
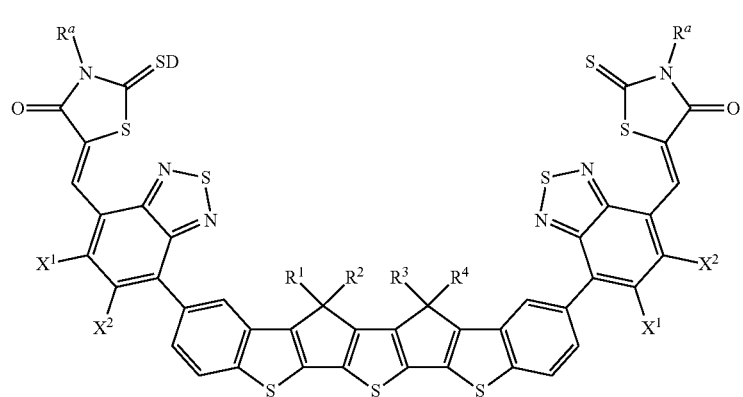
I6i I6k
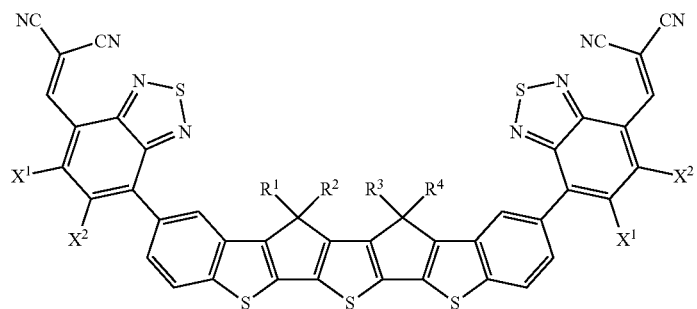
I6m
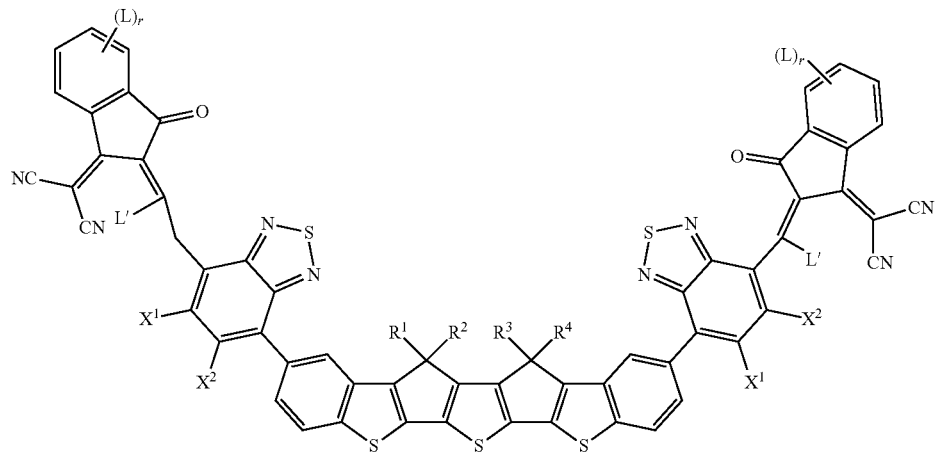
I7a
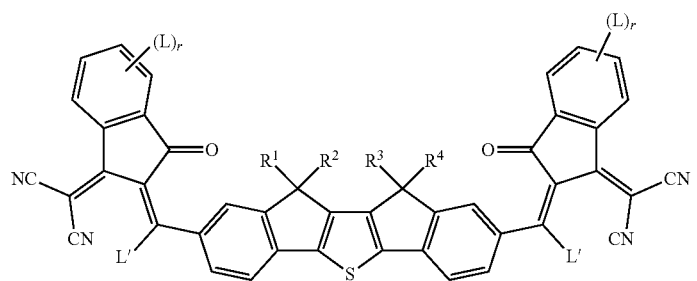
I7b
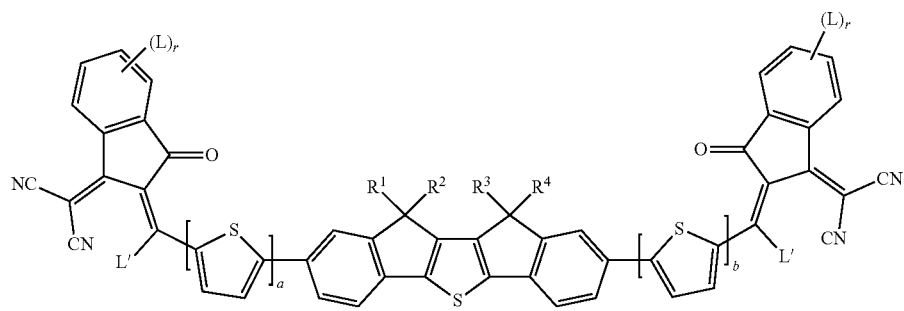

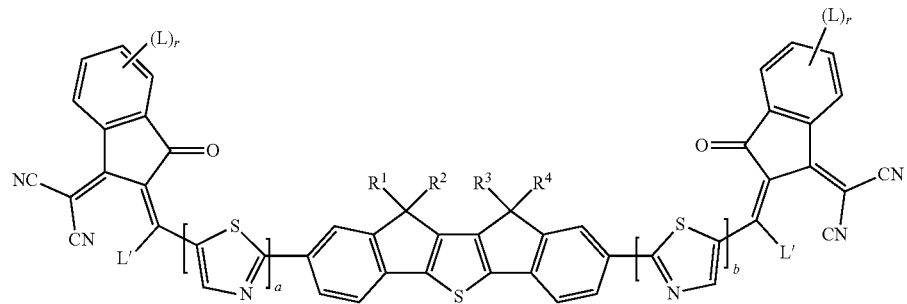
I7c
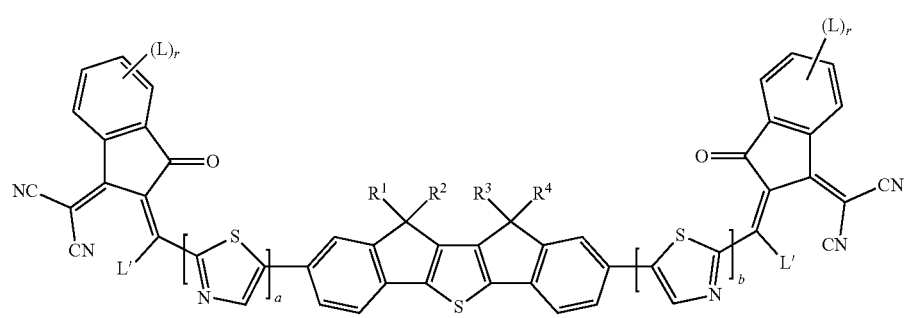
I7d
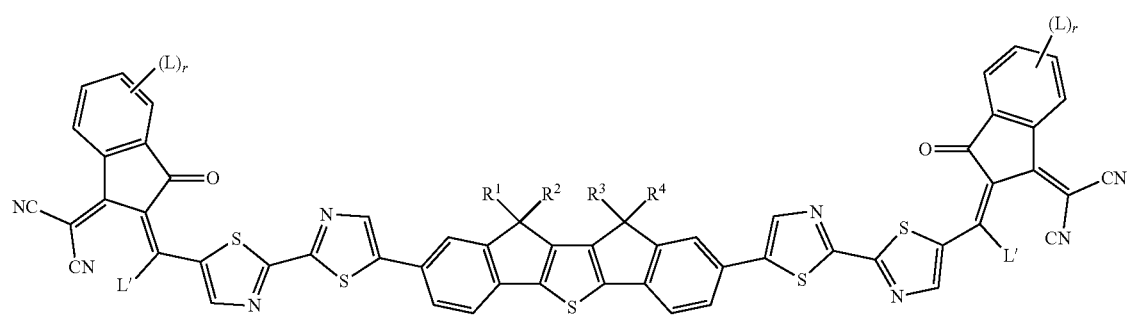
I7e
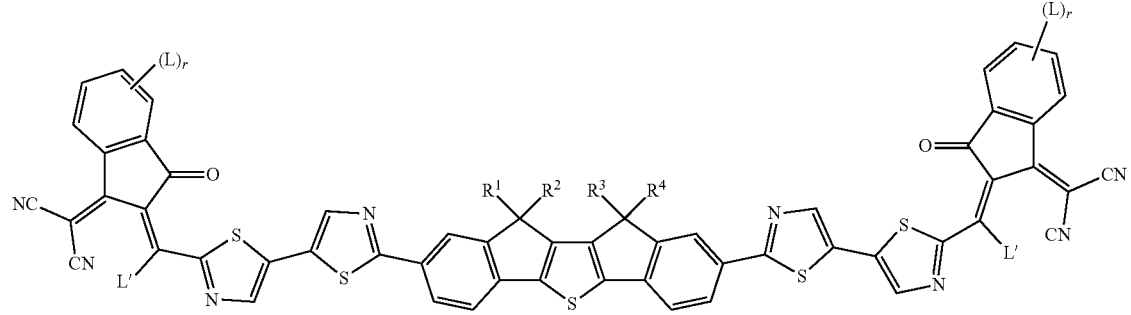
I7f

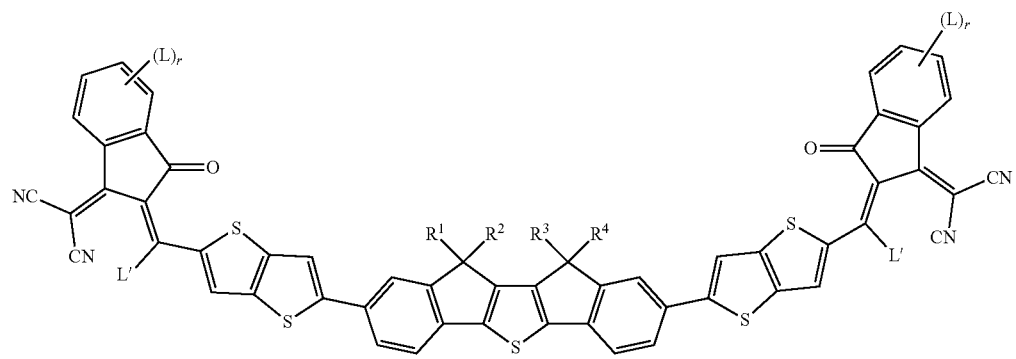
17g
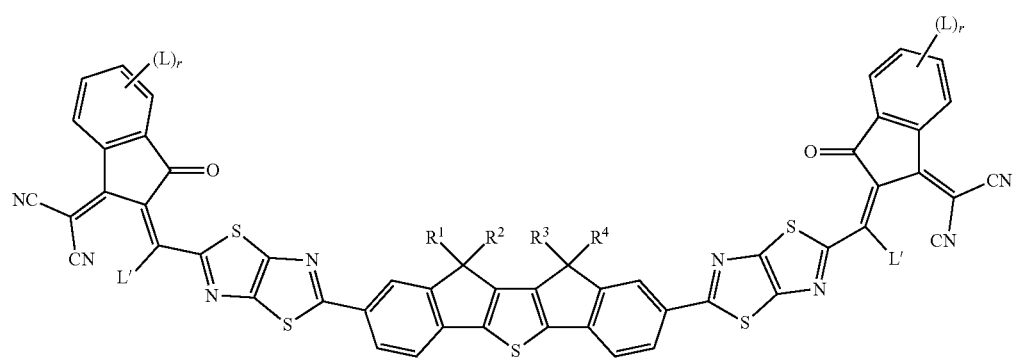
17h
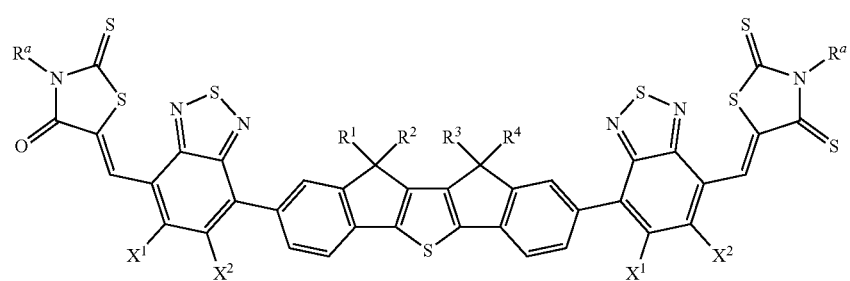
I7i
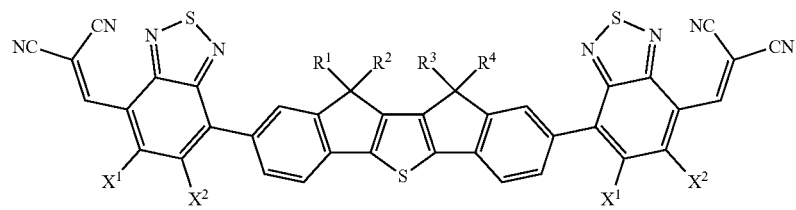
I7k
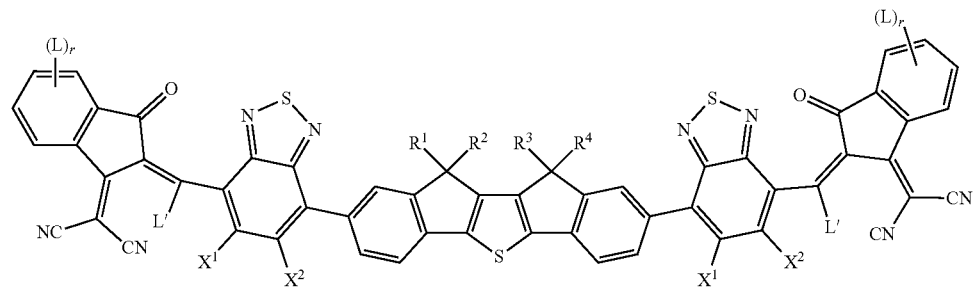
I7m

-continued
I8a
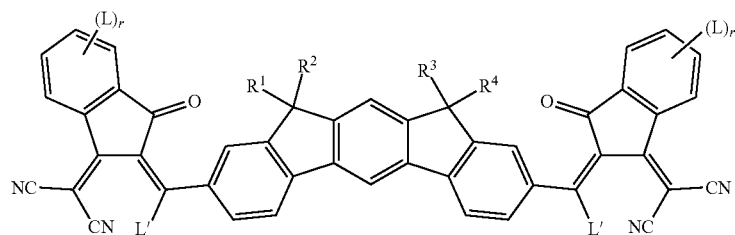
I8b
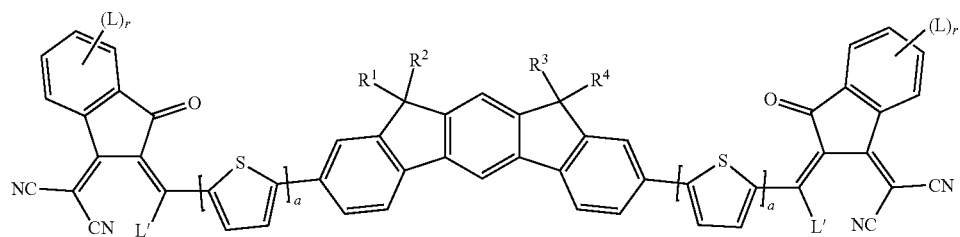
I8c
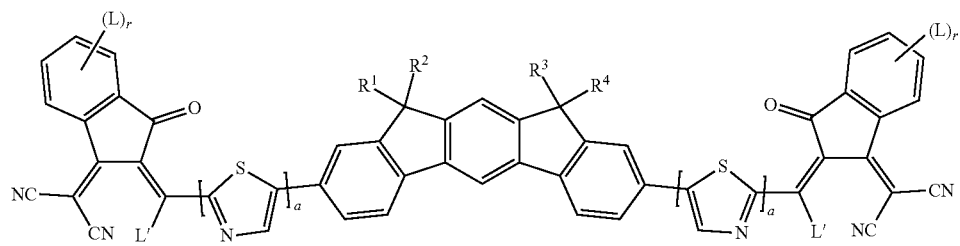
I8d
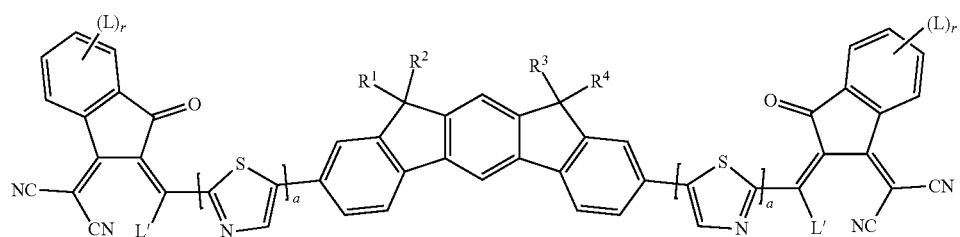
I8e
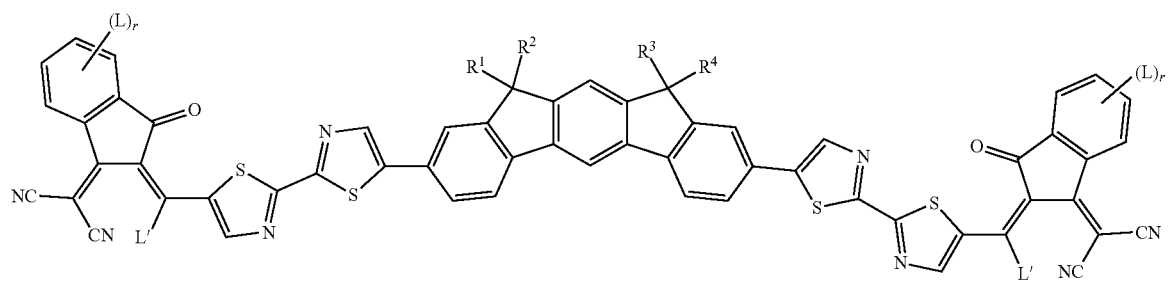
I8f
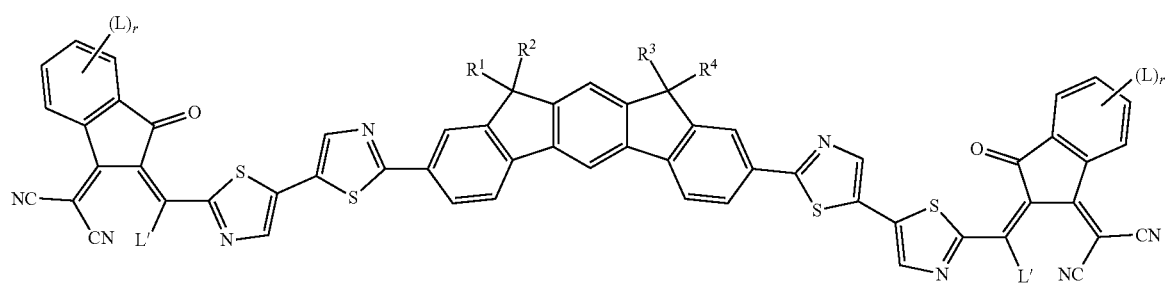

-continued
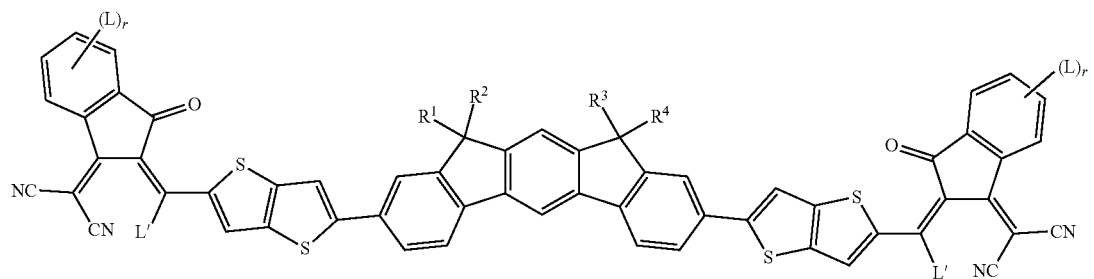
I8g
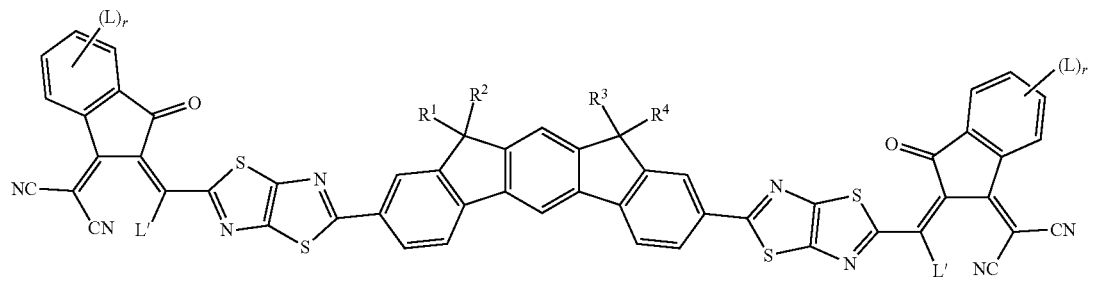
I8h
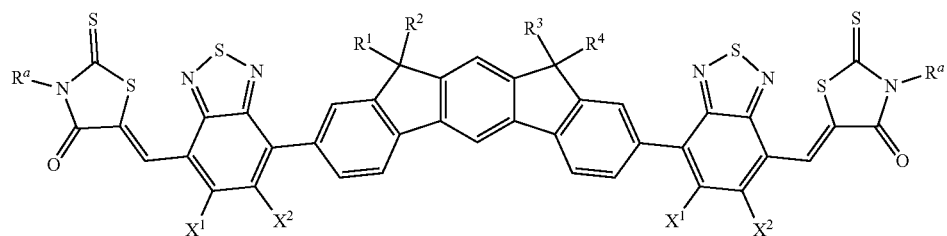
I8i
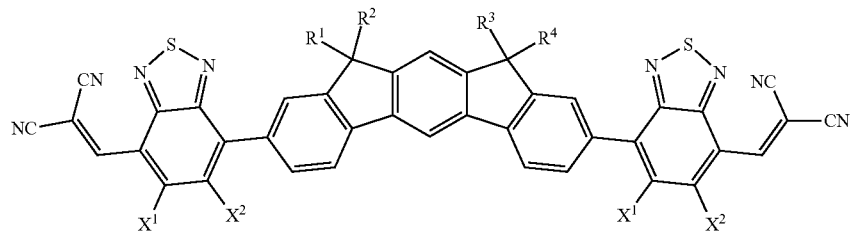
I8k
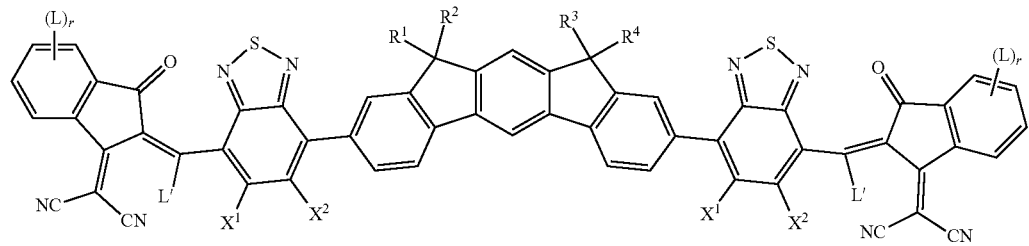
I8m
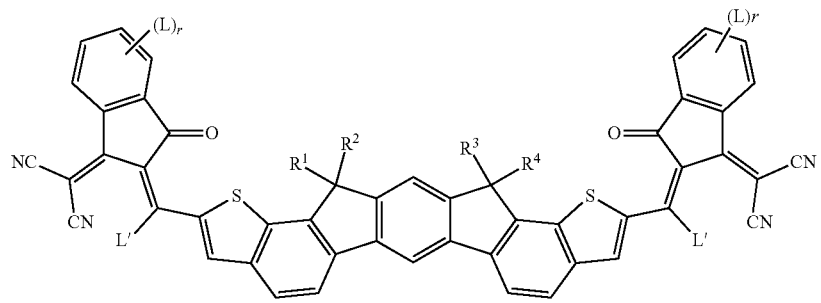
I9a

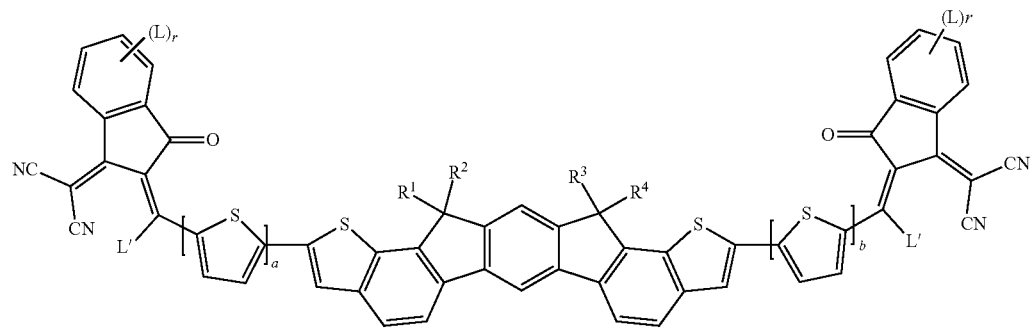
I9b
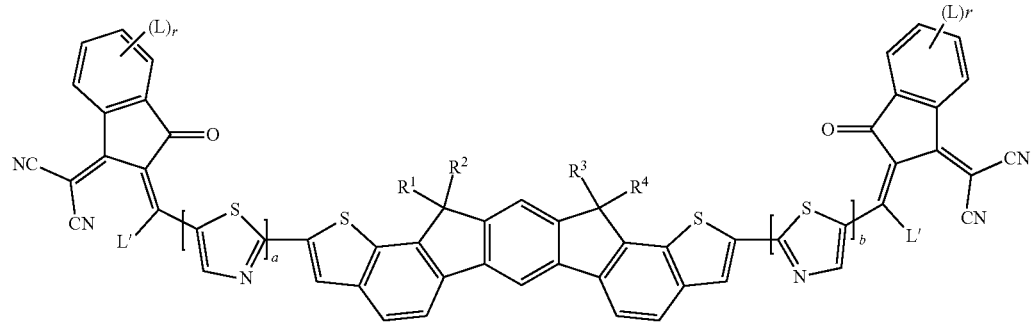
I9c
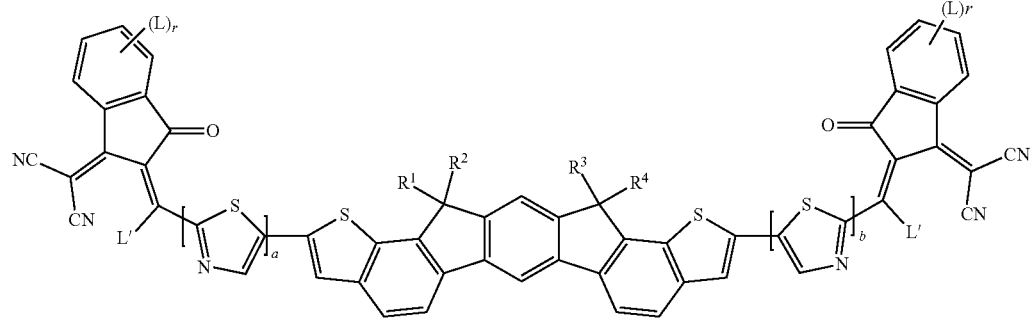
I9d
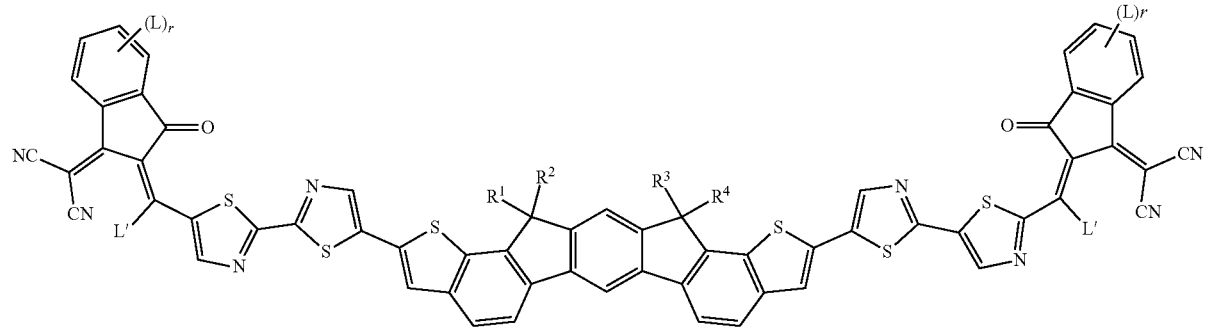
I9e

-continued
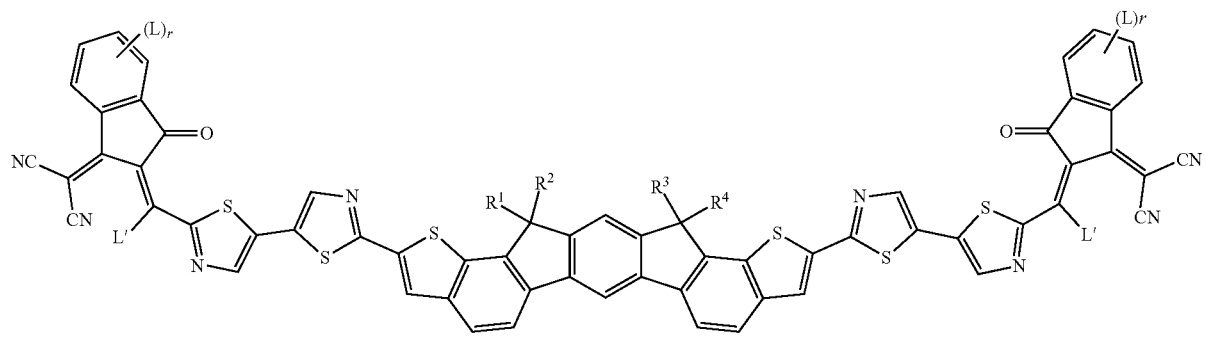
I9f
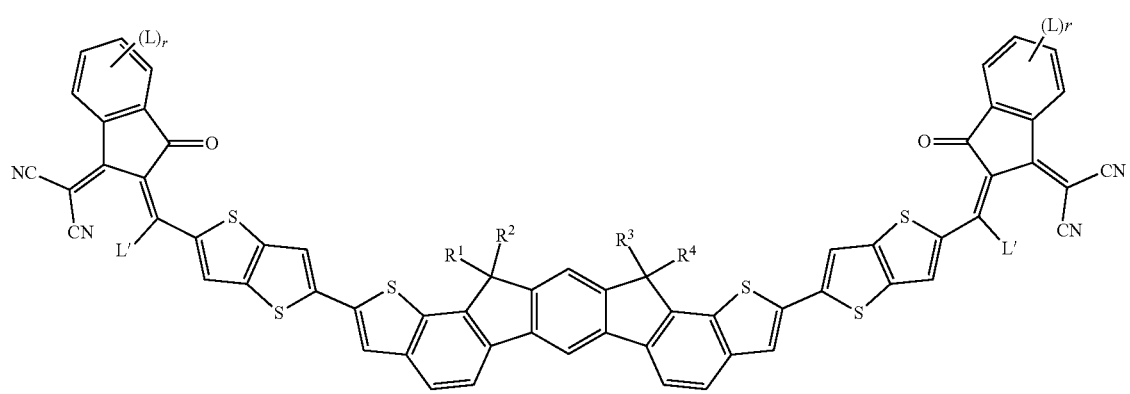
I9g
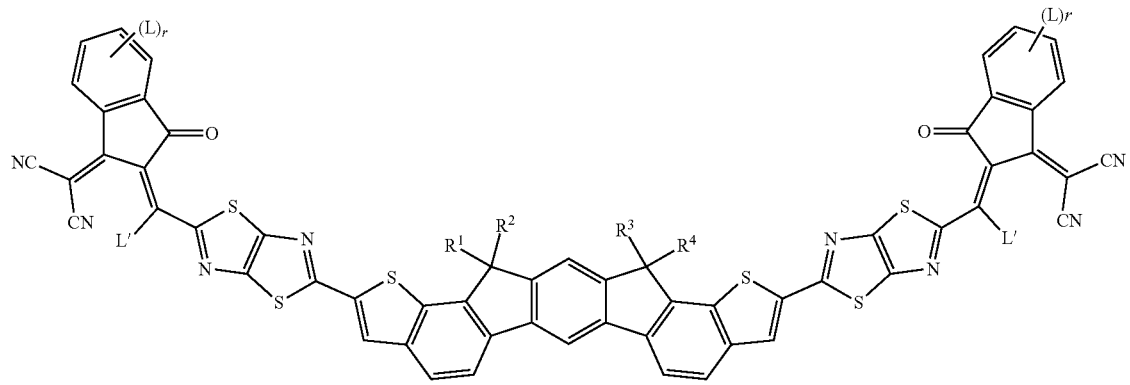
I9h
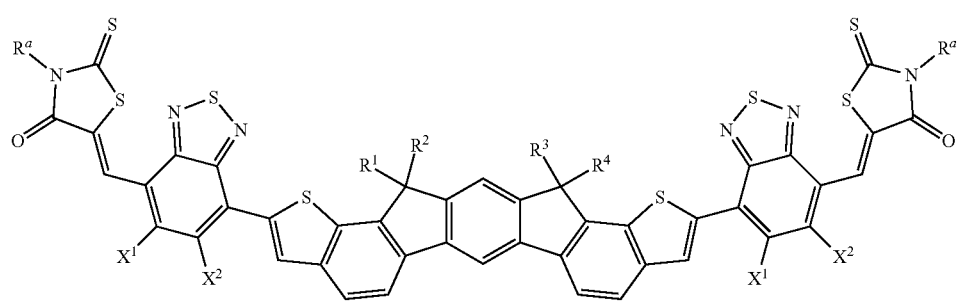
I9i

I9k
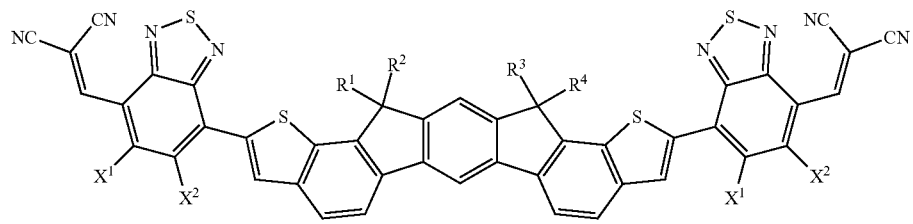
I9m
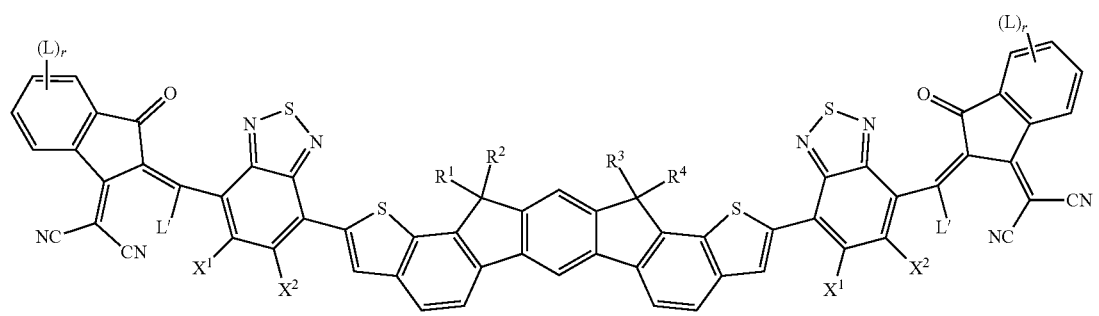
I10a
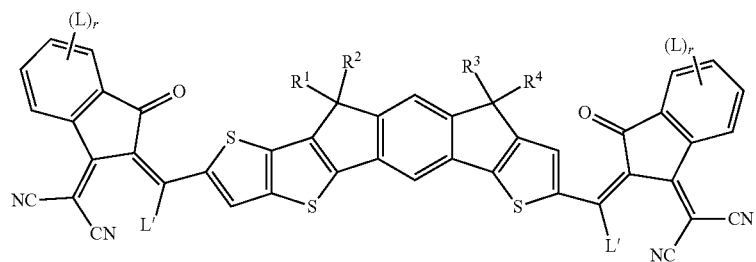
I10b
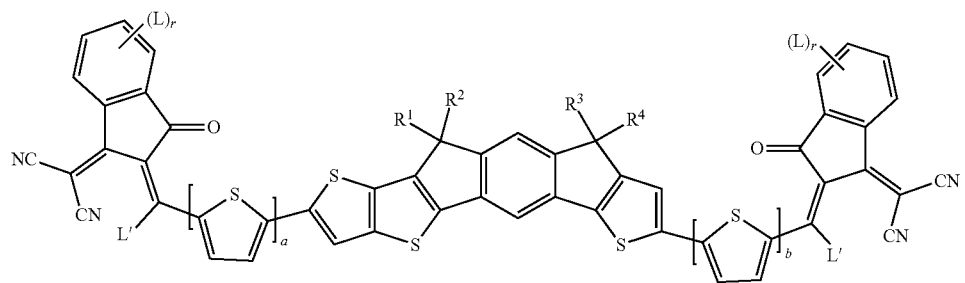
I10c
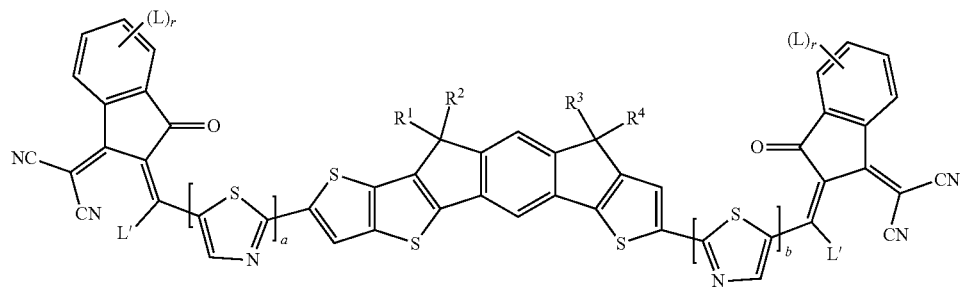

-continued
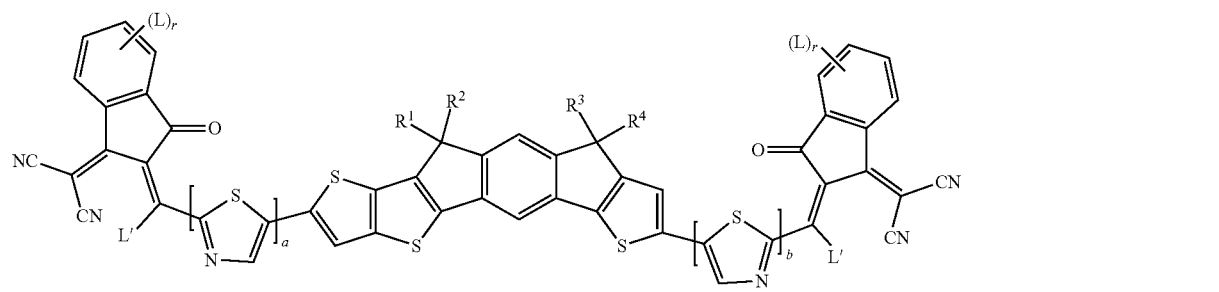
I10d
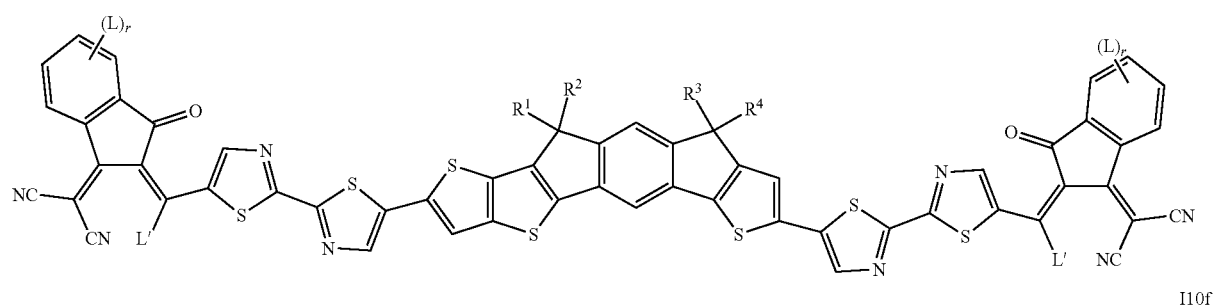
I10e
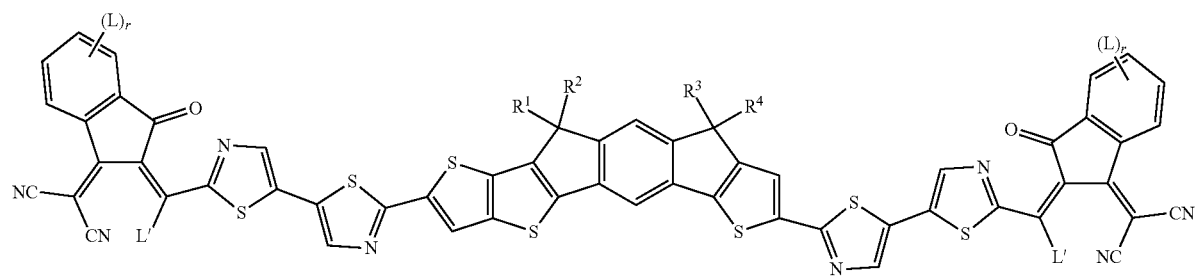
I10f
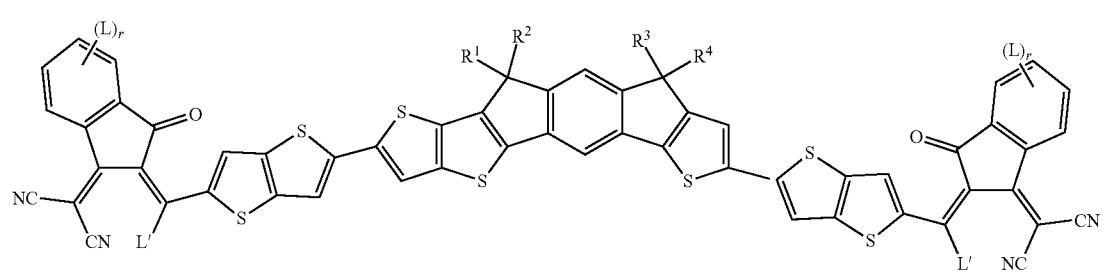
I10g
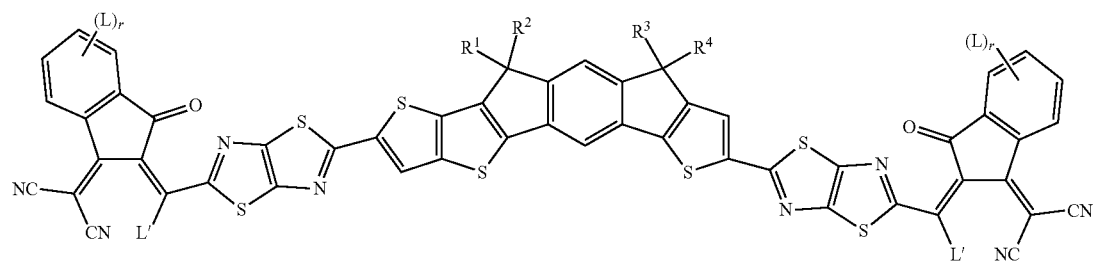
I10h -continued
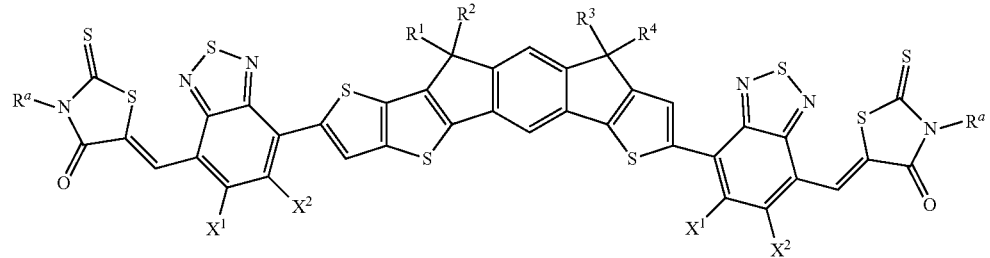
I10i
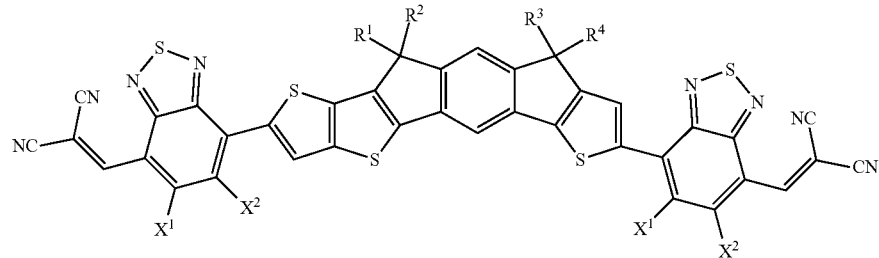
I10k
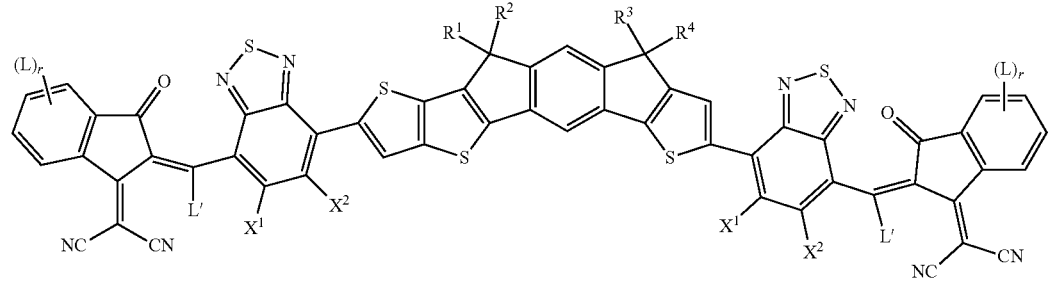
I10m
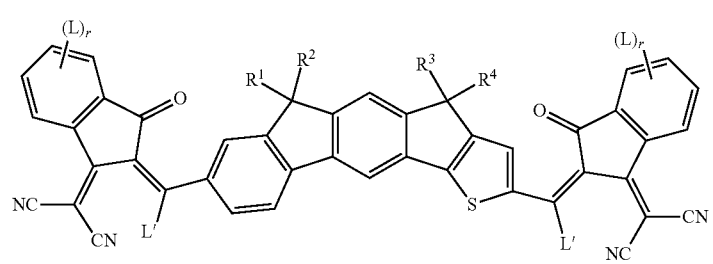
I11a
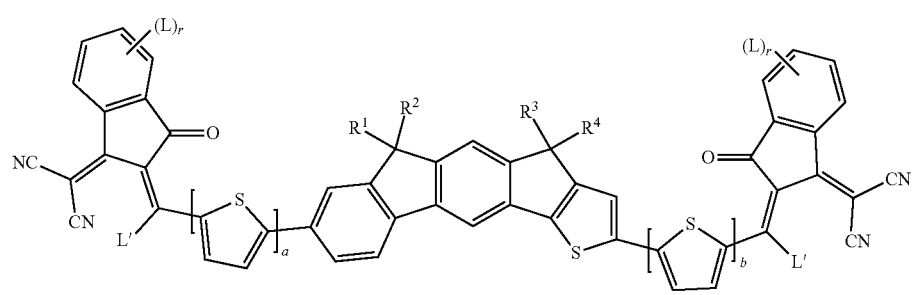
I11b -continued
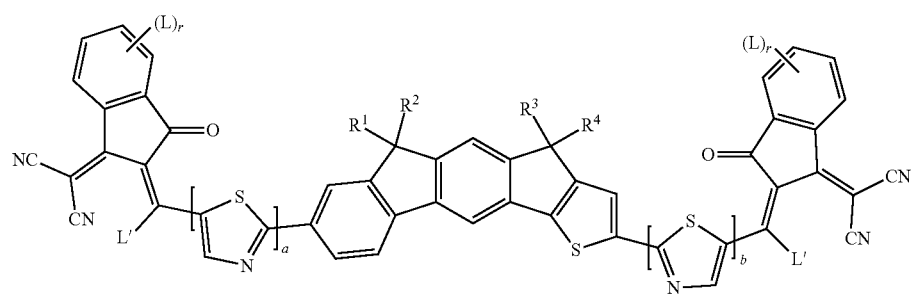
I11c
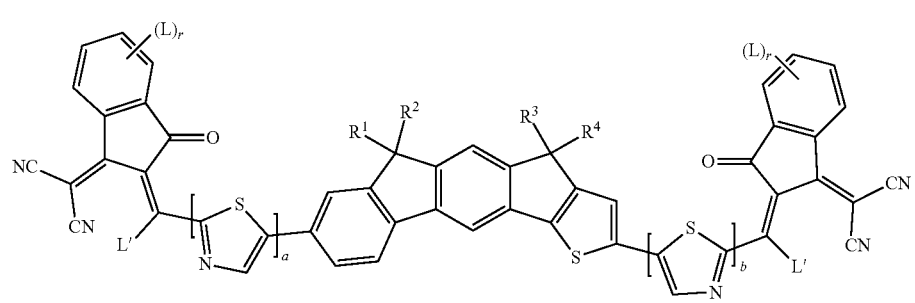
I11d
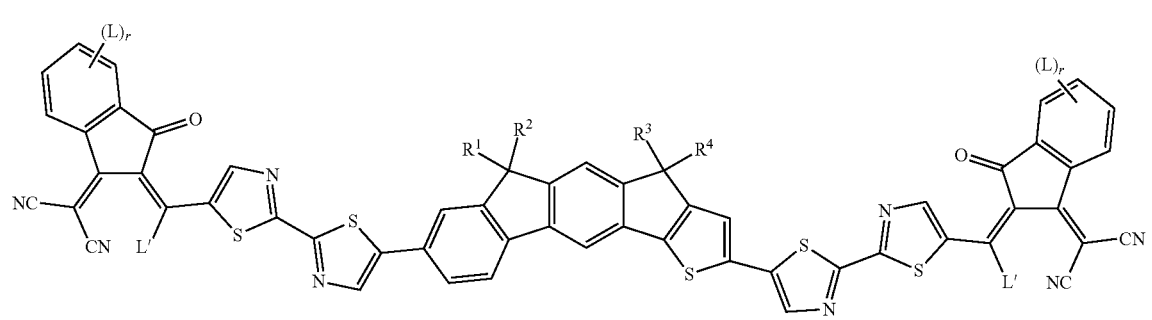
I11e
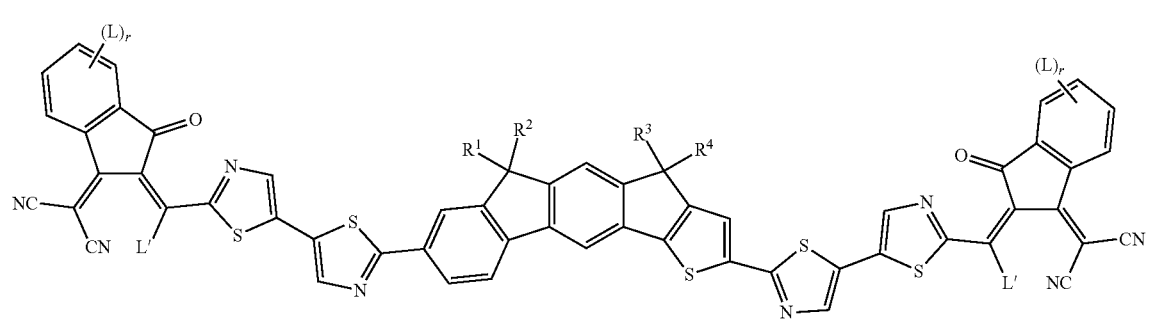
I11f
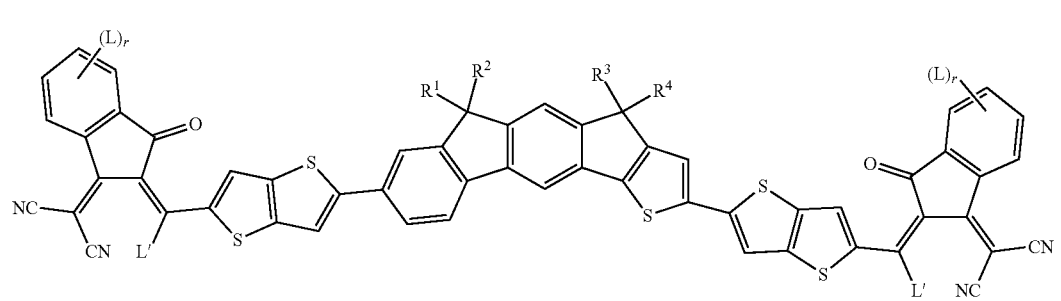
I11g -continued
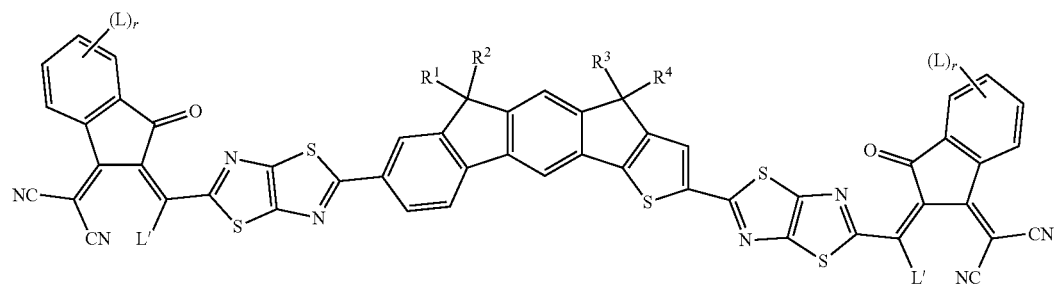
I11h
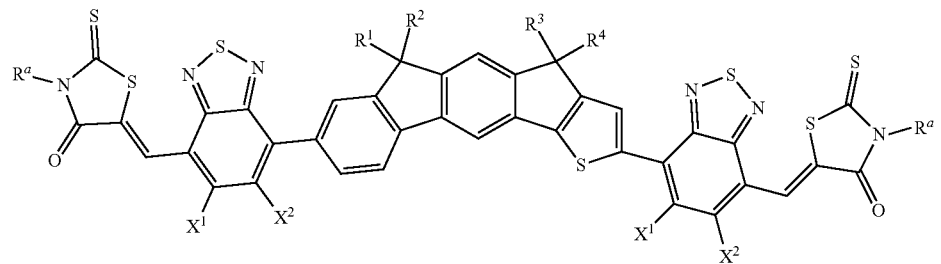
I11i
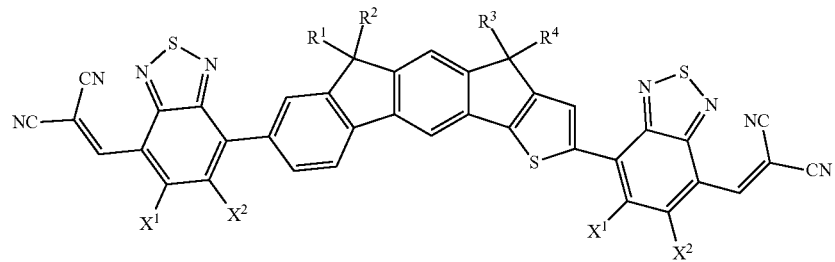
I11k
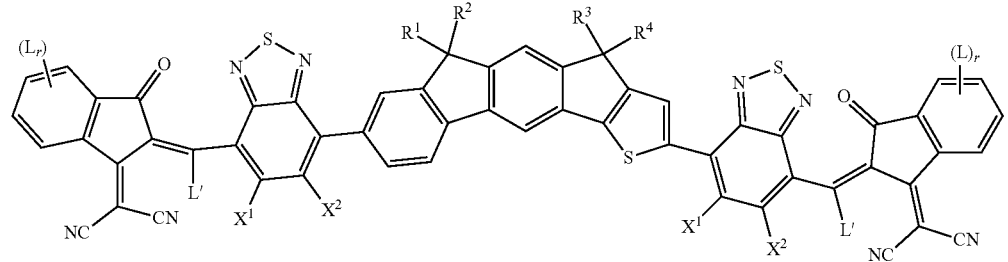
I11m
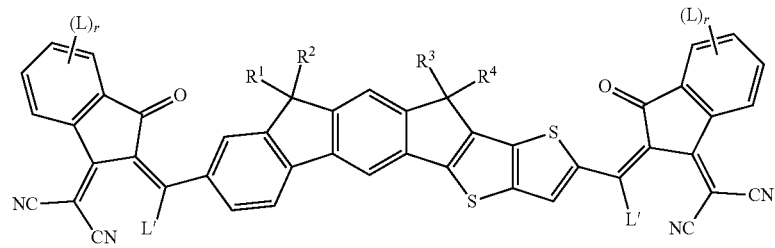
I12a
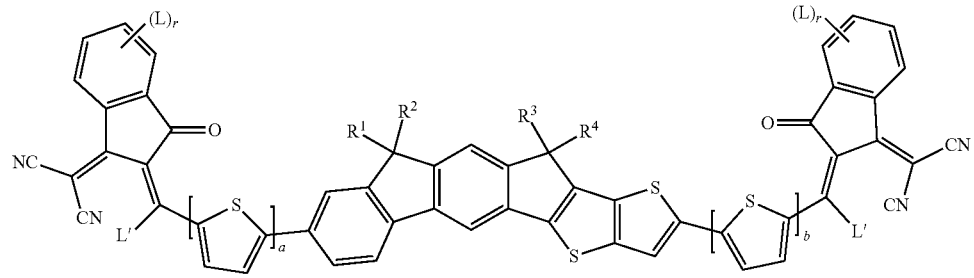
I12b -continued
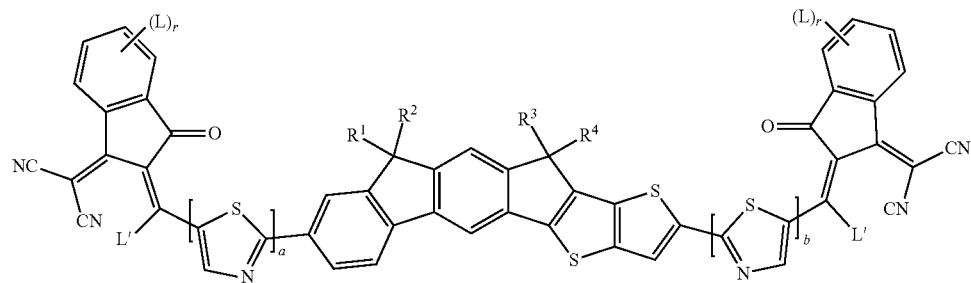
I12c
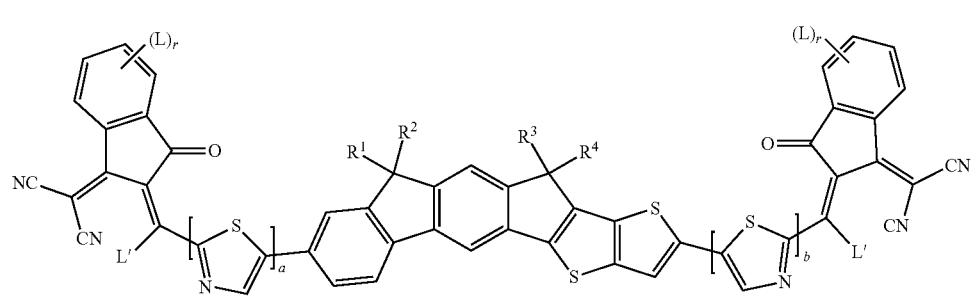
I12d
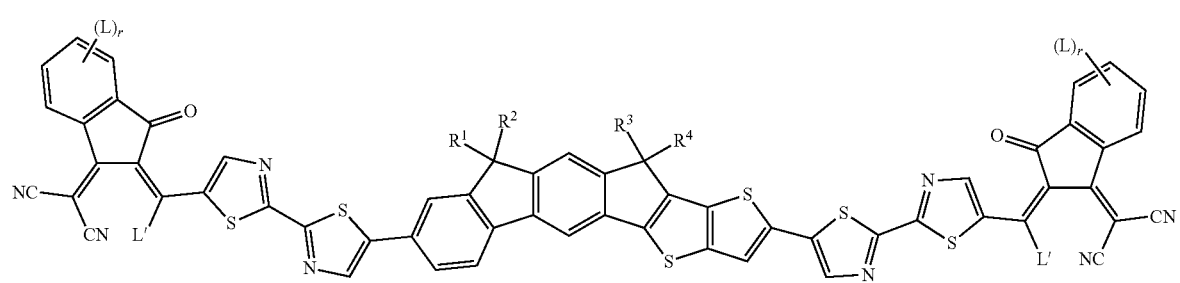
I12e
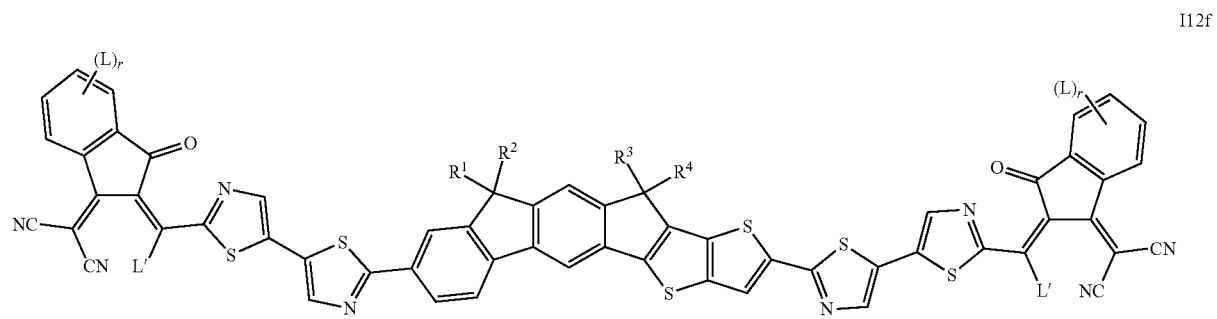
I12f
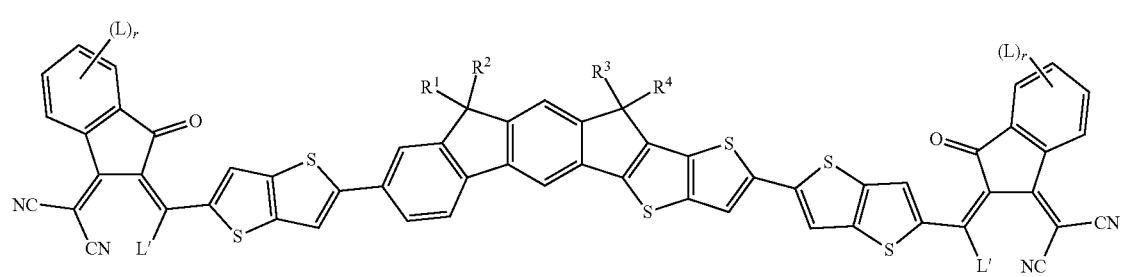
I12g

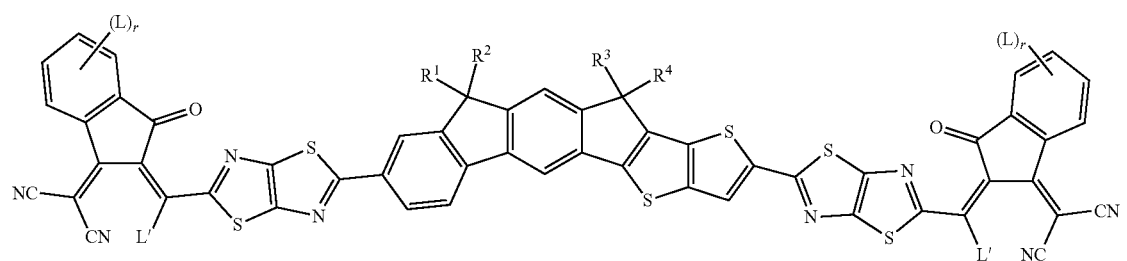
I12h
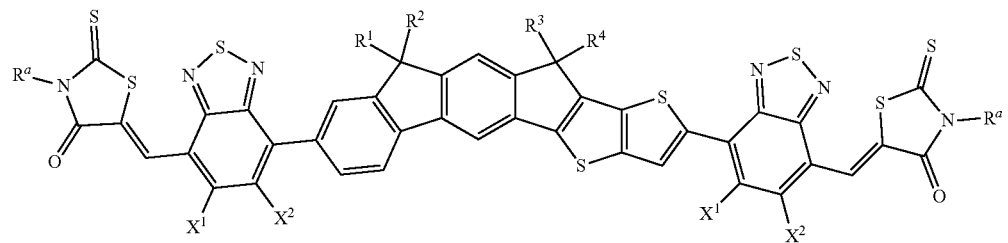
I12i
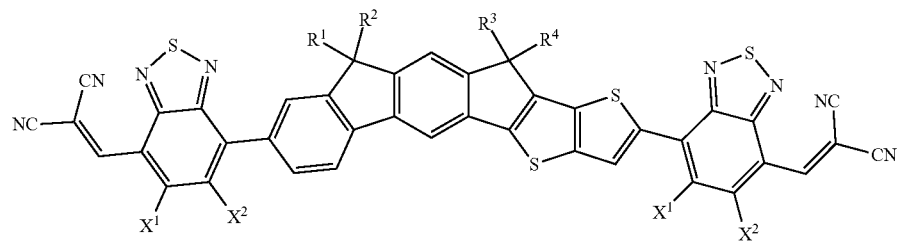
I12k
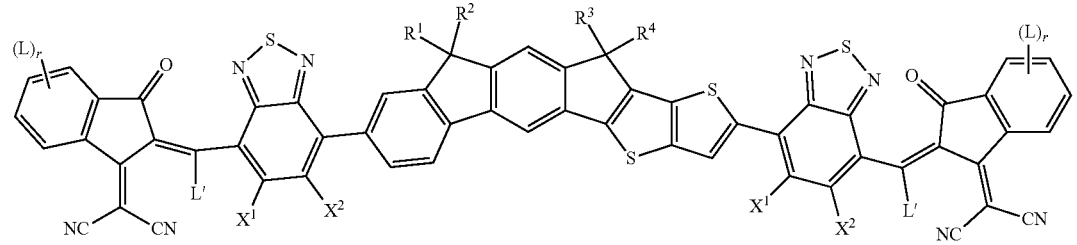
I12m
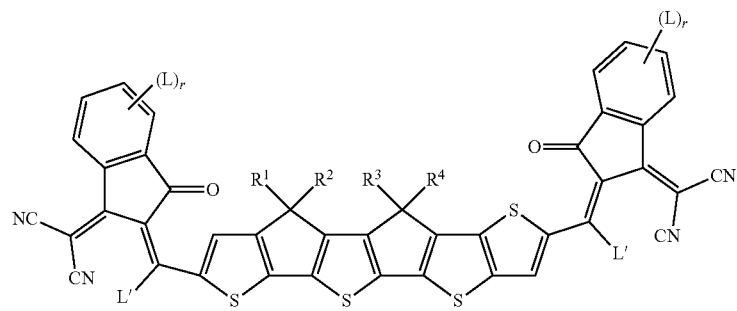
I13a -continued
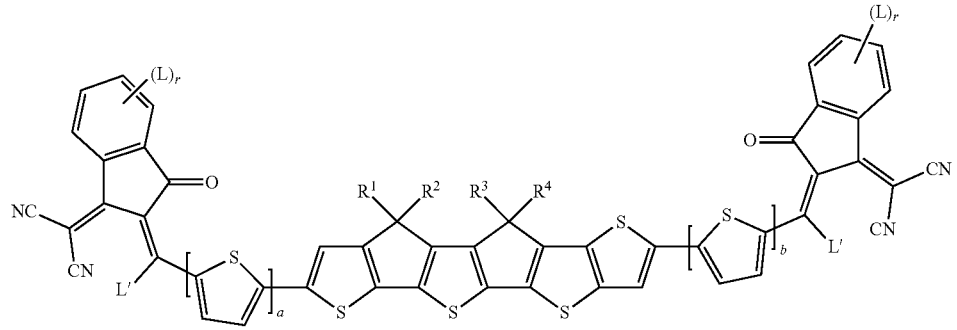
I13b
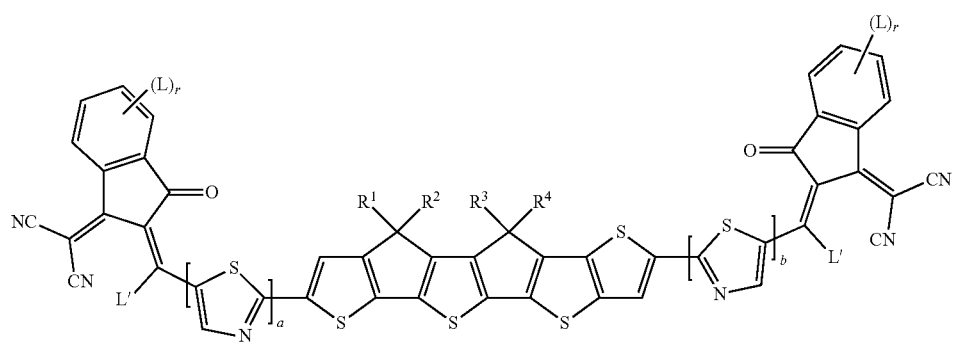
I13c
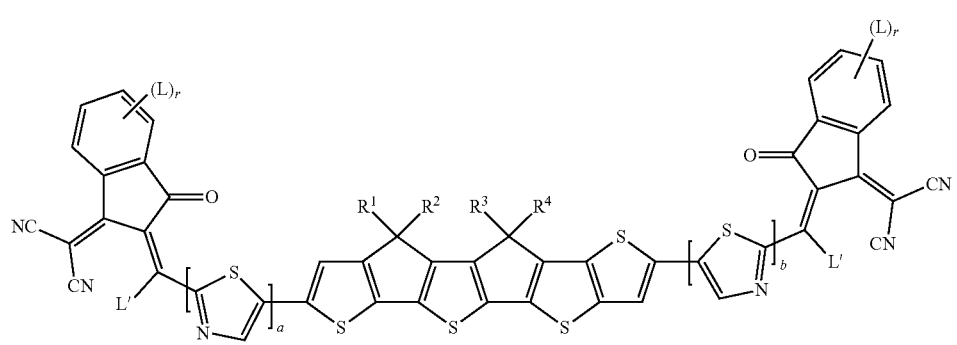
I13d
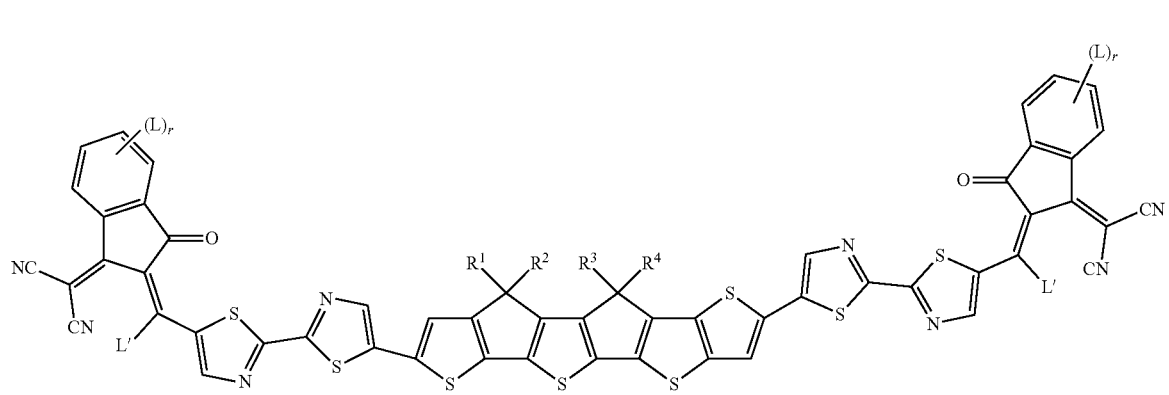
I13e -continued
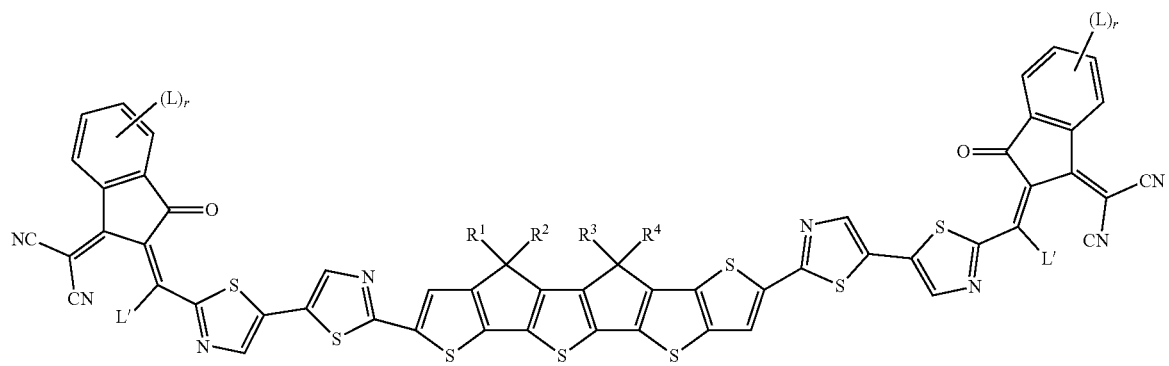
I13f
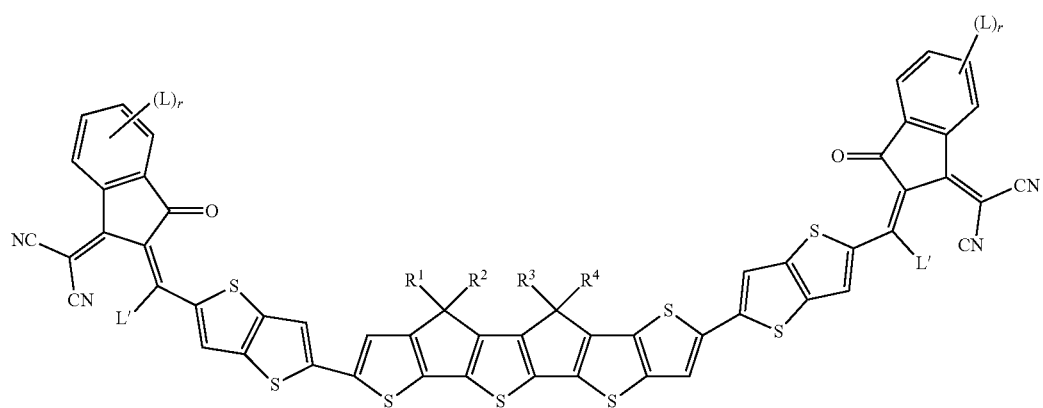
I13g
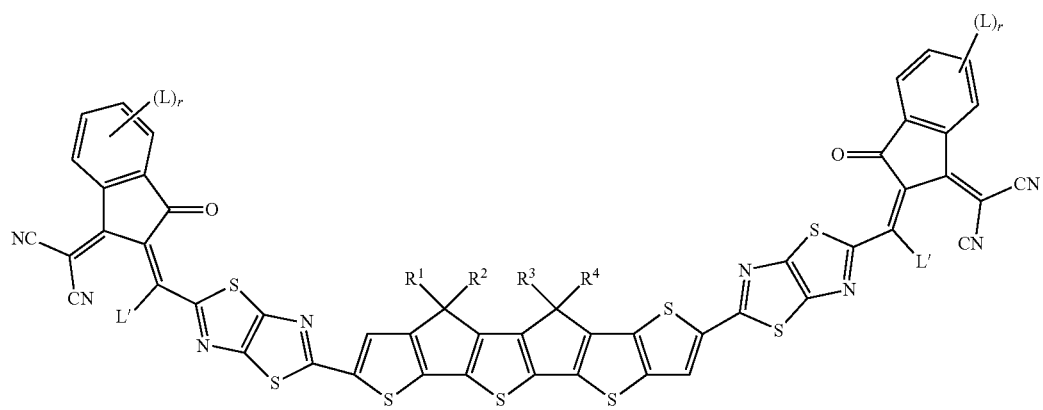
I13h
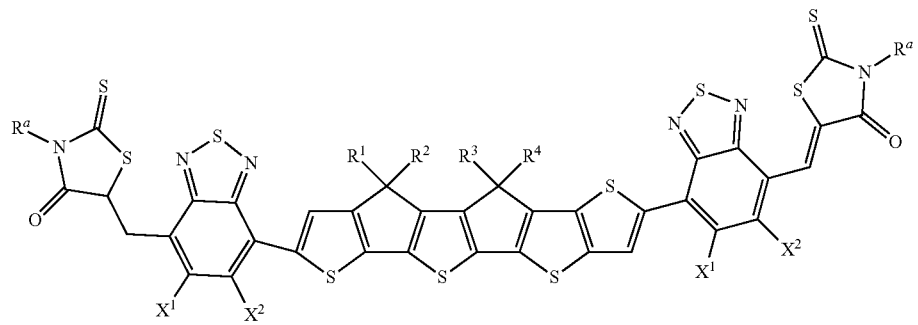
I13i I13k

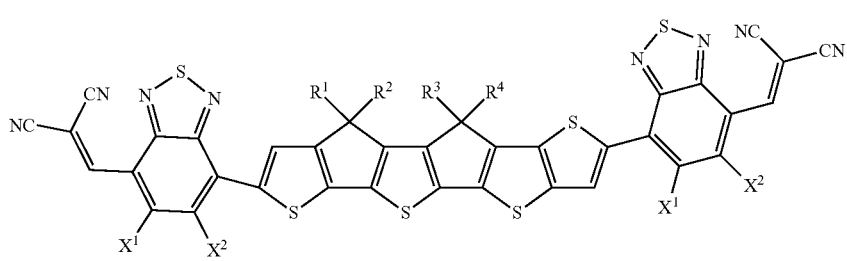

I13m

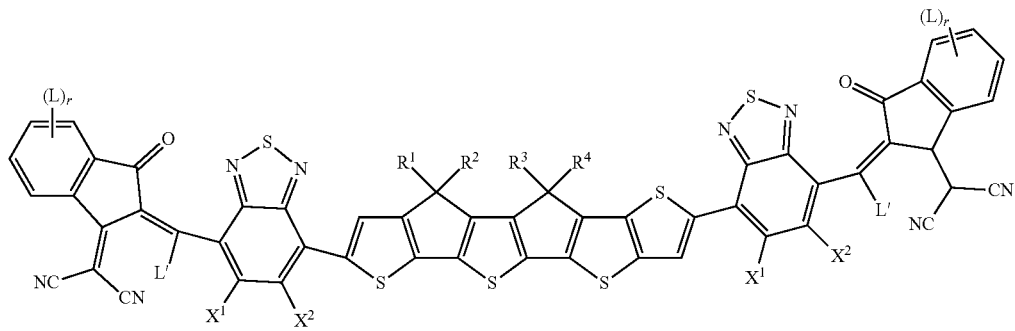

wherein R¹, R², R³, R⁴, L, L' and r have the meanings given above, and a and b are 1 or 2.

The above formulae I1a-I13m do also include their E- or Z-stereoisomers with respect to the C=C double bond of the terminal group in α-position to the adjacent group $Ar^{1-5}$, for example the following group

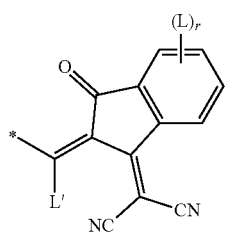

on each occurrence identically or differently may also denote

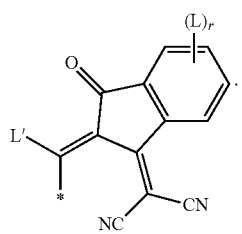

Preferably in formulae I1a-I13m L' is H. Further preferably in formulae I1a-I8i r is 0.

Preferably in formulae I1a-I13m R¹, R², R³ and R⁴ are selected from alkyl or alkoxy having 1 to 16 C atoms that is optionally fluorinated, very preferably methyl, Further preferably in formulae I1a-I13m R¹, R², R³ and R⁴ are selected from benzene that is optionally substituted, preferably in 4-position, 3,4,5-positions or 3,5-positions, with alkyl, alkoxy or thioalkyl having 1 to 16 C atoms. Most preferably in formulae I1a-I13m, R¹, R², R³ and R⁴ are selected from formulae SUB1-14 as defined above.

Another embodiment of the invention relates to a composition comprising a compound of formula I, and further comprising one or more electron donors or p-type semiconductors, preferably selected from conjugated polymers.

In a first preferred embodiment the compound of formula I is a conjugated polymer that comprises at least one electron donating unit ("donor unit") and at least one electron accepting unit ("acceptor unit"), and optionally at least one spacer unit separating a donor unit from an acceptor unit, wherein each donor and acceptor units is directly connected to another donor or acceptor unit or to a spacer unit, and wherein all of the donor, acceptor and spacer units are selected from arylene or heteroarylene that has from 5 to 20 ring atoms, is mono- or polycyclic, optionally contains fused rings, are is unsubstituted or substituted by one or more identical or different groups L as defined above.

Preferably the spacer units, if present, are located between the donor and acceptor units such that a donor unit and an acceptor unit are not directly connected to each other.

Preferred conjugated polymers comprise, very preferably consist of, one or more units of the formula U1 and one or more units of the formula U2

-(D-Sp)-  U1

-(A-Sp)-  U2 wherein D denotes a donor unit, A denotes an acceptor unit and Sp denotes a spacer unit, all of which are selected from arylene or heteroarylene that has from 5 to 20 ring atoms, is mono- or polycyclic, optionally contains fused rings, are is unsubstituted or substituted by one or more identical or different groups L as defined above.

Very preferred are polymers of formula Pi and Pii

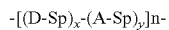   Pi

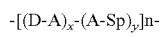   Pii wherein A, D and Sp are as defined in formula U1 and U2, x denotes the molar fraction of the units (D-Sp) or (D-A), y denotes the molar fraction of the units (A-Sp), x and y are each, independently of one another >0 and <1, with x+y=1, and n is an integer >1.

In the polymers of formula P1 and P2 and their subformulae, x and y are preferably from 0.1 to 0.9, very preferably from 0.3 to 0.7, most preferably from 0.4 to 0.6.

Preferred donor units or units D are selected from the following formulae

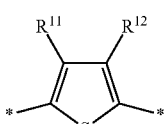 (D1)

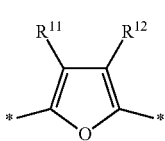 (D7)

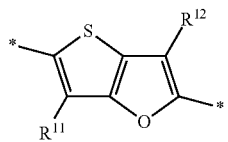 (D10)

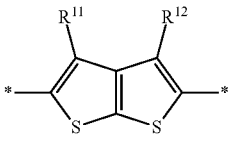 (D11)

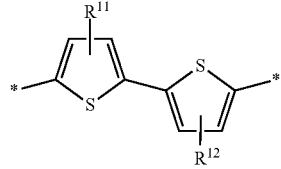 (D19)

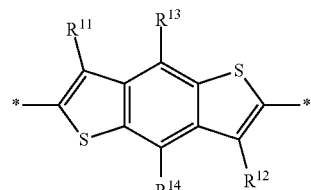 (D22)

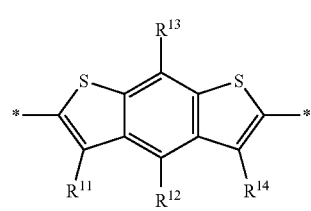 (D29)

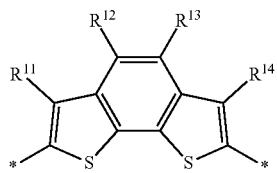 (D30)

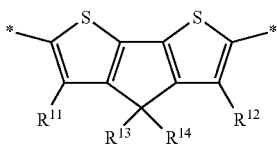 (D35)

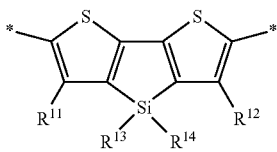 (D36)

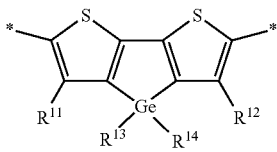 (D37)

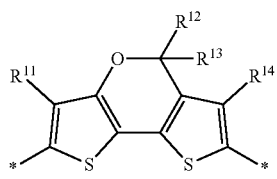 (D44)

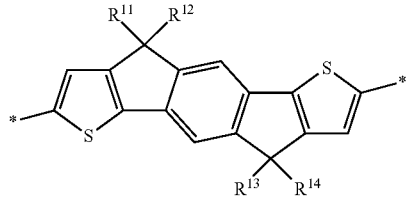 (D55)

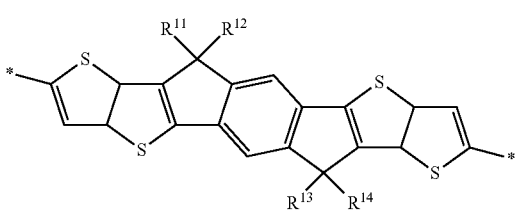 (D84)

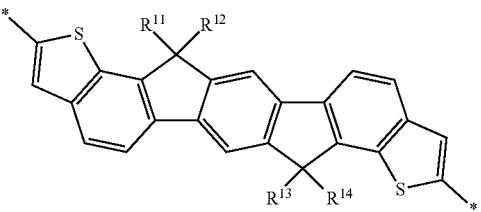 (D87)

(D88) 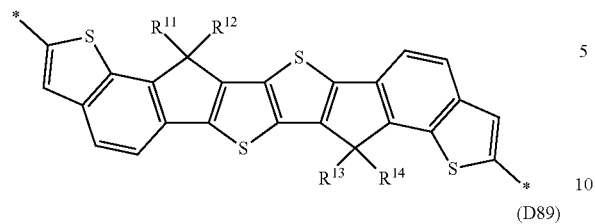
(D89) 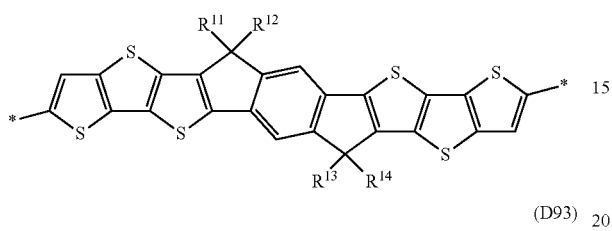
(D93) 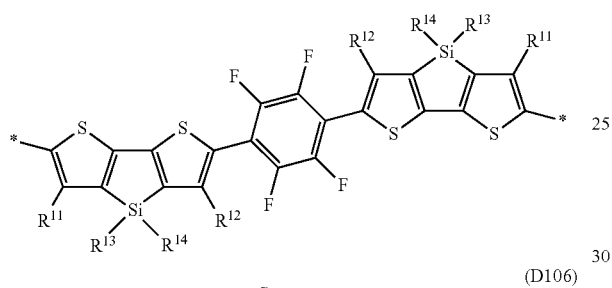
(D106) 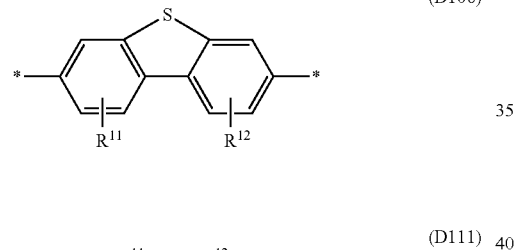
(D111) 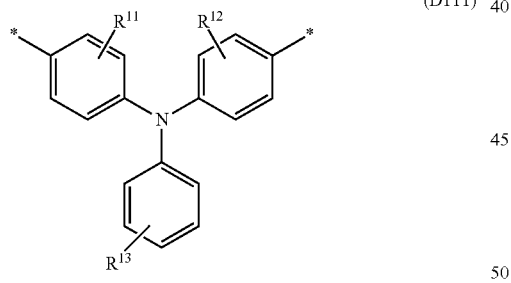
(D119) 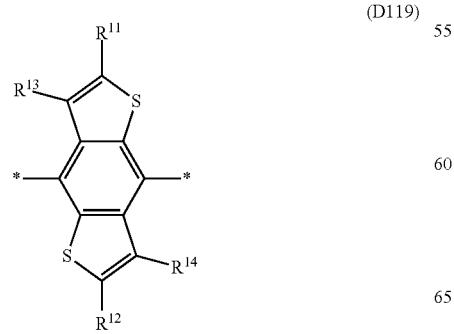
(D140) 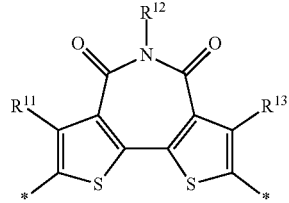
(D141) 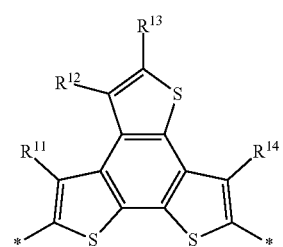
(D146) 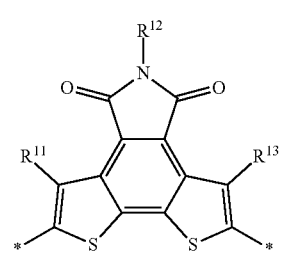
(D147) 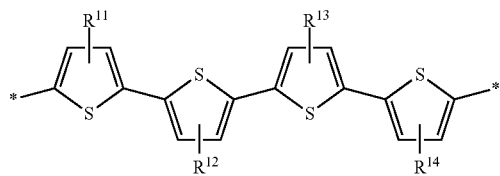
wherein $R^{11}$, $R^{12}$, $R^{13}$, $R^{14}$ independently of each other denote H or have one of the meanings of L as defined above.
Preferred acceptor units or units A are selected from the following formulae
(A1) 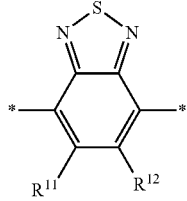
(A5) 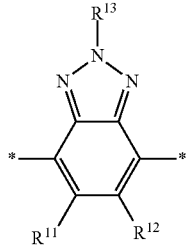

-continued
(A7) 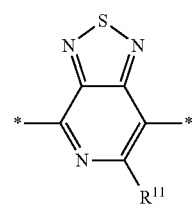
(A15) 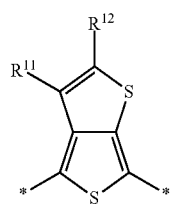
(A16) 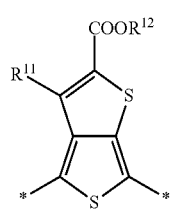
(A20) 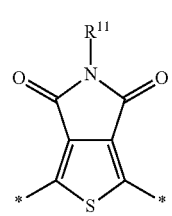
(A74) 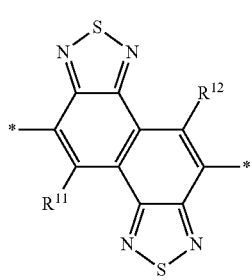
(A88) 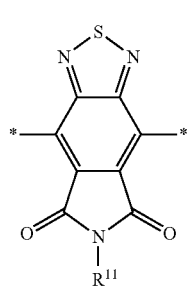
(A92) 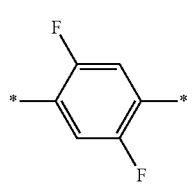
-continued
(A94) 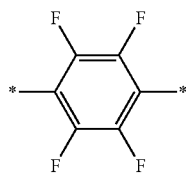
(A98) 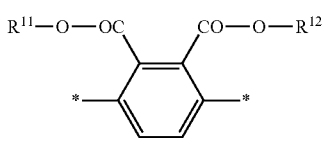
(A99) 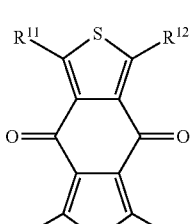
(A100) 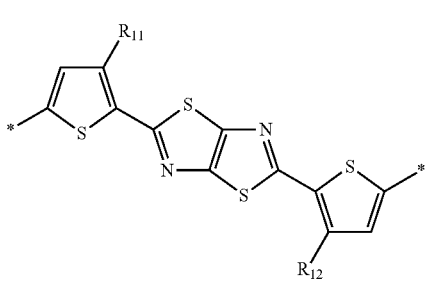
wherein $R^{11}$, $R^{12}$, $R^{13}$, $R^{14}$ independently of each other denote H or have one of the meanings of L as defined above.
Preferred spacer units or units Sp are selected from the following formulae
Sp1 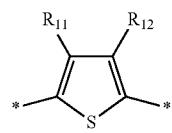
Sp2 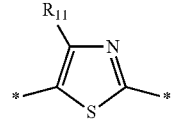
Sp3 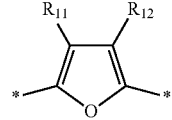
Sp4 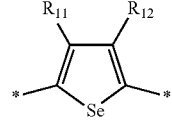

-continued

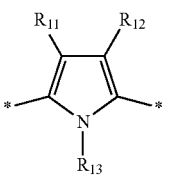
Sp5

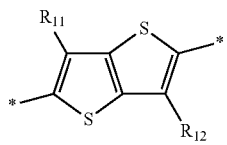
Sp6

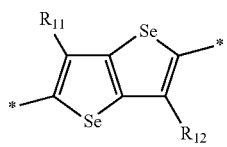
Sp7

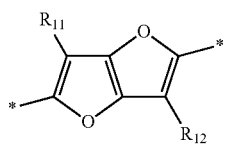
Sp8

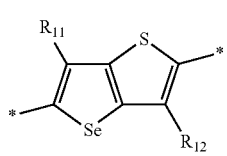
Sp9

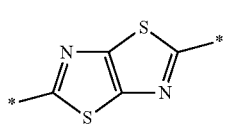
Sp10

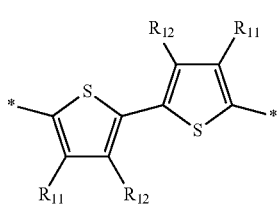
Sp11

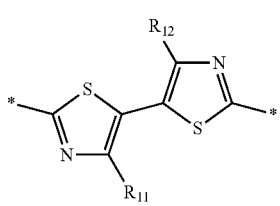
Sp12

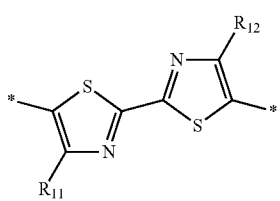
Sp13

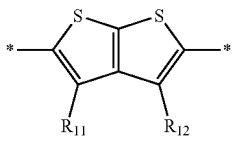
Sp14

Sp15

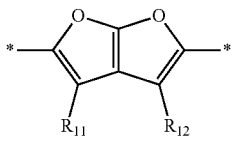
Sp16

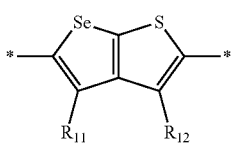
Sp17

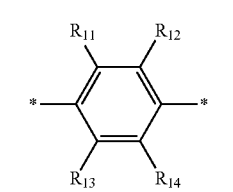
Sp18 wherein $R^{11}$, $R^{12}$, $R^{13}$, $R^{14}$ independently of each other denote H or have one of the meanings of L as defined above. In the formulae Sp1 to Sp18 preferably $R^{11}$ and $R^{12}$ are H.

Preferably the conjugated polymer contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A5, A7, A15, A16, A20, A74, A88, A92, A94 and A98, A99, A100 and c) optionally one or more spacer units selected from the group consisting of the formulae Sp1-Sp18, very preferably of the formulae Sp1, Sp6, Sp11 and Sp14, wherein the spacer units, if present, are preferably located between the donor and acceptor units such that a donor unit and an acceptor unit are not directly connected to each other.

In a second preferred embodiment the compound of formula I is a conjugated polymer that comprises, preferably consists of one or more, preferably one, two, three or four, distinct repeating units D, and one or more, preferably one, two or three, distinct repeating units A.

Preferably the conjugated polymer according to this second preferred embodiment contains from one to six, very preferably one, two, three or four distinct units D and from one to six, very preferably one, two, three or four distinct units A, wherein d1, d2, d3, d4, d5 and d6 denote the molar ratio of each distinct unit D, and a1, a2, a3, a4, a5 and a6 denote the molar ratio of each distinct unit A, and each of d1, d2, d3, d4, d5 and d6 is from 0 to 0.6, and d1+d2+d3+d4+d5+d6 is from 0.2 to 0.8, preferably from 0.3 to 0.7, and each of a1, a2, a3, a4, a5 and a6 is from 0 to 0.6, and a1+a2+a3+a4+a5+d6 is from 0.2 to 0.8, preferably from 0.3 to 0.7, and d1+d2+d3+d4+d5+d6+a1+a2+a3+a4+a5+a6 is from 0.8 to 1, preferably 1.

Preferably the conjugated polymer according to this second preferred embodiment contains, preferably consists of
a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A5, A7, A15, A16, A20, A74, A88, A92, A94, A98, A99 and A100.

In the above conjugated polymers, like those of formula P and its subformulae, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The conjugated polymers are preferably statistical or random copolymers.

Very preferred conjugated polymers are selected from the following subformulae

P1

P2

P3

P4

P5

-continued
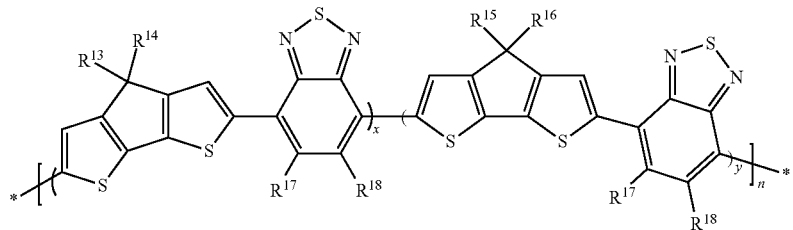
P6
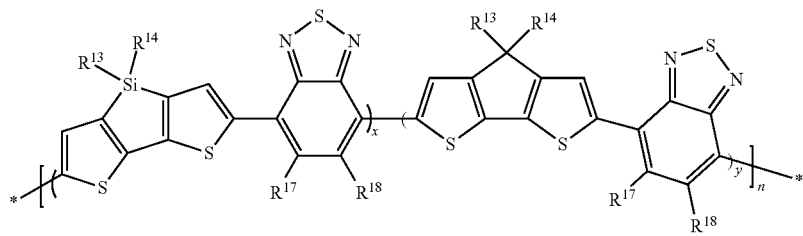
P7
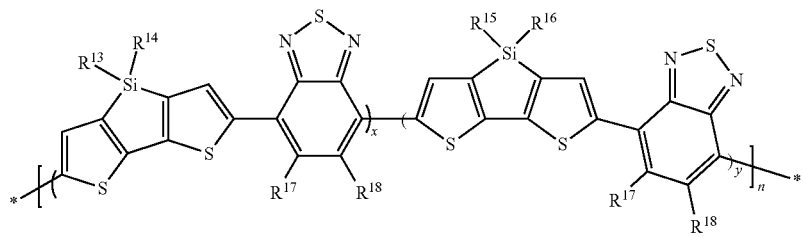
P8
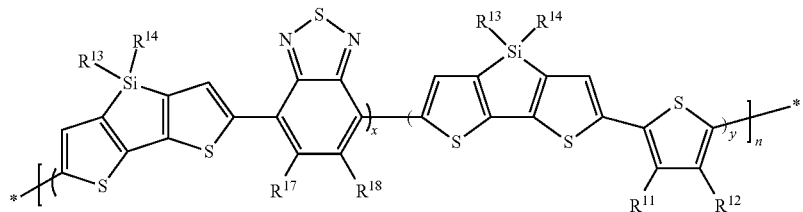
P9
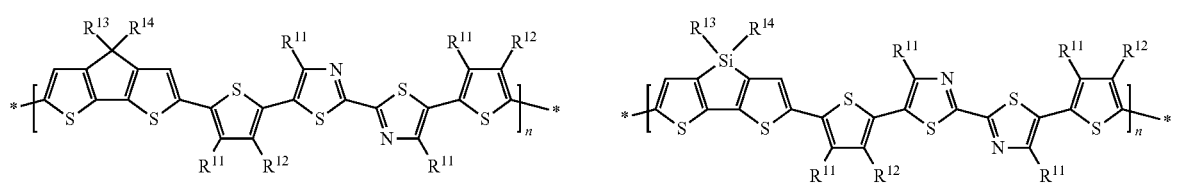
P10 P11
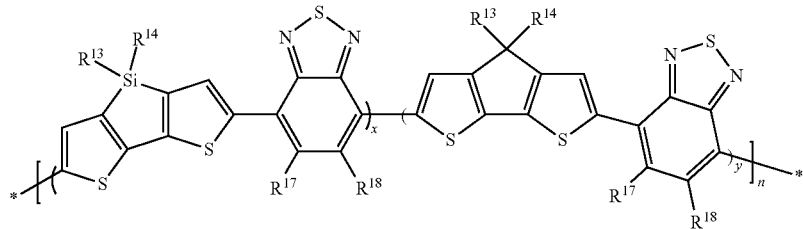
P12
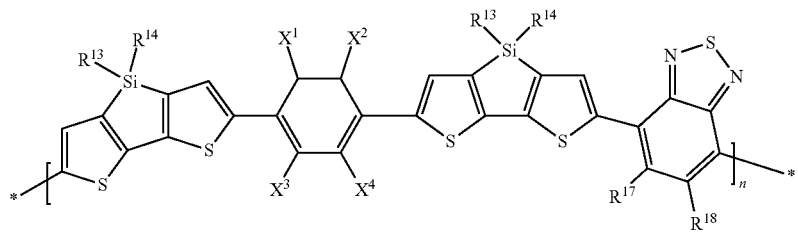
P13

-continued
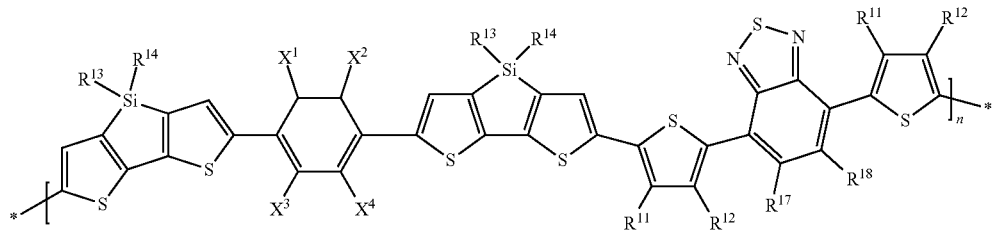
P14
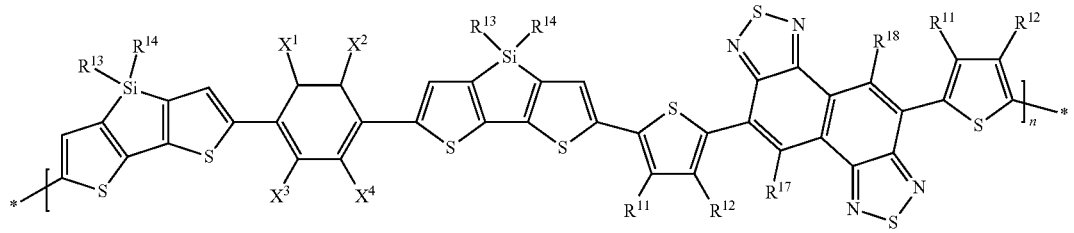
P15
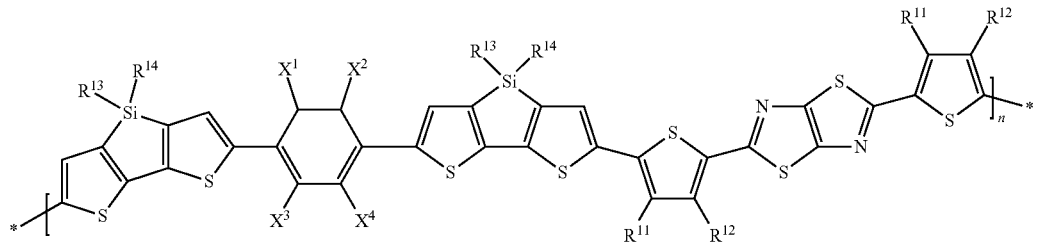
P16
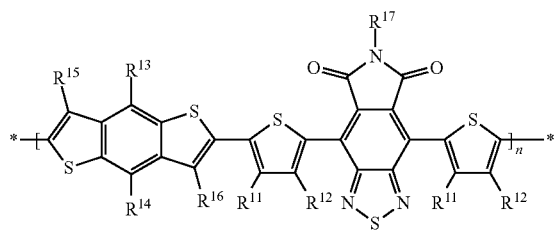
P17
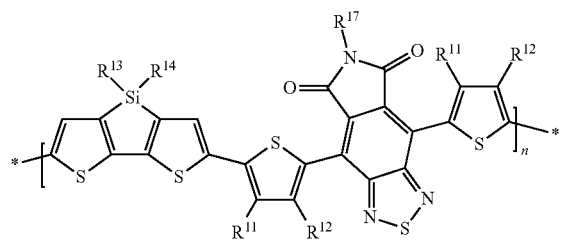
P18
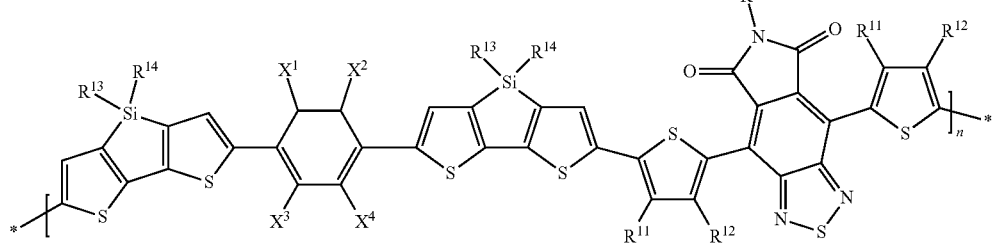
P19
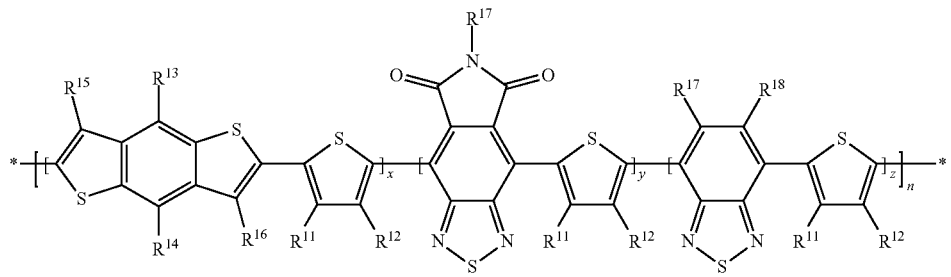
P20

-continued
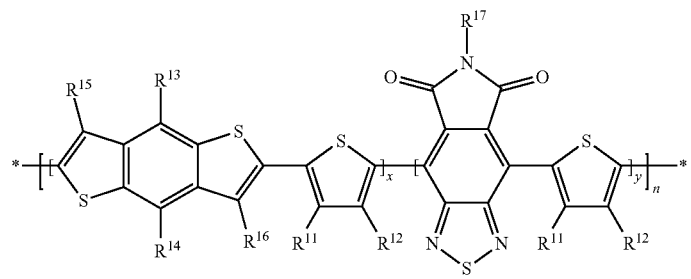
P21
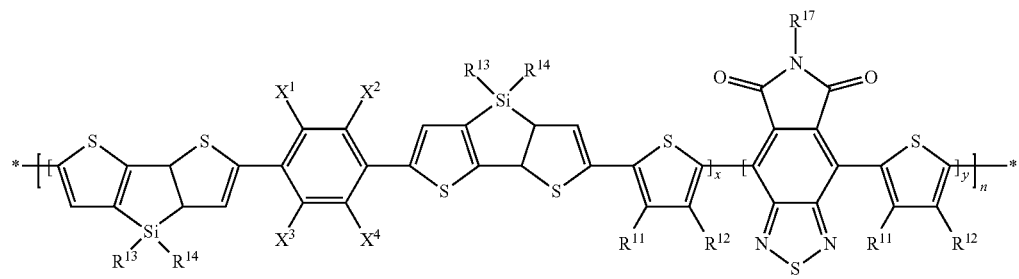
P22
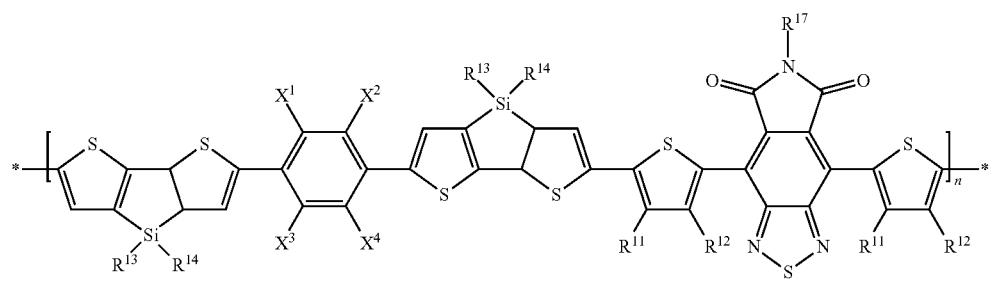
P23
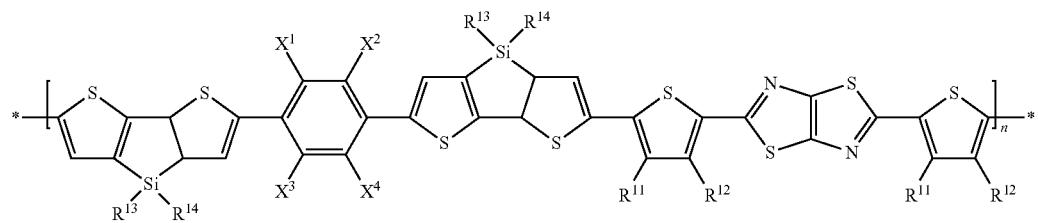
P24
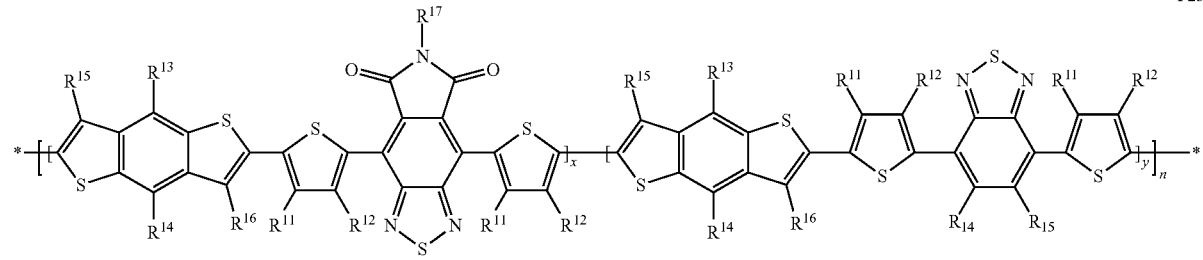
P25
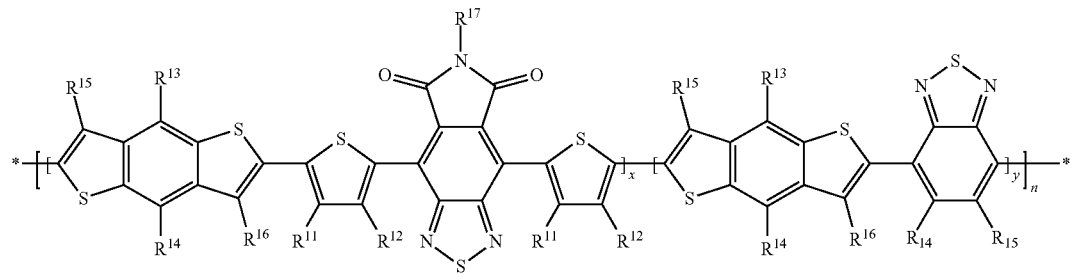
P26

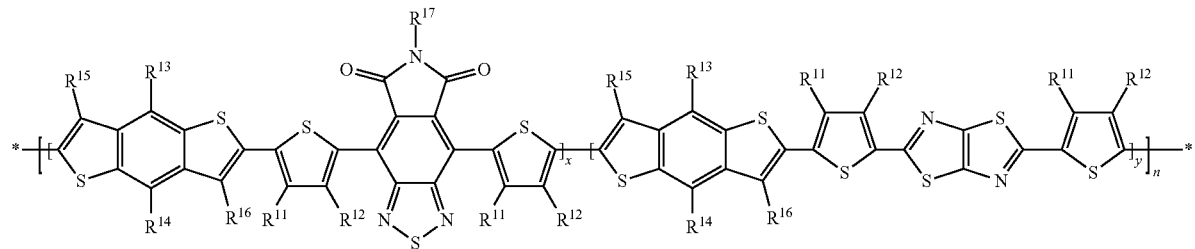
P27
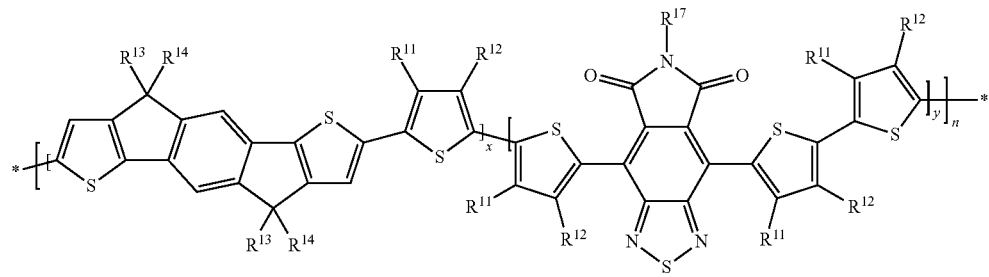
P28
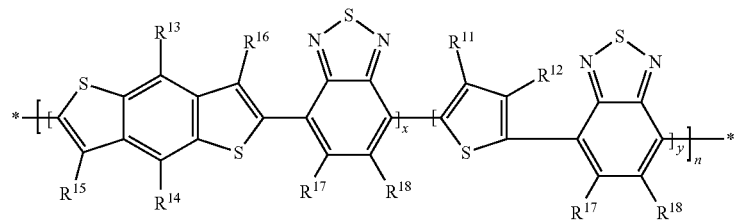
P29
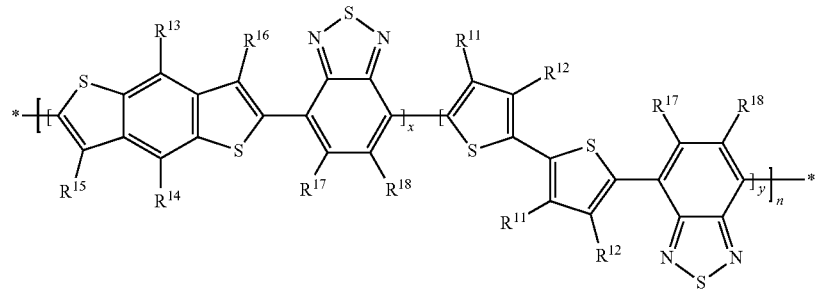
P30
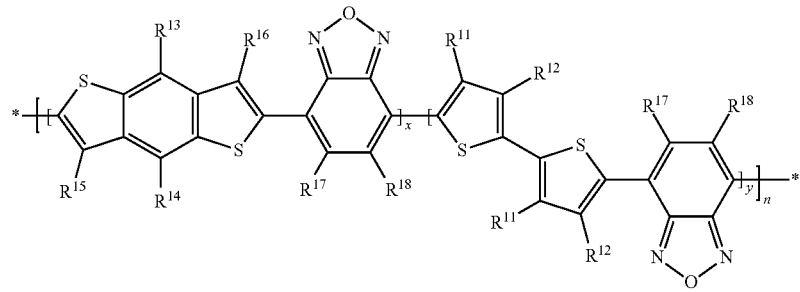
P31
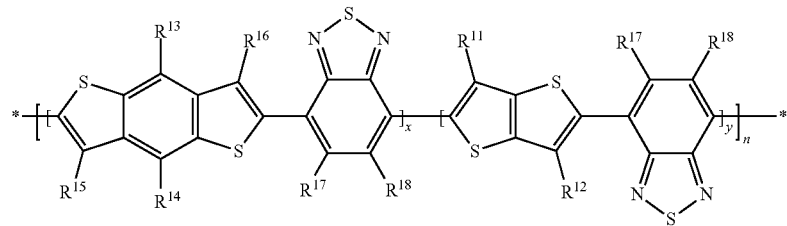
P32

-continued
P33
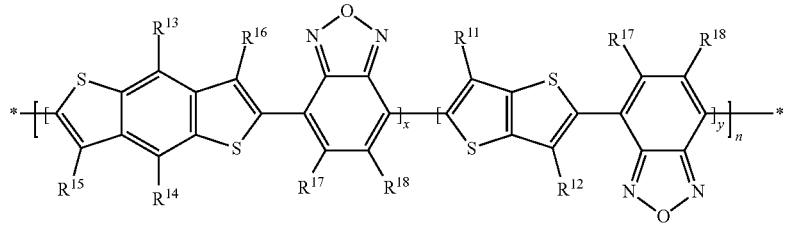
P34
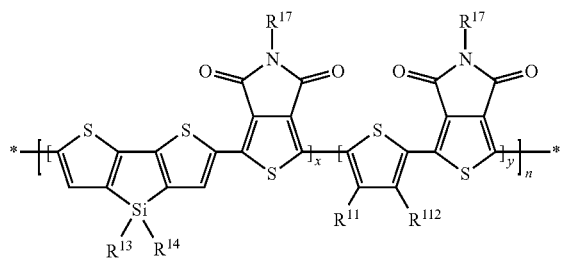
P35
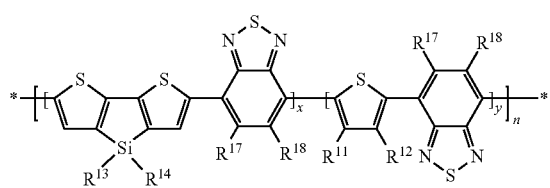
P36
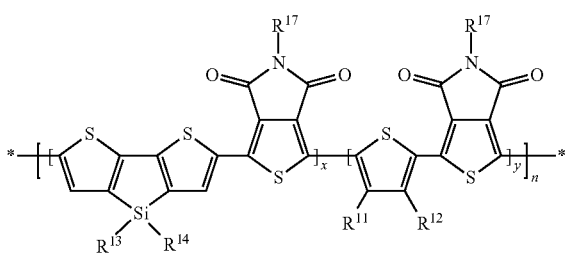
P37
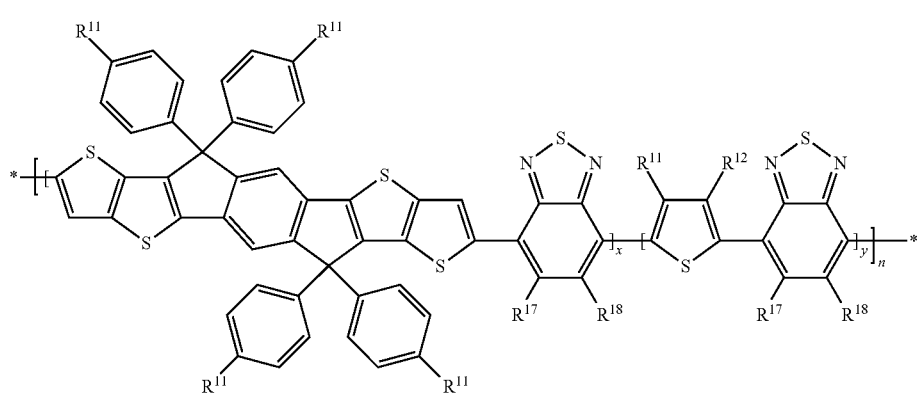
P38
P39
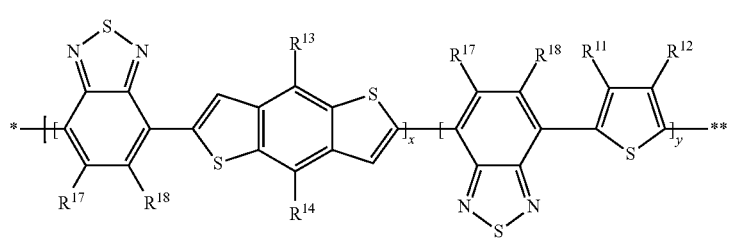

-continued
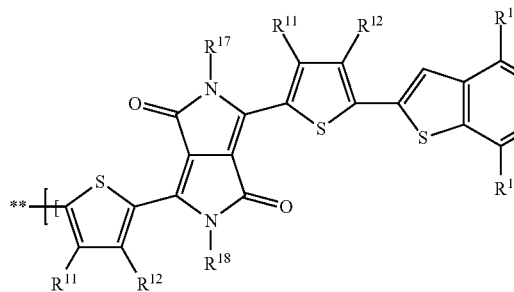
P40
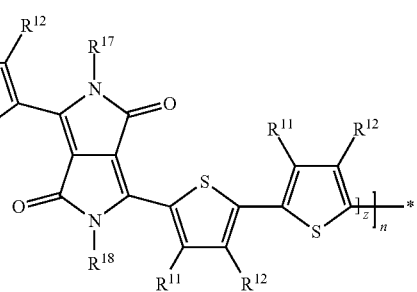
P41
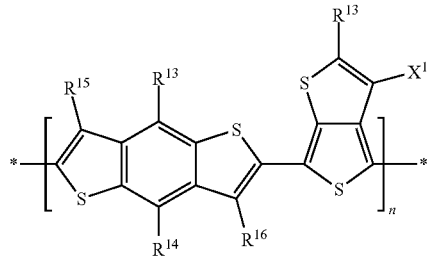
P42
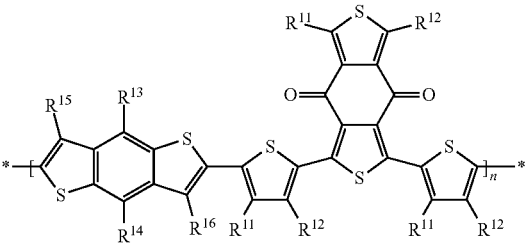
P43
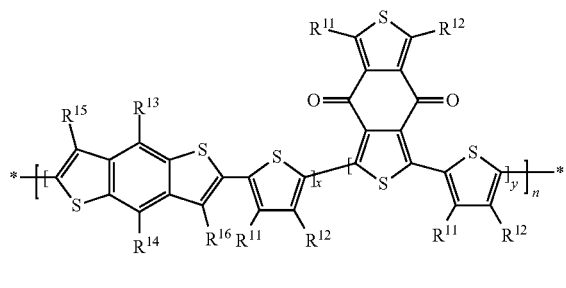
P44
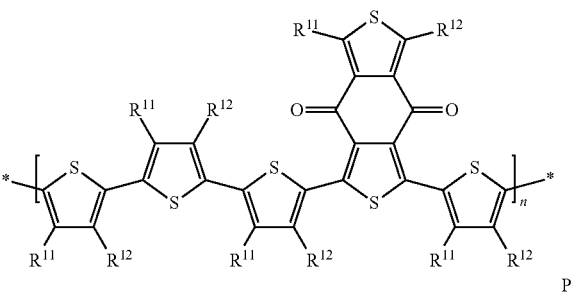
P45
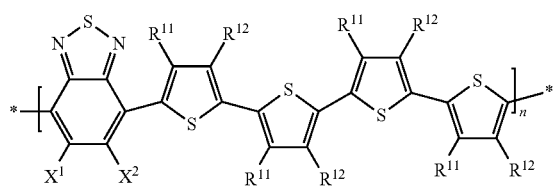
P46
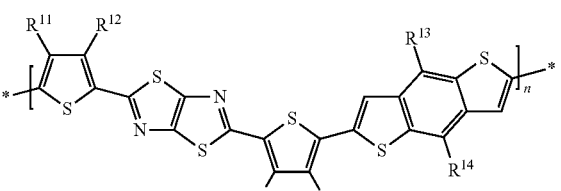
P47
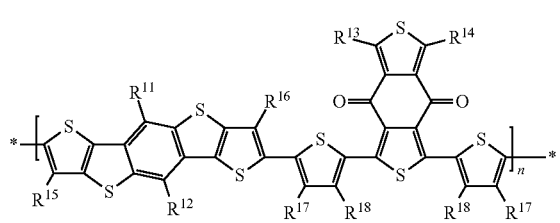
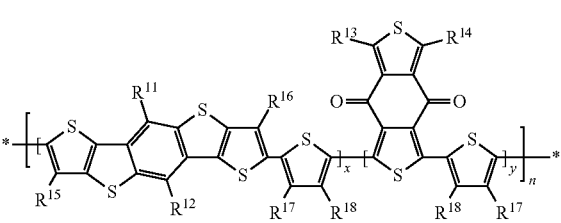
P48
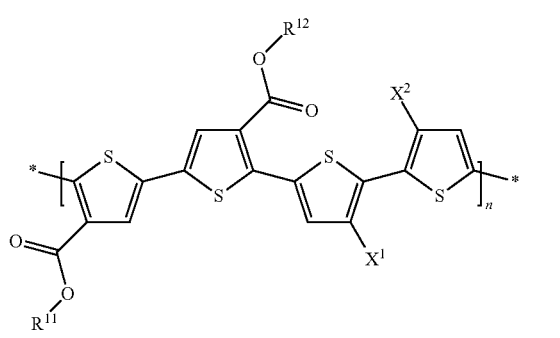

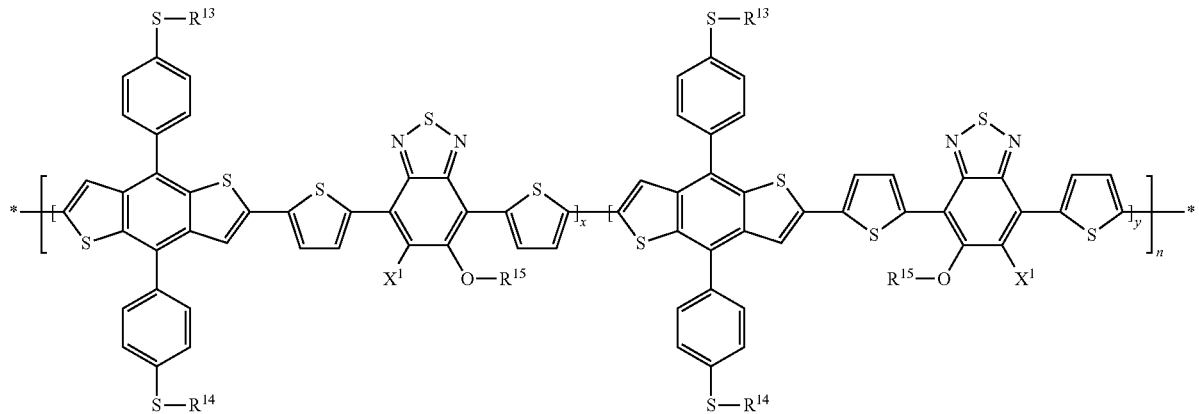

P49

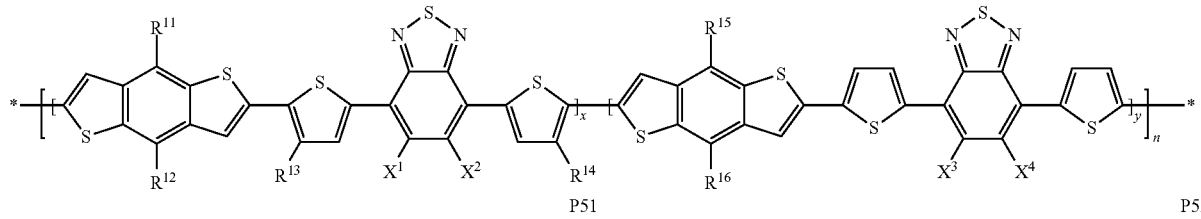

P50

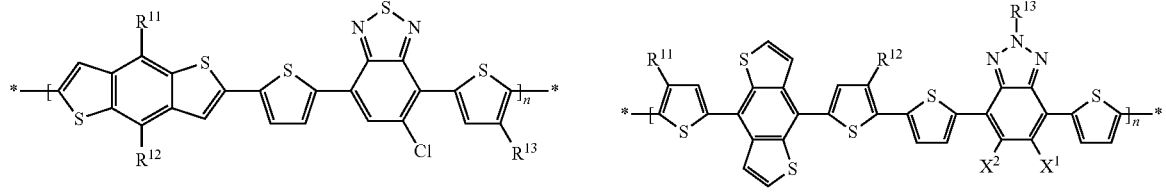

P51 P52 wherein R$^{11-17}$, x, y and n are as defined above, w and z have one of the meanings given for y, x+y+w+z=1, R$^{18}$ and R$^{19}$ have one of the meanings given for R$^1$, and X$^1$, X$^2$, X$^3$ and X$^4$ denote H, F or Cl.

In the formulae P1-P52 preferably one or more of X$^1$, X$^2$, X$^3$ and X$^4$ denote F, very preferably all of X$^1$, X$^2$, X$^3$ and X$^4$ denote F or X$^1$ and X$^2$ denote H and X$^3$ and X$^4$ denote F.

In the formulae P1-P52, preferably R$^{11}$ and R$^{12}$ are H. Further preferably R$^{11}$ and R$^{12}$, when being different from H, denote straight-chain or branched alkyl with 1 to 30, preferably 1 to 20, C atoms that is optionally fluorinated.

In the formulae P1-P52, preferably R$^{15}$ and R$^{16}$ are H, and R$^{13}$ and R$^{14}$ are different from H.

In the formulae P1-P52, preferably R$^{13}$, R$^{14}$, R$^{15}$ and R$^{16}$, when being different from H, are selected from the following groups:

the group consisting of straight-chain or branched alkyl, alkoxy or sulfanylalkyl with 1 to 30, preferably 1 to 20, C atoms that is optionally fluorinated, the group consisting of straight-chain or branched alkylcarbonyl or alkylcarbonyloxy with 2 to 30, preferably 2 to 20, C atoms, that is optionally fluorinated.

In the formulae P1-P52, preferably R$^{17}$ and R$^{18}$, when being different from H, are selected from the following groups:

the group consisting of straight-chain or branched alkyl, alkoxy or sulfanylalkyl with 1 to 30, preferably 1 to 20, C atoms that is optionally fluorinated, the group consisting of straight-chain or branched alkylcarbonyl or alkylcarbonyloxy with 2 to 30, preferably 2 to 20, C atoms, that is optionally fluorinated.

the group consisting of F and Cl.

Further preferred are conjugated polymers selected of formula PT $$R^{31}\text{-chain-}R^{32} \qquad \text{PT}$$

wherein "chain" denotes a polymer chain selected of formula Pi, Pii or P1-P44, and R$^{31}$ and R$^{32}$ have independently of each other one of the meanings of R$^{11}$ as defined above, or denote, independently of each other, H, F, Br, Cl, I, —CH$_2$Cl, —CHO, —CR'=CR''$_2$, —SiR'R''R''', —SiR'X'X'', —SiR'R''X', —SnR'R''R''', —BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of R$^0$ given in formula 1, and preferably denote alkyl with 1 to 12 C atoms, and two of R', R'' and R''' may also form a cyclosilyl, cyclostannyl, cycloborane or cycloboronate group with 2 to 20 C atoms together with the respective hetero atom to which they are attached.

Preferred endcap groups R$^{31}$ and R$^{32}$ are H, C$_{1-20}$ alkyl, or optionally substituted C$_{6-12}$ aryl or C$_{2-10}$ heteroaryl, very preferably H or phenyl.

The compounds of formula I and the conjugated polymers of formula P and PT can be synthesized according to or in analogy to methods that are known to the skilled person and are described in the literature. Other methods of preparation can be taken from the examples.

For example, the compounds of the present invention can be suitably prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al, *Angew. Chem. Int. Ed.*, 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, edcuts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as $Pd(Ph_3P)_4$. Another preferred phosphine ligand is tris(ortho-tolyl)phosphine, i.e. $Pd(o-ToI_3P)_4$. Preferred Pd(II) salts include palladium acetate, i.e. $Pd(OAc)_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl)phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula $-O-SO_2Z^1$ can be used wherein $Z^1$ is as described above. Particular examples of such leaving groups are tosylate, mesylate and triflate.

Especially suitable and preferred synthesis methods of the compounds of formula I and its subformulae are illustrated in the synthesis schemes shown hereinafter.

The synthesis of the polycyclic unit is exemplarily shown in Schemes 1-4.

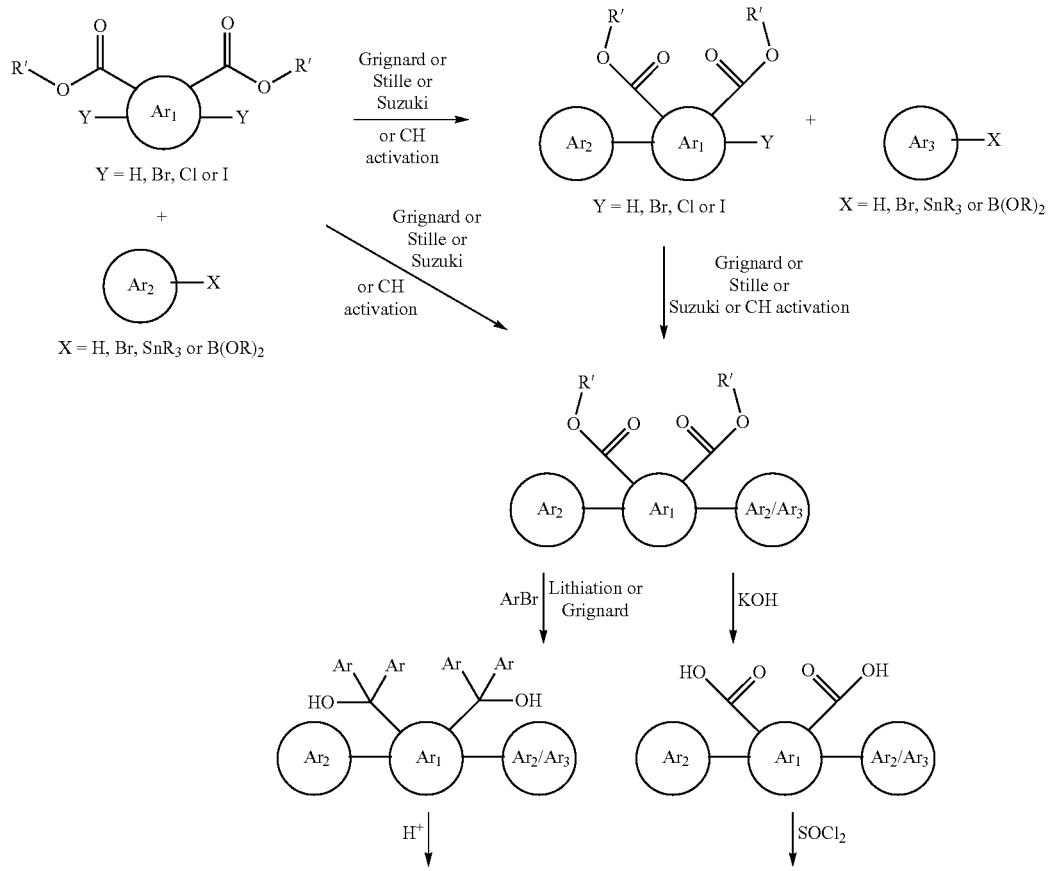

Scheme 1a

-continued
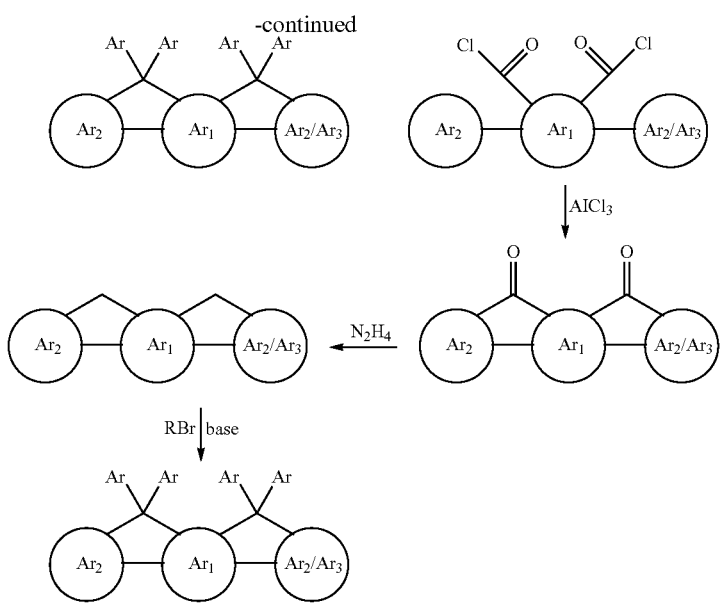
Scheme 1b
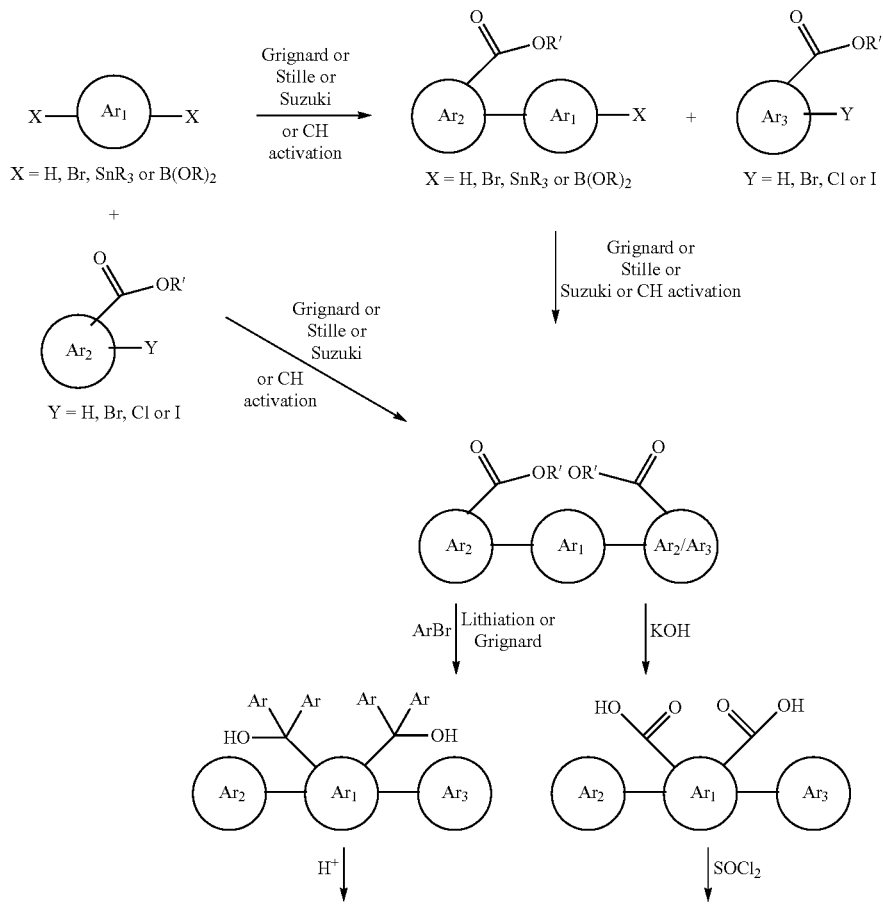

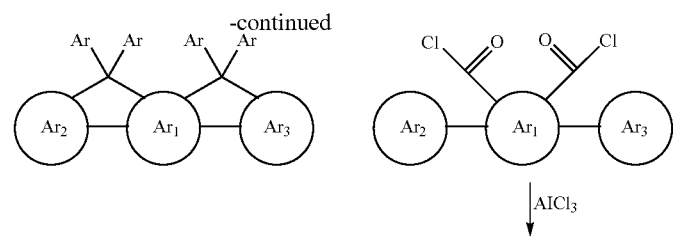
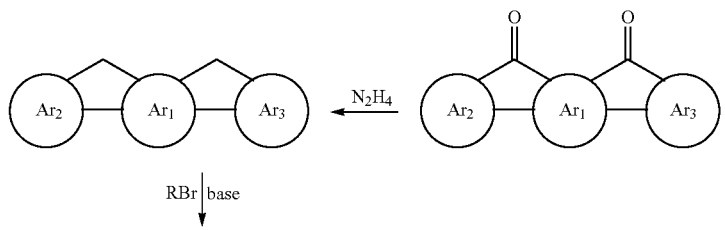
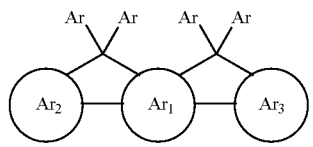
Scheme 2
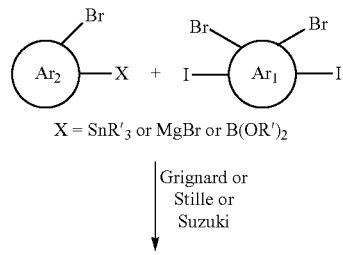
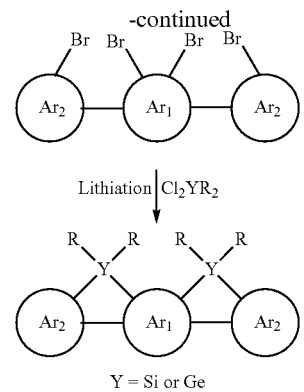
Y = Si or Ge
Scheme 3
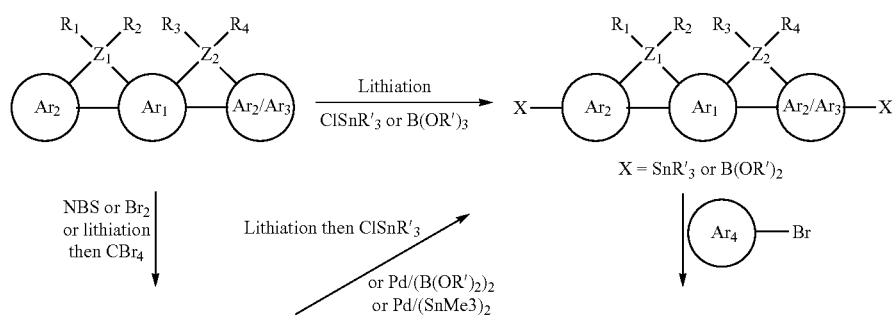

133 134
-continued
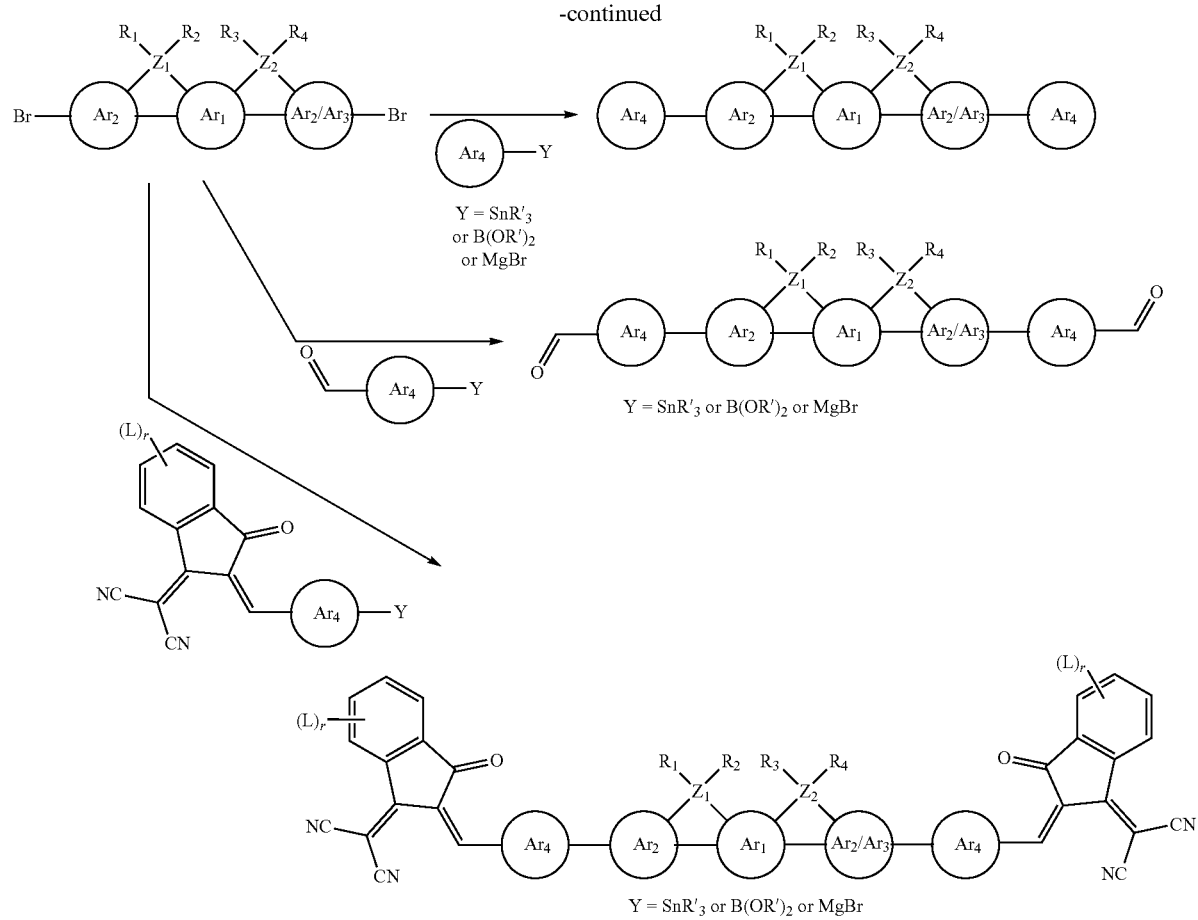
Scheme 4
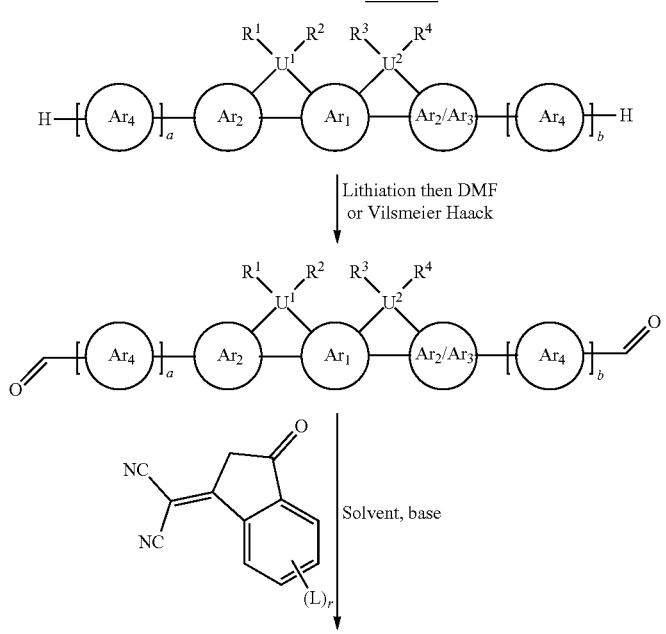

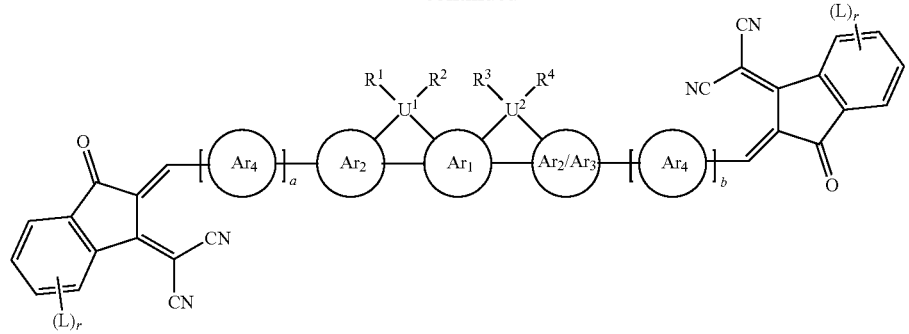

Novel methods of preparing compounds of formula I as described above and below are another aspect of the invention.

The compounds of formula I can also be used in compositions, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in OLED devices.

Thus, another aspect of the invention relates to a composition comprising one or more compounds of formula I and one or more small molecule compounds and/or polymers having one or more of a charge-transport, semiconducting, electrically conducting, photoconducting, hole blocking and electron blocking property.

These compositions blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds of formula I or compositions as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and/or mixtures thereof.

The concentration of the compounds or polymers in the solution is preferably 0.0001 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The compounds of formula I can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound of formula I by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent (s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds according to the present invention are useful as charge transport, semiconducting, electrically conducting, photoconducting or light emitting materials in optical, electrooptical, electronic, electroluminescent or photoluminescent components or devices. In these devices, the compounds of the present invention are typically applied as thin layers or films.

Thus, the present invention also provides the use of the semiconducting compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising compound or composition or organic semiconducting layer according to the present invention. Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular OPD and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

For use in OPV or OPD devices the compounds according to the present invention are preferably used in a composition that comprises or contains, more preferably consists of, one or more p-type (electron donor) semiconductors and one or more n-type (electron acceptor) semiconductors.

The n-type semiconductor is for example constituted by a compound of formula I.

The p-type semiconductor is preferably a conjugated polymer as defined above.

The composition can also comprise a compound of formula I as n-type semiconductor, a p-type semiconductor like a conjugated polymer, and a second n-type semiconductor, which is preferably a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

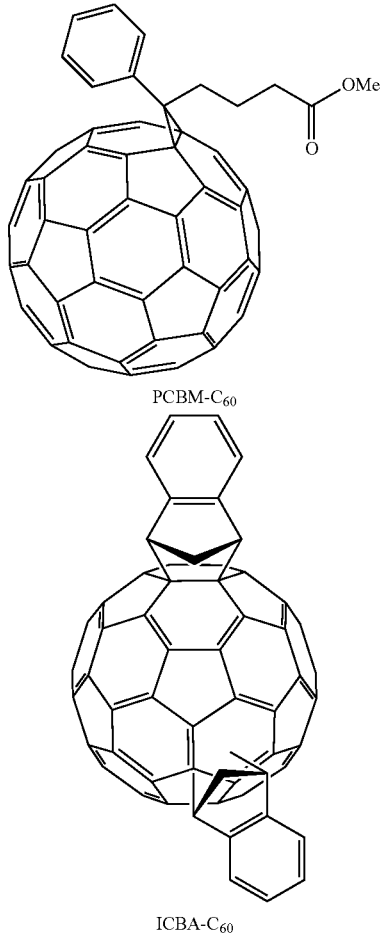

PCBM-C$_{60}$

ICBA-C$_{60}$

Preferably the compound according to the present invention is blended with another n-type semiconductor such as a fullerene or substituted fullerene of formula Full-I to form the active layer in an OPV or OPD device wherein,

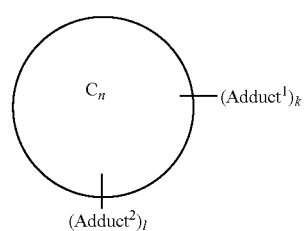

Full-I

C$_n$ denotes a fullerene composed of n carbon atoms, optionally with one or more atoms trapped inside, Adduct$^1$ is a primary adduct appended to the fullerene C$_n$ with any connectivity, Adduct$^2$ is a secondary adduct, or a combination of secondary adducts, appended to the fullerene C$_n$ with any connectivity, k is an integer ≥1, and l is 0, an integer ≥1, or a non-integer >0.

In the formula Full-I and its subformulae, k preferably denotes 1, 2, 3 or, 4, very preferably 1 or 2.

The fullerene C$_n$ in formula Full-I and its subformulae may be composed of any number n of carbon atoms Preferably, in the compounds of formula Full-I and its subformulae the number of carbon atoms n of which the fullerene C$_n$ is composed is 60, 70, 76, 78, 82, 84, 90, 94 or 96, very preferably 60 or 70.

The fullerene C$_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, (C$_{60-Ih}$)[5,6]fullerene, (C$_{70-D5h}$)[5,6]fullerene, (C$_{76-D2*}$)[5,6]fullerene, (C$_{84-D2*}$)[5,6]fullerene, (C$_{84-D2d}$)[5,6]fullerene, or a mixture of two or more of the aforementioned carbon based fullerenes.

The endohedral fullerenes are preferably metallofullerenes. Suitable and preferred metallofullerenes include, without limitation, La@C$_{60}$, La@C$_{82}$, Y@C$_{82}$, Sc$_3$N@C$_{80}$, Y$_3$N@C$_{80}$, Sc$_3$C$_2$@C$_{80}$ or a mixture of two or more of the aforementioned metallofullerenes.

Preferably the fullerene C$_n$ is substituted at a [6,6] and/or [5,6] bond, preferably substituted on at least one [6,6] bond.

Primary and secondary adduct, named "Adduct" in formula Full-I and its subformulae, is preferably selected from the following formulae

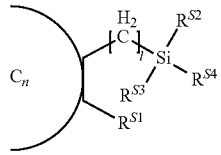

S-1

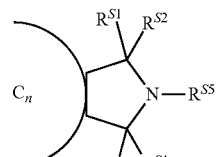

S-2

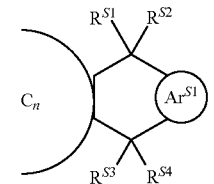

S-3

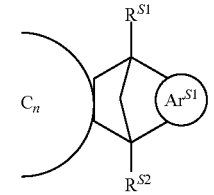

S-4

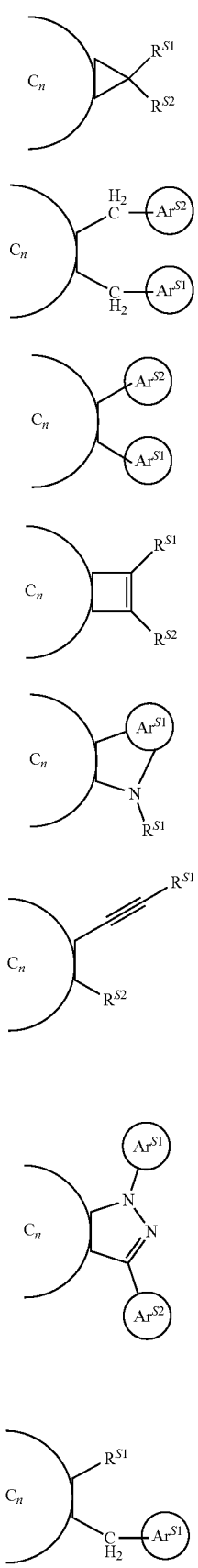
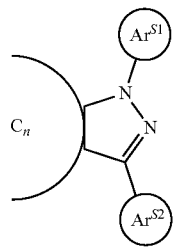

wherein

Ar$^{S1}$, Ar$^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of L as defined above and below, R$^{S1}$, R$^{S2}$, R$^{S3}$, R$^{S4}$ and R$^{S5}$ independently of each other denote H, CN or have one of the meanings of L as defined above and below.

Preferred compounds of formula Full-I are selected from the following subformulae:

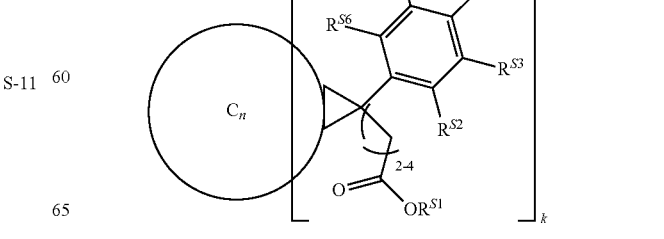

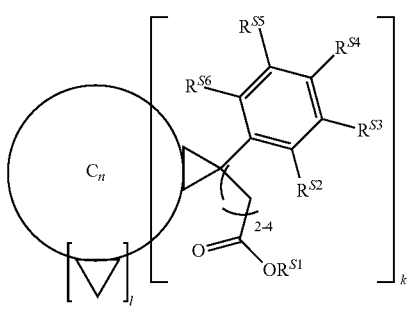
Full-Ib

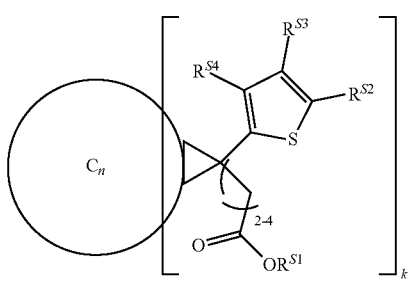
Full-Ic

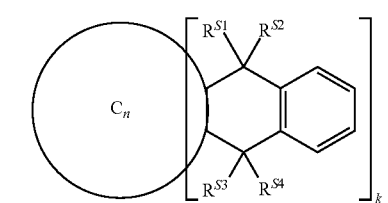
Full-Id

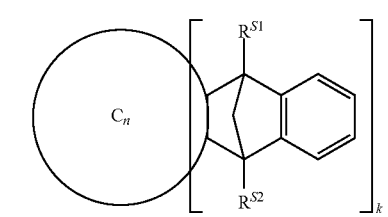
Full-Ie

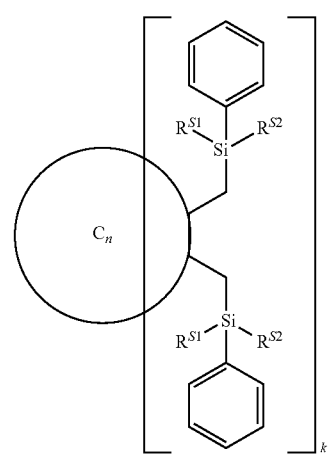
Full-If

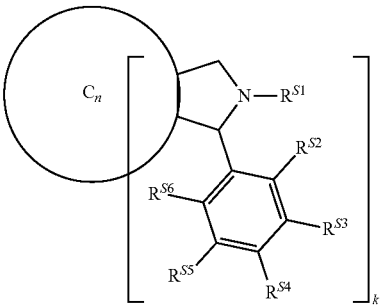
Full-Ig

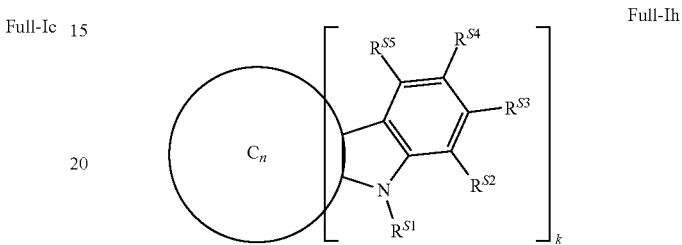
Full-Ih wherein $R^{S1}$, $R^{S2}$, $R^{S3}$, $R^{S4}$ $R^{S5}$ and $R^{S6}$ independently of each other denote H or have one of the meanings of L as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-1h), or bis-oQDM-C60.

The OPV or OPD device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrene-sulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly[(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a composition according to the present invention comprising a compound of formula I and a conjugated polymer, the ratio polymer:compound of formula I is preferably from 5:1 to 1:5 by weight, more preferably from 1:1 to 1:3 by weight, most preferably 1:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

To produce thin layers in BHJ OPV devices the compounds, compositions and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the mixture of a compound of formula I and a polymer must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode,
  an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF or PFN,
  a low work function electrode, preferably comprising a metal like for example aluminium, serving as cathode,
  wherein at least one of the electrodes, preferably the anode, is transparent to visible light, and
  wherein the n-type semiconductor is a compound of formula I.

A second preferred OPV device according to the invention is an inverted OPV device and comprises the following layers (in the sequence from bottom to top):
  optionally a substrate,
  a high work function metal or metal oxide electrode, comprising for example ITO, serving as cathode,
  a layer having hole blocking properties, preferably comprising a metal oxide like $TiO_x$ or $Zn_x$, or a poly(ethyleneimine),
  a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
  an optional conducting polymer layer or hole transport layer, preferably comprising an organic polymer or polymer blend, for example of PEDOT:PSS, nafion or a substituted triaryl amine derivative like for example TBD or NBD,
  an electrode comprising a high work function metal like for example silver, serving as anode,
  wherein at least one of the electrodes, preferably the cathode, is transparent to visible light, and
  wherein the n-type semiconductor is a compound of formula I.

In the OPV devices of the present invention the p-type and n-type semiconductor materials are preferably selected from the materials, like the compound/polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a perovskite-based solar cells, and to a DSSC or perovskite-based solar cells comprising a compound composition or polymer blend according to the present invention.

DSSCs and perovskite-based DSSCs can be manufactured as described in the literature, for example in Chem. Rev. 2010, 110, 6595-6663, Angew. Chem. Int. Ed. 2014, 53, 2-15 or in WO2013171520A1

The compounds and compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound and compositions according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
  wherein the semiconductor layer preferably comprises a compound of formula I.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass).

Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals*, 2000, 111-112, 31-34, Alcala, *J. Appl. Phys.*, 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science*, 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4{}_2^-$, $NO_3^-$, $ClO_4^-$, $BF_4^-$, $PF_6^-$, $AsF_6^-$, $SbF_6^-$, $FeCl_4^-$, $Fe(CN)_6{}^{3-}$, and anions of various sulfonic acids, such as $aryl-SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2{}^+)$ $(SbF_6^-)$, $(NO_2{}^+)$ $(SbCl_6^-)$, $(NO_2{}^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

EXAMPLES

Molecular structures were optimized at B3LYP/6-31G* level using Firefly QC package (see Alex A. Granovsky, Firefly version 8, www http://classic.chem.msu.su/gran/firefly/index.html), which is partially based on the GAMESS (US) source code (see M. W. Schmidt, K. K. Baldridge, J. A. Boatz, S. T. Elbert, M. S. Gordon, J. H. Jensen, S. Koseki, N. Matsunaga, K. A. Nguyen, S. Su, T. L. Windus, M. Dupuis, J. A. Montgomery J. Comput. Chem. 14, 1347-1363 (1993)).

$E_{HOMO}$ and $E_{LUMO}$ are defined as the eigenvalues of, respectively, the highest occupied and lowest unoccupied Kohn-Sham molecular orbitals, and are used as approximations of, respectively, ionisation potential (IP) and electron affinity (EA). $E_g$ is defined as $|E_{LUMO}-E_{HOMO}|$ and is the transport band gap of the material. $S^0$-$S^1$ is the vertical excitation energy from the ground state $S^0$ to the first singlet excited state $S^1$, and is used as the measure of the optical band gap $E_g$(opt).

An approximate relation between $E_{HOMO}$, $E_{LUMO}$ and $E_g$ of donor and acceptor materials in a bulk-heterojunction is known as the Scharber model [M. C. Scharber, D. Mühlbacher, M. Koppe, P. Denk, C. Waldauf, A. J. Heeger, C. J. Brabec, Adv. Mater. 2006, 18, 789-794]. It is widely accepted that when the donor material of the donor-acceptor blend absorbs light and forms an excited state, the excited electron must hop onto the neighbouring acceptor site in order for the free carriers to be formed. The driving force of this process is the energetic difference between the excited state of the donor material and the electron affinity (approximated by $E_{LUMO}$) of the acceptor material and has been empirically found to be at least ca. 0.35 eV for charge generation to be efficient [D. Veldman, S. C. J. Meskers, R. A. J. Janssen, Adv. Funct. Mater. 2009, 19, 1939-1948; M. C. Scharber, N. S. Sariciftci, Progr. Polym. Sci. 38 (2013)

1929-1940]. Therefore, tuning of acceptor's $E_{LUMO}$ is of paramount importance, lowering its value will increase the driving force for charge generation and may allow using lower-bandgap donor material, whilst increasing $E_{LUMO}$ may hinder charge generation. For the present OSC materials, owing to their small optical band gap, another mechanism is also possible: light absorption by the acceptor followed by hole injection to the donor material, driven by the energy difference between $E_{HOMO}$ of donor and acceptor, respectively [W. Zhao, D. Qian, S. Zhang, S. Li, O. Inganäs, F. Gao, J. Hou, Adv. Mater. 2016, DOI: 10.1002/adma.201600281]. This mechanism is responsible for non-negligible external quantum efficiency beyond the absorption edge of the donor material, and retaining of this advantage of the acceptor material requires careful tuning of HOMO energy.

Comparative Examples 1-2

Compounds C1 and C2, wherein the polycyclic central group has a "trans"-configuration, are calculated as a reference.

| No. | Structure | $E_{HOMO}$/eV | $E_{LUMO}$/eV | $E_g$/eV | $S^0$-$S^1$/eV |
|---|---|---|---|---|---|
| C1 | 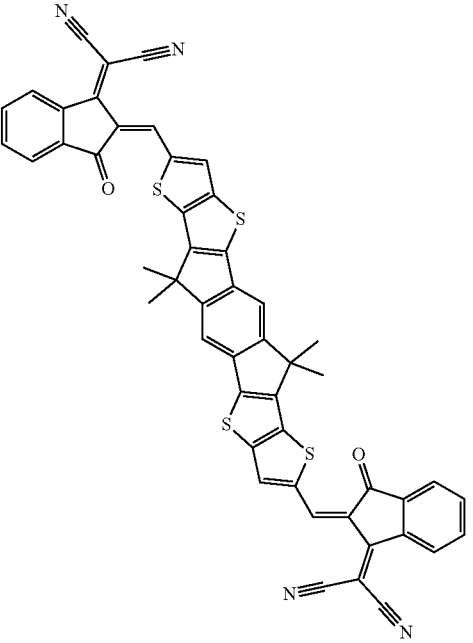 [SMILES: CC1(C)c2cc3c(cc2-c2sc4cc(/C=C5\C(=O)c6ccccc6C5=C(C#N)C#N)sc4c21)C(C)(C)c1c-3sc2cc(/C=C3\C(=O)c4ccccc4C3=C(C#N)C#N)sc12] | −5.54 | −3.41 | 2.13 | 1.86 |
| C2 | 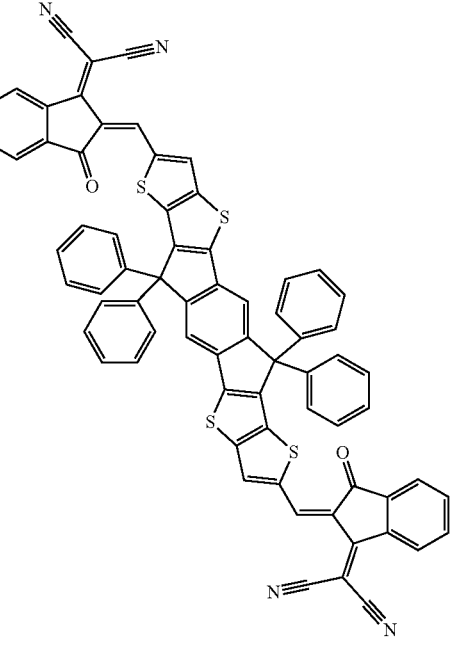 | −5.52 | −3.37 | 2.15 | 1.87 |

Examples 1-16
The computed values of $E_{HOMO}$, $E_{LUMO}$, $E_g$ and $S^0$-$S^1$ of compound C1 (whilst being different from experimentally determined IP, EA and $E_g$) are compared with the computed values of compounds 1-16 of formula I, wherein the polycyclic central group has a "cis"-configuration.
| No. | Structure | $E_{HOMO}$/eV | $E_{LUMO}$/eV | $E_g$/eV | $S^0$-$S^1$/eV |
|---|---|---|---|---|---|
| 1 | 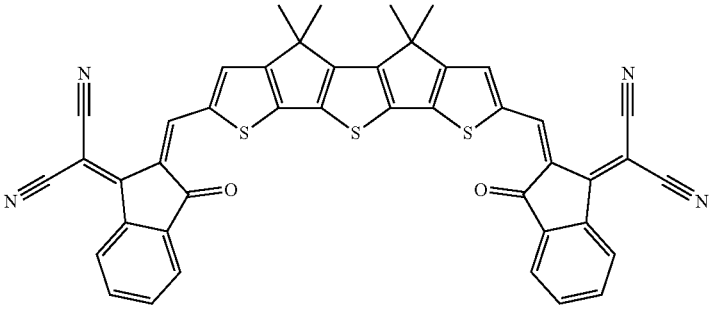 [SMILES: CC1(C)c2cc(/C=C3\C(=O)c4ccccc4C3=C(C#N)C#N)sc2-c2sc3c(c21)C(C)(C)c1cc(/C=C2\C(=O)c4ccccc4C2=C(C#N)C#N)sc1-3] | −5.59 | −3.59 | 1.99 | 1.98 |
| 2 | 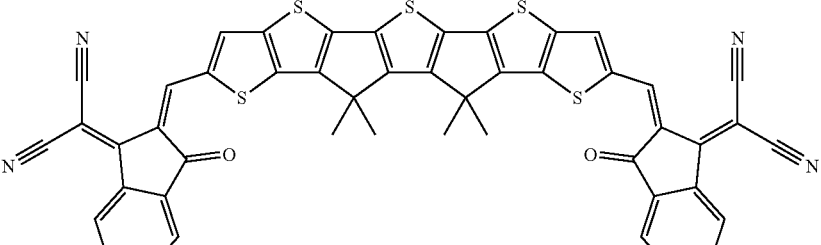 | −5.38 | −3.48 | 1.90 | 1.83 |
| 3 | 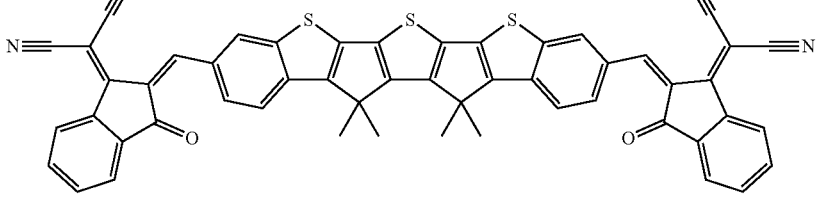 | −5.44 | −3.36 | 2.07 | 1.88 |
| 4 | 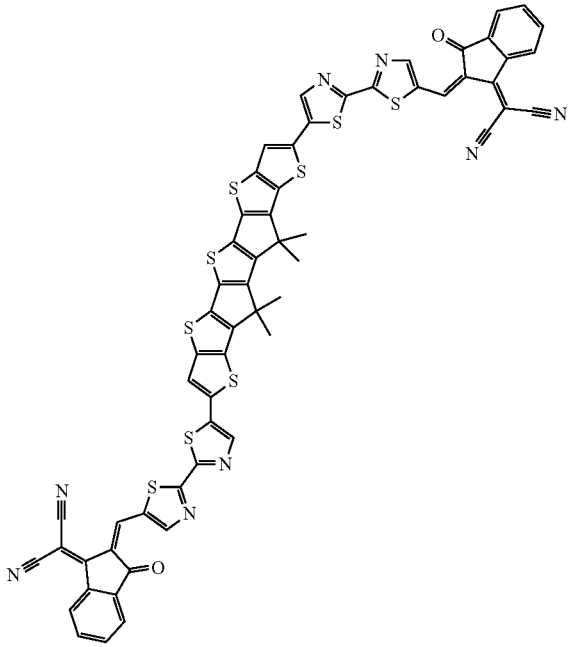 [SMILES: CC1(C)c2c(sc3c2C(C)(C)c2c-3sc3cc(-c4cnc(-c5ncc(/C=C6\C(=O)c7ccccc7C6=C(C#N)C#N)s5)s4)sc23)-c2sc3cc(-c4cnc(-c5ncc(/C=C6\C(=O)c7ccccc7C6=C(C#N)C#N)s5)s4)sc3c21] | −5.08 | −3.50 | 1.58 | 1.44 |

-continued

| No. | Structure | $E_{HOMO}$/eV | $E_{LUMO}$/eV | $E_g$/eV | $S^0$-$S^1$/eV |
|-----|-----------|---------------|---------------|----------|----------------|
| 5 | 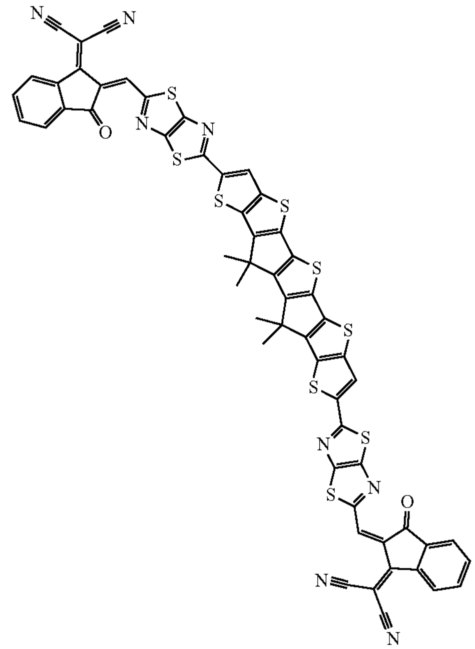 [SMILES: CC1(C)c2c(sc3c2C(C)(C)c2c-3sc3cc(-c4nc5sc(/C=C6\C(=O)c7ccccc7C6=C(C#N)C#N)nc5s4)sc23)-c2sc3cc(-c4nc5sc(/C=C6\C(=O)c7ccccc7C6=C(C#N)C#N)nc5s4)sc3c21] | −5.26 | −3.58 | 1.67 | 1.53 |
| 6 | 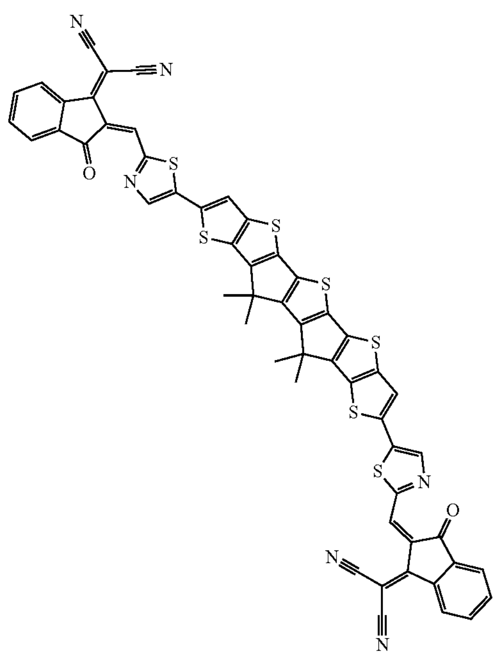 [SMILES: CC1(C)c2c(sc3c2C(C)(C)c2c-3sc3cc(-c4cnc(/C=C5\C(=O)c6ccccc6C5=C(C#N)C#N)s4)sc23)-c2sc3cc(-c4cnc(/C=C5\C(=O)c6ccccc6C5=C(C#N)C#N)s4)sc3c21] | −5.18 | −3.51 | 1.67 | 1.38 |

-continued

| No. | Structure | $E_{HOMO}$/eV | $E_{LUMO}$/eV | $E_g$/eV | $S^0$-$S^1$/eV |
|---|---|---|---|---|---|
| 7 | 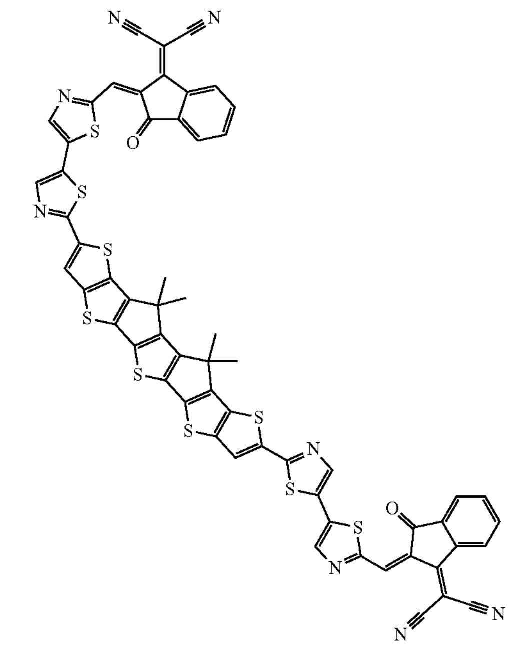 [SMILES: CC1(C)c2c(sc3c2C(C)(C)c2c-3sc3cc(-c4ncc(-c5cnc(/C=C6\C(=O)c7ccccc7C6=C(C#N)C#N)s5)s4)sc23)-c2sc3cc(-c4ncc(-c5cnc(/C=C6\C(=O)c7ccccc7C6=C(C#N)C#N)s5)s4)sc3c21] | −5.12 | −3.52 | 1.60 | 0.53 |
| 8 | 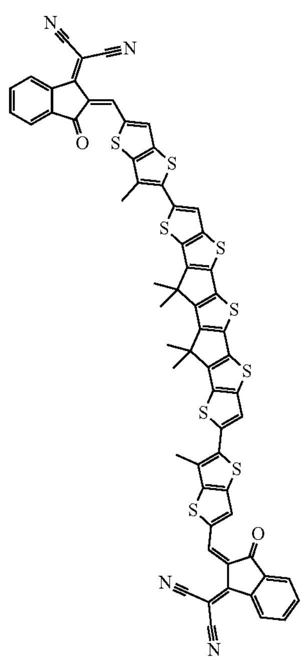 [SMILES: Cc1c(-c2cc3sc4c(c3s2)C(C)(C)c2c-4sc3c2C(C)(C)c2c-3sc3cc(-c4sc5cc(/C=C6\C(=O)c7ccccc7C6=C(C#N)C#N)sc5c4C)sc23)sc2cc(/C=C3\C(=O)c4ccccc4C3=C(C#N)C#N)sc12] | −5.01 | −3.32 | 1.69 | 1.54 |

-continued

| No. | Structure | $E_{HOMO}$/ eV | $E_{LUMO}$/ eV | $E_g$/eV | $S^0$-$S^1$/ eV |
|---|---|---|---|---|---|
| 9 | 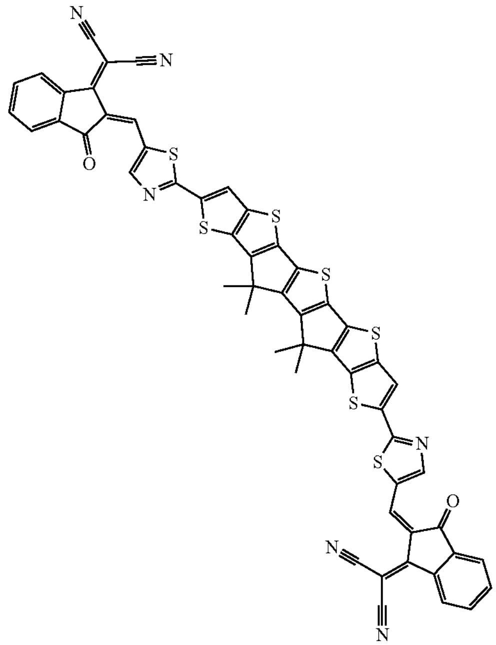 [SMILES: CC1(C)c2c(sc3c2C(C)(C)c2c-3sc3cc(-c4ncc(/C=C5\C(=O)c6ccccc6C5=C(C#N)C#N)s4)sc23)-c2sc3cc(-c4ncc(/C=C5\C(=O)c6ccccc6C5=C(C#N)C#N)s4)sc3c21] | −5.23 | −3.48 | 1.76 | 1.59 |
| 10 | 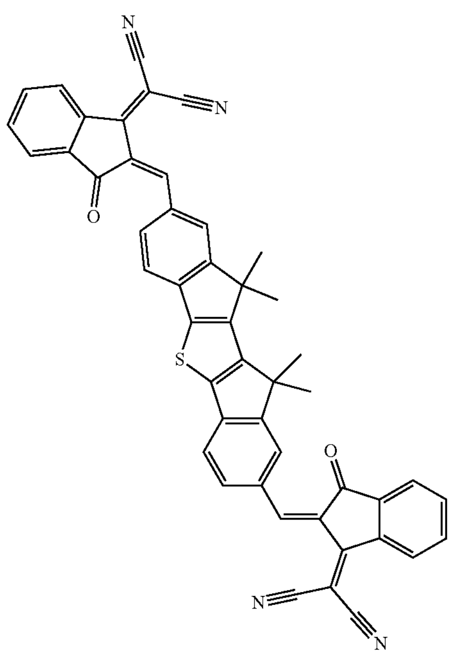 [SMILES: CC1(C)c2cc(/C=C3\C(=O)c4ccccc4C3=C(C#N)C#N)ccc2-c2sc3c(c21)C(C)(C)c1cc(/C=C2\C(=O)c4ccccc4C2=C(C#N)C#N)ccc1-3] | −5.72 | −3.41 | 2.31 | 2.16 |

-continued
| No. | Structure | $E_{HOMO}$/eV | $E_{LUMO}$/eV | $E_g$/eV | $S^0$-$S^1$/eV |
|---|---|---|---|---|---|
| 11 | 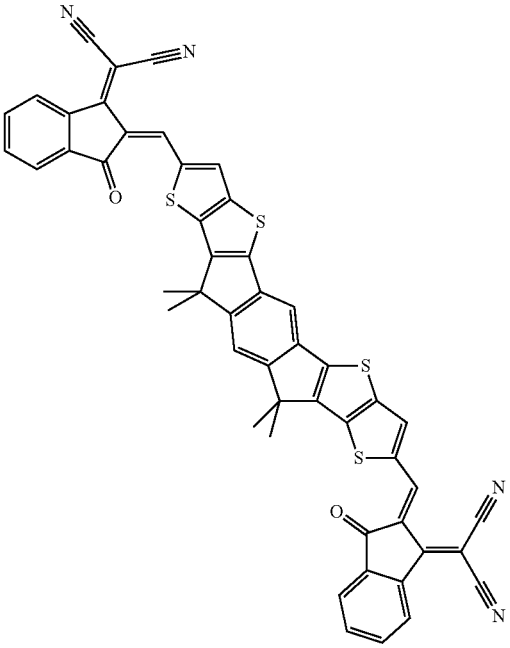 [SMILES: CC1(C)c2cc3c(cc2-c2sc4cc(/C=C5\C(=O)c6ccccc6C5=C(C#N)C#N)sc4c21)-c1sc2cc(/C=C4\C(=O)c5ccccc5C4=C(C#N)C#N)sc2c1C3(C)C] | −5.68 | −3.29 | 2.39 | 2.12 |
| 12 | 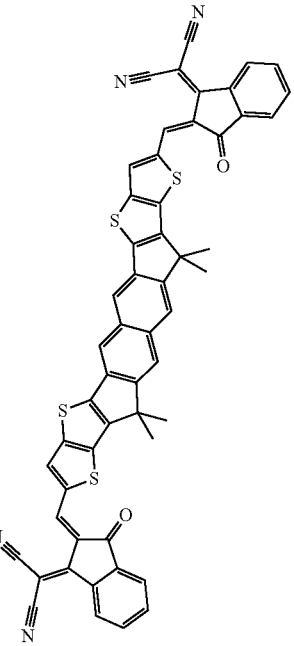 | −5.72 | −3.30 | 2.42 | 2.15 |
| 13 | 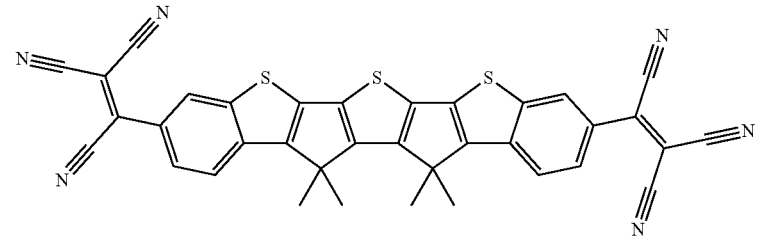 [SMILES: CC1(C)c2c(sc3c2C(C)(C)c2c-3sc3cc(C(C#N)=C(C#N)C#N)ccc23)-c2sc3cc(C(C#N)=C(C#N)C#N)ccc3c21] | −5.93 | −3.88 | 2.05 | 1.92 |

-continued

| No. | Structure | $E_{HOMO}$/eV | $E_{LUMO}$/eV | $E_g$/eV | $S^0$-$S^1$/eV |
|---|---|---|---|---|---|
| 14 | 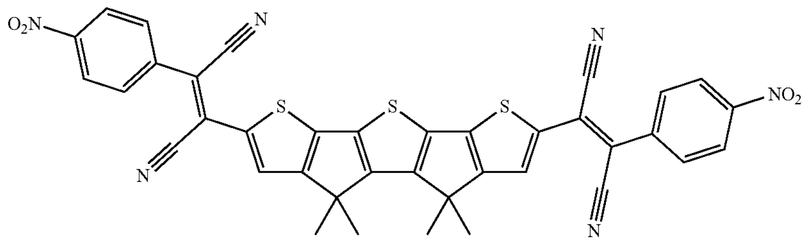 [SMILES: CC1(C)c2cc(/C(C#N)=C(\C#N)c3ccc([N+](=O)[O-])cc3)sc2-c2sc3c(c21)C(C)(C)c1cc(/C(C#N)=C(\C#N)c2ccc([N+](=O)[O-])cc2)sc1-3] | −5.76 | −3.74 | 2.02 | 1.95 |
| 15 | 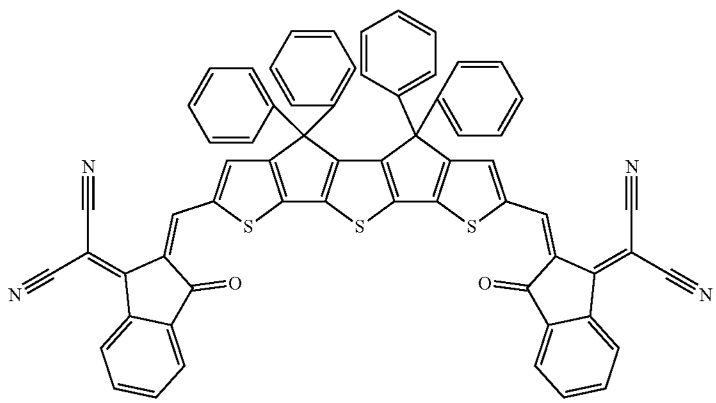 [SMILES: N#CC(C#N)=C1/C(=C/c2cc3c(s2)-c2sc4c(c2C3(c2ccccc2)c2ccccc2)C(c2ccccc2)(c2ccccc2)c2cc(/C=C3\C(=O)c5ccccc5C3=C(C#N)C#N)sc2-4)C(=O)c2ccccc21] | −5.48 | −3.51 | 1.87 | 1.96 |
| 16 | 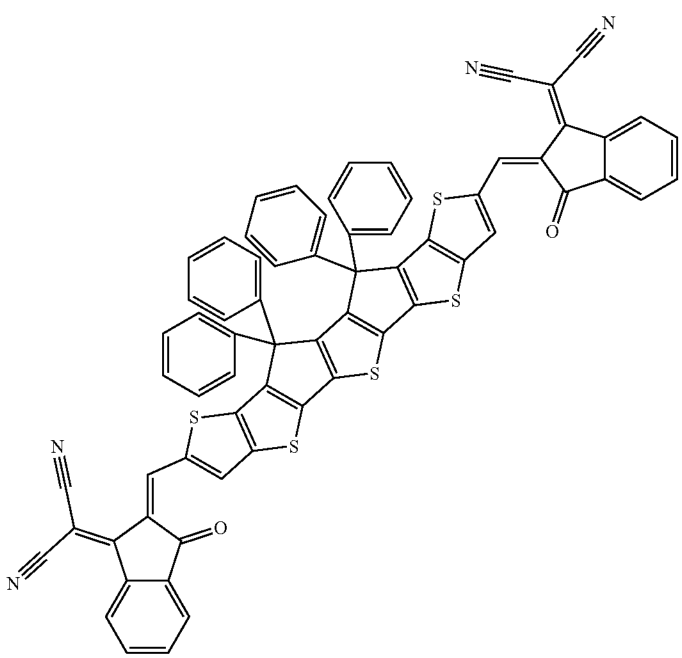 [SMILES: N#CC(C#N)=C1/C(=C/c2cc3sc4c(c3s2)C(c2ccccc2)(c2ccccc2)c2c-4sc3c2C(c2ccccc2)(c2ccccc2)c2c-3sc3cc(/C=C4\C(=O)c5ccccc5C4=C(C#N)C#N)sc23)C(=O)c2ccccc21] | −5.32 | −3.43 | 1.89 | 1.76 |

The $E_{LUMO}$ of compounds 1-16 are found to be close or slightly lower to that of compounds C1 and C2, indicating a similar or slightly stronger electron affinity. Calculated band gaps of compounds 1-16 are similar or slightly smaller than that of C1.

Example 17

Dimethyl-6,6'-(thiophene-2,5-diyl)bis(3-bromobenzoate)

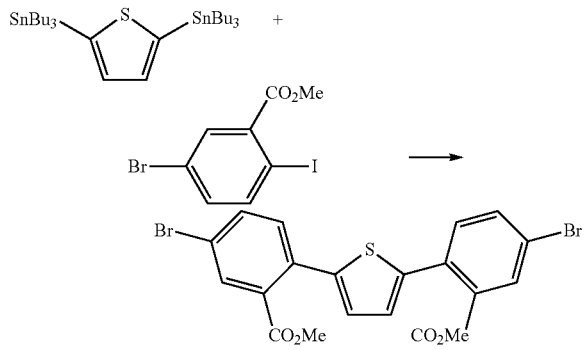

A solution of 2,5-bis(tributylstannyl)thiophene (15 g, 22.7 mmol), methyl 5-bromo-2-iodobenzoate (17.8 g, 52.1 mmol) and anhydrous toluene (350 cm³) was degassed by bubbling through a stream of nitrogen for 30 minutes. Tri-o-tolyl phosphine (0.17 g, 0.57 mmol) and bis(triphenylphosphine)palladium (II) dichloride (0.21 g, 0.29 mmol) were added and the degassing continued for 10 minutes. The reaction was stirred at 80° C. under nitrogen for 20 hours. After cooling to 23° C., the reaction mixture was poured into distilled water (250 cm³) and the organic layer decanted, washed with brine (2×100 cm³), dried over magnesium sulphate and filtered. Removal of the solvent in vacuo followed by purification by silica gel chromatography (dichloromethane:heptanes; 7:3) gave dimethyl-6,6'-(thiophene-2,5-diyl)bis(3-bromobenzoate) as a yellow solid (3.6 g, 31%). ¹H NMR (CDCl₃, 400 MHz, ppm, Hz): 7.89 (2H, d, J 2.3), 7.64 (2H, dd, J 2, 8.3), 7.40 (2H, d, J 8.3), 6.99 (2H, s), 3.80 (6H, s).

Thiophene-2,5-diylbis(3-bromo-6,1-phenylene))bis(bis(4-hexadecylphenyl)methanol

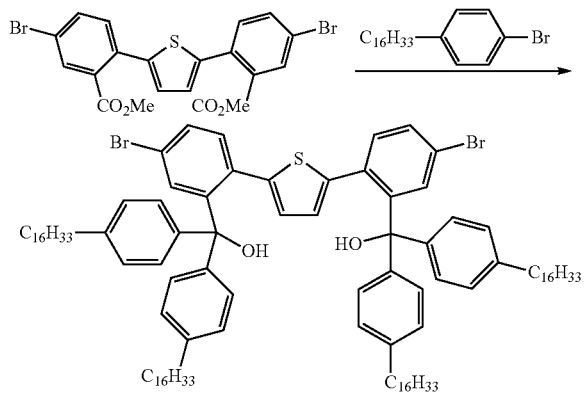

To a mixture of 1-bromo-4-hexadecylbenzene (13.4 g, 35.1 mmol) anhydrous tetrahydrofuran (170 cm³) at −65° C. was added dropwise n-butyllithium (15 cm³, 37.2 mmol, 2.5 M in hexanes) over 30 minutes. The resulting suspension was left to stir at −65° C. for 4 hours before dimethyl-6,6'-(thiophene-2,5-diyl)bis(3-bromobenzoate) (3.60 g, 7 mmol) was added in one portion. The reaction mixture was left to stir and to warm up slowly over 17 hours to 23° C. Distilled water (100 cm³) and tert-butyl methyl ether (100 cm³) were added and the mixture stirred for 30 minutes. The organic layer was decanted and the aqueous layer extracted by tert-butyl methyl ether (3×50 mL). All organics were combined, dried over sulphate magnesium, filtered and the solvent removed in vacuo. The solid was purified by silica gel chromatography (heptane:ethyl acetate; 95:5) to give thiophene-2,5-diylbis(3-bromo-6,1-phenylene))bis(bis(4-hexadecylphenyl)methanol) as a yellow oil which solidified slowly upon standing (7.0 g, 64%). ¹H NMR (CDCl₃, 400 MHz ppm, Hz): 7.39 (2H, dd, J 1.8, 7.8), 7.11 (8H, d, J 8.3), 7.04 (10H, m), 6.94 (2H, d, J 2.3), 5.90 (2H, s), 3.25 (2H, s), 2.61 (8H, m), 1.60 (8H, m), 1.24-1.29 (104H, m), 0.89 (12H, t, J 6.6).

2,8-Dibromo-10,10,11,11-tetrakis(4-hexadecylphenyl)-10,11-dihydrodiindeno[1,2-b:2',1'-d]thiophene

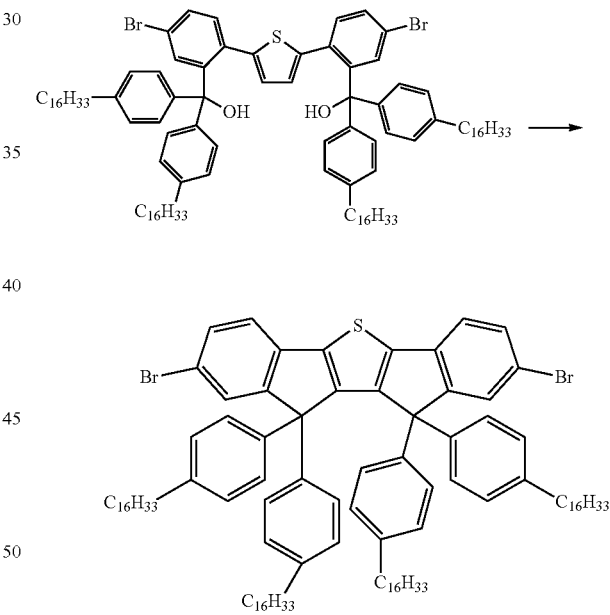

To a mixture of thiophene-2,5-diylbis(3-bromo-6,1-phenylene))bis(bis(4-hexadecylphenyl)methanol (7.4 g, 4.5 mmol) and dichloromethane (230 cm³) was added p-toluene sulfonic acid (1.7 mg, 9 mmol) and the reaction mixture heated at reflux for 6 hours. After cooling to 23° C., the suspension was filtered off. Purification by recrystallisation (2-butanone) gave 2,8-dibromo-10,10,11,11-tetrakis(4-hexadecylphenyl)-10,11-dihydrodiindeno[1,2-b:2',1'-d]thiophene as a beige solid (3.6 g, 50%). ¹H NMR (CDCl₃, 400 MHz, ppm, Hz): 7.31 (2H, dd, J 1.5, 6.6), 7.24 (2H, d, J 8.1), 7.17 (2H, d, J 1.5), 6.72 (8H, d, J 8.1), 6.61 (8H, d, J 8.1), 2.39-2.45 (8H, m), 1.52 (8H, m), 1.23-1.38 (104H, m), 0.89 (12H, t, J 6.6).

2,8-Di-(5-[1,3]dioxolan-2-yl-thiophen-2-yl)-10,10,11,11-tetrakis(4-hexadecylphenyl)-10,11-dihydrodiindeno[1,2-b:2',1'-d]thiophene

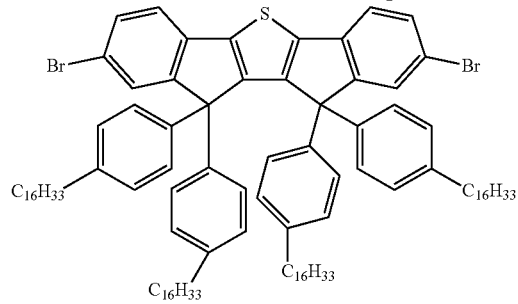

+

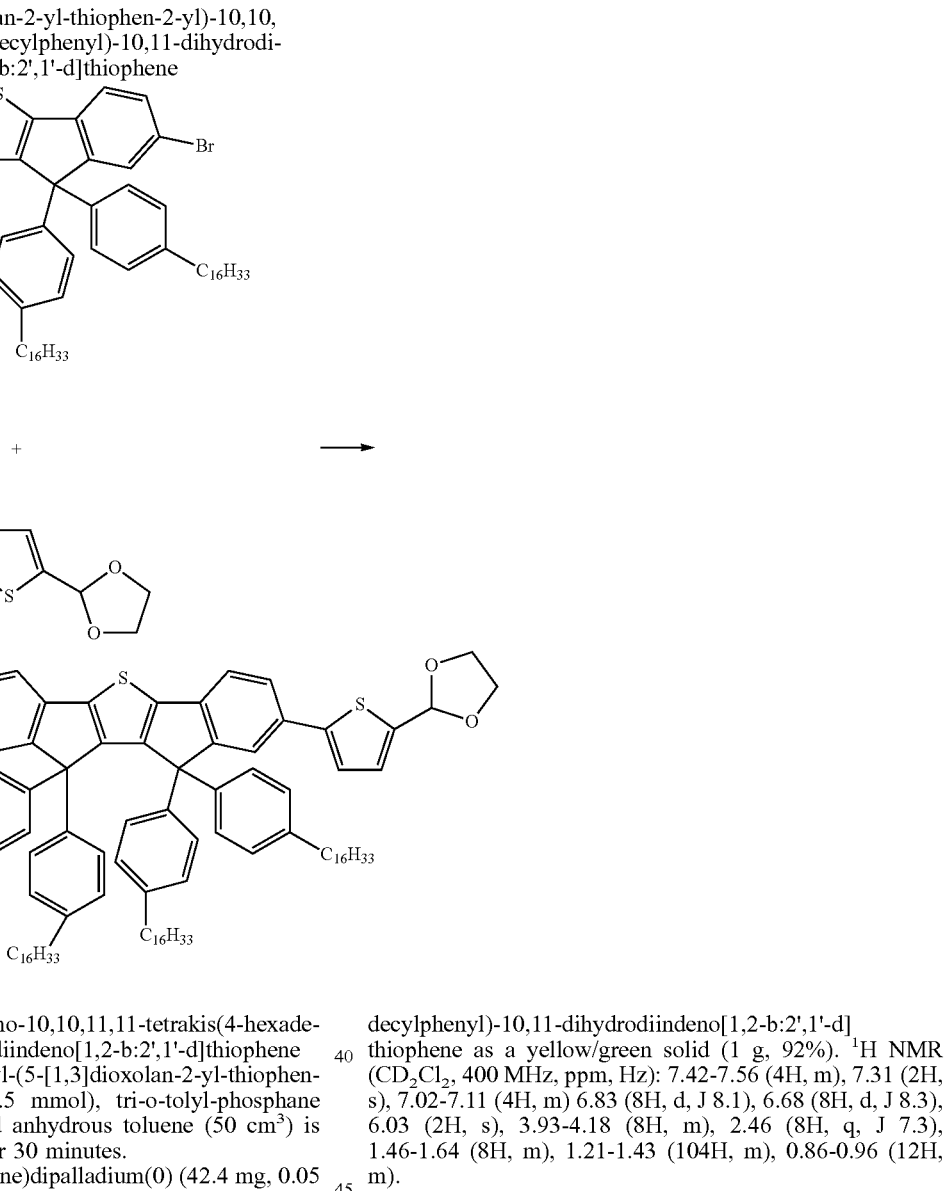

A solution of 2,8-dibromo-10,10,11,11-tetrakis(4-hexadecylphenyl)-10,11-dihydrodiindeno[1,2-b:2',1'-d]thiophene (1.0 g, 0.6 mmol), tributyl-(5-[1,3]dioxolan-2-yl-thiophen-2-yl)-stannane (1.1 g, 2.5 mmol), tri-o-tolyl-phosphane (56.4 mg, 0.2 mmol) and anhydrous toluene (50 cm$^3$) is degassed with nitrogen for 30 minutes.

Tris(dibenzylideneacetone)dipalladium(0) (42.4 mg, 0.05 mmol) is added and the degassing continued for 20 minutes. The reaction is stirred at 105° C. for 17 hours. The resulting reaction mixture is let cool to 25° C., removal of the solvent in vacuo followed by purification by silica gel chromatography (40-60 petrol:diethyl ether; 7:3) gave 2,8-di-(5-[1,3]dioxolan-2-yl-thiophen-2-yl)-10,10,11,11-tetrakis(4-hexadecylphenyl)-10,11-dihydrodiindeno[1,2-b:2',1'-d]thiophene as a yellow/green solid (1 g, 92%). $^1$H NMR (CD$_2$Cl$_2$, 400 MHz, ppm, Hz): 7.42-7.56 (4H, m), 7.31 (2H, s), 7.02-7.11 (4H, m) 6.83 (8H, d, J 8.1), 6.68 (8H, d, J 8.3), 6.03 (2H, s), 3.93-4.18 (8H, m), 2.46 (8H, q, J 7.3), 1.46-1.64 (8H, m), 1.21-1.43 (104H, m), 0.86-0.96 (12H, m).

2,8-Di-(5-carboxaldehyde-thiophen-2-yl)-10,10,11,11-tetrakis(4-hexadecylphenyl)-10,11-dihydrodiindeno[1,2-b:2',1'-d]thiophene

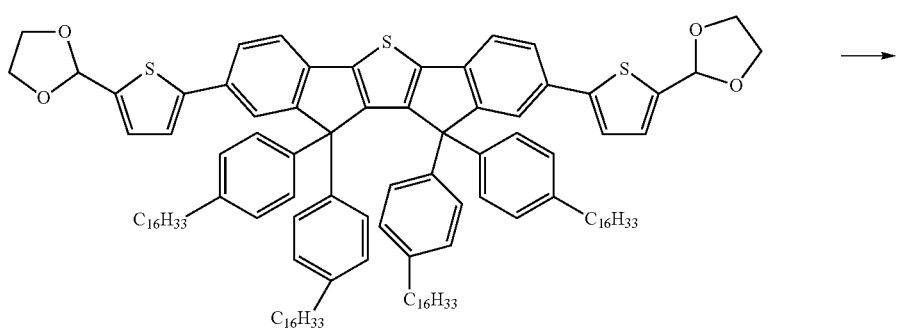

-continued

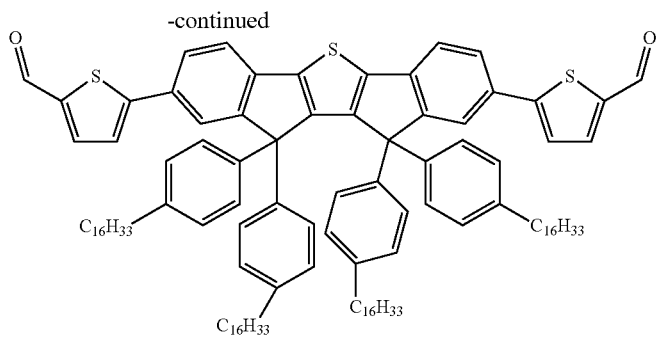

A solution of 2,8-di-(5-[1,3]dioxolan-2-yl-thiophen-2-yl)-10,10,11,11-tetrakis(4-hexadecylphenyl)-10,11-dihydrodiindeno[1,2-b:2',1'-d]thiophene (1.0 g, 0.6 mmol) in tetrahydrofuran (5 cm$^3$) at 20° C. was added dropwise concentrated hydrochloric acid (0.3 cm$^3$). The reaction mixture was stirred at 20° C. for 2 hours. The reaction was quenched with ice water (50 cm$^3$). The solution was extracted with diethyl ether (3×30 cm$^3$). The organic layers combined, dried over anhydrous magnesium sulfate and the solvent removed in vacuo. The crude product is dissolved in hot 40-60 petrol (20 cm$^3$) which is added dropwise into acetone (60 cm$^3$) to form a clear solution. On standing over 30 minutes an orange crystalline solid is formed, filtered, washed with ethanol to give 2,8-di-(5-carboxaldehyde-thiophen-2-yl)-10,10,11,11-tetrakis(4-hexadecylphenyl)-10,11-dihydrodiindeno[1,2-b:2',1'-d]thiophene as a light orange solid (850 mg, 90%). $^1$H NMR (CD$_2$Cl$_2$, 400 MHz, ppm, Hz): 9.78-9.88 (2H, s), 7.59-7.72 (4H, m), 7.53 (2H, d, J 8.1), 7.41 (2H, d, J 1.0), 7.31 (2H, d, J 4.2), 6.77-6.92 (8H, m), 6.61-6.75 (8H, m), 2.35-2.58 (8H, m), 1.45-1.64 (10H, m), 1.20-1.42 (104H, m), 0.91 (12H, t, J 6.7).

Compound 17

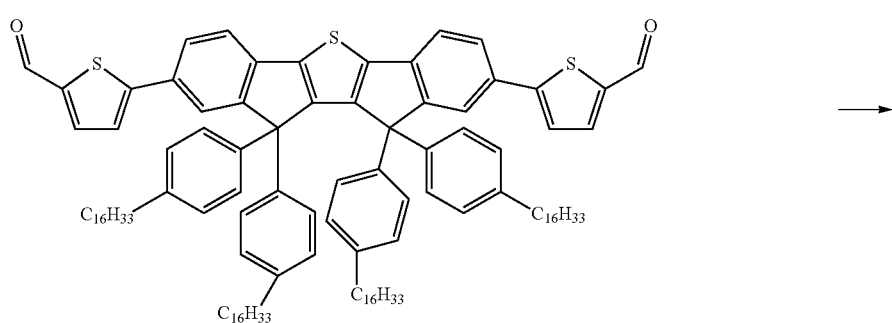

+

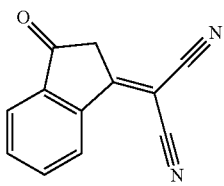

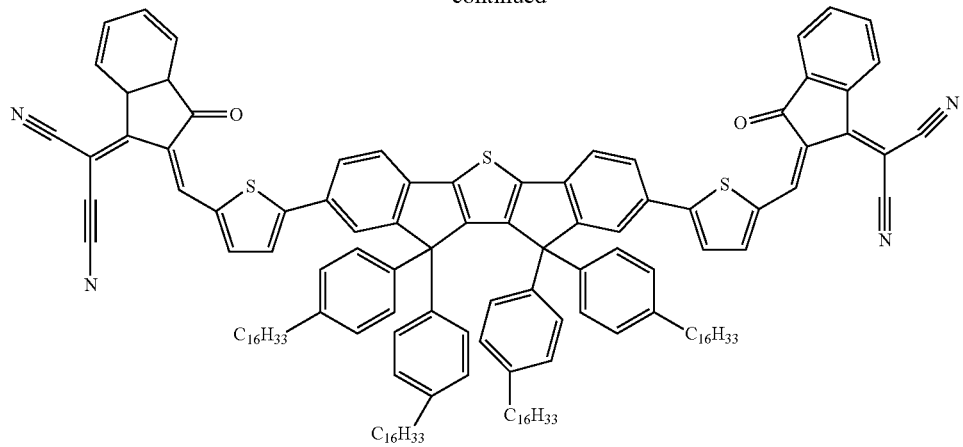

To a three-necked round-bottomed flask is added 2,8-di-(5-carboxaldehyde-thiophen-2-yl)-10,10,11,11-tetrakis(4-hexadecylphenyl)-10,11-dihydrodiindeno[1,2-b:2',1'-d]thiophene (0.8 g, 0.5 mmol), 2-(3-oxo-indan-1-ylidene)-malononitrile (0.65 g, 3.3 mmol), chloroform (50 cm$^3$) and pyridine (2.6 cm$^3$, 33.3 mmol). The mixture is degassed with nitrogen for 30 minutes and then heated to reflux for 12 hours. The resulting reaction mixture is let cool to 25° C. and poured into methanol (300 cm$^3$), stirred for 1 hour to form a fine suspension which was collected by filtration. The crude product is purified by column chromatography (dichloromethane) to give product 1 as a dark red solid (0.5 g, 52%). $^1$H NMR (CD$_2$Cl$_2$, 400 MHz, ppm, Hz): 8.68 (2H, s), 8.57 (2H, dd, J 6.6 1.2), 7.81 (2H, s), 7.63-7.73 (6H, m), 7.60 (2H, dd, J 8.1, 1.7), 7.35-7.42 (4H, m), 7.26 (2H, d, J 4.4), 6.77 (8H, d, J 8.3), 6.61 (8H, d, J 8.6), 2.36 (8H, m), 1.44 (8H, m), 1.09-1.31 (104H, m), 0.73-0.84 (12H, m).

Example 18

2,8-Dibromo-10,10,11,11-tetrakis(4-hexylphenyl)-10,11-dihydrodiindeno[1,2-b:2',1'-d]thiophene

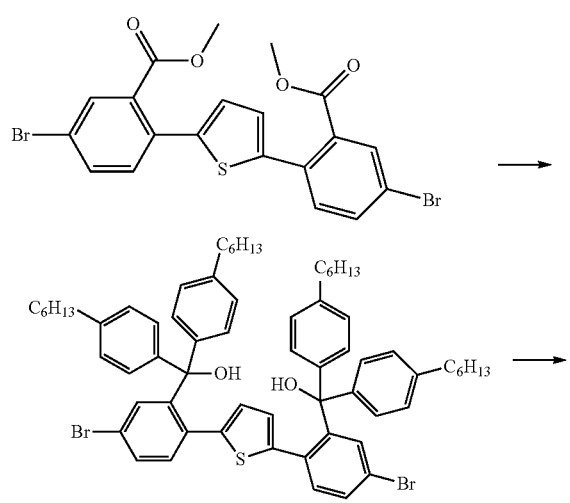

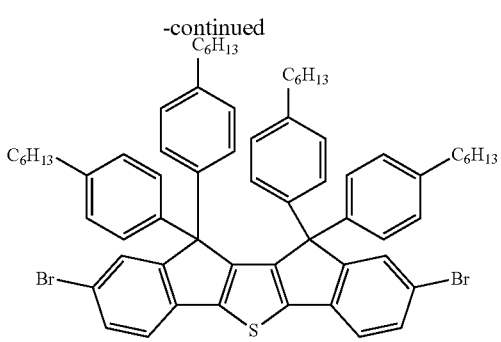

To a solution of 1-bromo-4-hexyl-benzene (6.24 g, 25.9 mmol) in anhydrous tetrahydrofuran (69 cm$^3$) at −78° C., n-butyllithium (10 cm$^3$, 25 mmol, 2.5 M in hexane) is added dropwise over 10 minutes. The reaction is allowed to stir at −78° C. for 80 minutes, before dimethyl-6,6'-(thiophene-2,5-diyl)bis(3-bromobenzoate) (1.65 g, 3.23 mmol) is added in one portion. The reaction mixture is stirred at 23° C. for 17 hours, quenched by the addition of water (100 cm$^3$) and stirred for 72 hours. The reaction is then extracted with ethyl acetate (2×50 cm$^3$) and the combined organic extracts washed with water (100 cm$^3$), extracting the aqueous layer with additional ethyl acetate (25 cm$^3$). The combined organic extracts are further washed with brine (100 cm$^3$), again extracting the aqueous layer with additional ethyl acetate (50 cm$^3$), before drying the combined organic extracts over anhydrous magnesium sulfate, filtered and the solvent removed in vacuo. Partial purification is by column chromatography eluting with a graded solvent system (40-60 petrol:dichloromethane; 4:1 to 3:2) to give the intermediate which is taken up in dichloromethane (125 cm$^3$) and the mixture degassed. Toluene-4-sulfonic acid monohydrate (955 mg, 5.02 mmol) is added and the reaction heated at reflux for 17 hours, before cooling to 23° C. diluting with water (100 cm$^3$). The organics are extracted with dichloromethane (2×25 cm$^3$) and the combined organic extracts washed with brine (100 cm$^3$) and the residual aqueous layer extracted with dichloromethane (25 cm$^3$). The combined organic extracts are then dried over anhydrous magnesium sulfate, filtered and the solvent removed in vacuo. Purification is by column chromatography eluting with a graded solvent system (40-60 petrol:dichloromethane; 1:0 to 3:1) followed by a further second column chromatography (40-

60 petrol) purification to give 2,8-dibromo-10,10,11,11-tetrakis(4-hexylphenyl)-10,11-dihydrodiindeno[1,2-b:2',1'-d]thiophene (902 mg, 26%) as a white crystalline solid. $^1$H NMR (400 MHz, CDCl$_3$, ppm, Hz) 7.31 (2H, dd, J 8.1, 1.4), 7.24 (2H, d, J 8.1), 7.17 (2H, d, J 1.2), 6.69-6.76 (8H, m), 6.57-6.63 (8H, m), 2.35-2.49 (8H, m), 1.47-1.55 (8H, m), 1.26-1.38 (24H, m), 0.86-0.94 (12H, m).

2,8-Di-(5-carboxaldehyde-thiophen-2-yl)-10,10,11,11-tetrakis(4-hexylphenyl)-10,11-dihydrodiindeno[1,2-b:2',1'-d]thiophene An oven dried nitrogen flushed flask is charged with 2,8-dibromo-10,10,11,11-tetrakis(4-hexylphenyl)-10,11-dihydrodiindeno[1,2-b:2',1'-d]thiophene (902 mg, 0.85 mmol) and anhydrous toluene (150 cm$^3$). Tributyl-(5-[1,3]dioxolan-2-yl-thiophen-2-yl)-stannane (0.93 cm$^3$, 2.0 mmol) is added. The solution is degassed with nitrogen for 30 minutes before tris(dibenzylideneacetone)dipalladium (62 mg, 0.07 mmol) and tri(o-tolyl)phosphine (78 mg, 0.26 mmol) are added and the degassing continued for a further 30 minutes. The reaction mixture is heated at 80° C. for 17 hours before concentration in vacuo. The resulting solid is triturated with methanol (5×10 cm$^3$) and collected by filtration to give the intermediate which is used without further purification. To a stirred solution of the intermediate in anhydrous tetrahydrofuran (81 cm$^3$) at 23° C., concentrated hydrochloric acid (0.65 cm$^3$, 5.7 mmol, 32%) is added dropwise. After 50 minutes, water (2.0 cm$^3$) is added and the reaction mixture stirred for a further 1 hour. The reaction mixture is then diluted with water (125 cm$^3$) and extracted with dichloromethane (4×25 cm$^3$). The combined organic extracts are then washed with brine (100 cm$^3$), additionally extracting the aqueous layer with dichloromethane (2×25 cm$^3$). The combined organic extracts are dried over anhydrous magnesium sulfate, filtered and the solvent removed in vacuo. Purification by column chromatography eluting with a graded solvent system (40-60 petrol:dichloromethane; 7:3 to 2:3) gives 2,8-di-(5-carboxaldehyde-thiophen-2-yl)-10,10,11,11-tetrakis(4-hexylphenyl)-10,11-dihydrodiindeno[1,2-b:2',1'-d]thiophene (586 mg, 61%) as an orange solid. $^1$H NMR (400 MHz, CDCl$_3$, ppm, Hz) 9.82 (2H, s), 7.64 (2H, d, J 3.9), 7.54 (2H, dd, J 8.0, 1.6), 7.44 (2H, d, J 8.3), 7.35 (2H, d, J 1.2), 7.24 (2H, d, J 3.9), 6.79 (8H, d, J 8.3), 6.63 (8H, d, J 8.3), 2.35-2.49 (8H, m), 1.47-1.56 (8H, m), 1.26-1.37 (24H, m), 0.85-0.92 (12H, m).

Compound 18

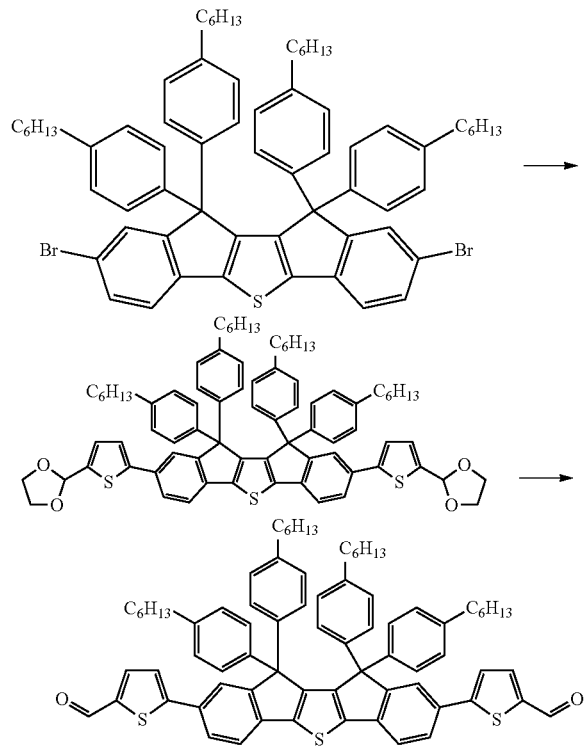

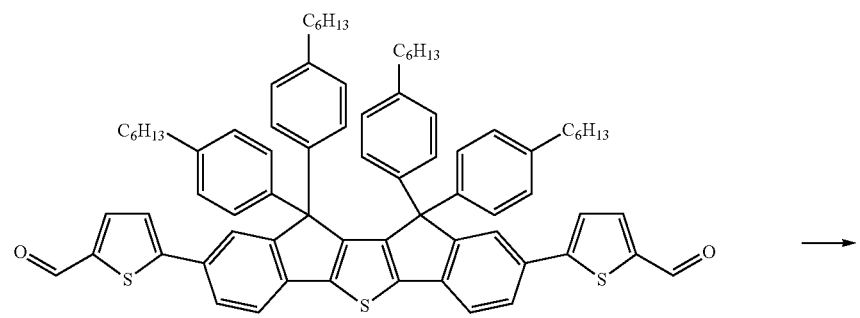

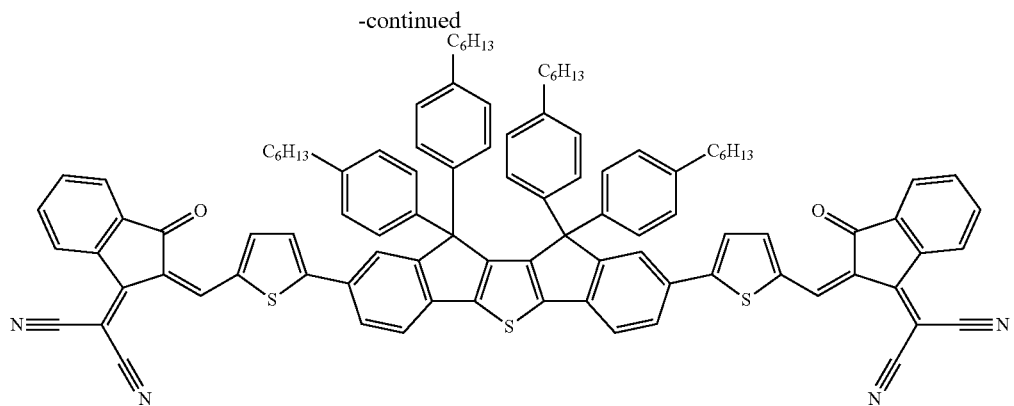

To a solution of 2,8-di-(5-carboxaldehyde-thiophen-2-yl)-10,10,11,11-tetrakis(4-hexylphenyl)-10,11-dihydrodiindeno[1,2-b:2',1'-d]thiophene (535 mg, 0.48 mmol) in anhydrous chloroform (51 cm$^3$) is added pyridine (2.7 cm$^3$, 33 mmol). The mixture is degassed with nitrogen for 20 minutes before 3-(dicyanomethylidene)indan-1-one (648 mg, 3.34 mmol) is added. The resulting solution is degassed for a further 10 minutes before stirring for 3 hours. The reaction mixture is then added to stirred methanol (500 cm$^3$), washing in with additional methanol (25 cm$^3$) and dichloromethane (25 cm$^3$). The precipitate is collected by filtration and washed with methanol (5×10 cm$^3$), warm methanol (5×10 cm$^3$), 40-60 petrol (3×10 cm$^3$), diethyl ether (3×10 cm$^3$), 80-100 petrol (3×10 cm$^3$) and acetone (3×10 cm$^3$) to give compound 2 (645 mg, 92%) as a blue/black solid. $^1$H NMR (400 MHz, CDCl$_3$, ppm, Hz) 8.77 (2H, s), 8.64-8.70 (2H, m), 7.89-7.94 (2H, m), 7.71-7.79 (6H, m), 7.61 (2H, dd, J 8.1, 1.7), 7.44 (2H, d, J 1.5), 7.38 (2H, d, J 8.1), 7.29 (2H, d, J 4.2), 6.85 (8H, d, J 8.3), 6.68 (8H, d, J 8.3), 2.38-2.52 (8H, m), 1.49-1.60 (8H, m), 1.24-1.40 (24H, m), 0.88 (12H, t, J 6.9).

Use Example A

Current-voltage characteristics are measured using a Keithley 2400 SMU while the solar cells are illuminated by a Newport Solar Simulator at 100 mW·cm$^{-2}$ white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics for a blend containing either Polymer 1, Polymer 2 or Polymer 3 having the structure shown below and acceptors coated from an organic solution. Details of the solution composition are shown in Table 1.

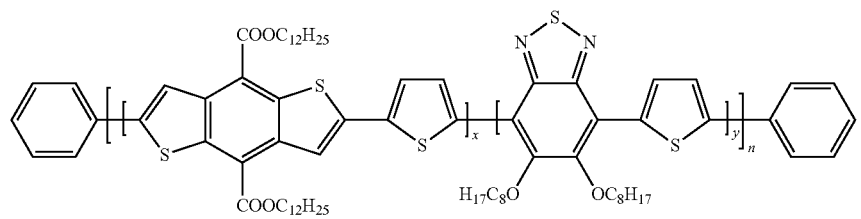

Polymer 1 and its preparation are disclosed in WO 2011/131280 A1.

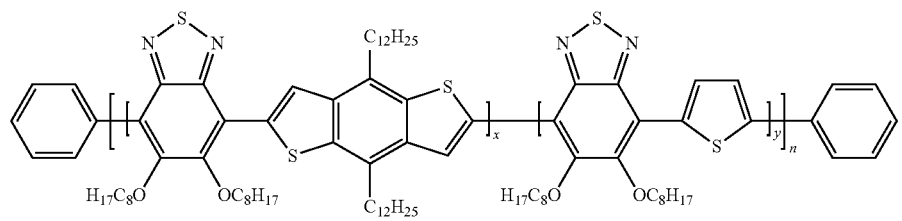

Polymer 2 and its preparation are disclosed in WO 2013/135339.

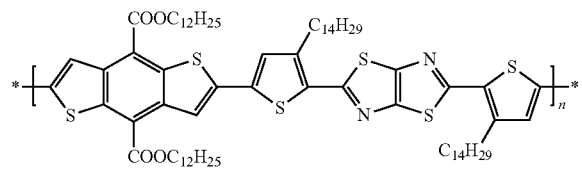

Polymer 3

Inverted Bulk Heterojunction Organic Photovoltaic Devices

Organic photovoltaic (OPV) devices are fabricated on pre-patterned ITO-glass substrates (130/sq.) purchased from LUMTEC Corporation. Substrates are cleaned using common solvents (acetone, iso-propanol, deionized-water) in an ultrasonic bath. A layer of commercially available aluminium zinc oxide (AlZnO, Nanograde) was applied as a uniform coating by doctor blade at 40° C. The AlZnO Films are then annealed at 100° C. for 10 minutes in air. Active material solutions (i.e. polymer+acceptor) are prepared to fully dissolve the solutes at a 23-30 mg·cm$^{-3}$ solution concentration. Thin films are blade-coated in air atmosphere to achieve active layer thicknesses between 50 and 800 nm as measured using a profilometer. A short drying period follows to ensure removal of any residual solvent.

Typically, blade-coated films are dried at 70° C. for 2 minutes on a hotplate. Next the devices are transferred into an air atmosphere. On top of the active layer 0.1 mL of a conducting polymer poly(ethylene dioxythiophene) doped with poly(styrene sulfonic acid) [PEDOT:PSS Clevios HTL Solar SCA 434 (Heraeus)] was spread and uniformly coated by doctor blade at 70° C. Afterwards Ag (100 nm) cathodes are thermally evaporated through a shadow mask to define the cells.

Table 1 shows the formulation characteristics of the individual photoactive material solutions comprising a polymer as electron donor component and a fullerene mixture or acceptor according to the present invention as electron acceptor component. Solutions C1 according to prior art contain fullerene PCBM-C60. Solutions 1 to 7 according to the present invention contain a mixture of compound 17 or 18 with previously described polymers, which differ in the nature of their polymer structure. The solvent is either o-dichlorobenzene (oDCB), or o-xylene (oXyl).

TABLE 1

Formulation characteristics

| No. | Acceptor | Polymer | Ratio Polymer:Acceptor | Concentration g/L | Solvent |
|---|---|---|---|---|---|
| C1 | PCBM-C60 | 1 | 1.00:2.00 | 30 | oDCB |
| 1 | Compound 17 | 1 | 1.00:1.50 | 25 | oDCB |
| 2 | Compound 17 | 1 | 1.00:1.50 | 25 | oXyl |
| 3 | Compound 17 | 2 | 1.00:1.30 | 23 | oDCB |
| 4 | Compound 17 | 2 | 1.00:1.30 | 23 | oXyl |
| 5 | Compound 17 | 3 | 1.00:1.30 | 23 | oDCB |
| 6 | Compound 17 | 3 | 1.00:1.30 | 23 | oXyl |
| 7 | Compound 18 | 1 | 1.00:1.30 | 23 | oDCB |

Inverted Device Properties

Table 2 shows the device characteristics for the individual OPV devices comprising a photoactive layer with a BHJ formed from the active material (acceptor/polymer) solutions of Table 1.

TABLE 2

Photovoltaic cell characteristics under simulated solar irradiation at 1 sun (AM1.5G).

| | Average Initial Performance | | | |
|---|---|---|---|---|
| No. | Voc mV | Jsc mA·cm$^{-2}$ | FF % | PCE % |
| C1 | 750 | 12.42 | 62.4 | 5.80 |
| 1 | 960 | 2.69 | 35.7 | 0.92 |
| 2 | 960 | 3.22 | 34.6 | 1.08 |
| 3 | 789 | 0.57 | 22.6 | 0.16 |
| 4 | 872 | 0.68 | 30.3 | 0.20 |
| 5 | 874 | 1.09 | 27.5 | 0.31 |
| 6 | 925 | 1.99 | 33.9 | 0.63 |
| 7 | 957 | 4.4 | 38.3 | 1.61 |

From Table 2 it can be seen that OPV devices with a BHJ prepared from compound 17 or 18 according to the invention, show high Voc values and functional OPV devices.

The experiments 1-7 show specific improvements in open circuit voltage (Voc) by comparison to $C_1$ and generated a photovoltaic effect.

Example 5

Bulk heterojunction organic photodetector devices (OPDs) Devices are fabricated onto glass substrates with six pre-patterned ITO dots of 5 mm diameter to provide the bottom electrode. The ITO substrates are cleaned using a standard process of ultrasonication in Decon90 solution (30 minutes) followed by washing with de-ionized water (×3) and ultrasonication in de-ionized water (30 minutes). The ZnO ETL layer was deposited by spin coating a ZnO nanoparticle dispersion onto the substrate and drying on a hotplate for 10 minutes at a temperature between 100 and 140° C. A formulation of Lisicon PV-D4650 and compound 1 was prepared at a ratio of 1:1.5 in o-xylene with 0-10% co-solvent at a concentration of 20 mg/ml, and stirred for 17 hours at 60° C. The active layer was deposited using blade coating (K101 Control Coater System from RK). The stage temperature was set to 30° C., the blade gap set between 2-15 μm and the speed set between 2-8 m/min targeting a final dry film thickness of 500-1 000 nm. Following coating the active layer was annealed at 100° C. for 15 minutes. The MoO$_3$ HTL layer was deposited by E-beam vacuum deposition from MoO$_3$ pellets at a rate of 1 Å/s, targeting 15 nm thickness. Finally, the top silver electrode was deposited by thermal evaporation through a shadow mask, to achieve Ag thickness between 30-80 nm.

The J-V curves are measured using a Keithley 4200 system under light and dark conditions at a bias from +5 to −5 V. The light source was a 580 nm LED with power 0.5 mW/cm$^2$.

The EQE of OPD devices are characterized between 400 and 1100 nm under −2V bias, using an External Quantum Efficiency (EQE) Measurement System from LOT-QuantumDesign Europe. EQE value at 650 nm for a device incorporating compound 17 is 17%.

The invention claimed is:

1. A compound of formula I

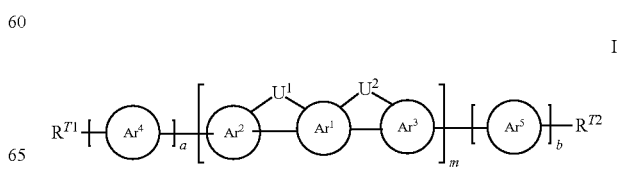

I wherein the individual radicals, independently of each other and on each occurrence identically or differently, have the following meanings $Ar^{1-3}$ are, each independently, arylene or heteroarylene that has from 5 to 20 ring atoms, is mono- or polycyclic, optionally contains fused rings, and is unsubstituted or substituted by one or more identical or different groups L, $Ar^{4,5}$ are, each independently, arylene or heteroarylene that has from 5 to 20 ring atoms, is mono- or polycyclic, optionally contains fused rings, and is unsubstituted or substituted by one or more identical or different groups L, or $CY^1=CY^2$ or —C≡C—, $Y^1$, $Y^2$ are, each independently, H, F, Cl or CN, $U^1$ is $CR^1R^2$, $SiR^1R^2$, $GeR^1R^2$, $NR^1$ or C=O, $U^2$ is $CR^3R^4$, $SiR^3R^4$, $GeR^3R^4$, $NR^3$ or C=O, $R^{1-4}$ are, each independently, H, F, Cl or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0=CR^{00}$—, —$CY^1=CY^2$— or —C≡C— in such a manner that O and/or S atoms are not linked directly to one another, and in which one or more H atoms are optionally replaced by F, Cl, Br, I or —CN, and in which one or more $OH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and a pair of $R^1$ and $R^2$ and/or a pair of $R^3$ and $R^4$ together with the C, Si or Ge atom to which they are attached, may also form a spiro group with 5 to 20 ring atoms which is mono- or polycyclic, does optionally contain fused rings, and is unsubstituted or substituted by one or more identical or different groups L $R^{T1}$, $R^{T2}$ are, each independently a carbyl or hydrocarbyl group with 1 to 30 C atoms that is optionally substituted by one or more groups L and optionally comprises one or more hetero atoms, and wherein at least one of $R^{T1}$ and $R^{T2}$ is an electron withdrawing group, L is F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, $NR^0R^{00}$, —C(=O)$NHR^0$, —C(=O)$NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30 C atoms that is optionally substituted and optionally comprises one or more hetero atoms, or is —O—C(=O)—$OR^0$, $R^0$, $R^{00}$ is H or straight-chain or branched alkyl with 1 to 20 C atoms that is optionally fluorinated, $X^0$ is halogen, a, b are, each independently, 0, 1, 2 or 3, and m is 1, 2 or 3.

2. The compound according to claim 1, wherein $Ar^{1-5}$ in formula I are selected from the following formulae and their mirror images $Ar^1$ is

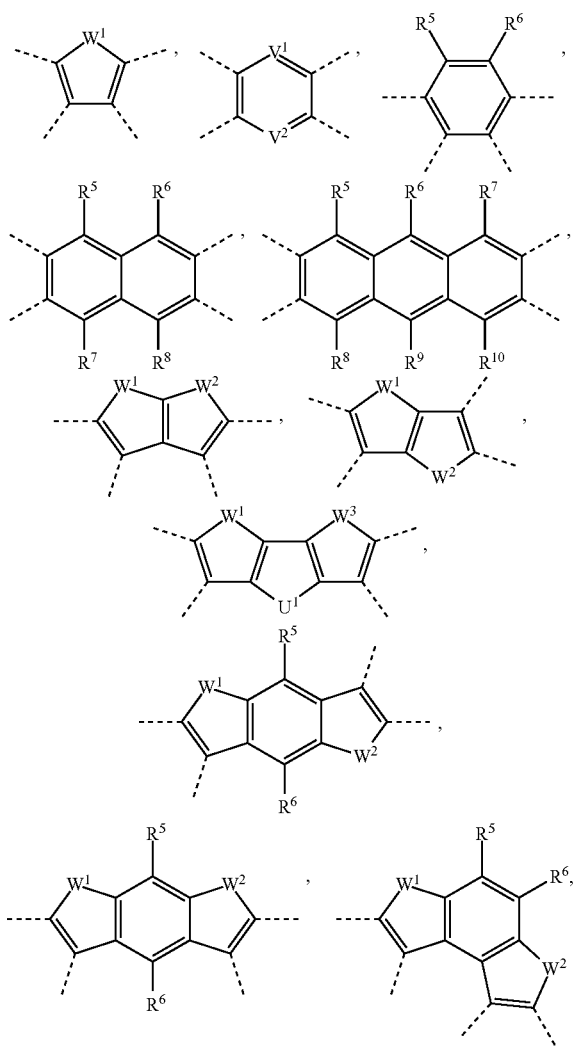

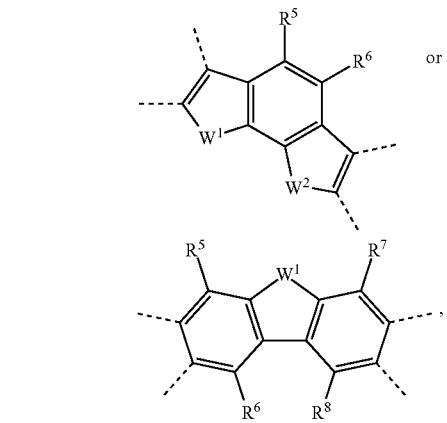

$Ar^2$ is

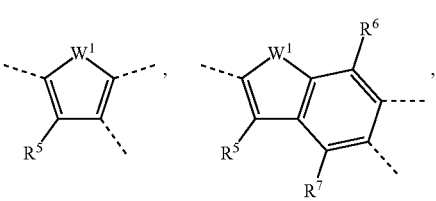

-continued

Ar³ is

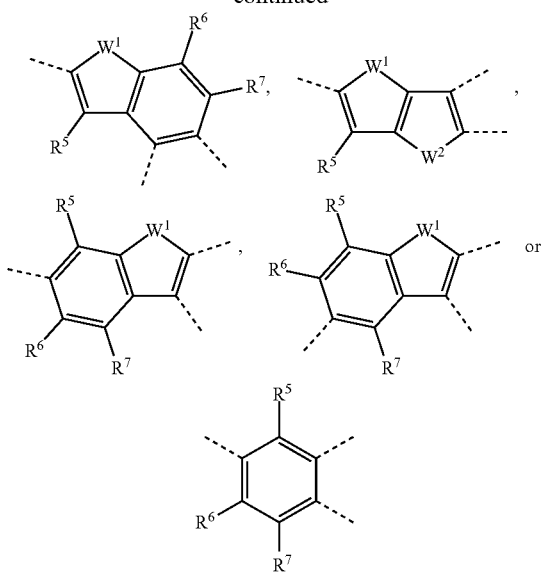

Ar⁴, Ar⁵ are each independently

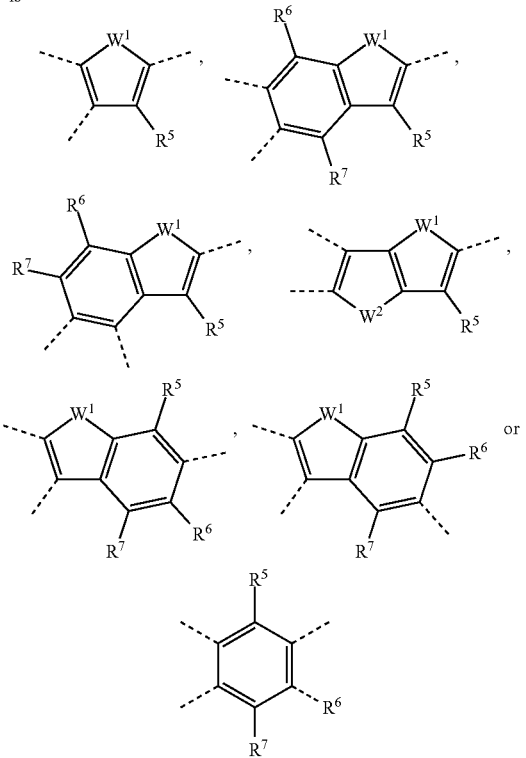

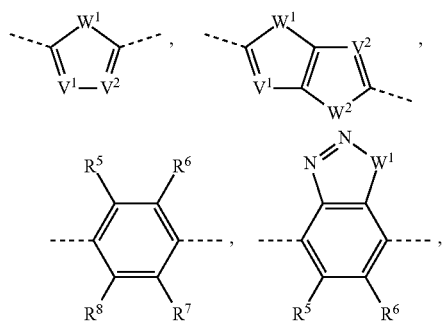

-continued

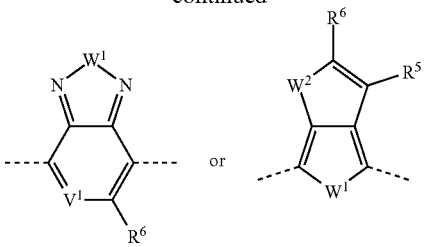

wherein the individual radicals, independently of each other and on each occurrence identically or differently, have the following meanings $U^1$ is $CR^1R^2$, $SiR^1R^2$, $GeR^1R^2$, $NR^1$ or C=O, $R^{1-2}$ are each independently H, F, Cl or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or —CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and a pair of $R^1$ and $R^2$ together with the C, Si or Ge atom to which they are attached, may also form a spiro group with 5 to 20 ring atoms which is mono- or polycyclic, does optionally contain fused rings, and is unsubstituted or substituted by one or more identical or different groups L $W^{1,2}$ are each independently S, O, Se or C=O, $V^1$ is $CR^5$ or N, $V^2$ is $CR^6$ or N, $R^{5-10}$ are each independently H, F, Cl, —CN or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or —CN, and in which one or more $OH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, $Y^1$, $Y^2$ are each independently H, F, Cl or CN, L is F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, —$NR^0R^{00}$, —C(=O)$NHR^0$, —C(=O)$NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30 C atoms that is optionally substituted and optionally comprises one or more hetero atoms, or is —O—C(=O)—OR⁰, R⁰, R⁰⁰ are each independently H or straight-chain or branched alkyl with 1 to 20 C atoms that is optionally fluorinated, and X⁰ is halogen.

3. The compound according to claim 1, wherein $Ar^{1-3}$ in formula I are selected from the following formulae and their mirror images $Ar^1$ is

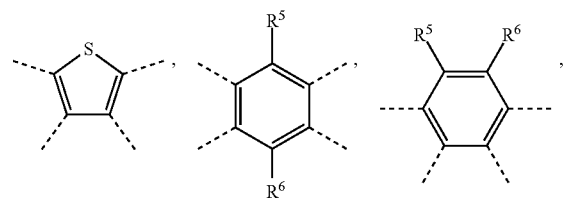

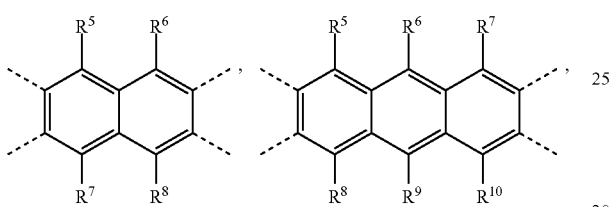

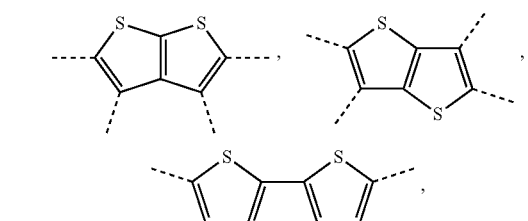

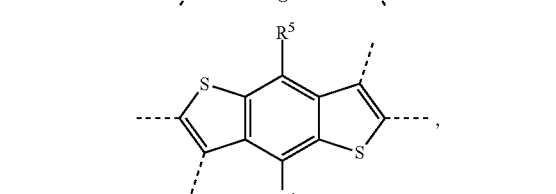

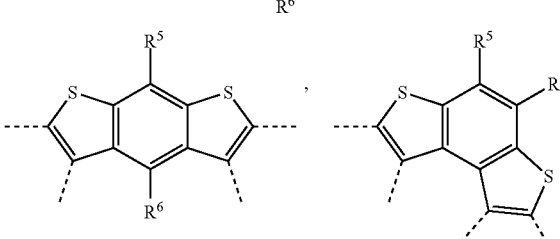

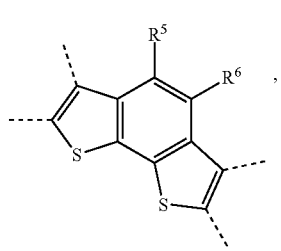

-continued

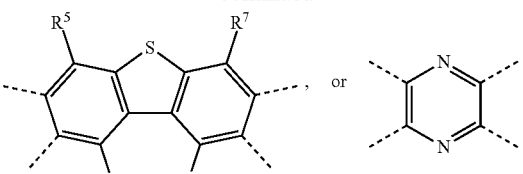

$Ar^2$

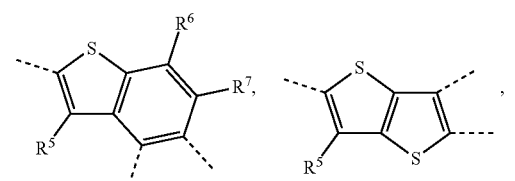

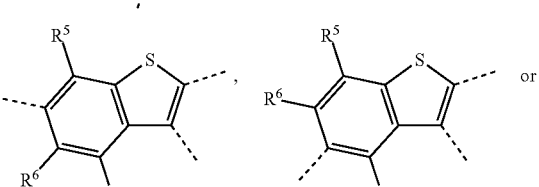

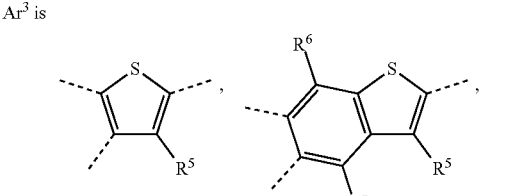

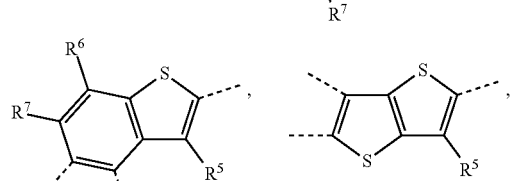

$Ar^3$ is

-continued

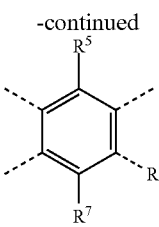

wherein $U^1$ is $CR^1R^2$, $SiR^1R^2$, $GeR^1R^2$, $NR^1$ or C=O, and $R^{1-2}$ are, each independently, H, F, Cl or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or —CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and a pair of $R^1$ and $R^2$ together with the C, Si or Ge atom to which they are attached, may also form a spiro group with 5 to 20 ring atoms which is mono- or polycyclic, does optionally contain fused rings, and is unsubstituted or substituted by one or more identical or different groups L $R^{5-10}$ are, each independently, H, F, Cl, —CN or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or —CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, $Y^1$, $Y^2$ are, each independently, H, F, Cl or CN, L are, each independently, F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, —$NR^0R^{00}$, —C(=O)$NHR^0$, —C(=O)$NR^0R^{00}$, —$SO_3R^0$, —$SO_2^0$, —OH, —$NO_2$, —$CF_3$, —$SF_5$, or optionally substituted silyl, or carbyl or hydrocarbyl with 1 to 30 C atoms that is optionally substituted and optionally comprises one or more hetero atoms, or is —O—C(=O)—$OR^0$, $R^0$, $R^{00}$ are, each independently, H or straight-chain or branched alkyl with 1 to 20 C atoms that is optionally fluorinated, and $X^0$ is halogen.

4. The compound according to claim 1, wherein $Ar^4$ and $Ar^5$ in formula I are selected from the following formulae and their mirror images

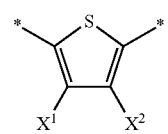
AR1

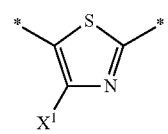
AR2

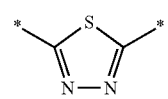
AR3

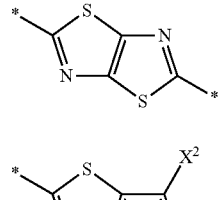
AR4

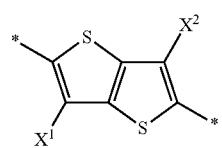
AR5

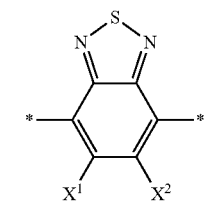
AR6

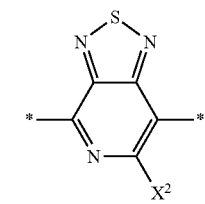
AR7

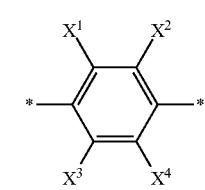
AR8

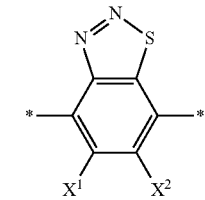
AR9

-continued

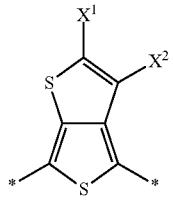
AR10 wherein
$X^1$ and $X^2$ are, each independently, H, F, Cl or straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or —CN, and in which one or more $OH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L,
$Y^1$, $Y^2$ are, each independently, H, F, Cl or CN,
L is F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, —$NR^0R^{00}$, —C(=O)$NHR^0$, —C(=O)$NR^0R^{00}$, —$SO_3R^0$, —$SO_2R^0$, —OH, —$NO_2$, —$CF_3$—$SF_5$, or optionally substituted silyl, or carbyl or hydrocarbyl with 1 to 30 C atoms that is optionally substituted and optionally comprises one or more hetero atoms, or is —O—C(=O)—$OR^0$,
$R^0$, $R^{00}$ are, each independently, H or straight-chain or branched alkyl with 1 to 20 C atoms that is optionally fluorinated,
$X^0$ is halogen.

5. The compound according to claim 1, wherein $R^{T1}$ and $R^{T2}$ are H, F, Cl, Br, —$NO_2$, —CN, —$CF_3$, R*, —$CF_2$—R*, —O—R*, —S—R*, —$SO_2$—R*, —$SO_3$—R*, —C(=O)—H, —C(=O)—R*, —C(=S)—R*, —C(=O)—$CF_2$—R*, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*, —NR*R**, —CR*=CR*R**, —C≡C—R*, —C≡C—SiR*RR*, —SiR*RR*, —CH=CH(CN), —CH=C(CN)$_2$, —C(CN)=C(CN)$_2$, —CH=C(CN)($R^a$), CH=C(CN)—C(=O)—OR*, —CH=C(CO—OR*)$_2$, —CH=C(CO—NR*R**)$_2$, or a group from the following formulae

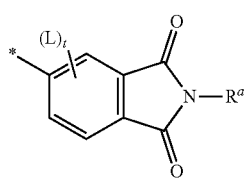
T1

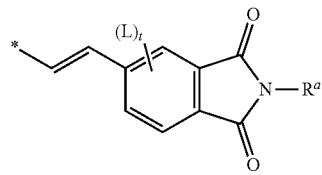
T2

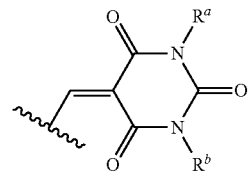
T3

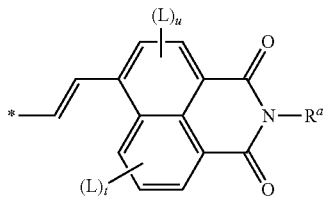
T4

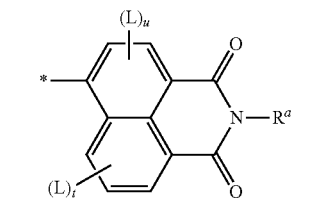
T5

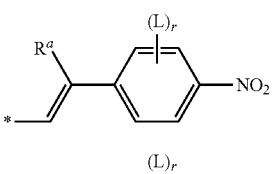
T6

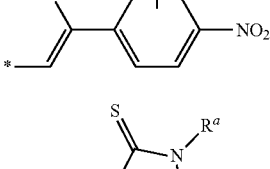
T7

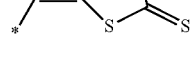
T8

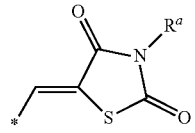
T9

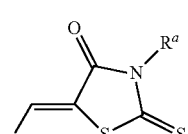
T10

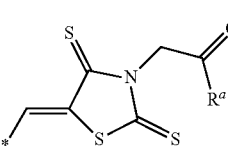
T11

| | |
|---|---|
| T12 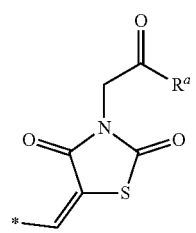 | T19 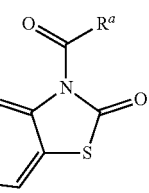 |
| T13 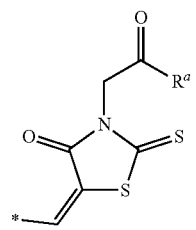 | T20 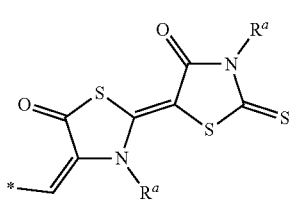 |
| T14 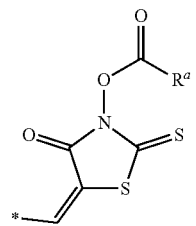 | T21 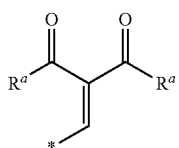 |
| T15 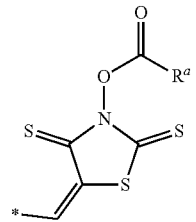 | T22 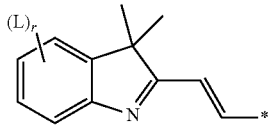 |
| T16 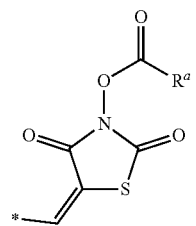 | T23 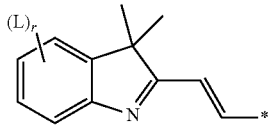 |
| T17 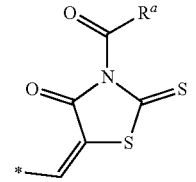 | T24 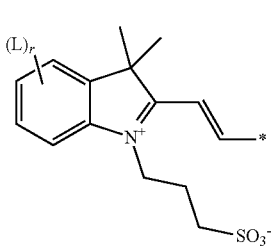 |
| T18 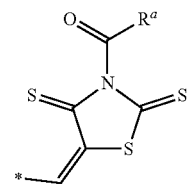 | T25 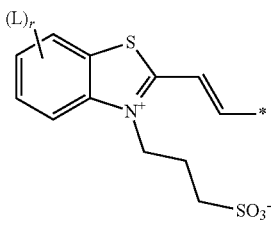 |
| | T26 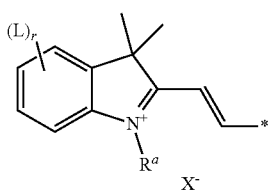 |

-continued
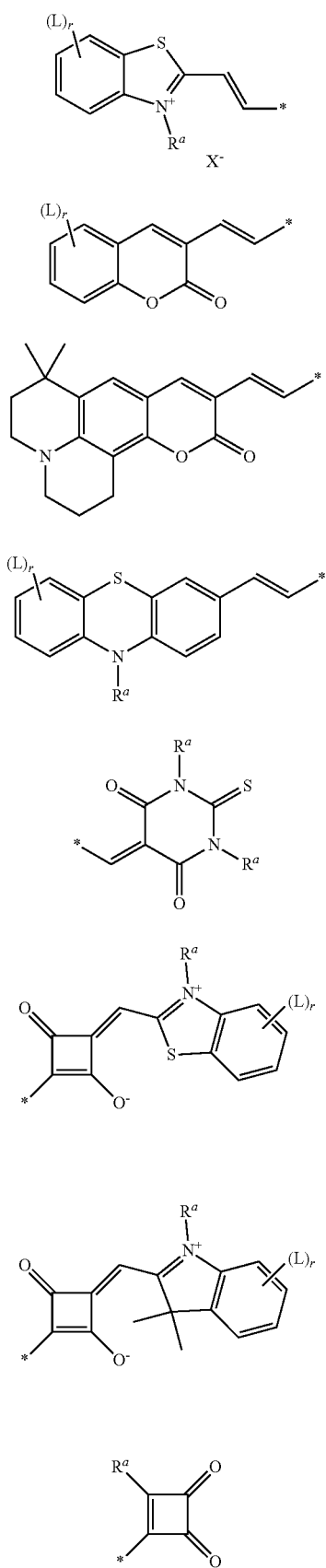
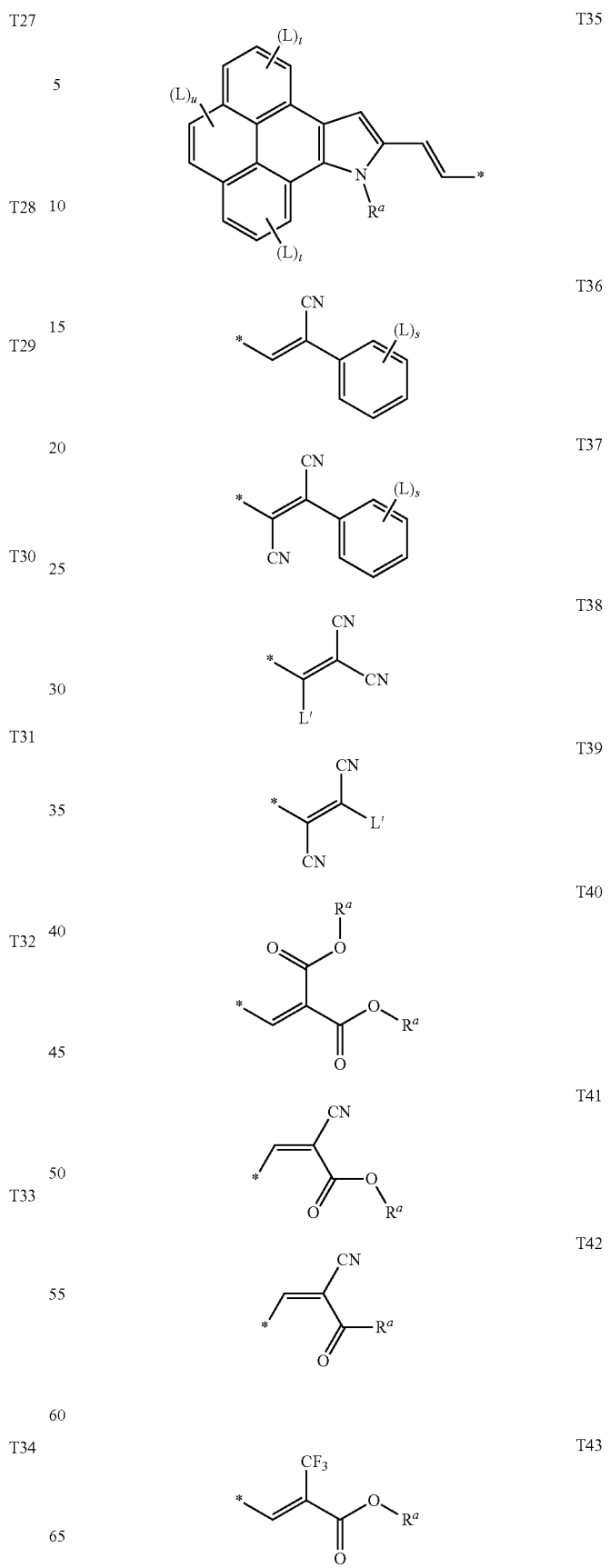

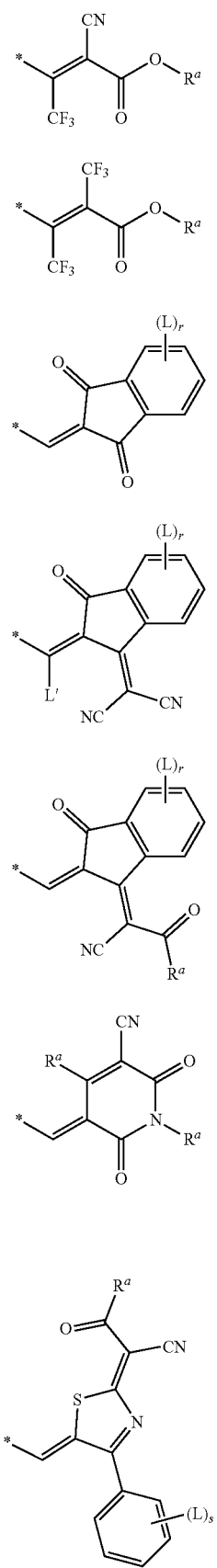
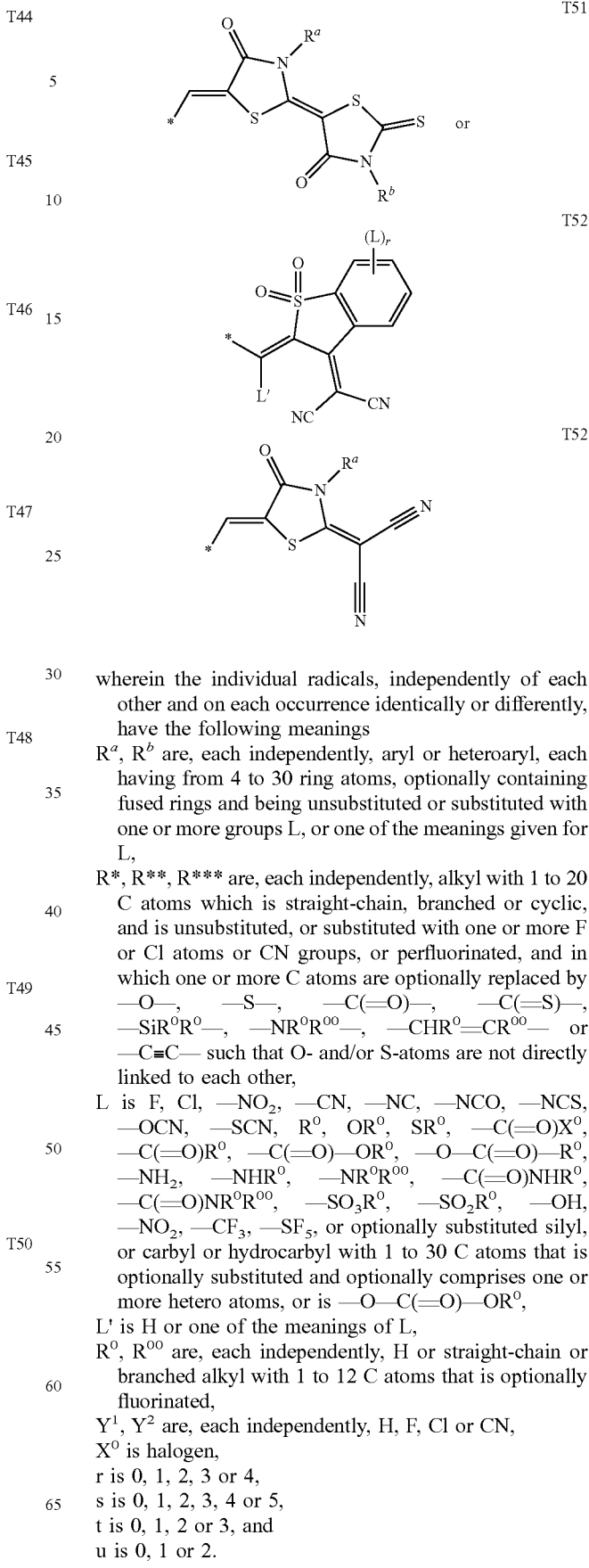

wherein the individual radicals, independently of each other and on each occurrence identically or differently, have the following meanings $R^a$, $R^b$ are, each independently, aryl or heteroaryl, each having from 4 to 30 ring atoms, optionally containing fused rings and being unsubstituted or substituted with one or more groups L, or one of the meanings given for L, $R^*$, $R^{}$, $R^{*}$ are, each independently, alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(=O)—, —C(=S)—, —SiR°R°—, —NR°R°°—, —CHR°=CR°°— or —C≡C— such that O- and/or S-atoms are not directly linked to each other, L is F, Cl, —NO$_2$, —CN, —NC, —NCO, —NCS, —OCN, —SCN, R°, OR°, SR°, —C(=O)X°, —C(=O)R°, —C(=O)—OR°, —O—C(=O)—R°, —NH$_2$, —NHR°, —NR°R°°, —C(=O)NHR°, —C(=O)NR°R°°, —SO$_3$R°, —SO$_2$R°, —OH, —NO$_2$, —CF$_3$, —SF$_5$, or optionally substituted silyl, or carbyl or hydrocarbyl with 1 to 30 C atoms that is optionally substituted and optionally comprises one or more hetero atoms, or is —O—C(=O)—OR°, L' is H or one of the meanings of L, R°, R°° are, each independently, H or straight-chain or branched alkyl with 1 to 12 C atoms that is optionally fluorinated, $Y^1$, $Y^2$ are, each independently, H, F, Cl or CN, X° is halogen, r is 0, 1, 2, 3 or 4, s is 0, 1, 2, 3, 4 or 5, t is 0, 1, 2 or 3, and u is 0, 1 or 2.

6. The compound according to claim 1, wherein both $R^{T1}$ and $R^{T2}$ denote an electron withdrawing group.

7. The compound according to claim 1, wherein $R^{T1}$ and $R^{T2}$ are of the following formulae

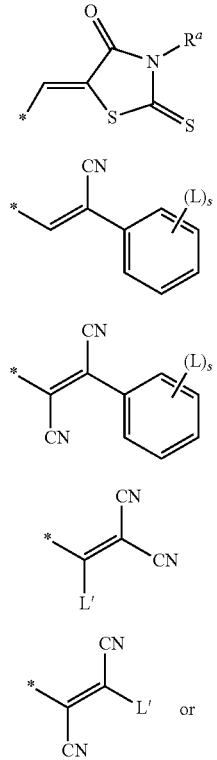

wherein

L is F, Cl, —NO$_2$, —CN, —NC, —NCO, —NCS, —OCN, —SCN, R$^0$, OR$^0$, SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O)NR$^0$R$^{00}$, —SO$_3$R$^0$, —SO$_2$R$^0$, —OH, —NO$_2$, —CF$_3$, —SF$_5$, or optionally substituted silyl, or carbyl or hydrocarbyl with 1 to 30 C atoms that is optionally substituted and optionally comprises one or more hetero atoms, or is —O—C(=O)—OR$^0$, R$^0$, R$^{00}$ are, each independently, H or straight-chain or branched alkyl with 1 to 12 C atoms that is optionally fluorinated, $Y^1$, $Y^2$ are, each independently, H, F, Cl or CN, X$^0$ is halogen, r is 0, 1, 2, 3 or 4, and s is 0, 1, 2, 3, 4 or 5.

8. The compound according to claim 1, which is of the following formulae

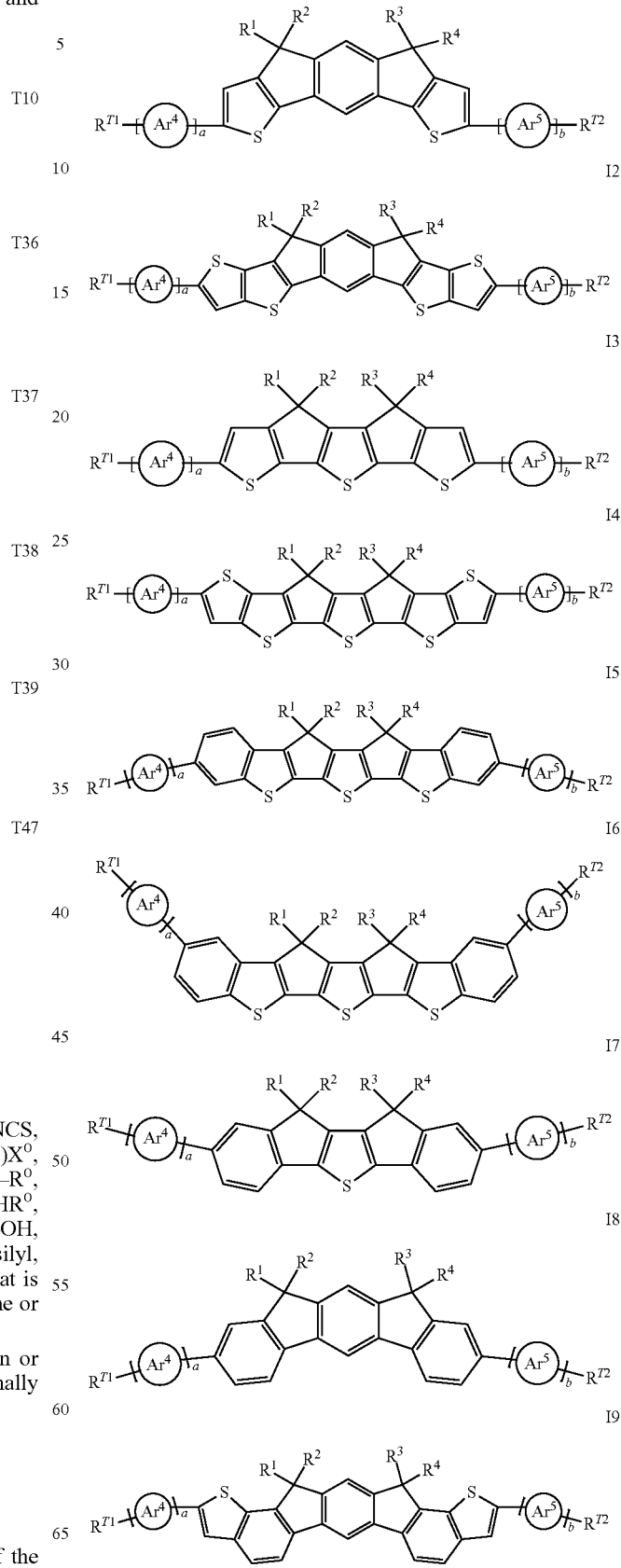

-continued

I10
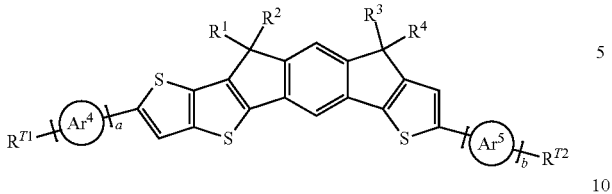

I11
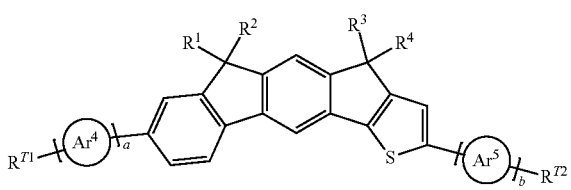

I12
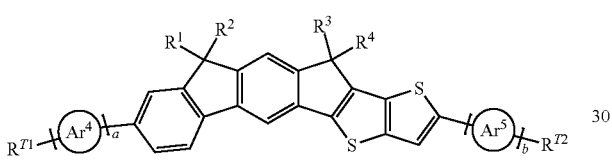

I13
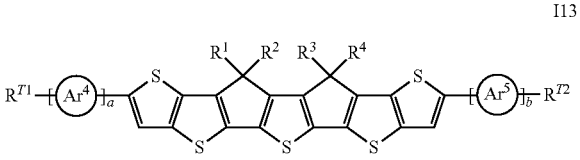

wherein

Ar$^{4,5}$ are, each independently, arylene or heteroarylene that has from 5 to 20 ring atoms, is mono- or polycyclic, optionally contains fused rings, and is unsubstituted or substituted by one or more identical or different groups L, or CY$^1$=CY$^2$ or —C≡C—, Y$^1$, Y$^2$ are, each independently, H, F, Cl or CN, R$^{1-4}$ are, each independently, H, F, Cl or straight-chain, branched or cyclic alkyl with 1 to 30 C atoms, in which one or more CH$_2$ groups are optionally replaced by —O—, —S—, —C(=O)—, —C(=S)—, —C(=O)—O—, —O—C(=O)—, —NR$^o$—, —SiR$^o$R$^{oo}$—, —CF$_2$—, —CR$^o$=CR$^{oo}$—, —CY$^1$=CY$^2$— or —C≡C— in such a manner that O and/or S atoms are not linked directly to one another, and in which one or more H atoms are optionally replaced by F, Cl, Br, I or —CN, and in which one or more CH$_2$ or CH$_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups L, and a pair of R$^1$ and R$^2$ and/or a pair of R$^3$ and R$^4$ together with the C, Si or Ge atom to which they are attached, may also form a spiro group with 5 to 20 ring atoms which is mono- or polycyclic, does optionally contain fused rings, and is unsubstituted or substituted by one or more identical or different groups L, R$^{T1}$, R$^{T2}$ are, each independently, a carbyl or hydrocarbyl group with 1 to 30 C atoms that is optionally substituted by one or more groups L and optionally comprises one or more hetero atoms, and wherein at least one of R$^{T1}$ and R$^{T2}$ is an electron withdrawing group, L is F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, or optionally substituted silyl, or carbyl or hydrocarbyl with 1 to 30 C atoms that is optionally substituted and optionally comprises one or more hetero atoms, or is —O—C(=O)—OR$^o$, R$^o$, R$^{oo}$ are, each independently, H or straight-chain or branched alkyl with 1 to 20 C atoms that is optionally fluorinated, X$^o$ is halogen, and a, b are, each independently 0, 1, 2 or 3.

9. The compound according to claim 1, wherein

R$^{1-4}$ are each independently alkyl or alkoxy with 1 to 16 C atoms which is optionally fluorinated or aryl or heteroaryl that is mono- or polycyclic, optionally contains fused rings, has 4 to 30 ring atoms, and is optionally substituted by one or more groups L, L is F, Cl, —NO$_2$, —CN, —NC, —NCO, —NCS, —OCN, —SCN, R$^o$, OR$^o$, SR$^o$, —C(=O)X$^o$, —C(=O)R$^o$, —C(=O)—OR$^o$, —O—C(=O)—R$^o$, —NH$_2$, —NHR$^o$, —NR$^o$R$^{oo}$, —C(=O)NHR$^o$, —C(=O)NR$^o$R$^{oo}$, —SO$_3$R$^o$, —SO$_2$R$^o$, —OH, —NO$_2$, —CF$_3$, —SF$_5$, or optionally substituted silyl, or carbyl or hydrocarbyl with 1 to 30 C atoms that is optionally substituted and optionally comprises one or more hetero atoms, or is —O—C(=O)—OR$^o$, R$^o$, R$^{oo}$ are, each independently, H or straight-chain or branched alkyl with 1 to 20 C atoms that is optionally fluorinated, and X$^o$ is halogen.

10. A composition comprising one or more compounds according to claim 1, and further comprising one or more compounds having one or more of a semiconducting, hole or electron transporting, hole or electron blocking, electrically conducting, photoconducting, photoactive or light emitting properties, and/or a binder.

11. The composition, comprising one or more compounds having one or more of a semiconducting, hole or electron transporting, hole or electron blocking, electrically conducting, photoconducting, photoactive or light emitting properties, and/or a binder, and one or more n-type semiconductors, at least one of which is a compound according to claim 1, and one or more p-type semiconductors.

12. The composition of claim 10, comprising one or more p-type semiconductors selected from conjugated polymers.

13. The composition of claim 12, wherein the conjugated polymers are of the following formulae P1
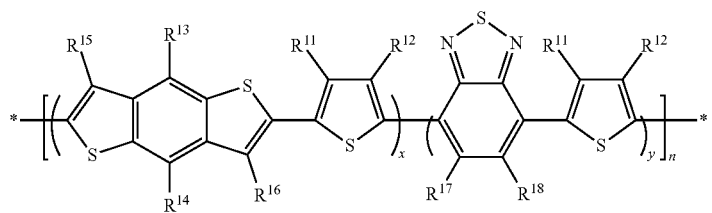
P2
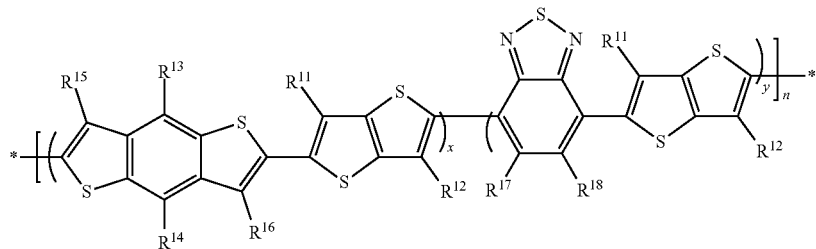
P3
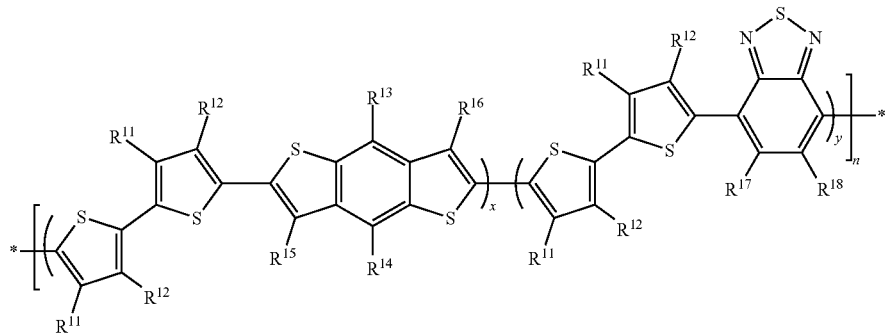
P4
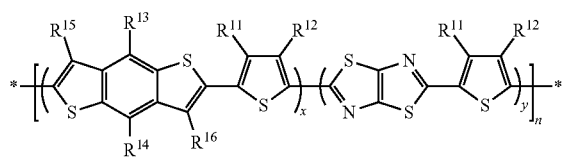
P5
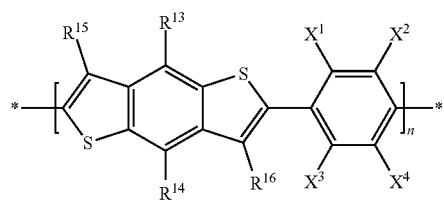
P6
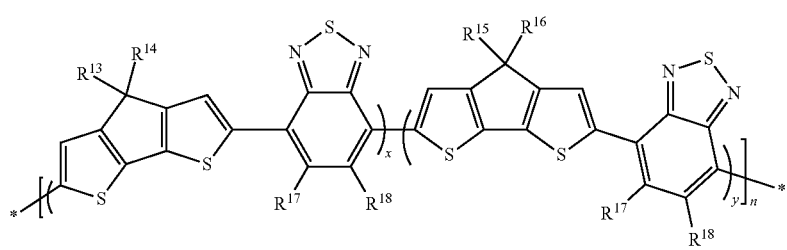
P7
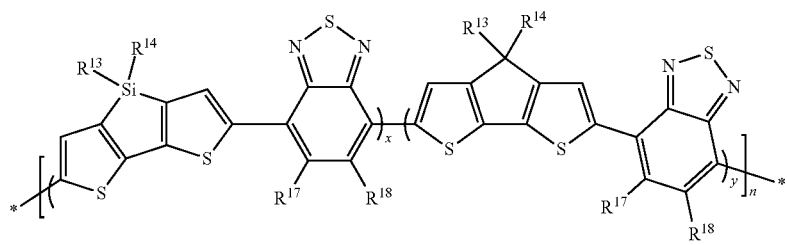

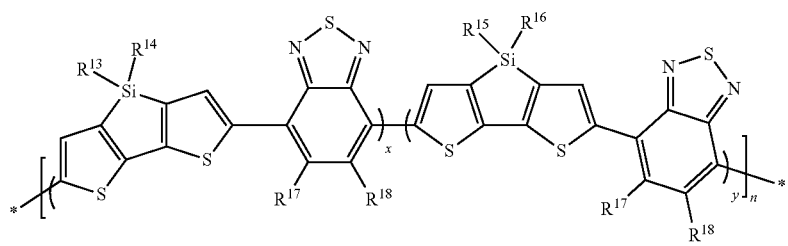
P8
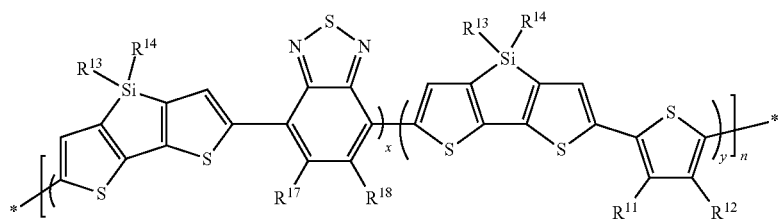
P9
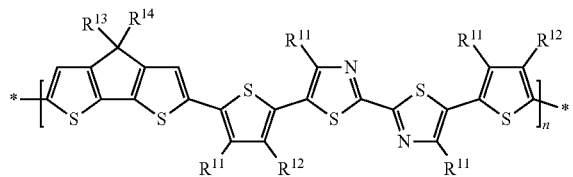
P10
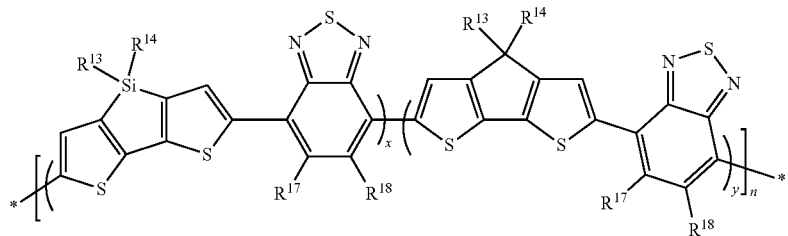
P11
P12
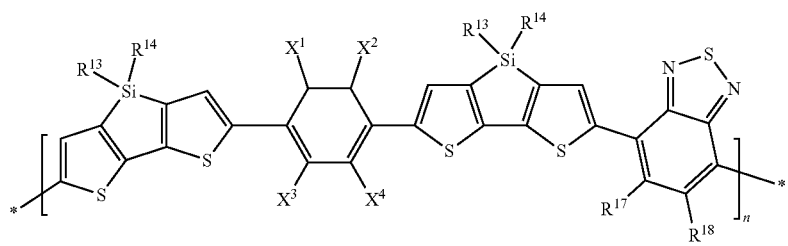
P13
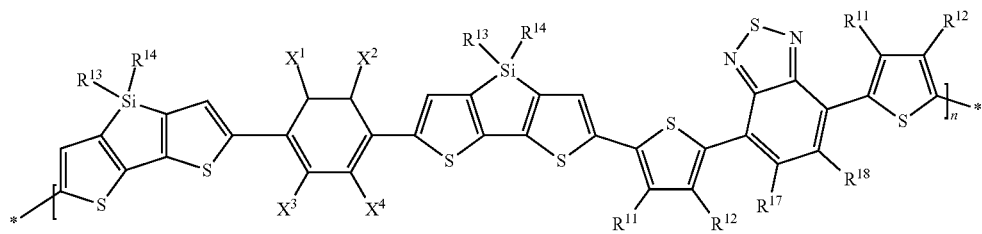
P14

-continued
P15
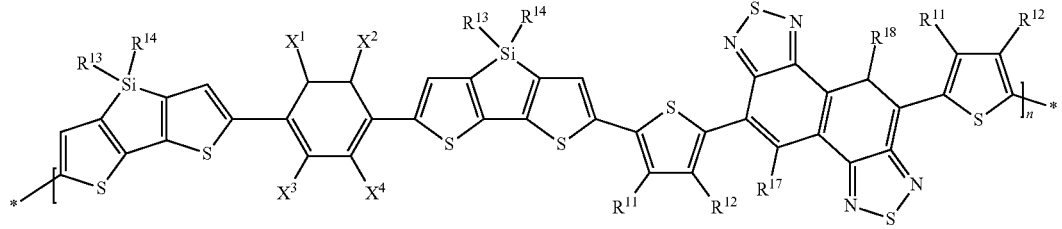
P16
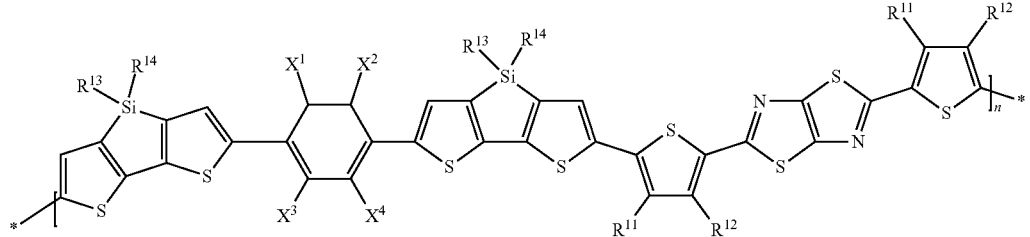
P17
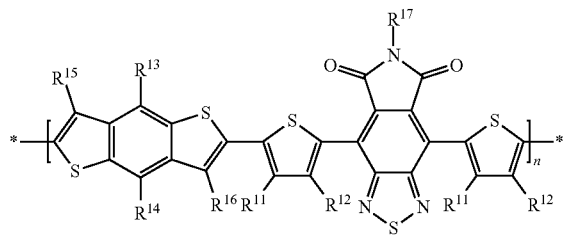
P18
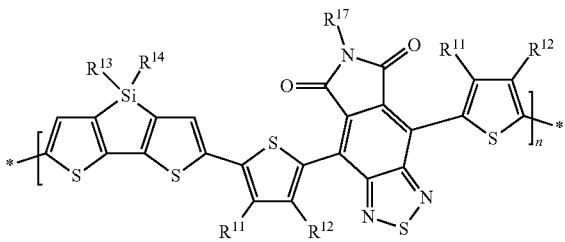
P19
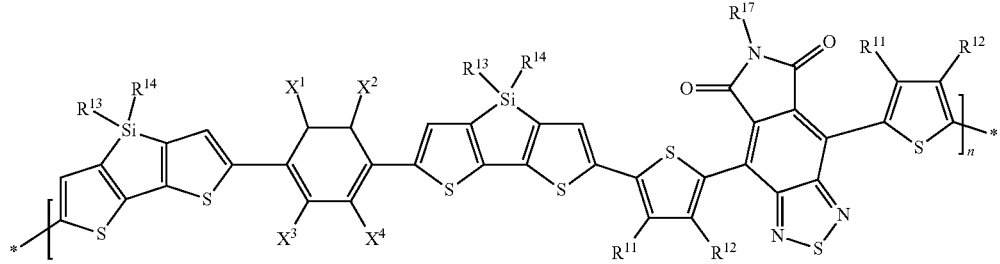
P20
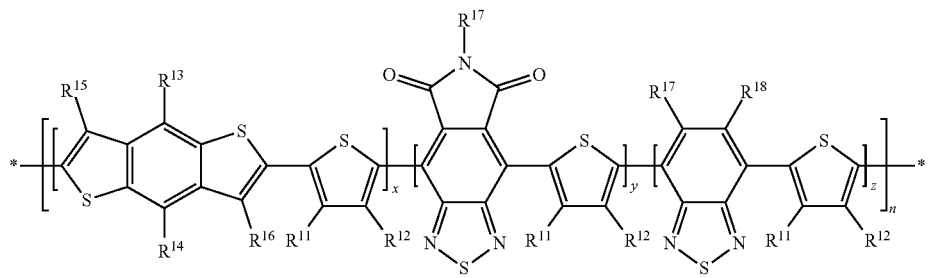
P21
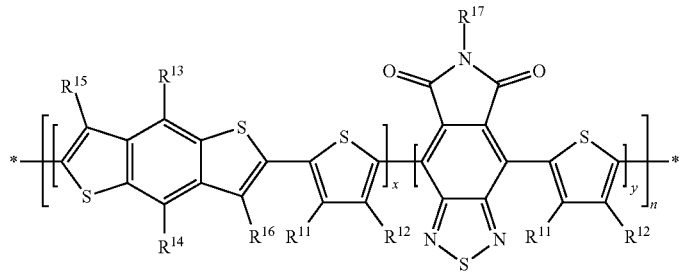

-continued
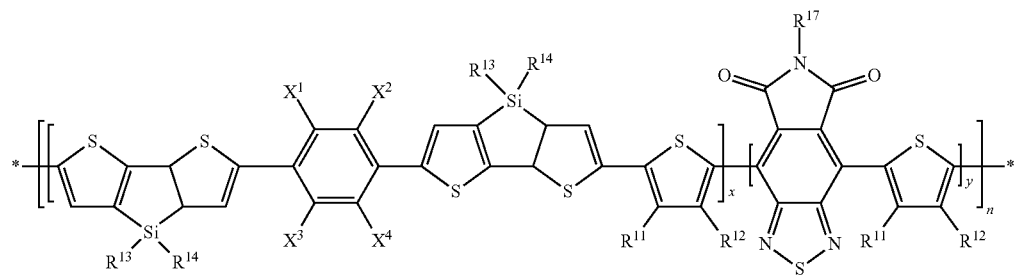
P22
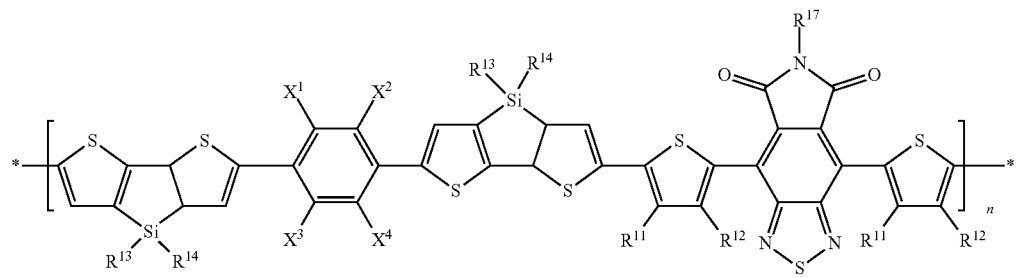
P23
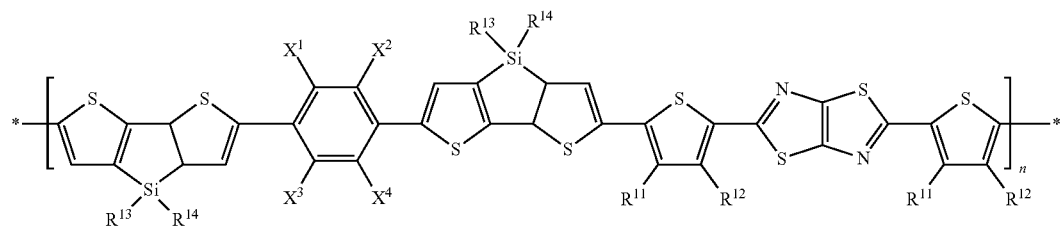
P24
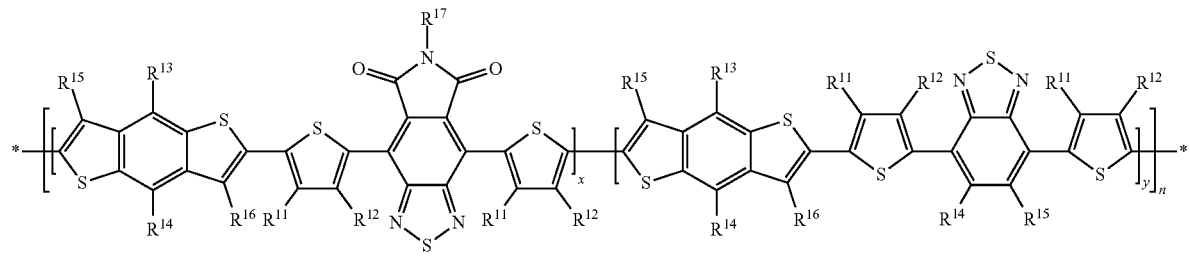
P25
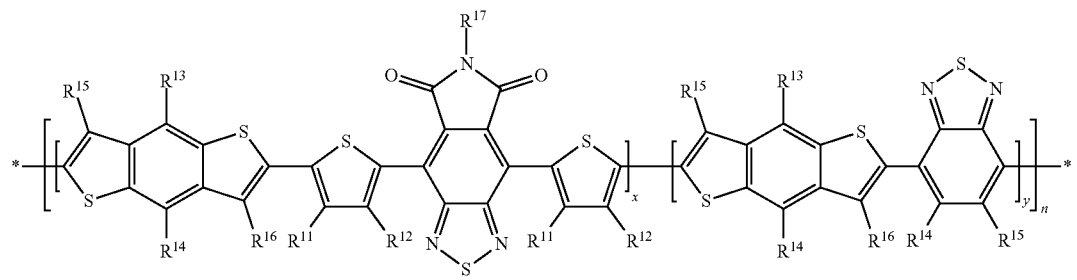
P26
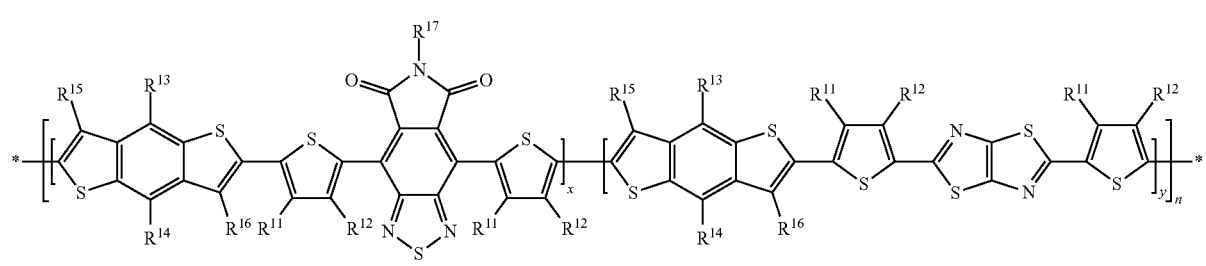
P27

-continued
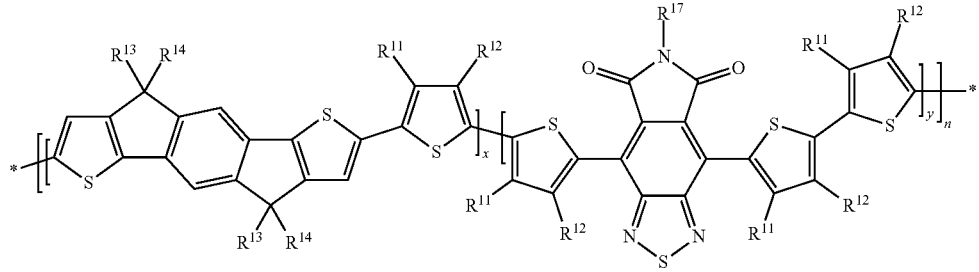
P28
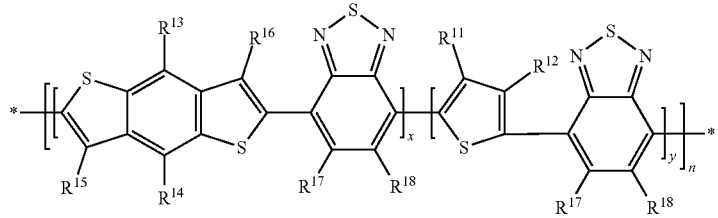
P29
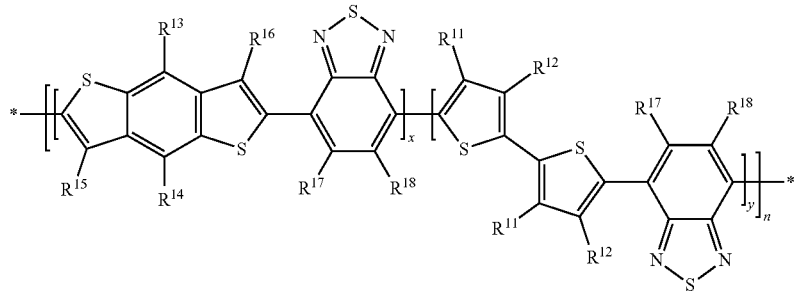
P30
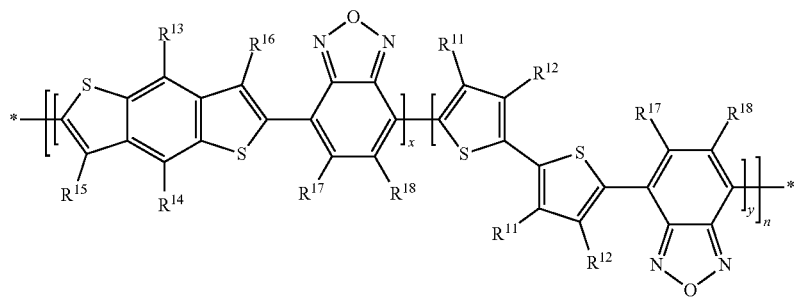
P31
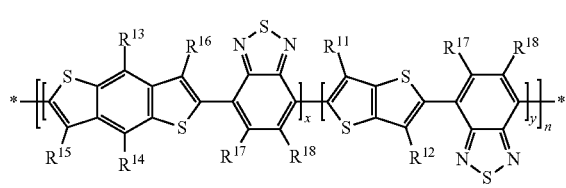
P32
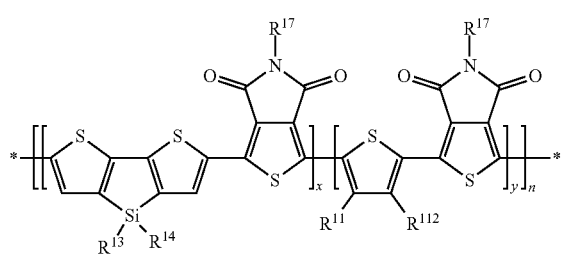
P34
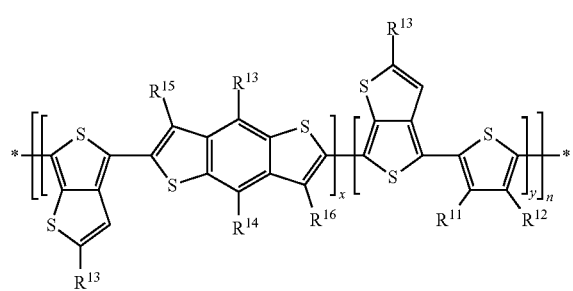
P33
P35

-continued
P36
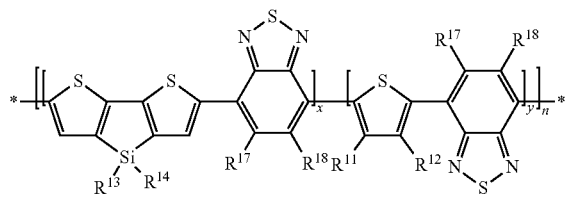
P37
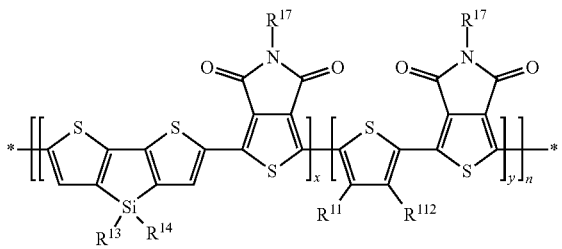
P38
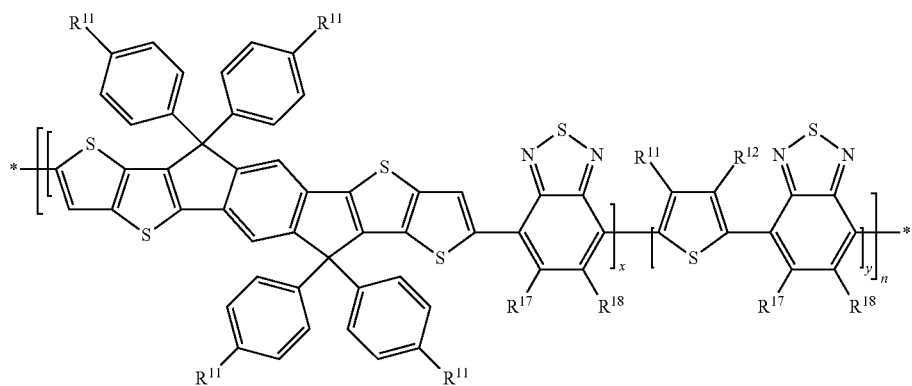
P39
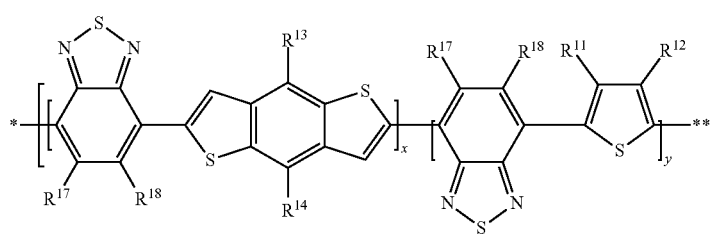
P39
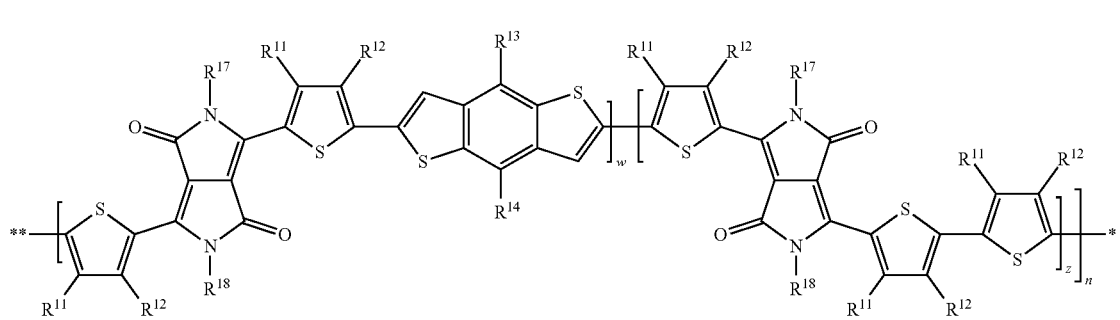
P40
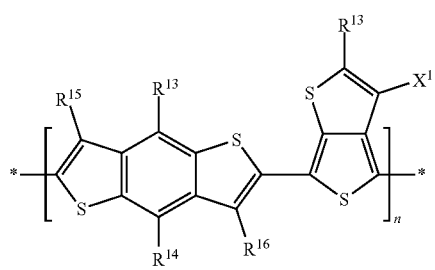
P41
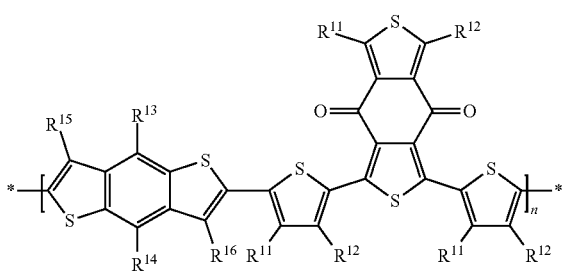

-continued
P42
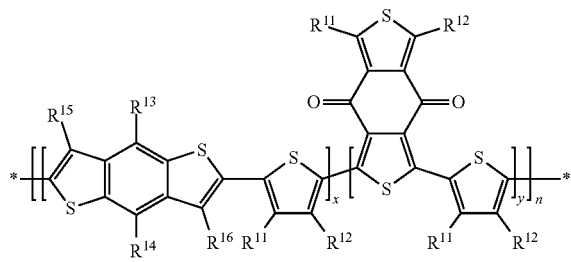
P43
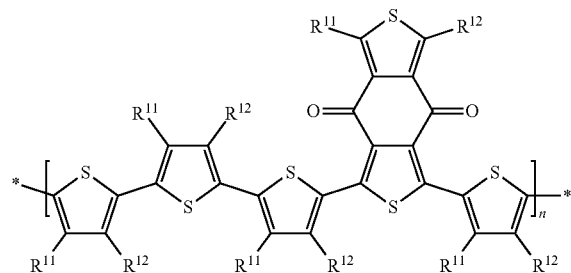
P44
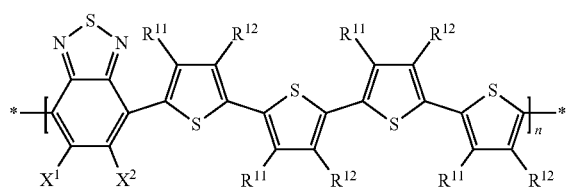
P45
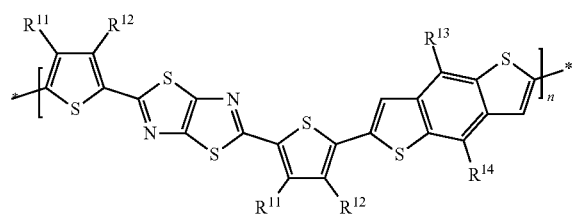
P46
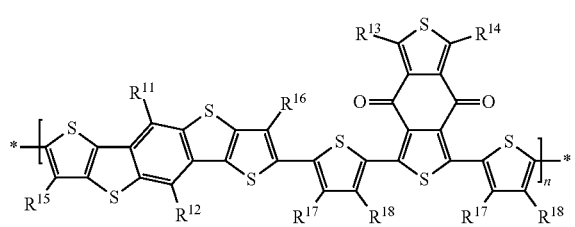
P47
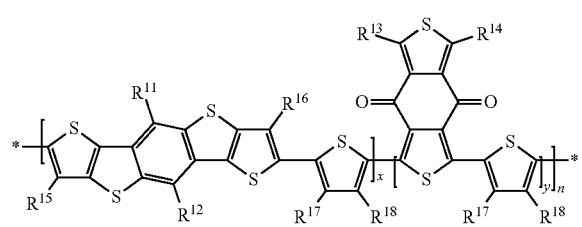
P48
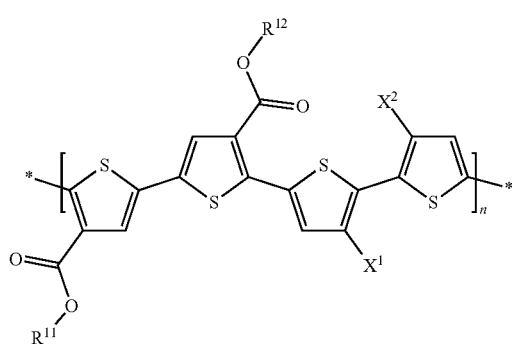
P49
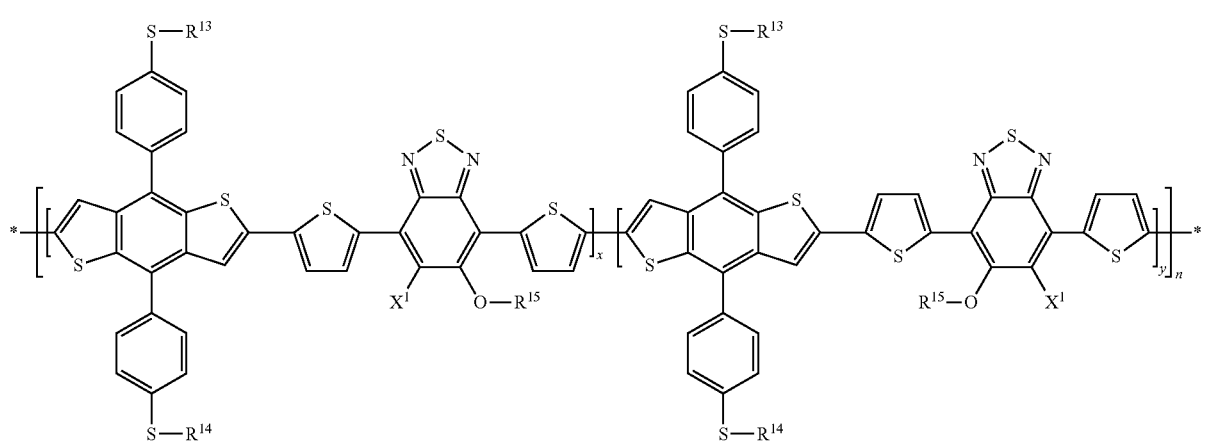

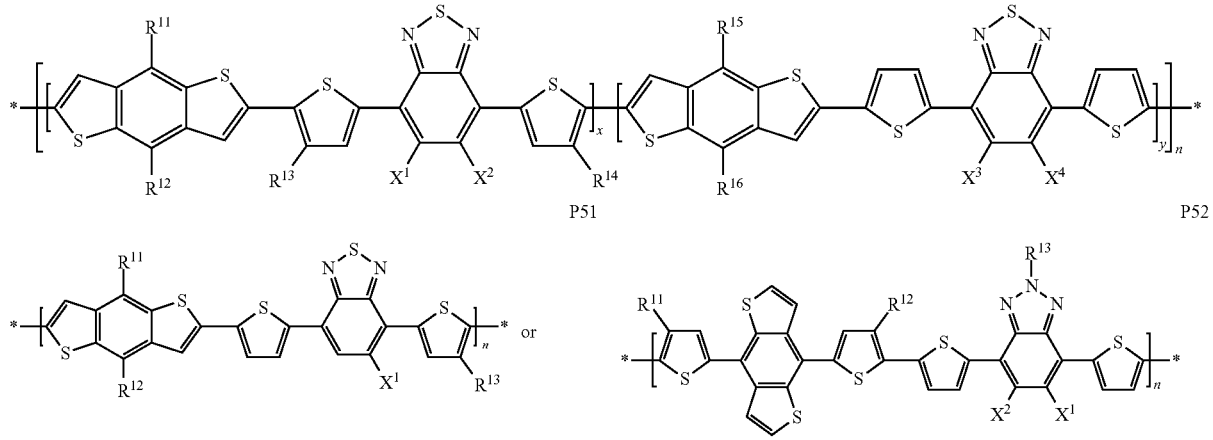

wherein R¹¹⁻¹⁹ independently of each other denote H or have one of the meanings of L, L is F, Cl, —NO₂, —CN, —NC, —NCO, —NCS, —OCN, —SCN, R°, OR°, SR°, —C(=O)X°, —C(=O)R°, —C(=O)—OR°, —O—C(=O)—R°, —NH₂, —NHR°, —NR°R°°, —C(=O)NHR°, —C(=O)NR°R°°, —SO₃R°, —SO₂R°, —OH, —NO₂, —CF₃, —SF₅, or optionally substituted silyl, or carbyl or hydrocarbyl with 1 to 30 C atoms that is optionally substituted and optionally comprises one or more hetero atoms, or is —O—C(=O)—OR°, R°, R°° are, each independently, H or straight-chain or branched alkyl with 1 to 20 C atoms that is optionally fluorinated, X° is halogen, X¹, X², X³ and X⁴ each independently denote H, F or Cl, x and y are each, independently of one another >0 and <1, with x+y=1, and n is an integer >1.

14. The composition according to claim 10, comprising one or more n-type semiconductors selected from fullerenes or fullerene derivatives.

15. A bulk heterojunction (BHJ) formed from a composition according to claim 10.

16. A formulation comprising one or more compounds according to claim 1, or a composition comprising said one or more compounds and one or more compounds having one or more of a semiconducting, hole or electron transporting, hole or electron blocking, electrically conducting, photoconducting, photoactive or light emitting properties, and/or a binder, and one or more organic solvents.

17. An electronic or optoelectronic device, or a component thereof, or an assembly comprising it, which comprises a compound according to claim 1, or a composition comprising compound and one or more compounds having one or more of a semiconducting, hole or electron transporting, hole or electron blocking, electrically conducting, photoconducting, photoactive or light emitting properties, and/or a binder.

18. The electronic or optoelectronic device according to claim 17, which is selected from the group consisting of organic field effect transistors (OFET), organic thin film transistors (OTFT), organic light emitting diodes (OLED), organic light emitting transistors (OLET), organic light emitting electro-chemical cells (OLEC), organic photovoltaic devices (OPV), organic photodetectors (OPD), organic solar cells, dye-sensitized solar cells (DSSC), perovskite-based solar cells, organic photoelectrochemical cells (OPEC), laser diodes, Schottky diodes, photoconductors, photodetectors, thermoelectric devices and LC windows.

19. The component according to claim 17, which is selected from the group consisting of charge injection layers, charge transport layers, interlayers, planarising layers, anti-static films, polymer electrolyte membranes (PEM), conducting substrates and conducting patterns.

20. The assembly according to claim 17, which is selected from the group consisting of integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

* * * * *